United States Patent
Nishide et al.

(10) Patent No.: US 11,844,268 B2
(45) Date of Patent: Dec. 12, 2023

(54) ORGANIC COMPOUND AND ORGANIC LIGHT-EMITTING ELEMENT

(71) Applicant: CANON KABUSHIKI KAISHA, Tokyo (JP)

(72) Inventors: Yosuke Nishide, Kanagawa (JP); Hirokazu Miyashita, Kanagawa (JP); Satoru Shiobara, Kanagawa (JP); Hiroki Ohrui, Kanagawa (JP); Naoki Yamada, Tokyo (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 521 days.

(21) Appl. No.: 17/084,128

(22) Filed: Oct. 29, 2020

(65) Prior Publication Data
US 2021/0143335 A1 May 13, 2021

(30) Foreign Application Priority Data

Nov. 12, 2019 (JP) ................. 2019-204601
Nov. 22, 2019 (JP) ................. 2019-211187
Jul. 14, 2020 (JP) ................. 2020-120637

(51) Int. Cl.
*H01L 51/50* (2006.01)
*H10K 85/60* (2023.01)
(Continued)

(52) U.S. Cl.
CPC ......... *H10K 85/624* (2023.02); *C07D 213/06* (2013.01); *C07D 213/22* (2013.01); *C07D 215/06* (2013.01); *C07D 237/30* (2013.01); *C07D 253/04* (2013.01); *C07D 307/91* (2013.01); *C07D 333/54* (2013.01); *C07D 333/76* (2013.01); *C07D 345/00* (2013.01); *C07D 401/10* (2013.01);
(Continued)

(58) Field of Classification Search
None
See application file for complete search history.

(56) References Cited

U.S. PATENT DOCUMENTS

| 2011/0251446 | A1 | 10/2011 | Kamatani | |
| 2014/0231787 | A1* | 8/2014 | Ishige | H10K 50/11 257/40 |
| 2021/0036232 | A1* | 2/2021 | Shiobara | C07D 307/91 |

* cited by examiner

*Primary Examiner* — Gregory D Clark
(74) *Attorney, Agent, or Firm* — Canon U.S.A., Inc., IP Division

(57) ABSTRACT

An organic compound represented by formula [1]. The compounds are of the class of diacenaphthochrysene compound, useful as organic light emitting device.

[1]

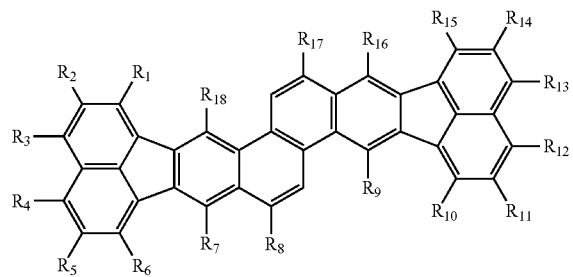

In the formula [1], $R_1$ to $R_{18}$ are each independently selected from the group consisting of a hydrogen atom and a substituent.

33 Claims, 6 Drawing Sheets

(51) Int. Cl.
  *C07D 401/10* (2006.01)
  *C07D 253/04* (2006.01)
  *C07D 307/91* (2006.01)
  *C07D 333/76* (2006.01)
  *C07D 333/54* (2006.01)
  *C07D 345/00* (2006.01)
  *C07D 493/04* (2006.01)
  *C07D 213/06* (2006.01)
  *C07D 213/22* (2006.01)
  *C07D 215/06* (2006.01)
  *C07D 471/04* (2006.01)
  *C07D 237/30* (2006.01)
  *H10K 50/13* (2023.01)
  *H10K 50/854* (2023.01)
  *H10K 59/12* (2023.01)
  *H10K 59/65* (2023.01)

(52) U.S. Cl.
  CPC ......... *C07D 471/04* (2013.01); *C07D 493/04* (2013.01); *H10K 85/654* (2023.02); *H10K 85/6574* (2023.02); *H10K 85/6576* (2023.02); *H10K 50/13* (2023.02); *H10K 50/854* (2023.02); *H10K 59/12* (2023.02); *H10K 59/65* (2023.02)

ORGANIC COMPOUND AND ORGANIC LIGHT-EMITTING ELEMENT

BACKGROUND OF THE INVENTION

Field of the Invention

The present disclosure relates to an organic compound and an organic light-emitting element including the organic compound.

Description of the Related Art

Organic light-emitting elements (also referred to as organic electroluminescent elements or organic EL elements) are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state.

Recent remarkable progress in organic light-emitting elements can achieve low driving voltage, various emission wavelengths, high-speed response, and reductions in the thickness and weight of light-emitting devices.

The standards of sRGB and AdobeRGB have been employed as a color reproduction range used for displays, and materials that reproduce the color reproduction range have been demanded. In recent years, BT-2020 has been selected as the standard that further widens the color reproduction range.

Luminescent organic compounds have been enthusiastically created to date. This is because it is important to create compounds having good light-emitting properties in order to provide high-performance organic light-emitting elements. US2011/0251446 (hereinafter PTL 1) discloses compounds 1-a, 1-A, and 1-B below.

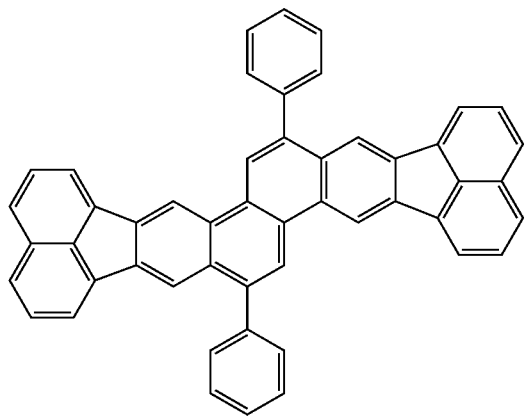

1-a

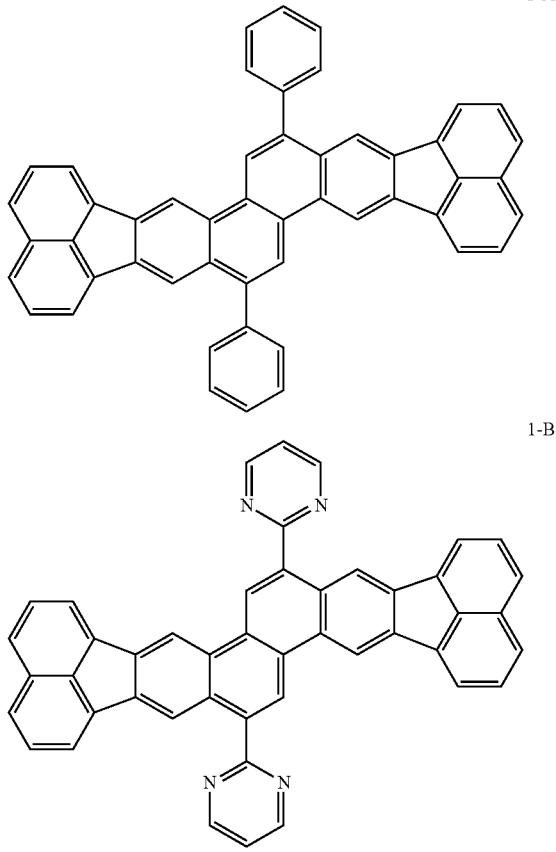

1-A

1-B

The compound 1-a described in PTL 1 is a blue light-emitting material, and is desired to have further improved light emission efficiency in the form of thin film. The compound 1-a is also desired to have further improved electron acceptability. Organic light-emitting elements including such a compound are desired to have further improved light emission efficiency or durability.

The compounds 1-A and 1-B described in PTL 1 are blue light-emitting materials, and are desired to have further improved electron acceptability. Furthermore, the color purity of blue light emission is desirably further improved in consideration of the color reproduction range of blue that corresponds to the standards of sRGB, AdobeRGB, and BT2020. Organic light-emitting elements including such compounds are desired to have further improved color purity or durability.

SUMMARY OF THE INVENTION

In view of the foregoing, the present disclosure provides a blue light-emitting material that contributes to high light emission efficiency due to reduced concentration quenching and that has high electron acceptability due to high reduction potential and has a high color purity.

The present disclosure also provides a blue light-emitting material having high electron acceptability due to high reduction potential and a high color purity. The present disclosure also provides an organic light-emitting element having a high color purity and high driving durability. The present disclosure also provides an organic light-emitting element having high light emission efficiency and high driving durability. One embodiment of the present disclosure provides an organic compound represented by formula [1].

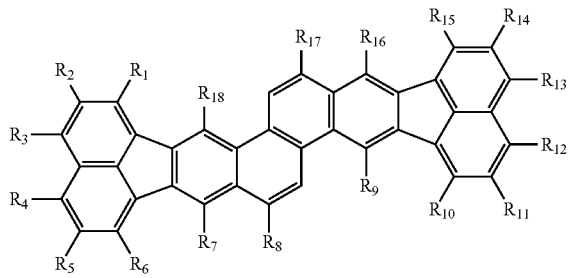

[1]

In the formula [1], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, a silyl group, and a group represented by any one of formulae [2], [3], and [102] to [104]. At least one of $R_1$ to $R_{18}$ represents a group represented by any one of the formulae [2], [3], and [102] to [104].

The group represented by any one of the formulae [2] and [3] is a group bonded at any one of $R_{19}$ to $R_{32}$.

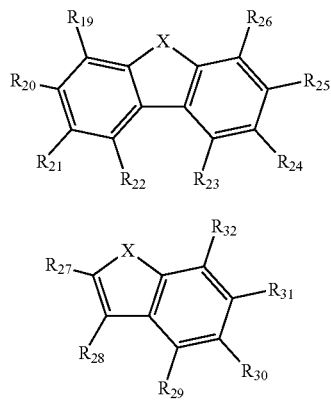

[2]

[3]

In the formulae [2] and [3], $R_{19}$ to $R_{32}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, and a silyl group. $R_{19}$ to $R_{32}$ may form a ring with a group adjacent thereto.

Each X is independently selected from the group consisting of an oxygen atom, a sulfur atom, a selenium atom, and a tellurium atom.

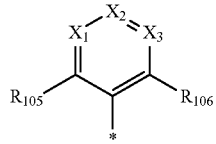

[102]

In the formula [102], $X_1$ to $X_3$ represent a carbon atom having a hydrogen atom or a substituent Y or a nitrogen atom, the carbon atom or the nitrogen atom constituting a ring. At least one of $X_1$ to $X_3$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group.

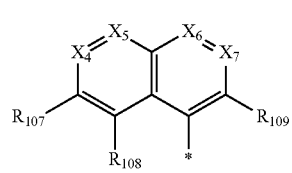

[103]

In the formula [103], $X_4$ to $X_7$ represent a carbon atom having a hydrogen atom or a substituent Y or a nitrogen atom, the carbon atom or the nitrogen atom constituting a ring. At least one of $X_4$ to $X_7$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ to $R_{109}$ represent groups each independently selected from the group consisting of a hydrogen atom, a substituted or unsubstituted alkyl group, a substituted or unsubstituted aryl group, and a substituted or unsubstituted heterocyclic group.

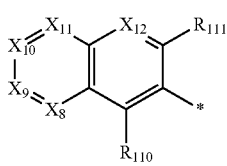

[104]

In the formula [104], $X_8$ to $X_{12}$ represent a carbon atom having a hydrogen atom or a substituent Y or a nitrogen atom, the carbon atom or the nitrogen atom constituting a ring. At least one of $X_8$ to $X_{12}$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

One embodiment of the present disclosure provides an organic compound represented by formula [101].

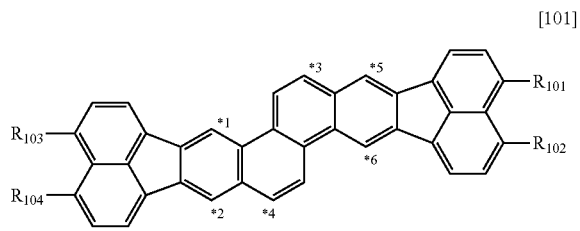

[101]

In the formula [101], a group having an azine skeleton and represented by any one of formulae [102] to [104] is bonded at a position * to at least one of positions *1 to *6. When the group having an azine skeleton and represented by any one of the formulae [102] to [104] is bonded to a plurality of the positions *1 to *6, the groups having an azine skeleton and represented by any one of the formulae [102] to [104] may be the same or different.

$R_{101}$ to $R_{104}$ represent groups each independently selected from the group consisting of a hydrogen atom, a substituted or unsubstituted aryl group, and a substituted or unsubstituted aryloxy group.

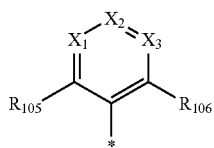

[102]

In the formula [102], $X_1$ to $X_3$ represent a carbon atom having a hydrogen atom or a substituent Y or a nitrogen atom, the carbon atom or the nitrogen atom constituting a ring. At least one of $X_1$ to $X_3$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group.

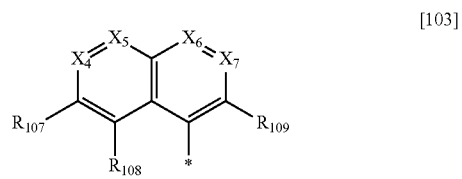

[103]

In the formula [103], $X_4$ to $X_7$ represent a carbon atom having a hydrogen atom or a substituent Y or a nitrogen atom, the carbon atom or the nitrogen atom constituting a ring. At least one of $X_4$ to $X_7$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ to $R_{109}$ represent groups each independently selected from the group consisting of a hydrogen atom, a substituted or unsubstituted alkyl group, a substituted or unsubstituted aryl group, and a substituted or unsubstituted heterocyclic group.

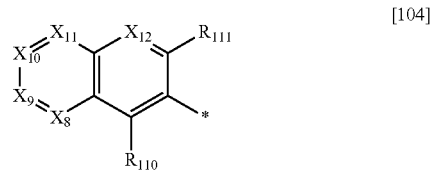

[104]

In the formula [104], $X_8$ to $X_{12}$ represent a carbon atom having a hydrogen atom or a substituent Y or a nitrogen atom, the carbon atom or the nitrogen atom constituting a ring. At least one of $X_8$ to $X_{12}$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

Further features of the present disclosure will become apparent from the following description of exemplary embodiments with reference to the attached drawings.

DESCRIPTION OF THE EMBODIMENTS

Organic Compound Represented by Formula [1]

Figure 1:
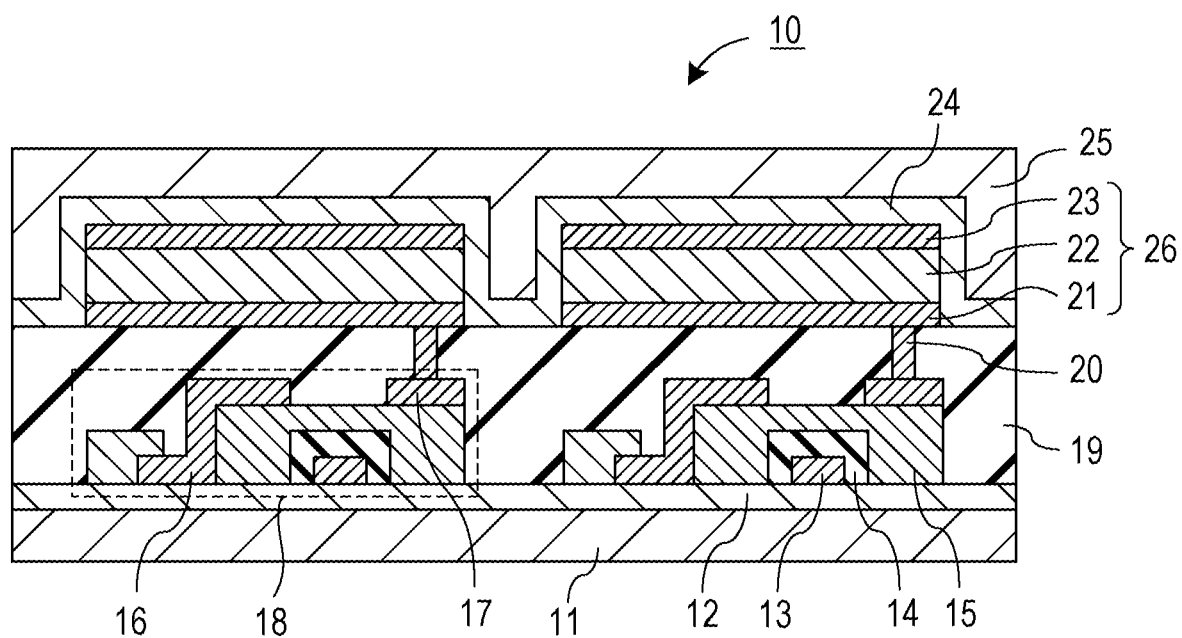
FIG. 1 is a schematic sectional view illustrating an example of a display apparatus including an organic light-emitting element according to an embodiment of the present disclosure.

First, an organic compound according to this embodiment will be described. The novel organic compound according to this embodiment is an organic compound represented by formula [1].

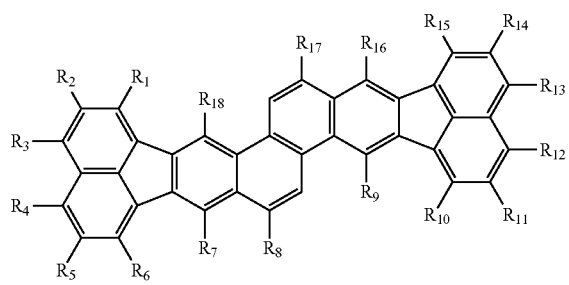

[1]

In the formula [1], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, a silyl group, and a group represented by any one of formulae [2], [3], and [102] to [104]. At least one of $R_1$ to $R_{18}$ represents a group represented by any one of the formulae [2], [3], and [102] to [104].

The group represented by any one of the formulae [2] and [3] is a group bonded at any one of $R_{19}$ to $R_{32}$.

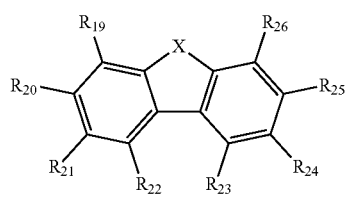

[2]

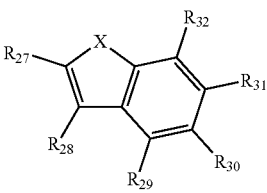

[3]

In the formulae [2] and [3], $R_{19}$ to $R_{32}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, and a silyl group. $R_{19}$ to $R_{32}$ may form a ring with a group adjacent thereto.

Each X is independently selected from the group consisting of an oxygen atom, a sulfur atom, a selenium atom, and a tellurium atom.

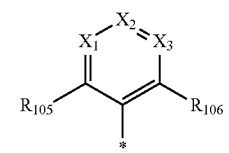

[102]

In the formula [102], $X_1$ to $X_3$ represent a carbon atom having a hydrogen atom or a substituent Y or a nitrogen atom, the carbon atom or the nitrogen atom constituting a ring. At least one of $X_1$ to $X_3$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group.

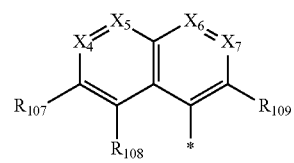

[103]

In the formula [103], $X_4$ to $X_7$ represent a carbon atom having a hydrogen atom or a substituent Y or a nitrogen atom, the carbon atom or the nitrogen atom constituting a ring. At least one of $X_4$ to $X_7$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ to $R_{109}$ represent groups each independently selected from the group consisting of a hydrogen atom, a substituted or unsubstituted alkyl group, a substituted or unsubstituted aryl group, and a substituted or unsubstituted heterocyclic group.

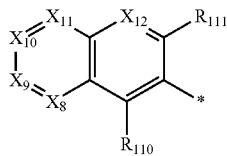

[104]

In the formula [104], $X_8$ to $X_{12}$ represent a carbon atom having a hydrogen atom or a substituent Y or a nitrogen atom, the carbon atom or the nitrogen atom constituting a ring. At least one of $X_8$ to $X_{12}$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

The group represented by any one of the formulae [2], [3], and [102] to [104] may be a group represented by any one of the formulae [2] and [3]. The number of groups represented by any one of the formulae [2], [3], and [102] to [104] is not particularly limited, and is preferably 1 to 4 and more preferably 1 or 2. Preferably, at least one of $R_3$, $R_4$, $R_7$, $R_8$, $R_9$, $R_{12}$, $R_{13}$, $R_{16}$, $R_{17}$, and $R_{18}$ represents a group represented by any one of the formulae [2], [3], and [102] to [104]. More preferably, at least one of $R_7$, $R_8$, $R_9$, $R_{16}$, $R_{17}$, and $R_{18}$ represents a group represented by any one of the formulae [2], [3], and [102] to [104]. The group represented by any one of the formulae [2] and [3] may be a group bonded at any one of $R_{22}$, $R_{23}$, and $R_{29}$. The group represented by any one of the formulae [2] and [3] may be a dibenzofuranyl group or a dibenzothiophenyl group.

$R_1$ to $R_{18}$ may be each independently selected from the group consisting of a hydrogen atom and a group represented by any one of the formulae [2], [3], and [102] to [104]. $R_1$, $R_6$, $R_{19}$, and $R_{15}$ may represent a hydrogen atom, $R_3$, $R_4$, $R_{12}$, and $R_{13}$ may represent a hydrogen atom, and $R_7$, $R_9$, $R_{16}$, and $R_{18}$ may represent a hydrogen atom.

In this embodiment, non-limiting examples of the halogen atom represented by $R_1$ to $R_{32}$ include fluorine, chlorine, bromine, and iodine.

Non-limiting examples of the alkyl group represented by $R_1$ to $R_{32}$ include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. Among them, the alkyl group may be an alkyl group having 1 to 10 carbon atoms.

Non-limiting examples of the alkoxy group represented by $R_1$ to $R_{32}$ include a methoxy group, an ethoxy group, a propoxy group, an 2-ethyl-octyloxy group, and a benzyloxy group. Among them, the alkoxy group may be an alkoxy group having 1 to 6 carbon atoms.

Non-limiting examples of the amino group represented by $R_1$ to $R_{32}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, and an N-piperidyl group.

Non-limiting examples of the aryl group represented by $R_1$ to $R_{32}$ include a phenyl group, a naphthyl group, an indenyl group, a biphenyl group, a terphenyl group, a fluorenyl group, a phenanthryl group, and a triphenylenyl group. Among them, the aryl group may be an aryl group having 6 to 18 carbon atoms.

Non-limiting examples of the aryloxy group represented by $R_1$ to $R_{32}$ include a phenoxy group and a thienyloxy group. Among them, the aryloxy group may be an aryloxy group having 6 to 18 carbon atoms.

Non-limiting examples of the silyl group represented by $R_1$ to $R_{32}$ include a trimethylsilyl group and a triphenylsilyl group.

Non-limiting examples of a substituent that may be further introduced to the alkyl group, the alkoxy group, the amino group, the aryl group, and the aryloxy group include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; amino groups such as a dimethylamino group, a diethylamino group, a dibenzylamino group, a diphenylamino group, and a ditolylamino group; alkoxy groups such as a methoxy group, an ethoxy group, and a propoxy group; aryloxy groups such as a phenoxy group; halogen atoms such as fluorine, chlorine, bromine, and iodine; a thienyl group; and a thiol group.

Examples of the group represented by the formula [102] include groups represented by formulae [105] to [109].

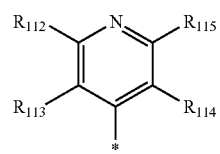

[105]

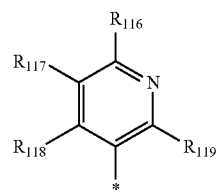

[106]

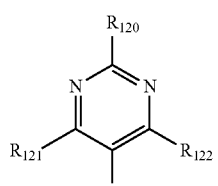

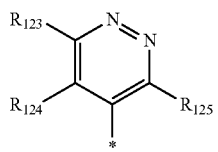

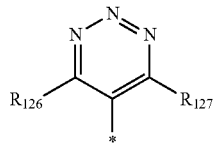

In the formulae [105] to [109], $R_{112}$ to $R_{127}$ represent groups each independently selected from the group consisting of a hydrogen atom, a substituted or unsubstituted alkyl group, a substituted or unsubstituted aryl group, and a substituted or unsubstituted heterocyclic group.

Examples of the group represented by the formula [103] or [104] include groups represented by formulae [110] to [118].

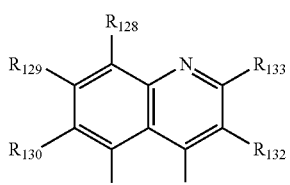

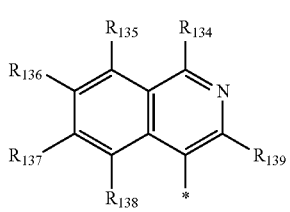

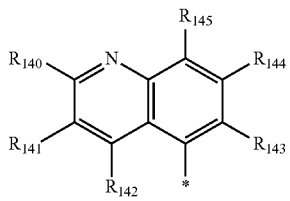

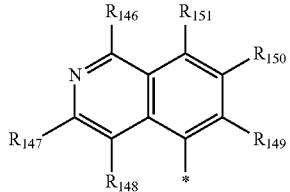

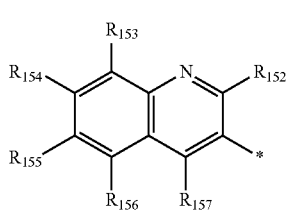

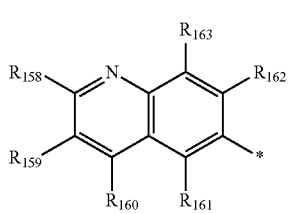

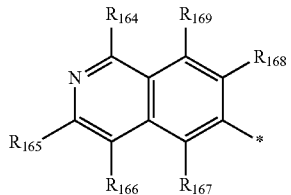

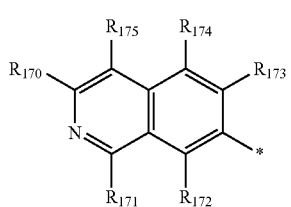

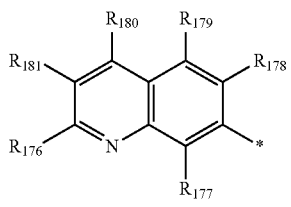

In the formulae [110] to [118], $R_{128}$ to $R_{181}$ represent groups each independently selected from the group consisting of a hydrogen atom, a substituted or unsubstituted alkyl group, a substituted or unsubstituted aryl group, and a substituted or unsubstituted heterocyclic group.

Examples of the group represented by the formula [103] or [104] also include groups represented by formulae [119] to [124].

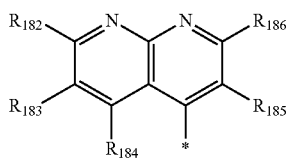

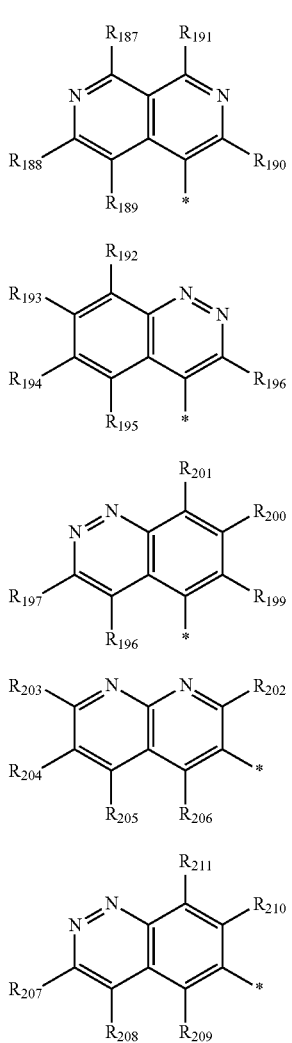

In the formulae [119] to [124], $R_{128}$ to $R_{211}$ represent groups each independently selected from the group consisting of a hydrogen atom, a substituted or unsubstituted alkyl group, a substituted or unsubstituted aryl group, and a substituted or unsubstituted heterocyclic group.

Examples of the group represented by the formula [103] or [104] also include groups with $X_6$ and $X_7$ representing a carbon atom and groups with $X_{12}$ representing a carbon atom.

[120] Non-limiting examples of the alkyl group represented by Y and $R_{105}$ to $R_{111}$ include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. Among them, the alkyl group may be an alkyl group having 1 to 10 carbon atoms.

[121] Non-limiting examples of the aryl group represented by Y and $R_{105}$ to $R_{211}$ include a phenyl group, a naphthyl group, an indenyl group, a biphenyl group, a terphenyl group, a fluorenyl group, a phenanthryl group, and a triphenylenyl group. Among them, the aryl group may be an aryl group having 6 to 18 carbon atoms.

[122] Non-limiting examples of the heterocyclic group represented by Y and $R_{105}$ to $R_{211}$ include a pyridyl group, a pyrimidyl group, a pyrazyl group, a triazyl group, an oxazolyl group, an oxadiazolyl group, a thiazolyl group, a thiadiazolyl group, a carbazolyl group, an acridinyl group, and a phenanthrolyl group. Among them, the heterocyclic group may be a heterocyclic group having 3 to 15 carbon atoms.

[123] Non-limiting examples of the aryloxy group represented by Y include a phenoxy group and a thienyloxy group.

Non-limiting examples of the silyl group represented by Y include a trimethylsilyl group and a triphenylsilyl group.

[124] Non-limiting examples of the substituent that may be further introduced to the alkyl group, the aryl group, the heterocyclic group, and the aryloxy group include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heterocyclic groups such as a pyridyl group and a pyrrolyl group; alkoxy groups such as a methoxy group, an ethoxy group, and a propoxy group; and aryloxy groups such as a phenoxy group.

Next, a method for synthesizing the organic compound according to this embodiment will be described. The organic compound according to this embodiment is synthesized through, for example, the following reaction scheme.

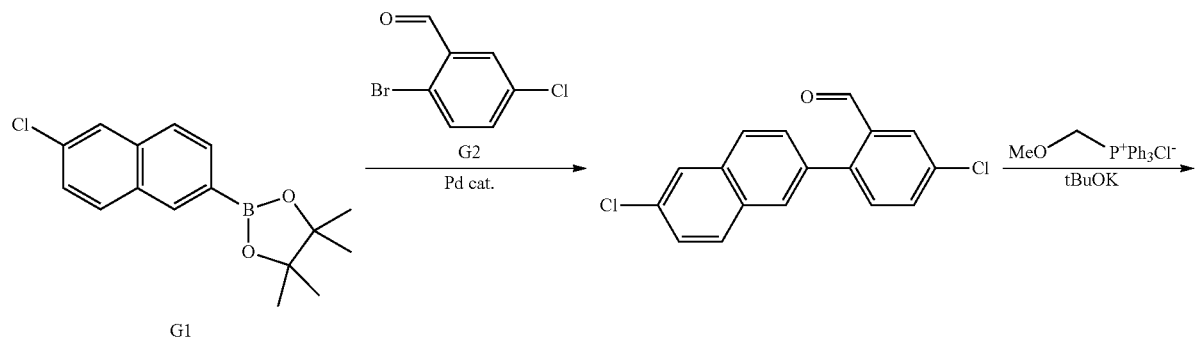

-continued

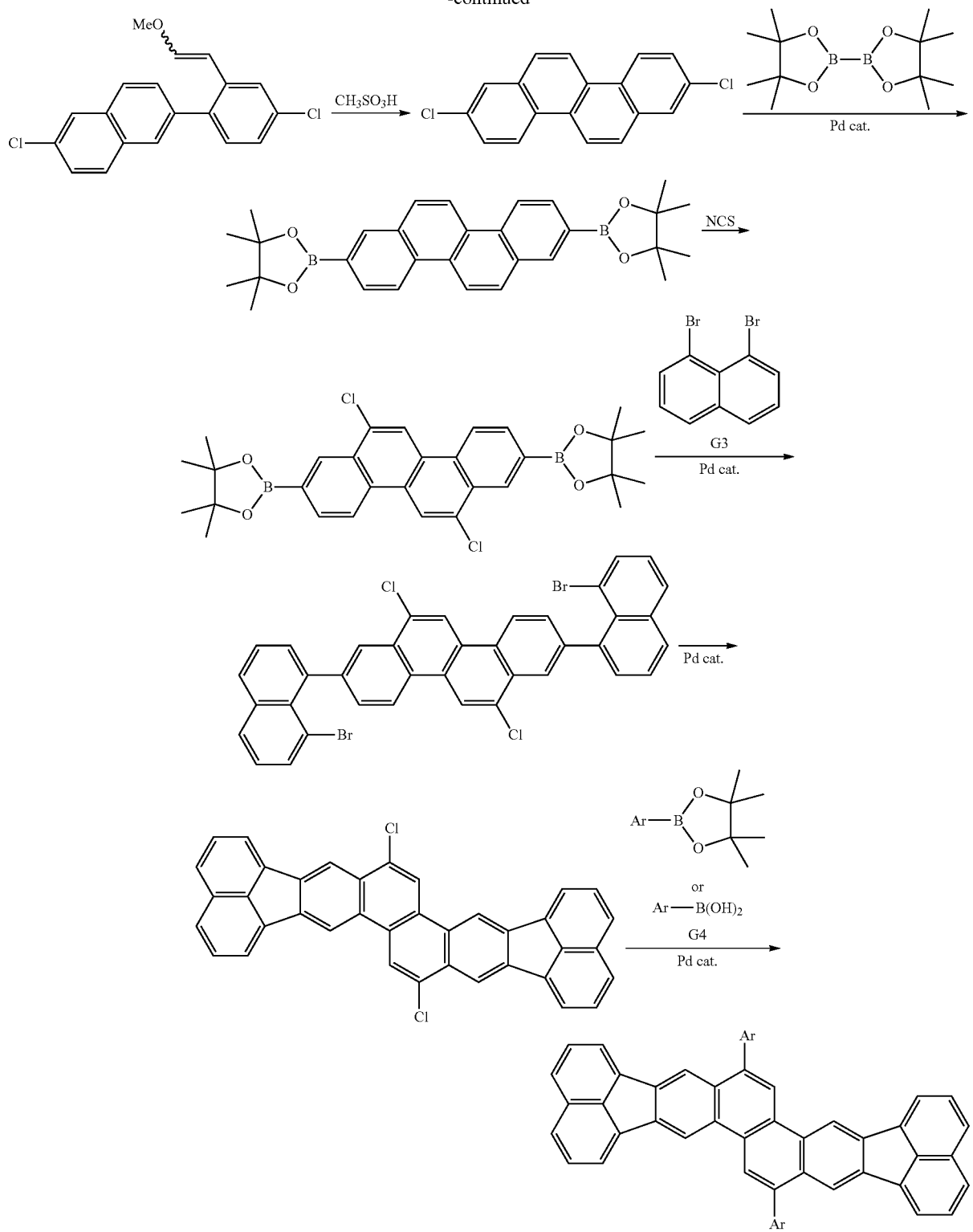

Herein, the organic compound represented by the formula [1] can be obtained by appropriately changing G1 to G4. The details of the synthesis method will be described in Examples.

Since the organic compound according to this embodiment has the following features, the organic compound is a chemically stable compound that contributes to emitting blue light with a high color purity and high efficiency and has a high reduction potential (in a direction away from the vacuum level in terms of LUMO). By using the organic compound according to this embodiment, an organic light-emitting element having a high color purity, high light emission efficiency, and high durability can also be provided.

(1) When the basic skeleton has, as an electron-withdrawing substituent, a benzochalcogenophene derivative group represented by any one of the formulae [2] and [3] (hereafter may be simply referred to as a "benzochalcogenophene derivative group"), high electron acceptability and blue light emission with a high color purity are achieved.

(2) When the basic skeleton has a benzochalcogenophene derivative group as a substituent for reducing concentration quenching, light emission efficiency in the form of thin film is improved.

The basic skeleton according to this embodiment is a basic skeleton in which all of $R_1$ to $R_{18}$ of the compound represented by the formula [1] represent a hydrogen atom.

For these features, the characteristics of the basic skeleton of the organic compound according to this embodiment will be described by comparing the organic compound with comparative compounds having a structure similar to that of the organic compound according to this embodiment. Specifically, the comparative compounds are a comparative compound 1-a described in PTL 1 and a comparative compound 1-b similar to the organic compound according to this embodiment.

Comparative compound 1-a

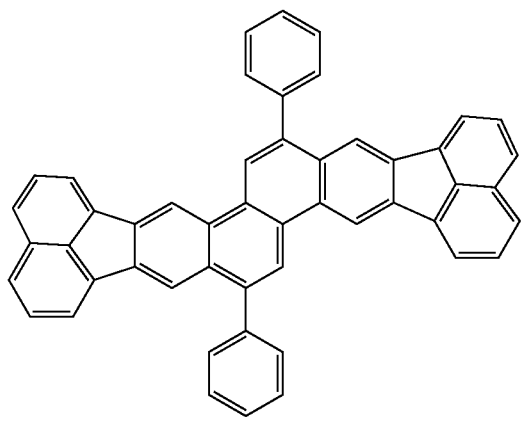

Comparative compound 1-b

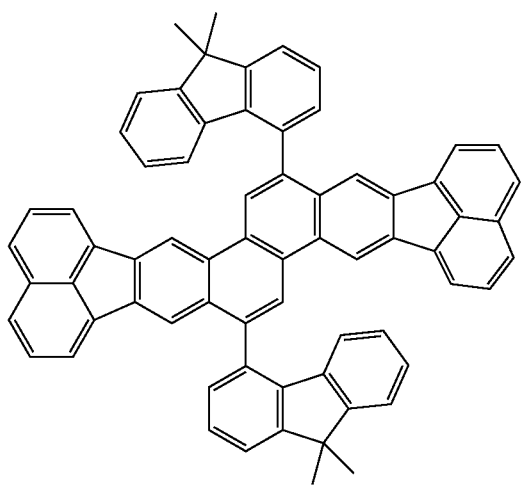

Exemplary compound A1

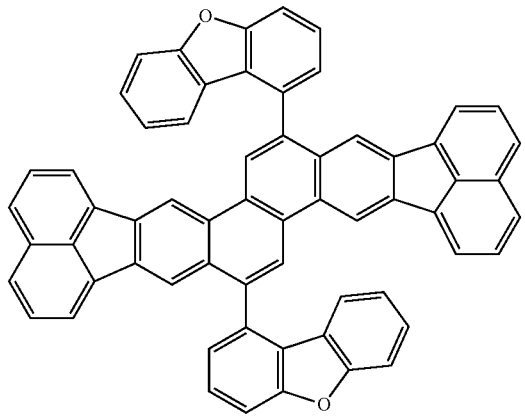

Herein, one of the organic compounds according to this embodiment is an exemplary compound A1 in which $R_1$ to $R_7$, $R_9$ to $R_{16}$, and $R_{18}$ represent a hydrogen atom and $R_8$ and $R_{17}$ represent a dibenzofuranyl group in the formula [1].

(1) When the basic skeleton has a benzochalcogenophene derivative group as an electron-withdrawing substituent, high electron acceptability and blue light emission with a high color purity are achieved.

When the organic compound represented by the formula [1] is made, the present inventors have focused on the basic skeleton itself.

To emit blue light with a high color purity, the basic skeleton itself needs to be in a blue region with a high color purity. In this embodiment, the desired emission wavelength region is a blue region with a high color purity, which is specifically a region in which the maximum emission wavelength in a dilute solution is 430 nm or more and 450 nm or less. The basic skeleton according to this embodiment is a basic skeleton suitable for desired blue light emission.

The basic skeleton according to this embodiment contributes to emitting blue light with a high color purity, but the compound has a large band gap and low electron acceptability. Organic light-emitting materials need to have high charge stability. To achieve this, high electron acceptability is required. In organic light-emitting elements, carrier recombination caused when an organic compound sandwiched between electrodes is repeatedly oxidized and reduced between its molecules allows the organic compound to have an excited state and a ground state in a repeated manner. Consequently, the organic light-emitting elements emit light. Therefore, the compound that is unstable in terms of charge transfer is chemically changed to a different compound through an oxidation-reduction process and in an excited state. This impairs the intrinsic element characteristics, which decreases the luminance of the organic light-emitting element and deteriorates the durability of the element during continuous driving. To suppress such deterioration, charge stability is required and thus high electron acceptability is required.

Accordingly, the present inventors have focused on an increase in reduction potential as one of design strategies for materials having high electron acceptability, and have found the compound represented by the formula [1]. Specifically, by introducing a benzochalcogenophene derivative group serving as an electron-withdrawing substituent to the basic skeleton, the electron acceptability is improved, which can further improve the charge stability.

In Table 1, the exemplary compound A1 according to this embodiment and the comparative compounds 1-a and 1-b are compared with each other in terms of the reduction potential determined by CV measurement and the maximum emission wavelength in a diluted toluene solution. To show the effect of a chalcogen atom that is a feature of this embodiment, the comparative compound 1-b is a comparative compound that is similar to the exemplary compound A1, but does not have a chalcogen atom.

The emission wavelength was measured by photoluminescence measurement of a diluted toluene solution at an excitation wavelength of 350 nm at room temperature using an F-4500 manufactured by Hitachi, Ltd. The reduction potential was determined by cyclic voltammetry (CV) measurement. The CV measurement was performed using a DMF solution of 0.1 M tetrabutylammonium perchlorate (for reduction potential measurement). The reference electrode was Ag/Ag$^+$, the counter electrode was Pt, and the working electrode was glassy carbon. The scanning speed of voltage was 1.0 V/s. The measurement instrument was an electrochemical analyzer 660C manufactured by ALS.

TABLE 1

| Name of compound | Molecular structure | Reduction potential (V) | Maximum emission wavelength (nm) |
| --- | --- | --- | --- |
| Comparative compound 1-a | 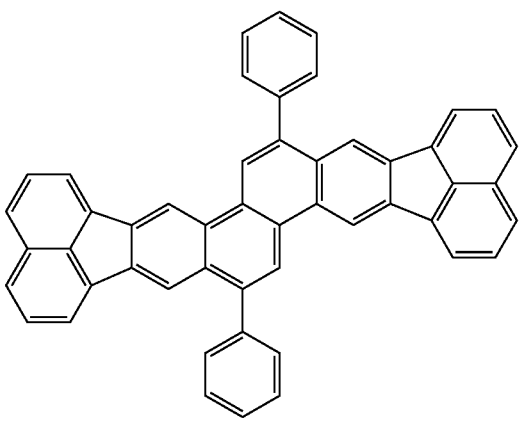 [SMILES: c1ccc(-c2cc3c4cc5c(cc4c(-c4ccccc4)cc3c3cc4c(cc23)-c2cccc3cccc-4c23)-c2cccc3cccc-5c23)cc1] | −2.10 | 448 |
| Comparative compound 1-b | 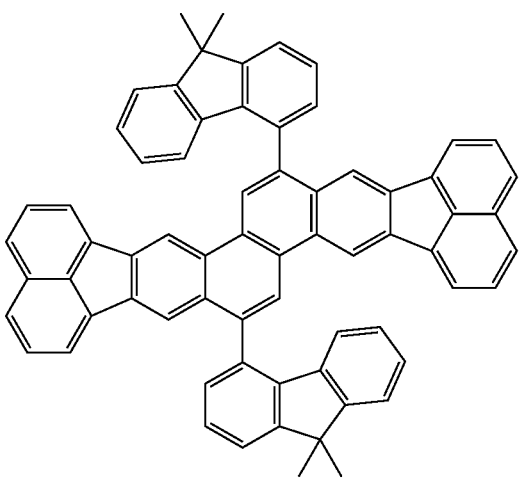 [SMILES: CC1(C)c2ccccc2-c2c(-c3cc4c5cc6c(cc5c(-c5cccc7c5-c5ccccc5C7(C)C)cc4c4cc5c(cc34)-c3cccc4cccc-5c34)-c3cccc4cccc-6c34)cccc21] | −2.10 | 445 |
| Exemplary compound A1 | 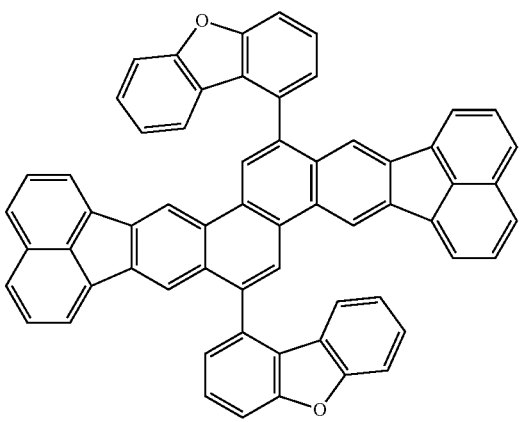 [SMILES: c1cc2c3c(cccc3c1)-c1cc3c(cc1-2)c(-c1cccc2oc4ccccc4c12)cc1c2cc4c(cc2c(-c2cccc5oc6ccccc6c25)cc31)-c1cccc2cccc-4c12] | −2.07 | 444 |

Table 1 shows that the reduction potential of the compound according to this embodiment having a benzochalcogenophene derivative group as an electron withdrawing substituent is higher than that of the comparative compounds 1-a and 1-b. This shows that the electron acceptability of the compound according to this embodiment is improved. Furthermore, compared with the comparative compound 1-a having an emission wavelength of 448 nm, the exemplary compound A1 according to this embodiment exhibits blue light emission with a high color purity. As described above, it has been found that the benzochalcogenophene derivative group provides unique effects of blue light emission with a high color purity and high reduction potential.

(2) When the basic skeleton has a benzochalcogenophene derivative group as a substituent for reducing concentration quenching, light emission efficiency in the form of thin film is improved.

The basic skeleton according to this embodiment exhibits blue light emission with a high color purity, but has high planarity. Therefore, the light emission efficiency decreases by concentration quenching in the form of thin film. If the efficiency decreases in the form of thin film, the light emission efficiency also decreases even when the compound is used for organic light-emitting elements. The concentration quenching needs to be reduced by introducing a substituent, but this effect is dependent on the type of substituent. For the substituent, in this embodiment, the present inventors have focused on the effect of suppressing intermolecular interaction by bulky fused ring structure as one of design strategies for reducing concentration quenching, and have found the compound represented by the formula [1].

Specifically, by introducing a benzochalcogenophene derivative group having a bulky fused ring structure to the basic skeleton, the light emission efficiency in the form of thin film can be improved. In Table 2, the exemplary compound A1 according to this embodiment and the comparative compound 1-a are compared with each other in terms of emission quantum yield in a diluted toluene solution and in a deposited film (single film). The emission quantum yield is expressed as a ratio obtained when the emission quantum yield of the comparative compound 1-a is 1.0.

The deposited film was formed on a glass substrate by performing vacuum vapor deposition through resistance heating in a vacuum chamber. The emission quantum yield was measured by placing the glass substrate subjected to vapor deposition in an integrating sphere C9920-02 manufactured by Hamamatsu Photonics K.K. and performing photoluminescence measurement at room temperature at an excitation wavelength of 350 nm.

Table 2 shows that the emission quantum yield of the compound A1 according to this embodiment is improved by the substituent having a bulky fused ring structure compared with the comparative compound 1-a. This shows that the effect of reducing concentration quenching is improved in the compound according to this embodiment.

TABLE 2

| Name of compound | Molecular structure | Quantum yield/ toluene solution | Quantum yield/ deposited film |
|---|---|---|---|
| Comparative compound 1-a | 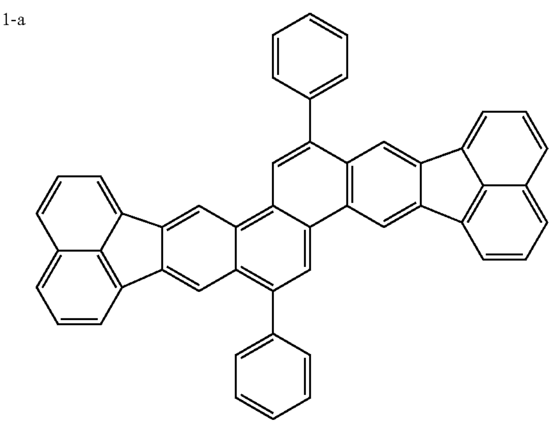 | 1.0 | 1.0 |
| Exemplary compound A1 | 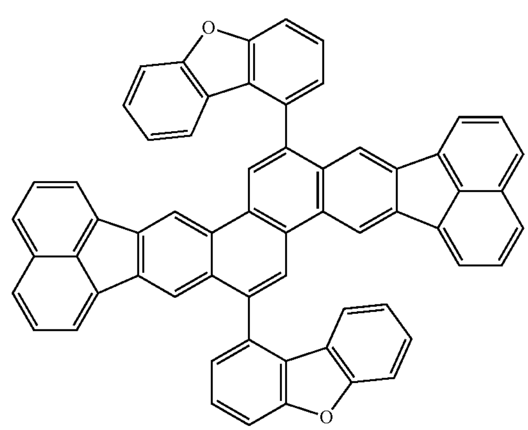 [SMILES: c1cc2c3c(cccc3c1)-c1cc3c(cc1-2)c(-c1cccc2oc4ccccc4c12)cc1c2cc4c(cc2c(-c2cccc5oc6ccccc6c25)cc31)-c1cccc2cccc-4c12] | 1.0 | 1.1 |

In the organic compound represented by the formula [1], a benzochalcogenophene derivative group may be introduced to at least one of $R_7$, $R_8$, $R_9$, $R_{16}$, $R_{17}$, and $R_{18}$.

The basic skeleton according to this embodiment has a large ratio of long axis and short axis. Therefore, if the substituent is not introduced near the center of gravity, the distance between basic skeleton planes is small in the form of thin film, which increases the intermolecular interaction. This may cause concentration quenching and decrease in sublimability. Therefore, the substituent may be introduced near the center of the molecule. In particular, it has been described above that the benzochalcogenophene derivative group provides a large effect.

The organic compound according to this embodiment has a glass transition temperature, which is as high as 120° C. or higher. This is because the organic compound has a benzochalcogenophene derivative group having a fused ring structure. If the organic compound has high crystallinity or a glass transition temperature of lower than 120° C. when used for organic light-emitting elements, crystallization is caused during the process of producing an element or during driving of an element, which decreases the efficiency and the durability life. Therefore, low crystallinity and high glass transition temperature are characteristics required to realize an excellent organic light-emitting element.

In the formula [1], the group represented by any one of the formulae [2] and [3] may be a group bonded at any one of $R_{22}$, $R_{23}$, and $R_{29}$. This is because the organic compound in which the group represented by any one of the formulae [2] and [3] is a group bonded at any one of $R_{22}$, $R_{23}$, and $R_{29}$ exhibits blue light emission with a higher color purity and higher reduction potential than other organic compounds according to this embodiment.

Table 3 shows the maximum emission wavelength in a diluted toluene solution and the reduction potential determined by CV measurement for the exemplary compounds A1, B1, and B9 according to this embodiment. This shows that the exemplary compound A1 in which the group represented by any one of the formulae [2] and [3] is a group bonded at any one of $R_{22}$, $R_{23}$, and $R_{29}$ has the shortest wavelength and the highest reduction potential.

TABLE 3

| Name of compound | Molecular structure | Maximum emission wavelength (nm) | Reduction potential (V) |
| --- | --- | --- | --- |
| Exemplary compound A1 | 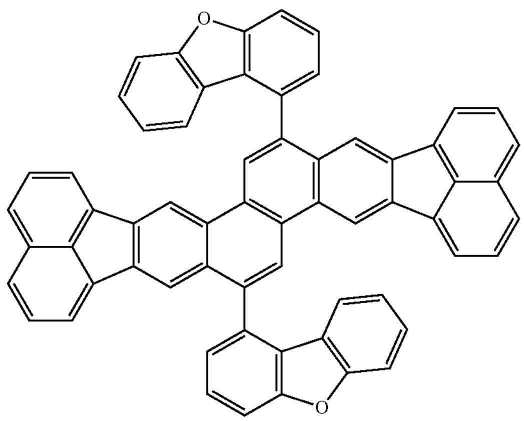 [SMILES: c1cc2c3c(cccc3c1)-c1cc3c(cc1-2)c(-c1cccc2oc4ccccc4c12)cc1c2cc4c(cc2c(-c2cccc5oc6ccccc6c25)cc31)-c1cccc2cccc-4c12] | 444 | −2.07 |
| Exemplary compound B1 | 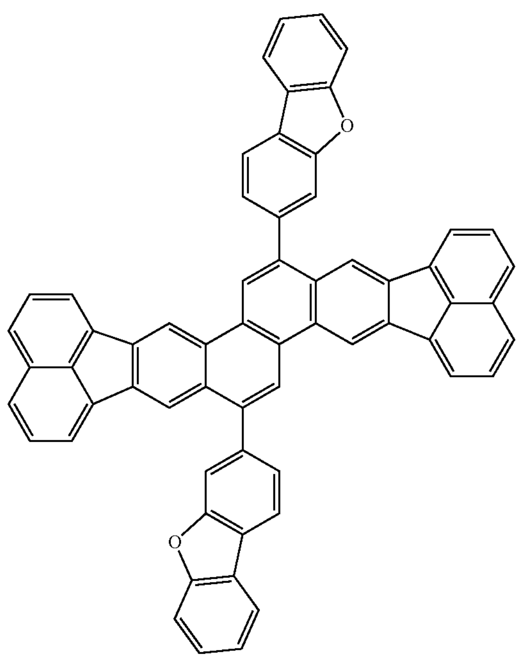 [SMILES: c1cc2c3c(cccc3c1)-c1cc3c(cc1-2)c(-c1ccc2c(c1)oc1ccccc12)cc1c2cc4c(cc2c(-c2ccc5c(c2)oc2ccccc25)cc31)-c1cccc2cccc-4c12] | 448 | −2.08 |

TABLE 3-continued

| Name of compound | Molecular structure | Maximum emission wavelength (nm) | Reduction potential (V) |
|---|---|---|---|
| Exemplary compound B9 | 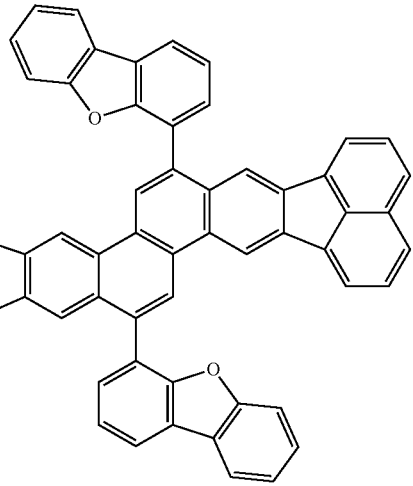 | 449 | −2.10 |

As described above, the organic compound according to this embodiment has the above features (1) and (2). Therefore, the organic compound is a chemically stable compound that contributes to emitting blue light with a higher color purity and higher efficiency and has higher reduction potential than the comparative compound. Accordingly, by using the organic compound according to this embodiment, an organic light-emitting element having a high color purity, high light emission efficiency, and high durability can be provided.

The organic compound according to this embodiment will be specifically described below. However, this embodiment is not limited thereto.

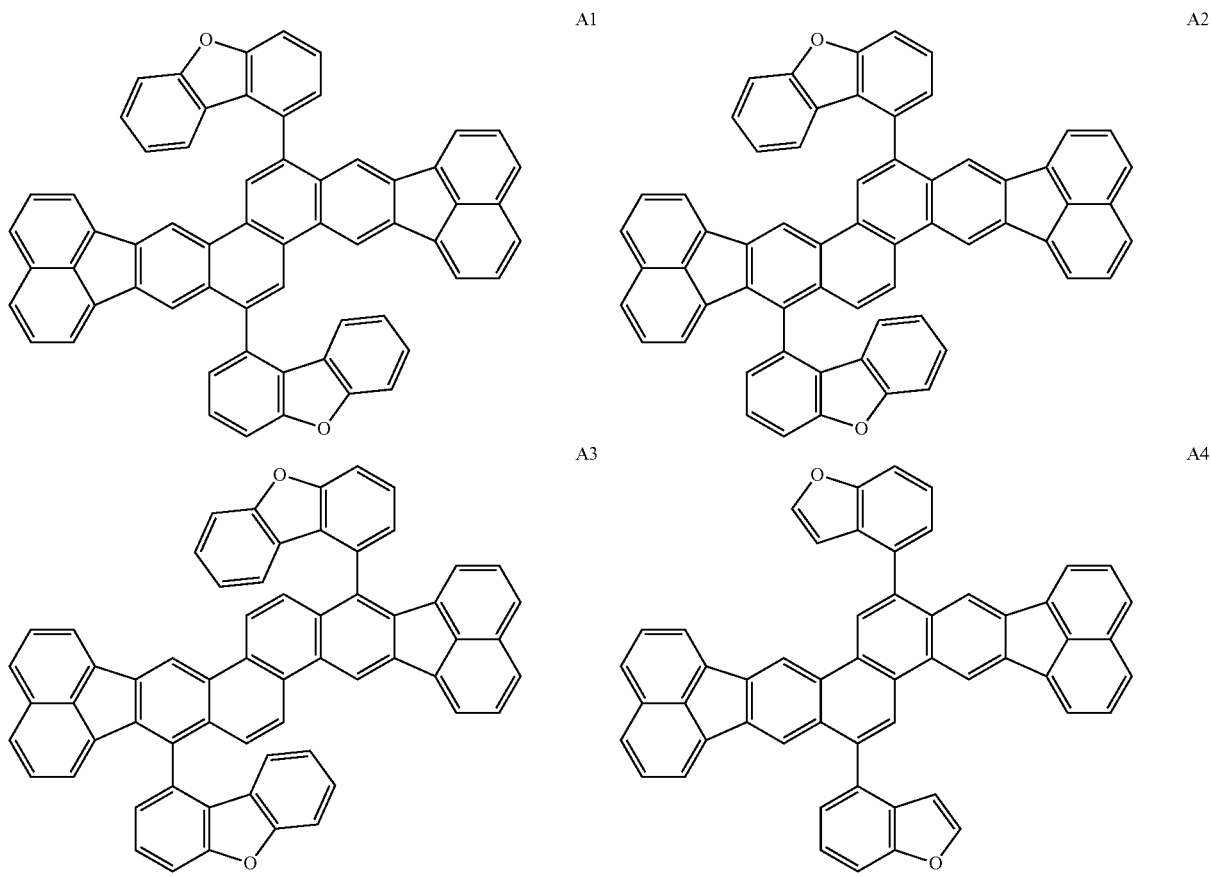

-continued
| | |
|---|---|
| A5 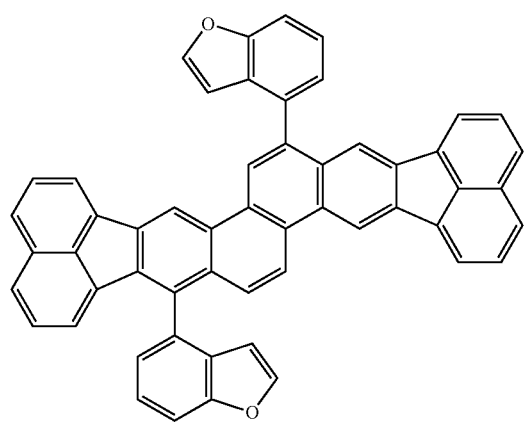 | A6 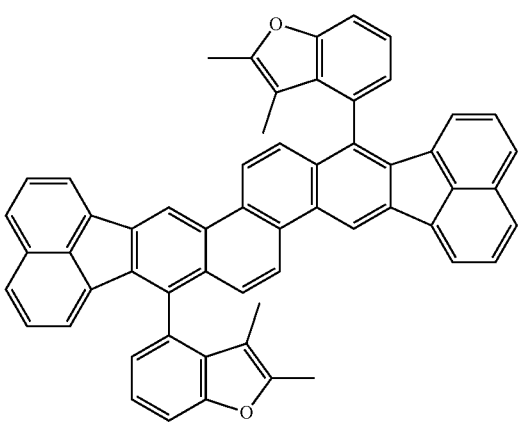 |
| A7 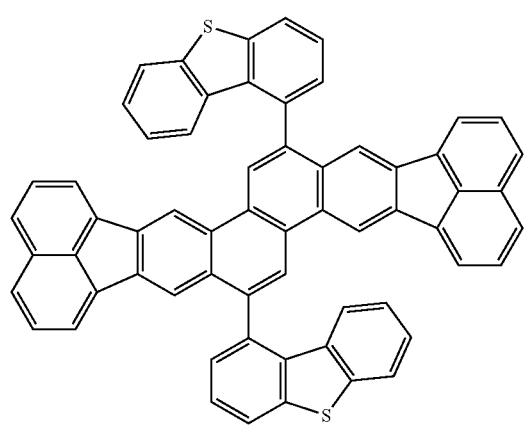 | A8 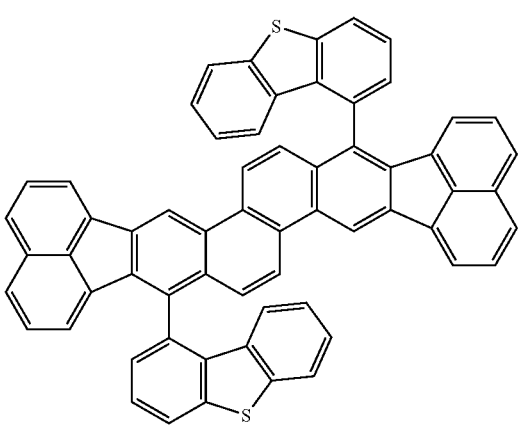 |
| A9 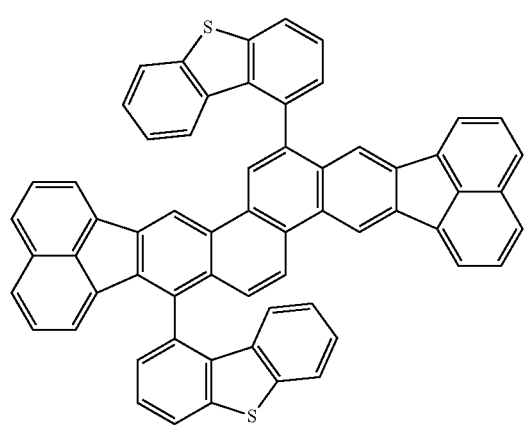 | A10 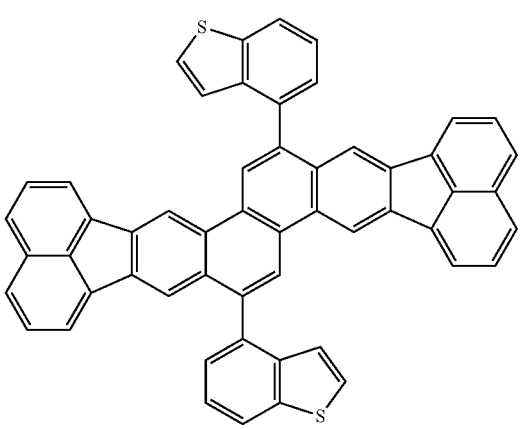 |

-continued
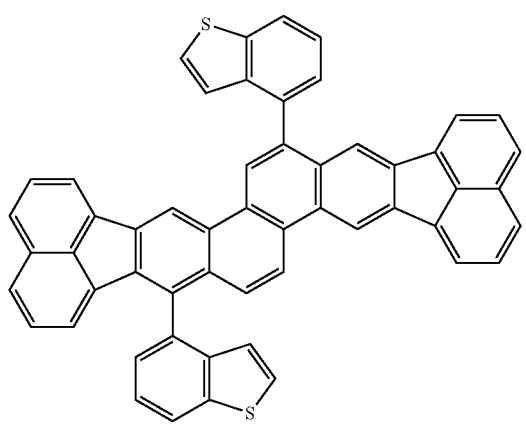
A11
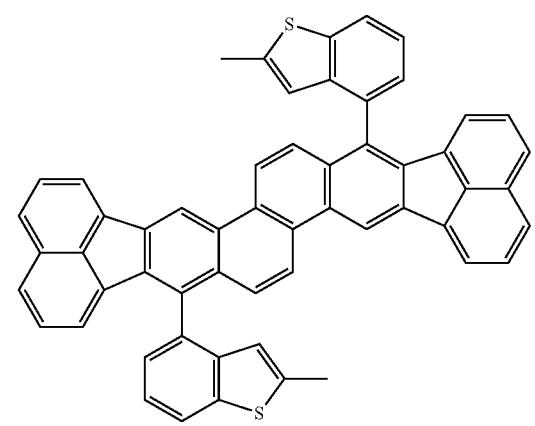
A12
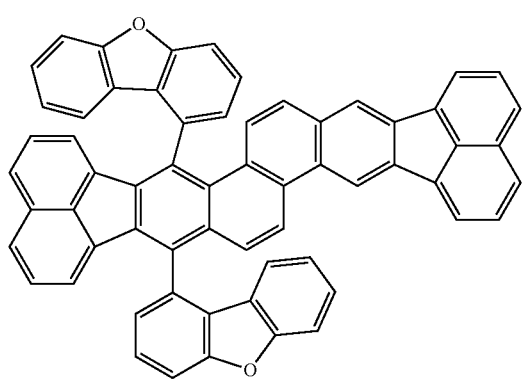
A13
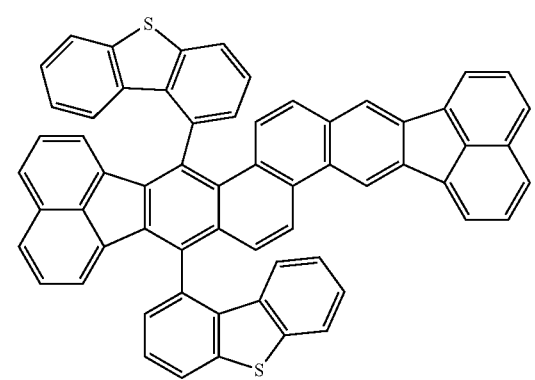
A14
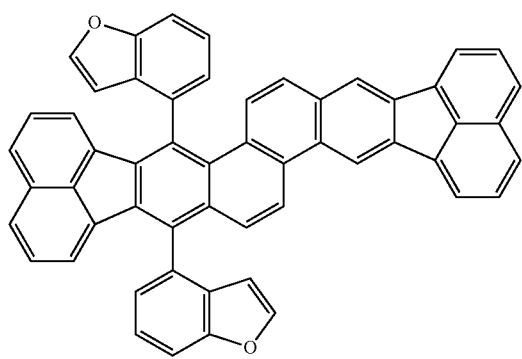
A15
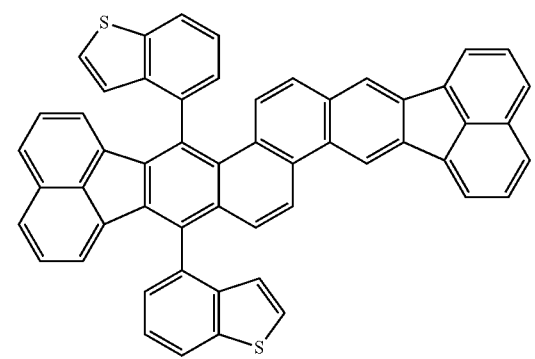
A16
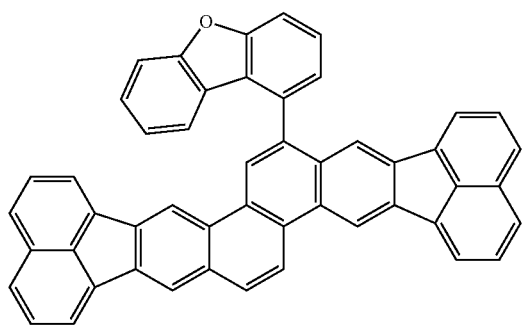
A17
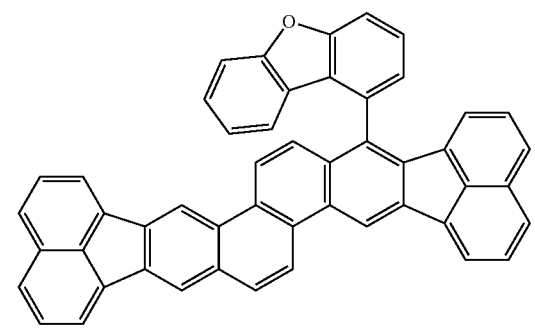
A18

-continued
A19
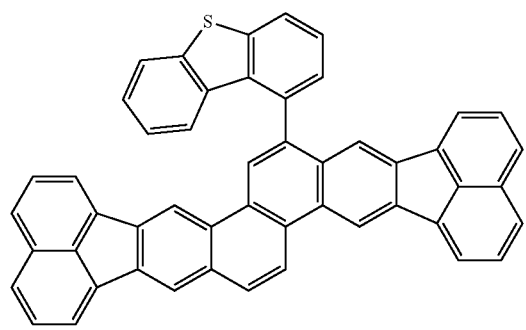
A20
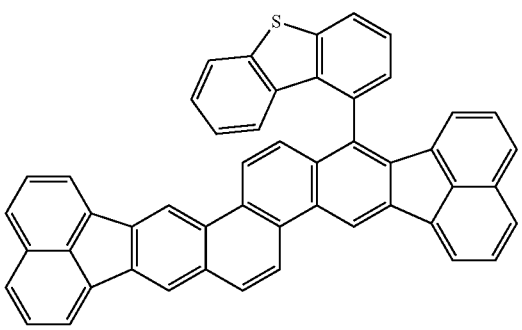
A21
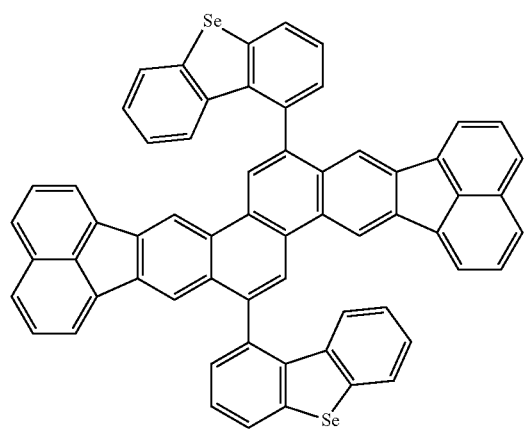
A22
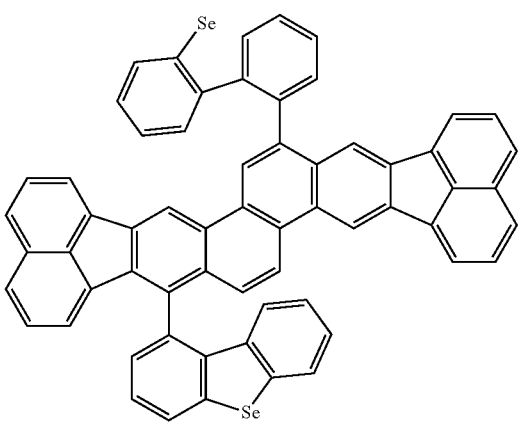
A23
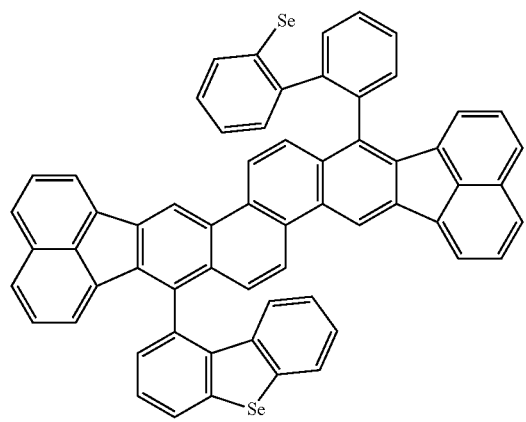
A24
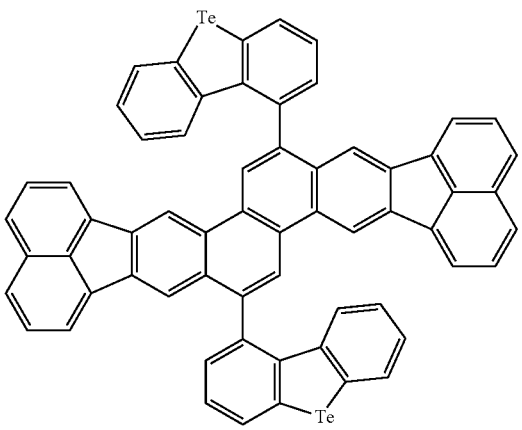
A25
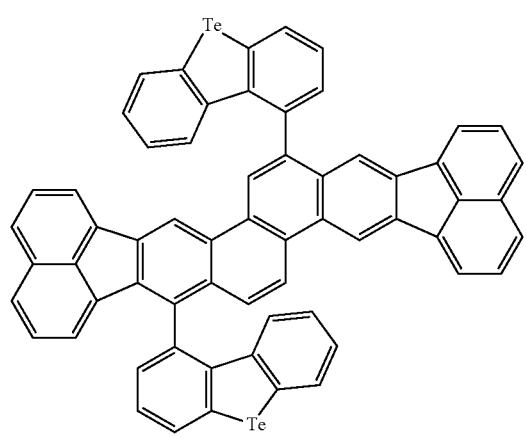
A26
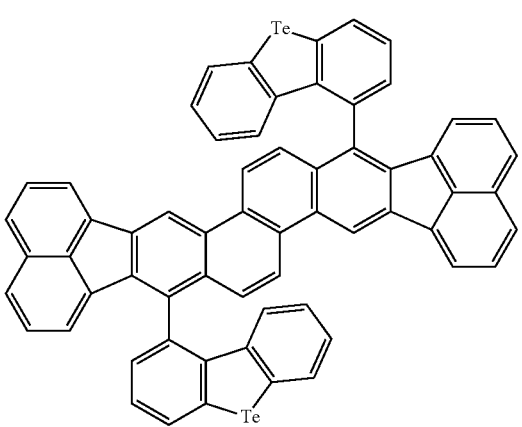

-continued
A27
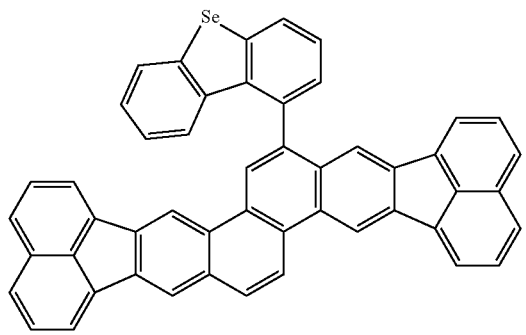
A28
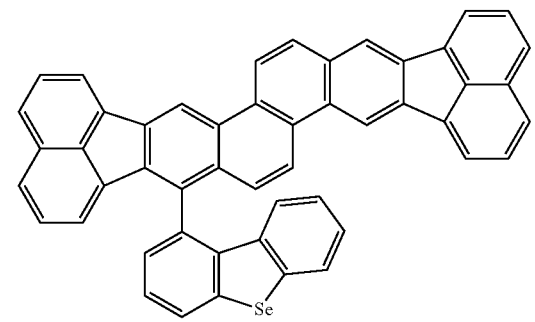
B1
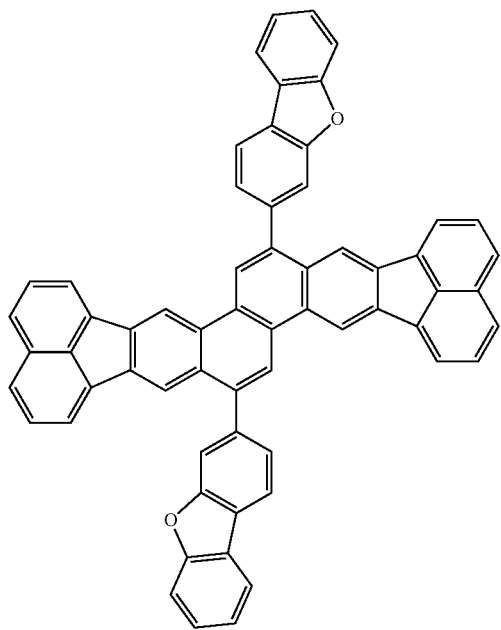
B2
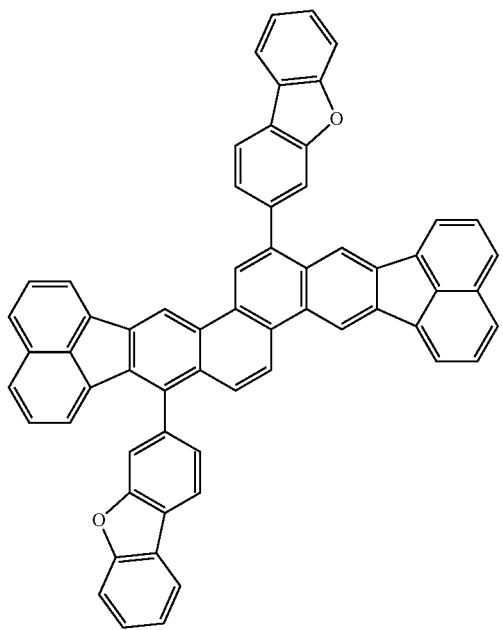
B3
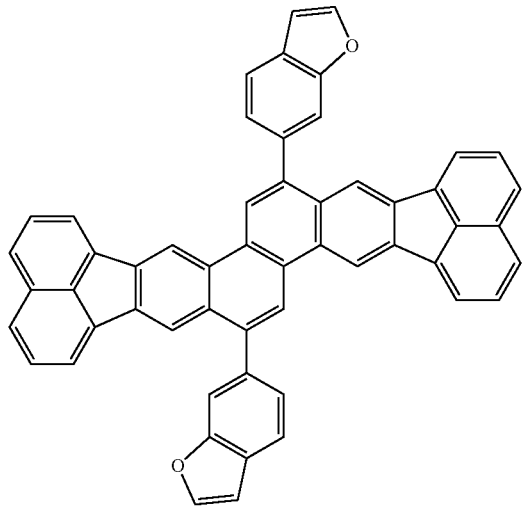
B4
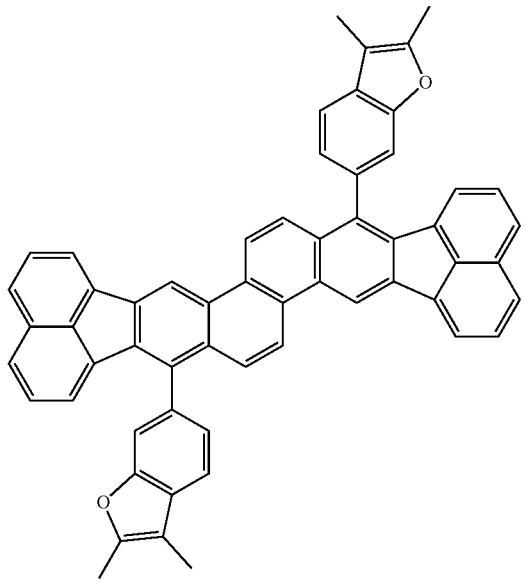

-continued
B5
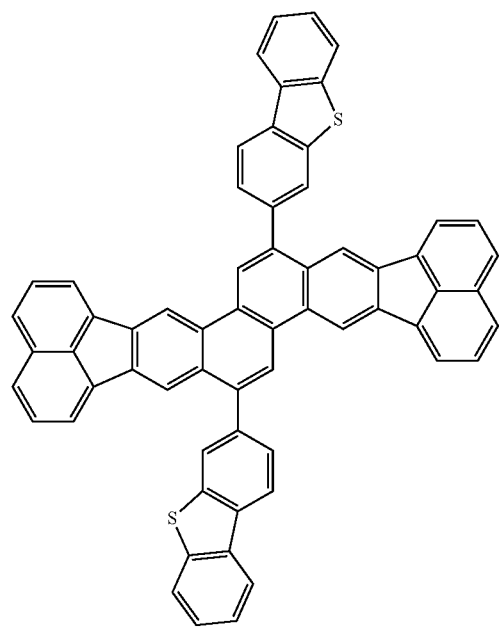
B6
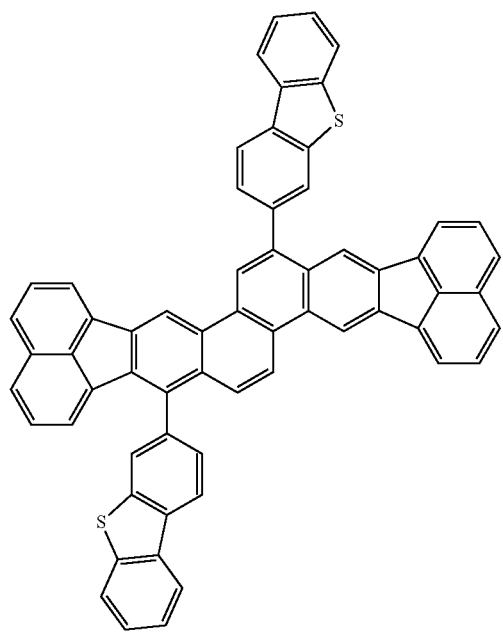
B7
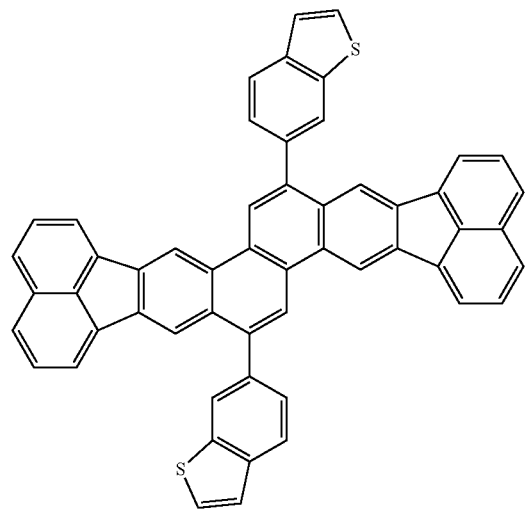
B8
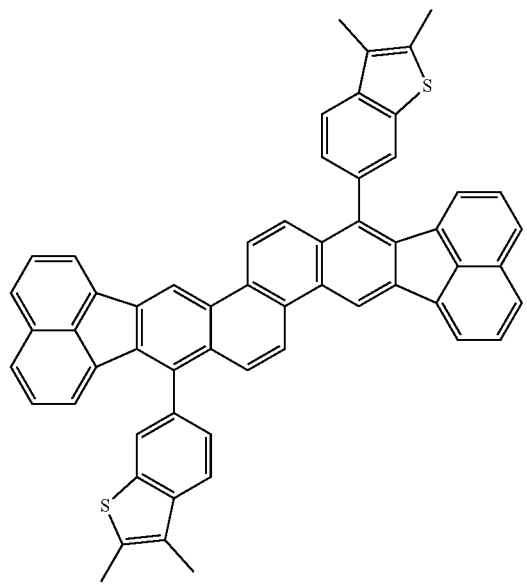

-continued
B9
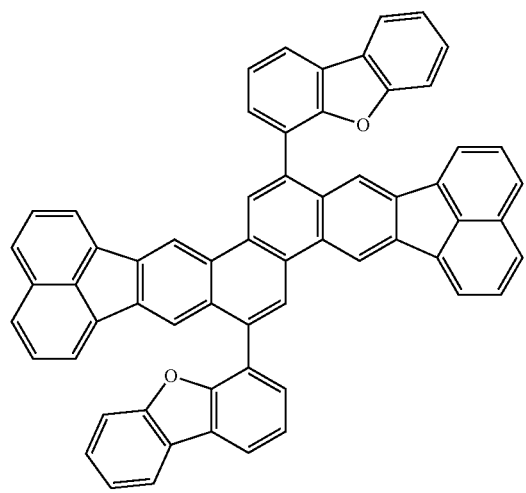
B10
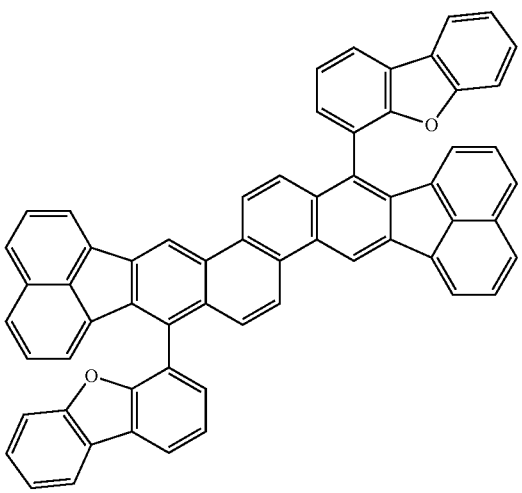
B11
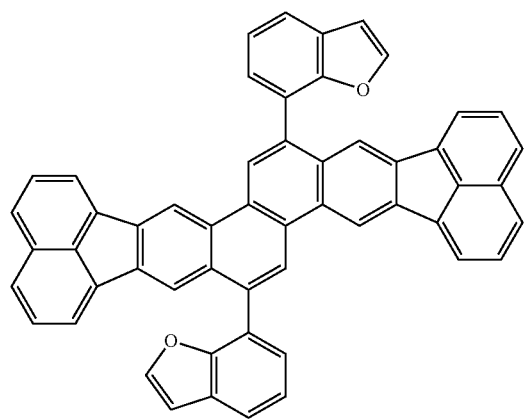
B12
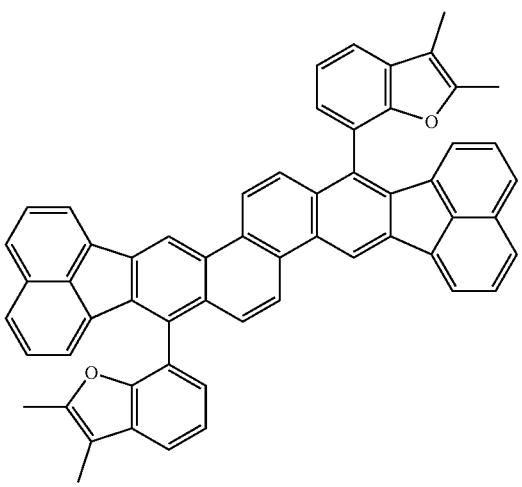
B13
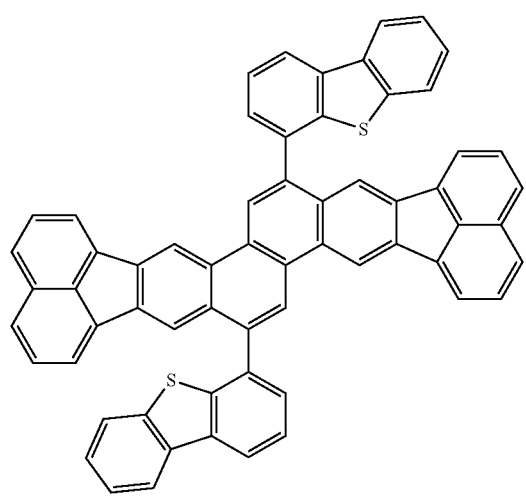
B14
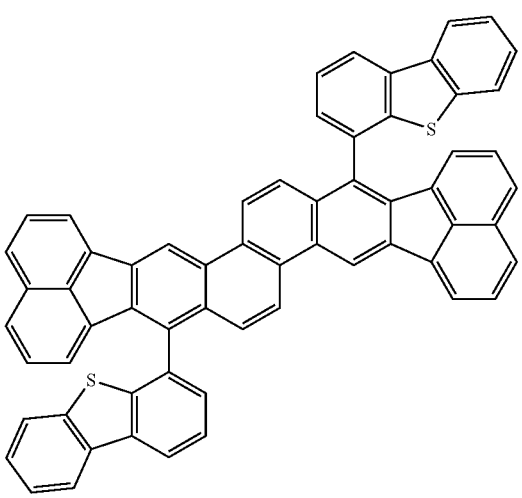

-continued
B15
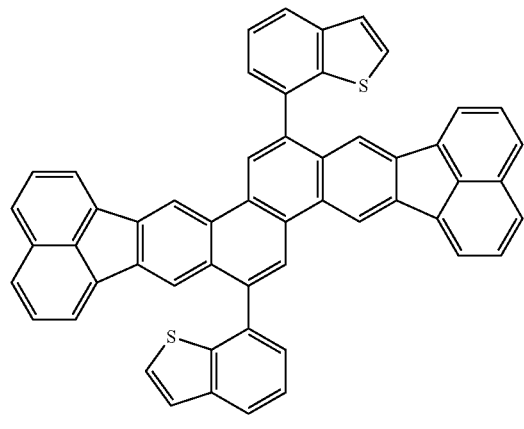
B16
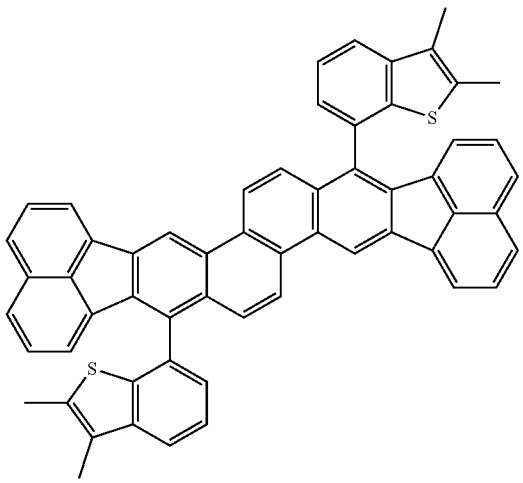
B17
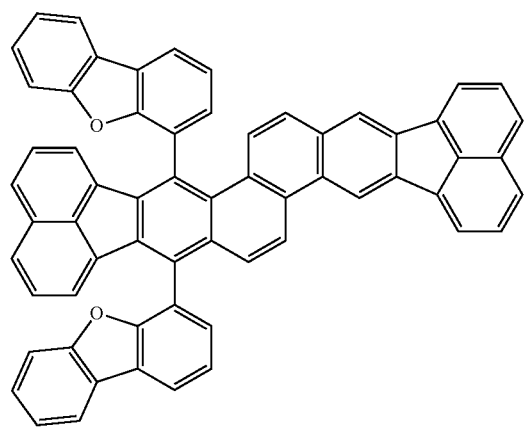
B18
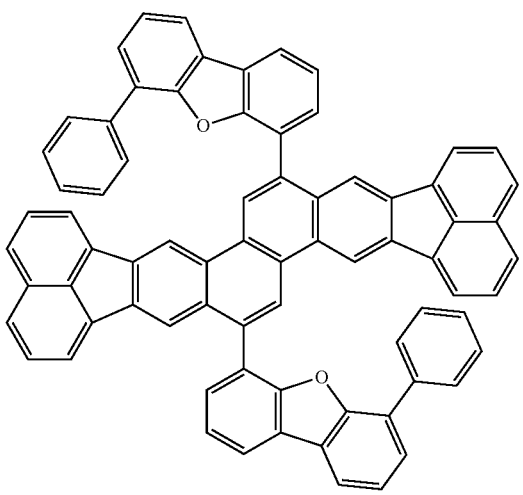
B19
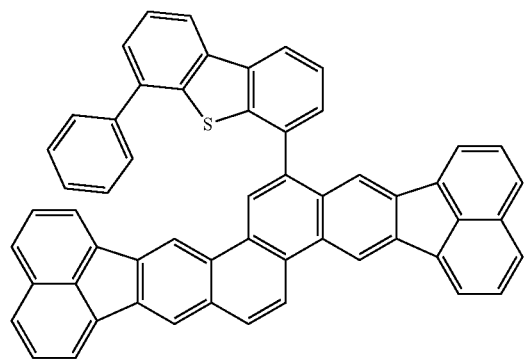

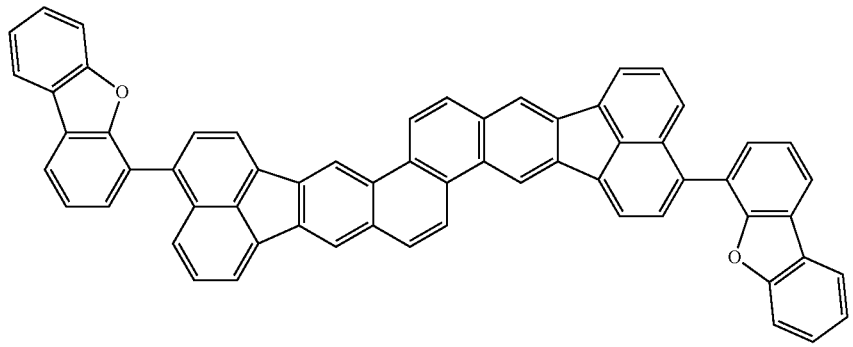

-continued
B25
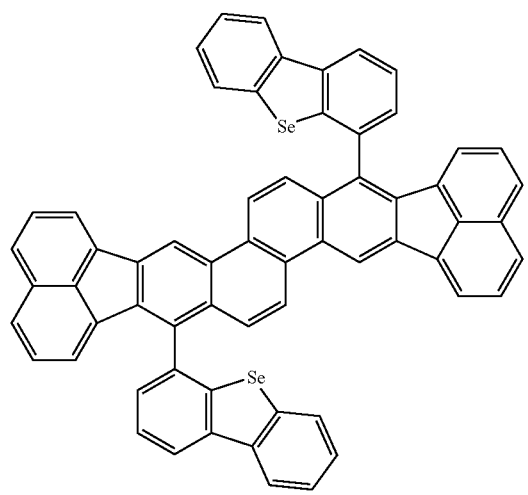
B26
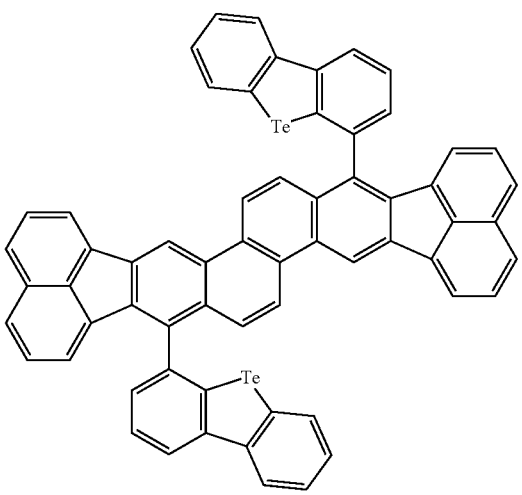
B27
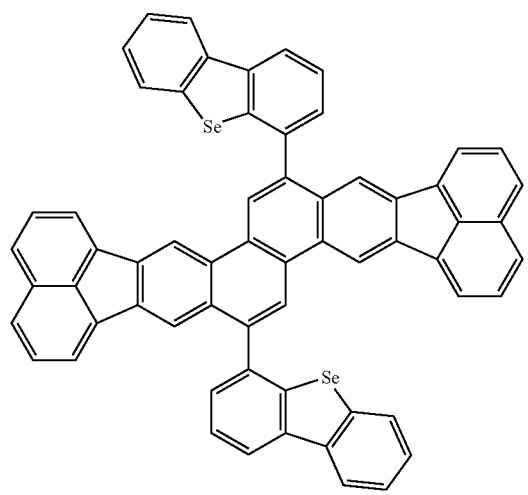
B28
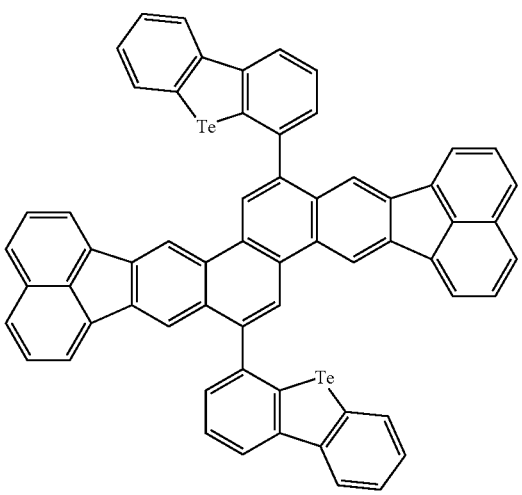 [SMILES: c1cc2c3c(cccc3c1)-c1cc3c(cc1-2)c(-c1cccc2c1oc1ccccc12)cc1c2cc4c(cc2c(-c2cccc5c2oc2ccccc25)cc31)-c1cccc2cccc-4c12]
C1
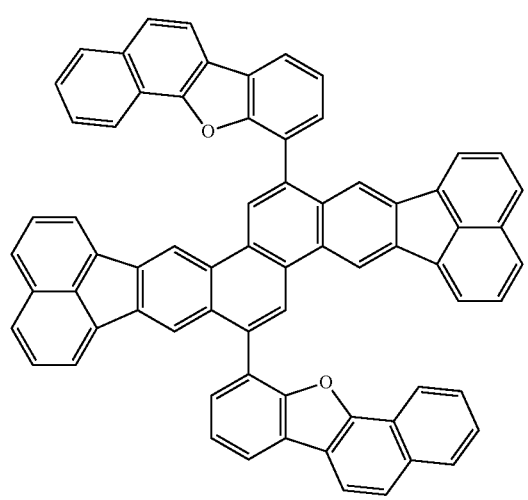
C2
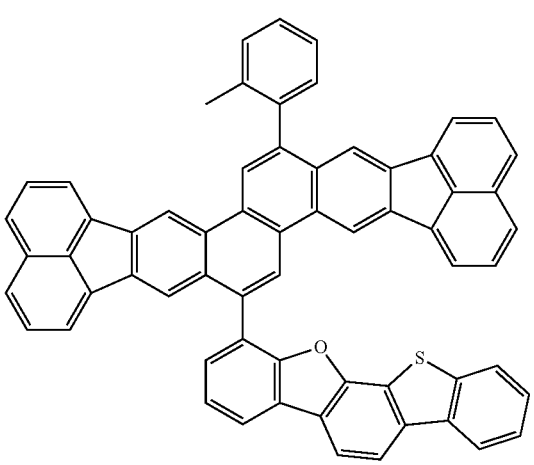

C3
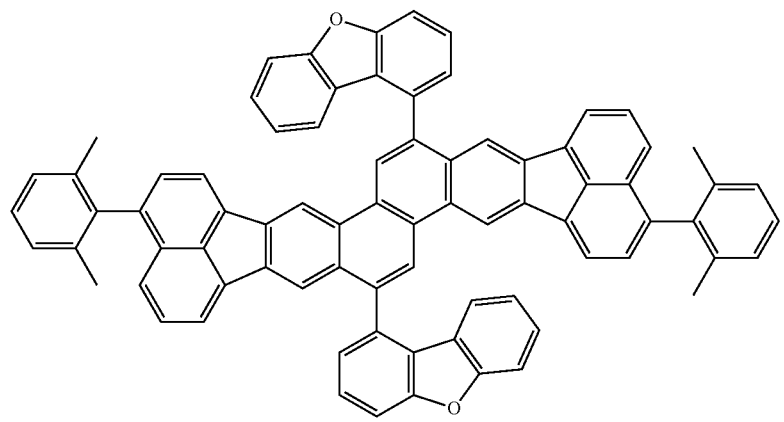
C4
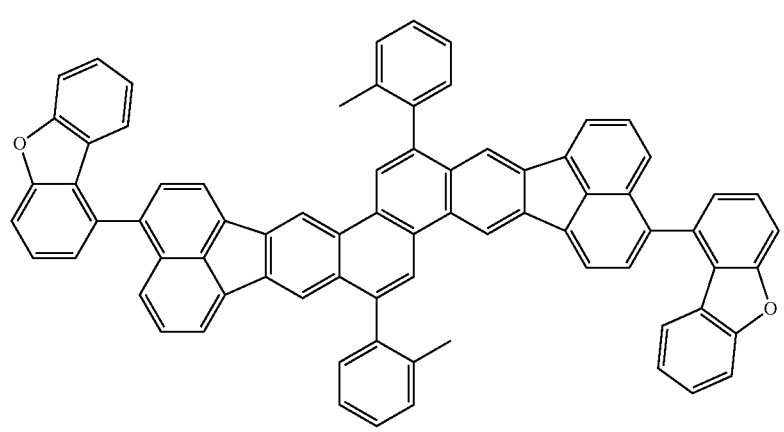
C5
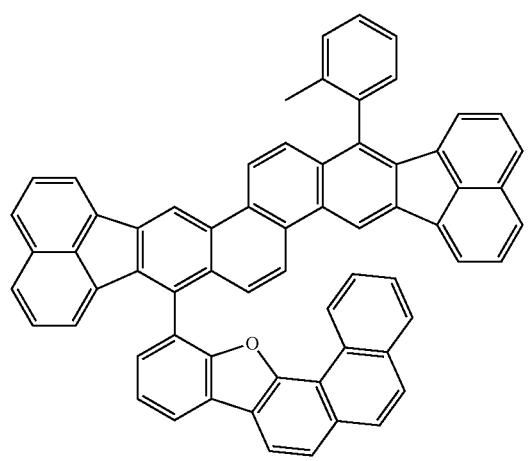

-continued
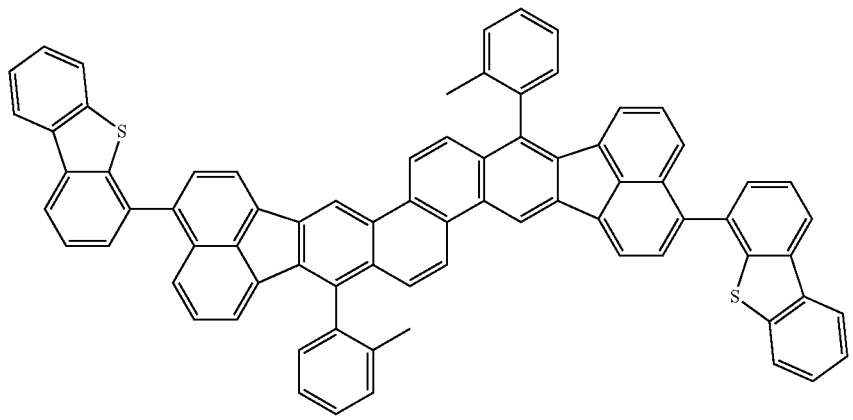
C6
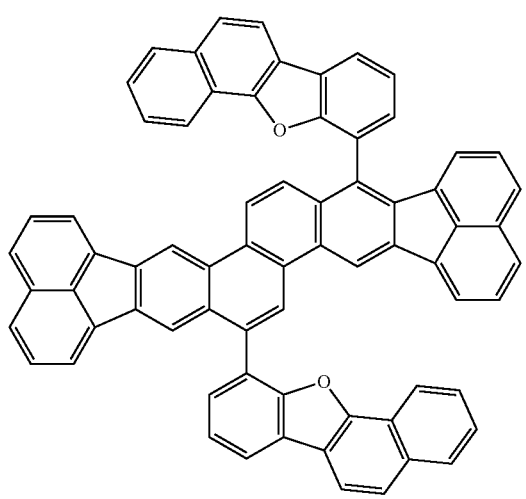
C7
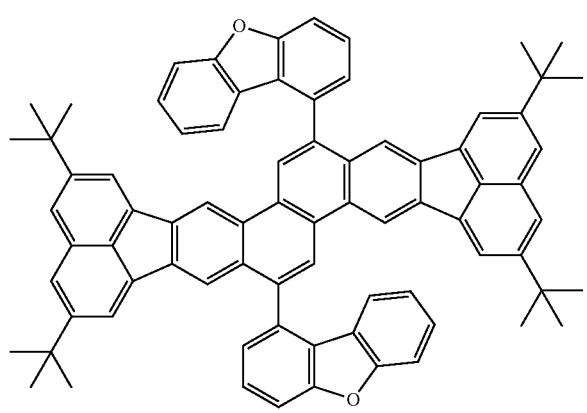
C8
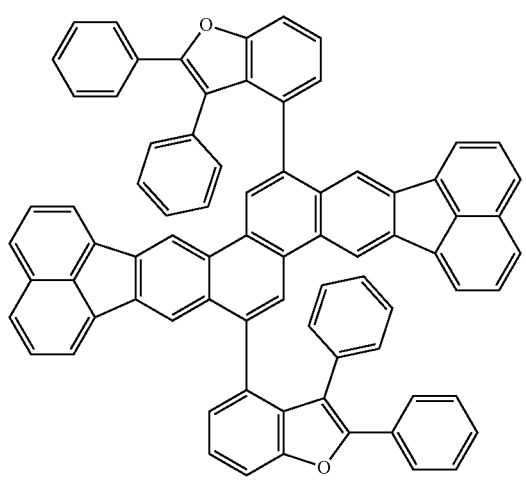
C9

-continued
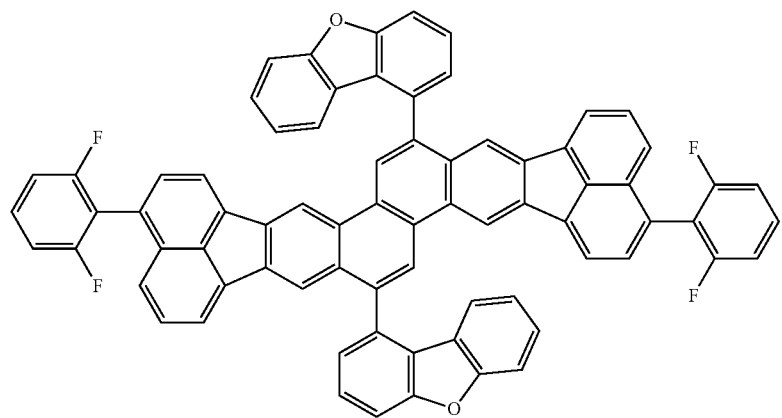
C10
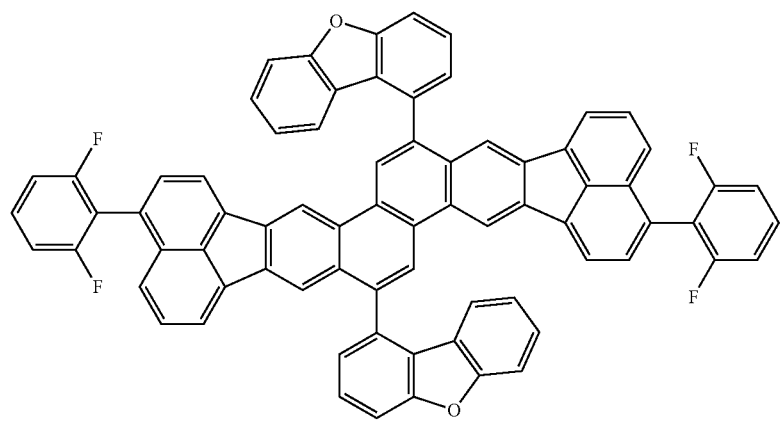
C11
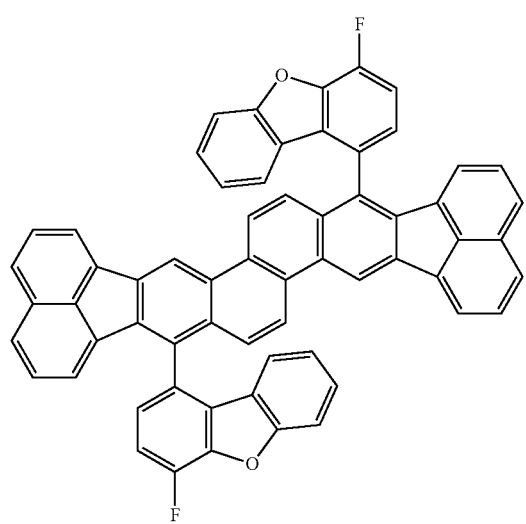
C12
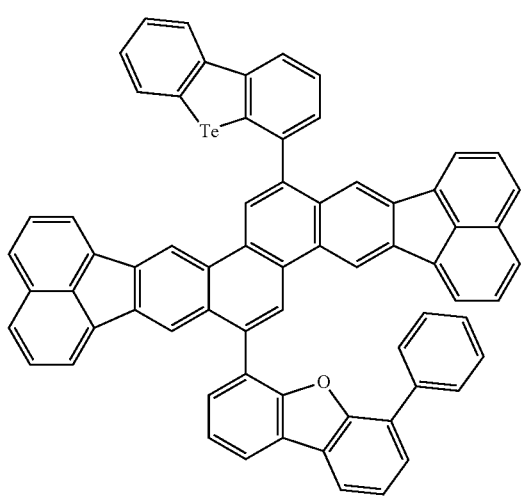
C13

-continued
C14
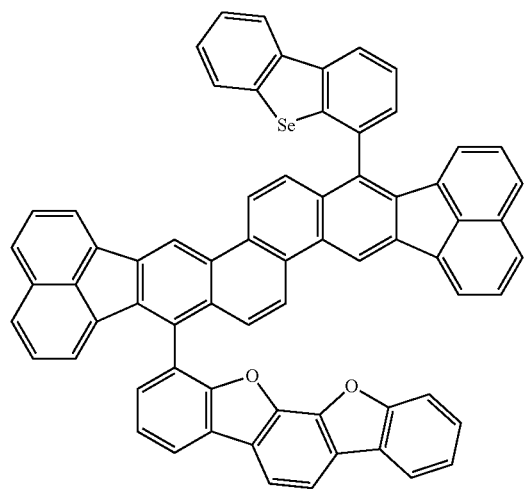
C15
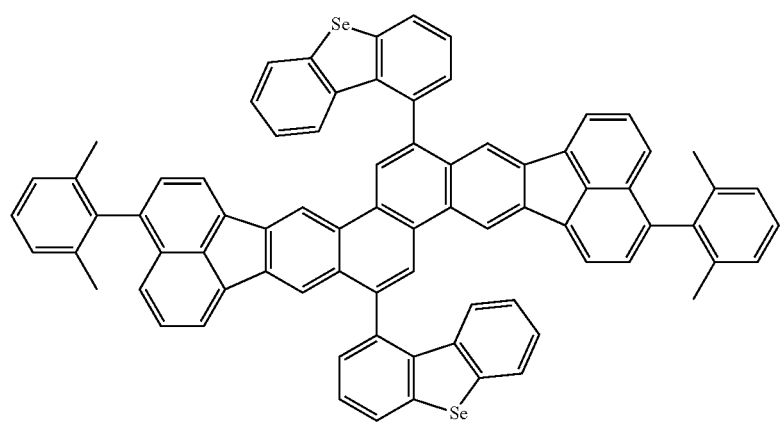
C16
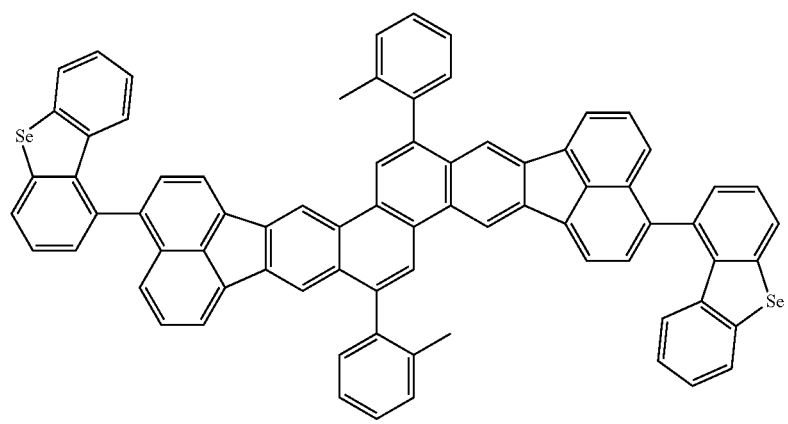

-continued
D1
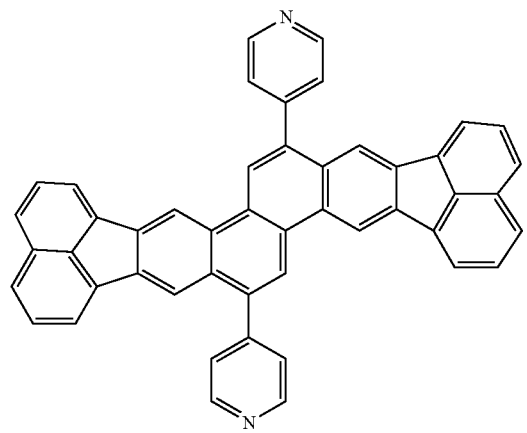
D2
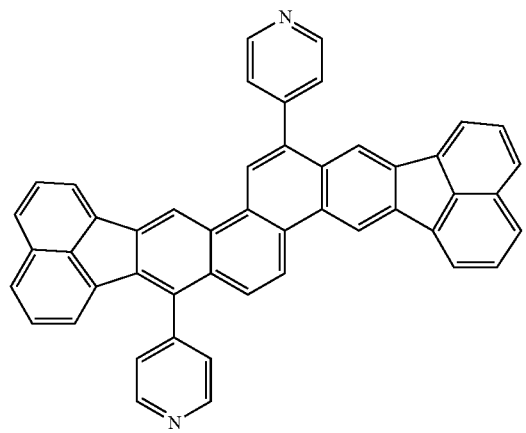
D3
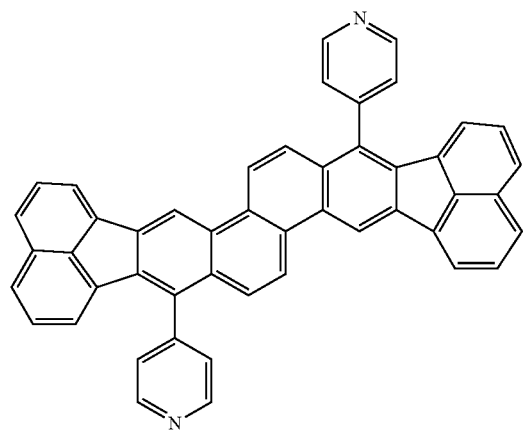
D4
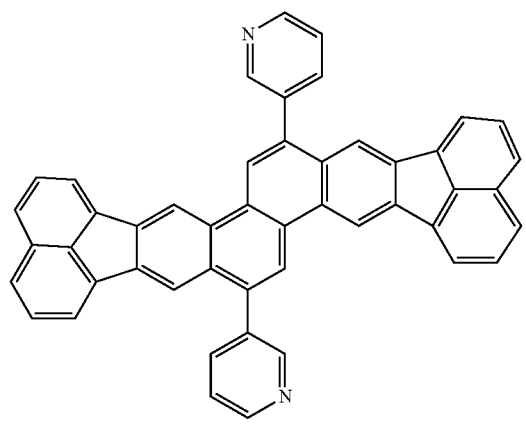
D5
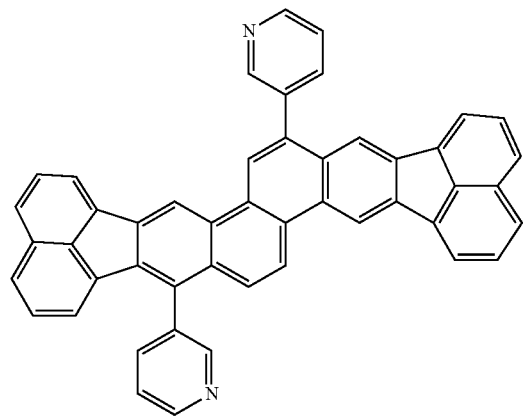
D6
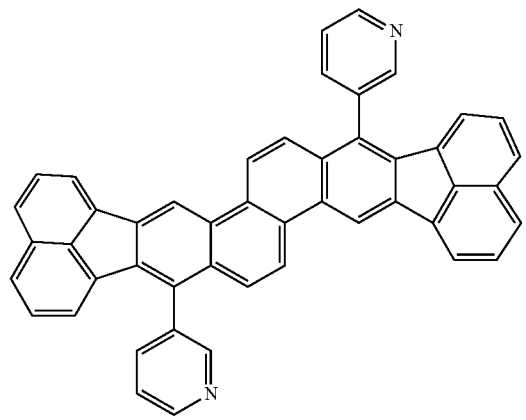

-continued
D7
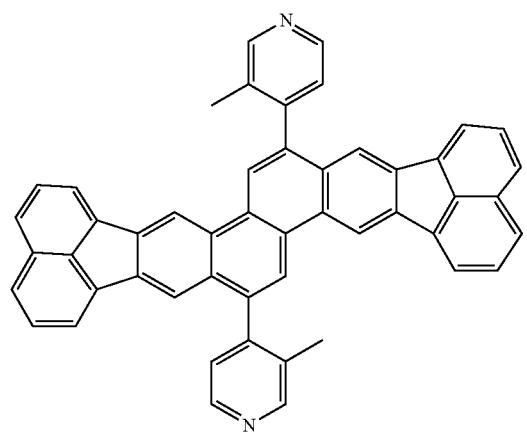
D8
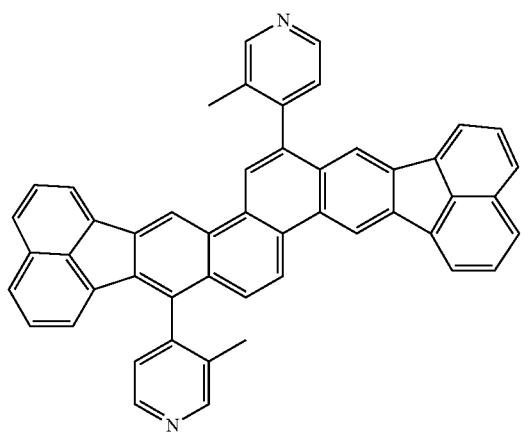
D9
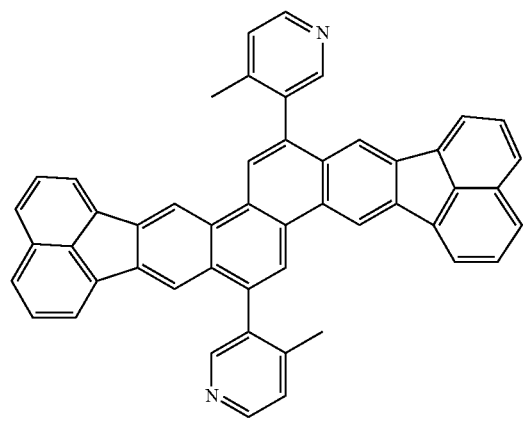
D10
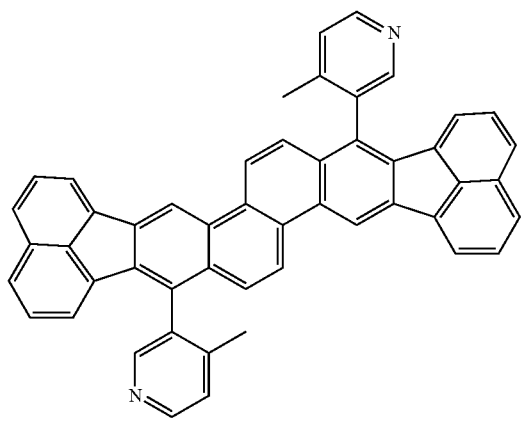
D11
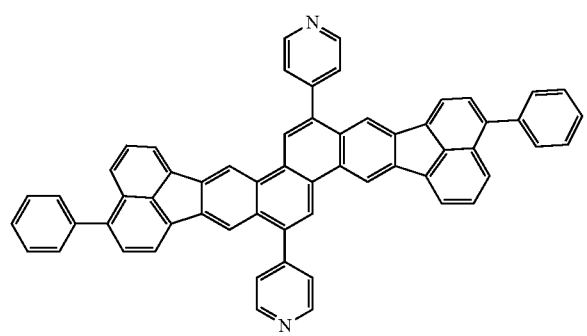
D12
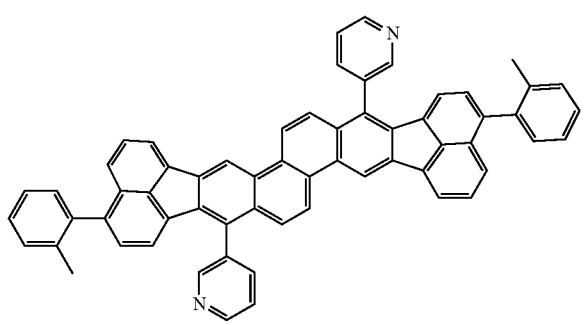
D13
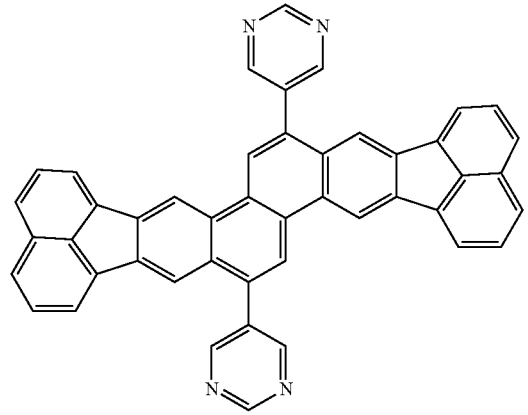
D14
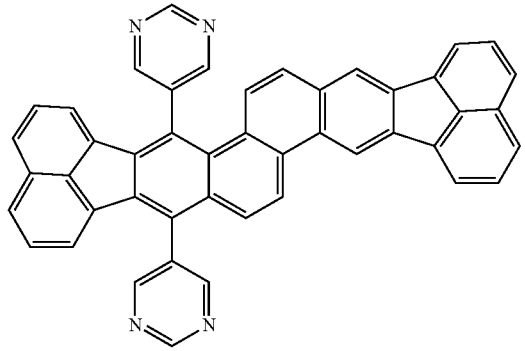

-continued
D15
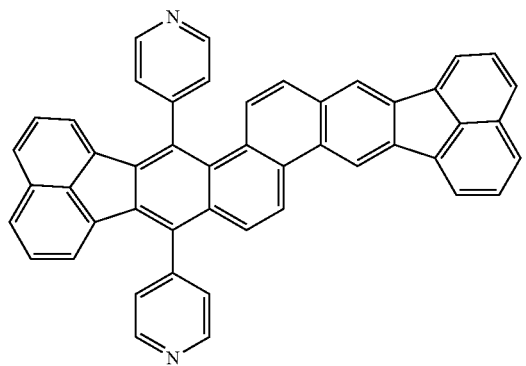
D16
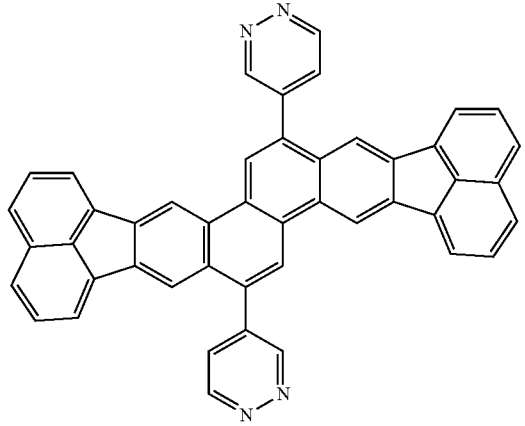
D17
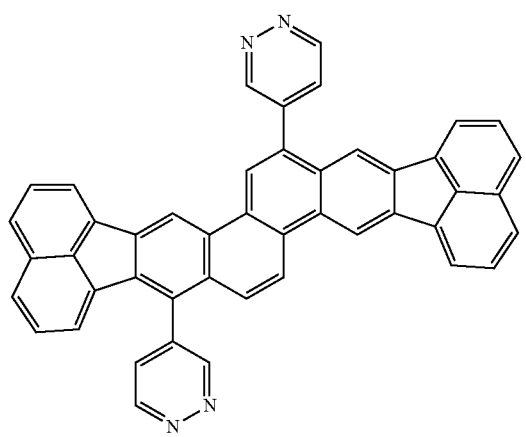
D18
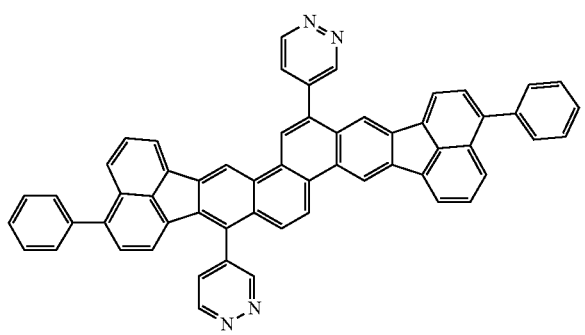
D19
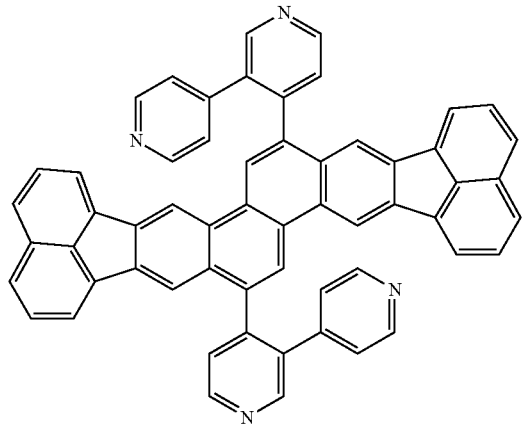
D20
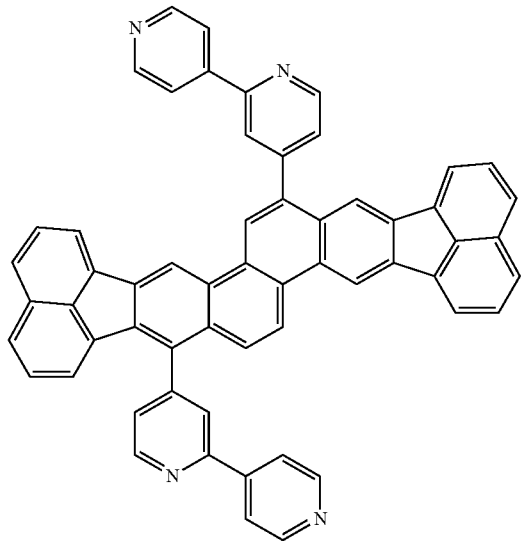

-continued
D21
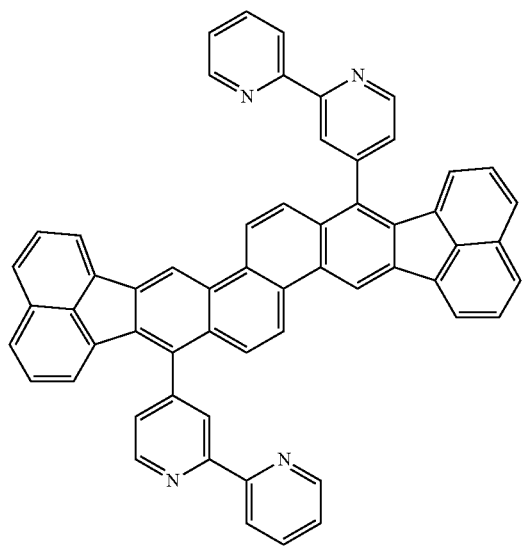
D22
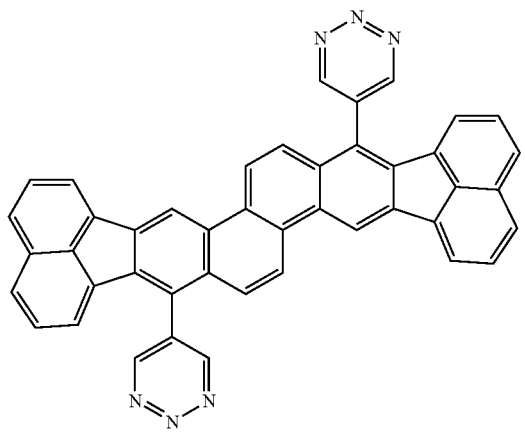
D23
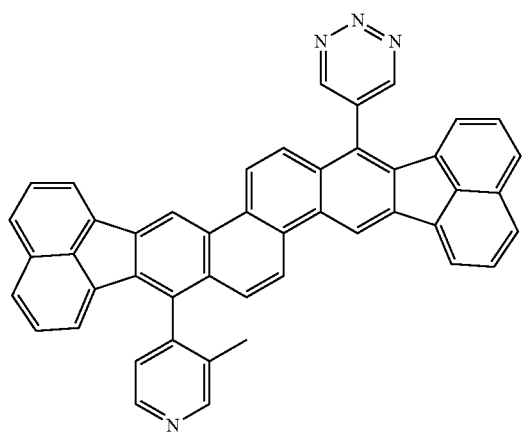
D24
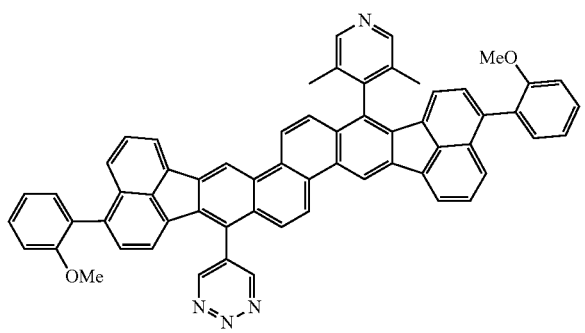
D25
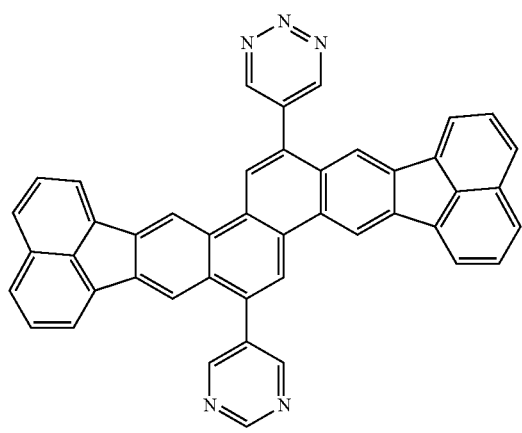
D26
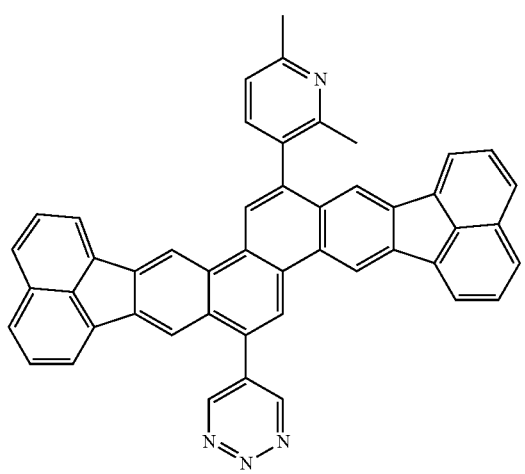

-continued
D27
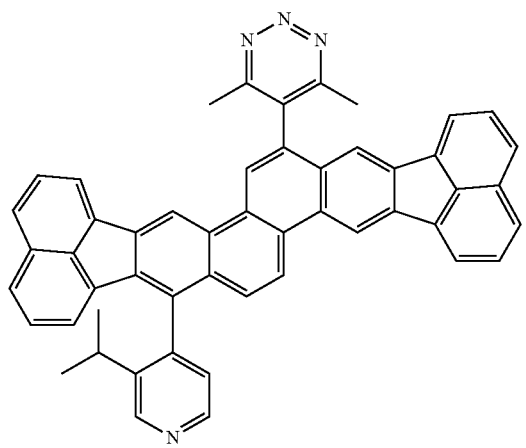
D28
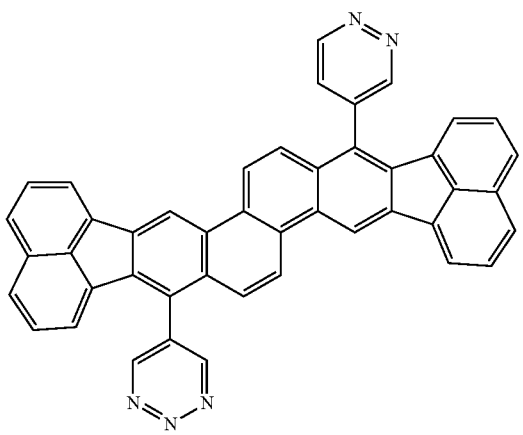
D29
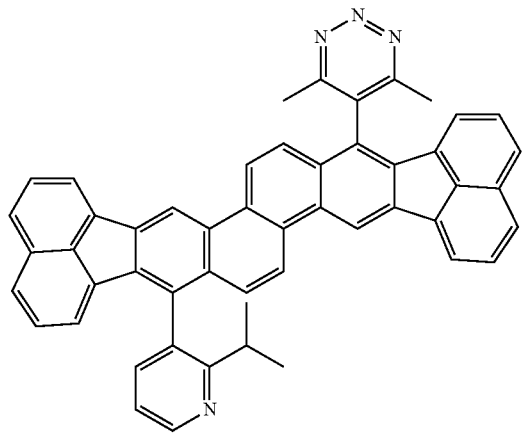
D30
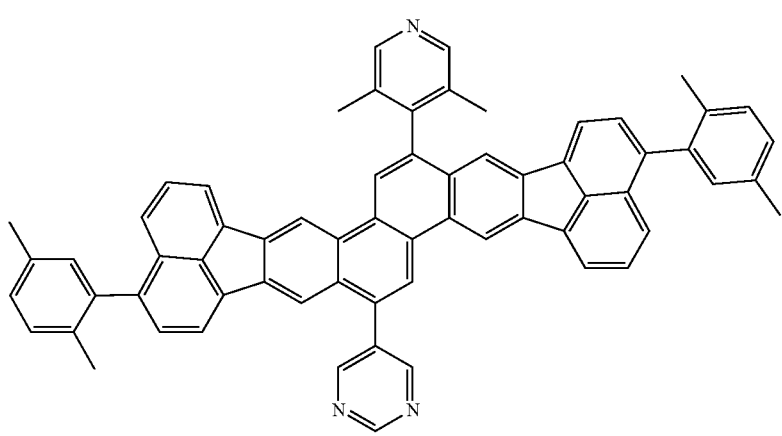

-continued
D31
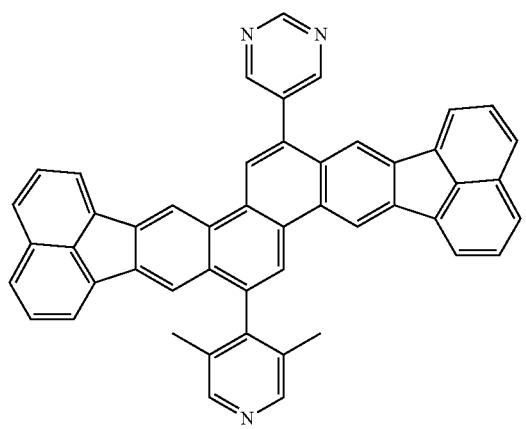
D32
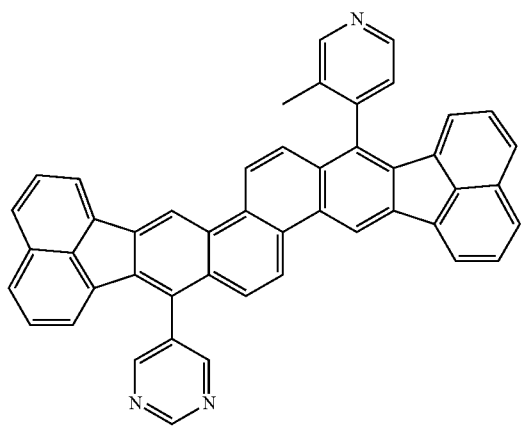
D33
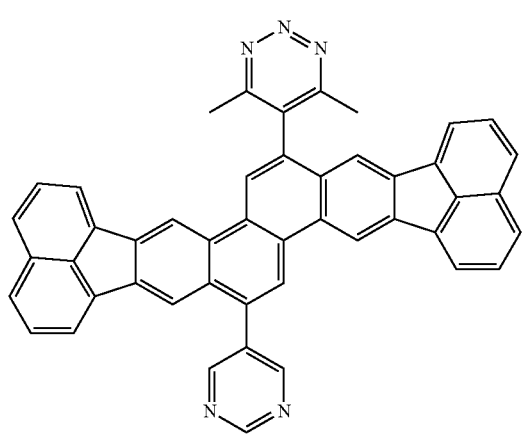
E1
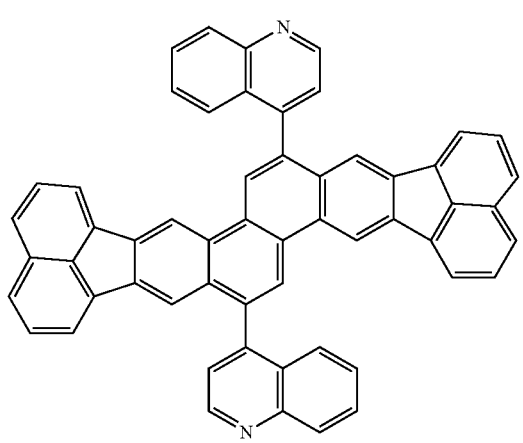
E2
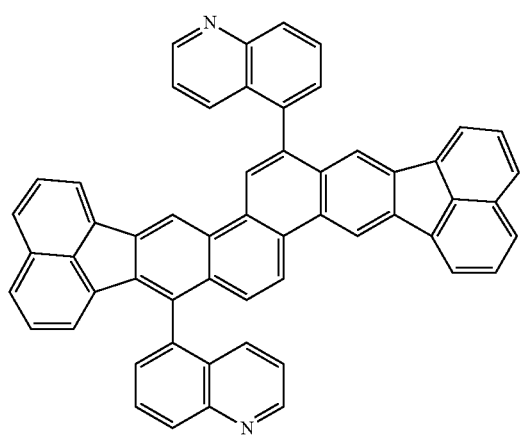
E3
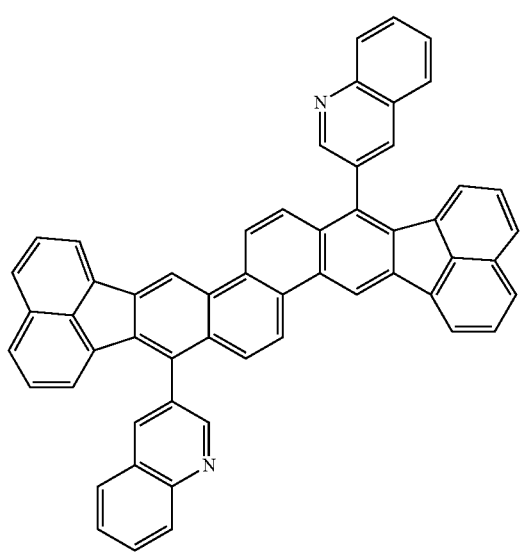

-continued
65
E4
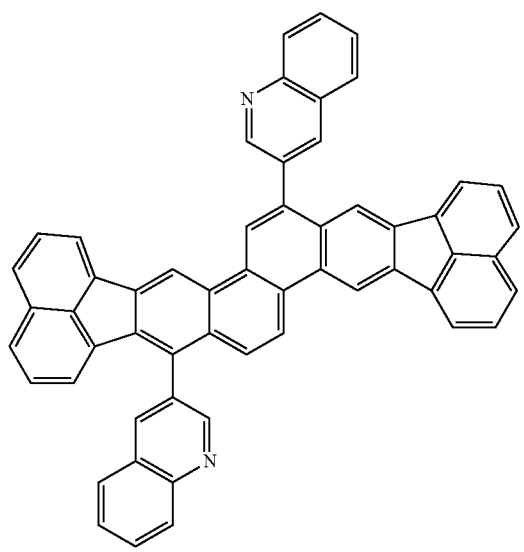
66
E5
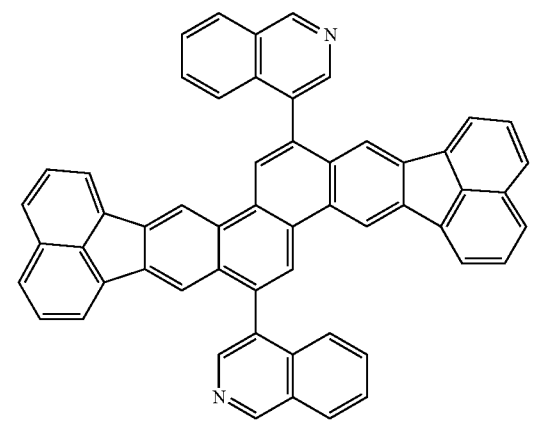
E6
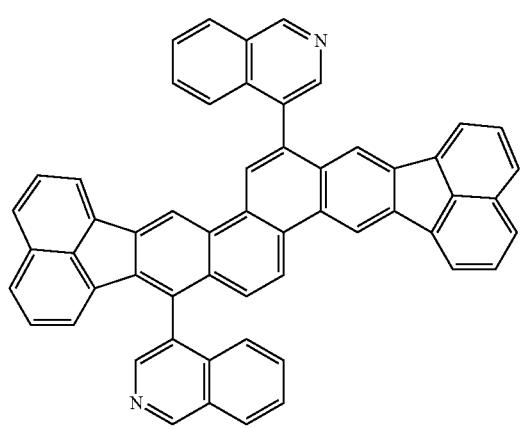
E7
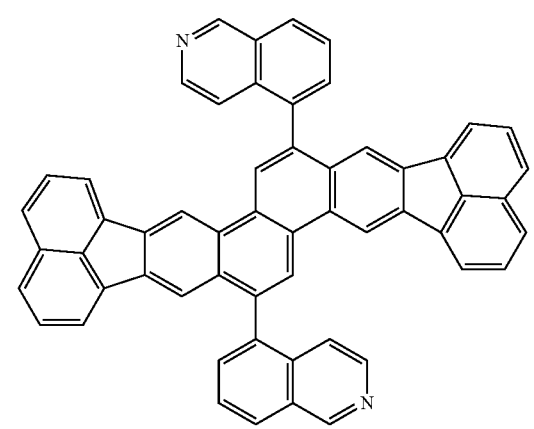
E8
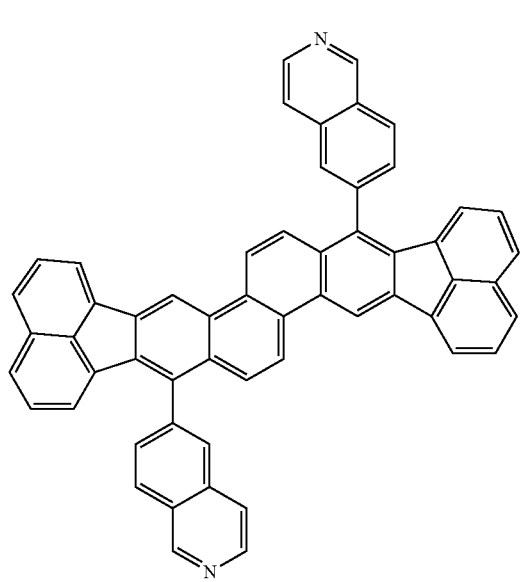
E9
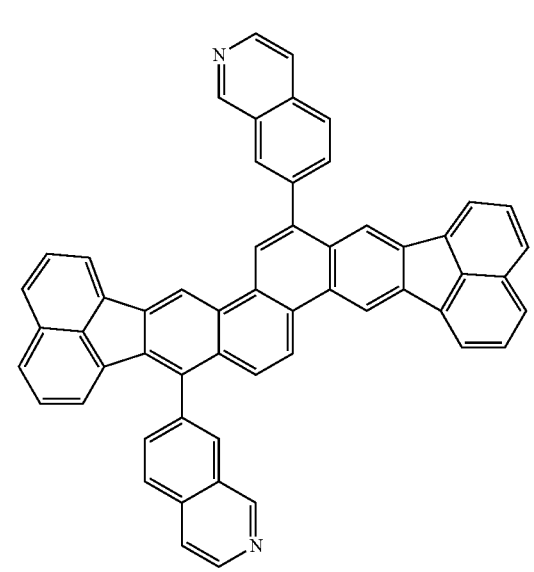

-continued
E10
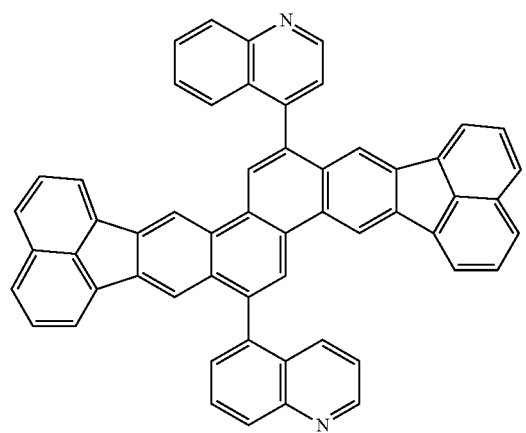
E11
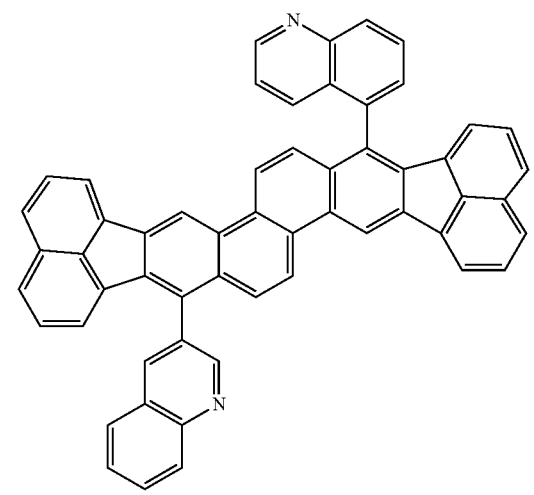
E12
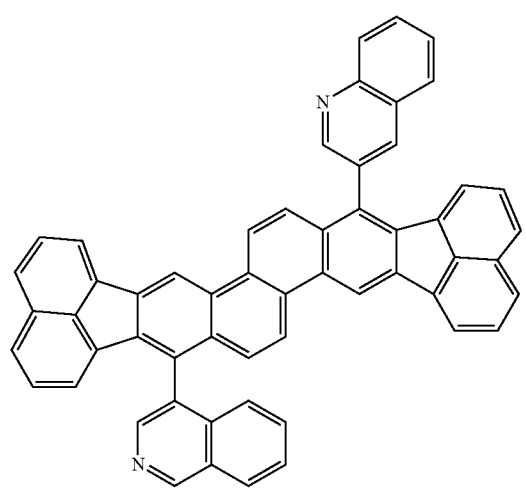
F1
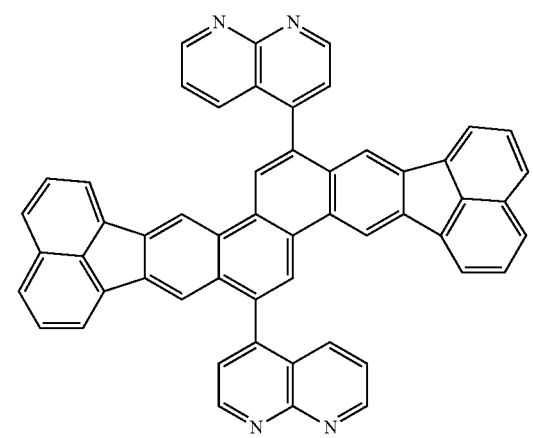
F2
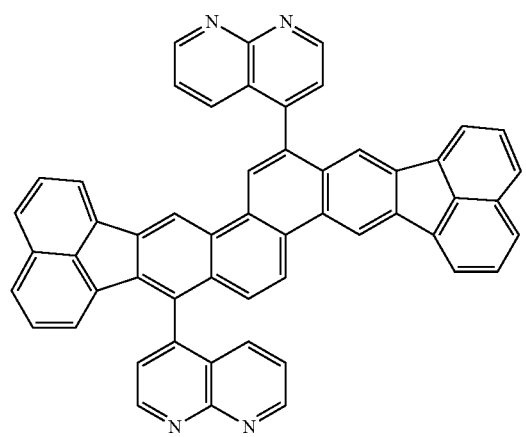
F3
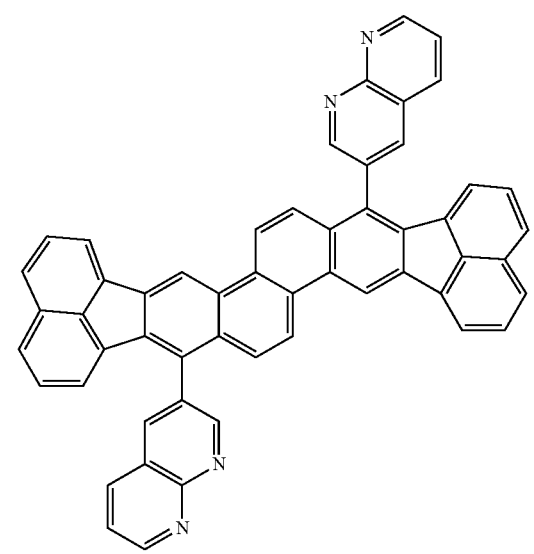

-continued
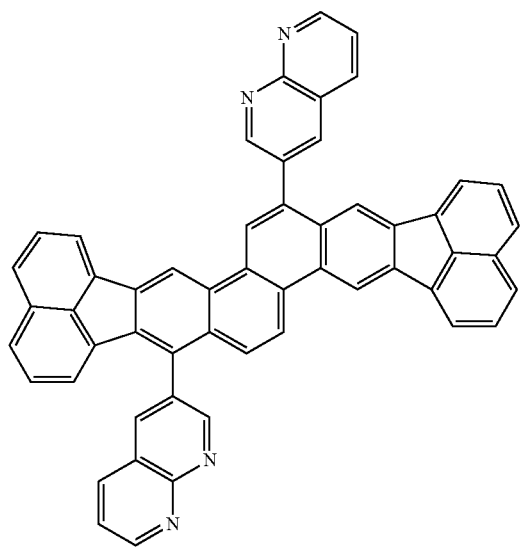
F4
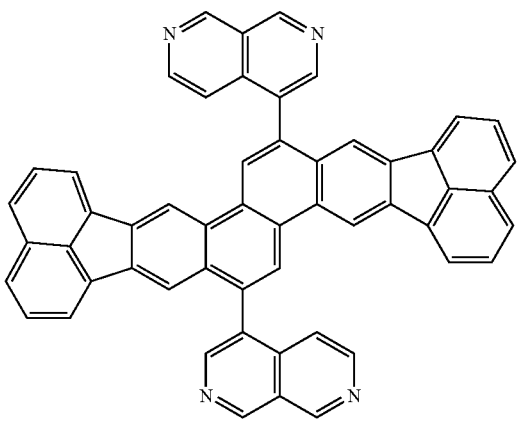
F5
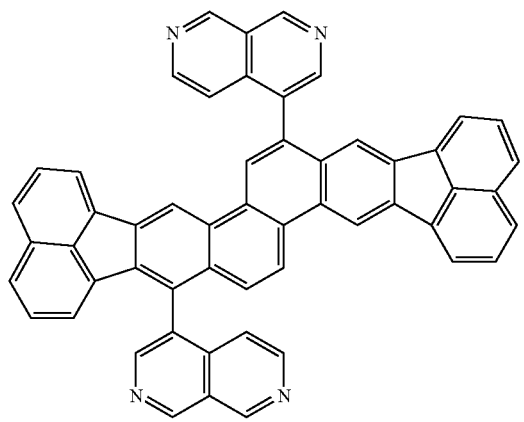
F6
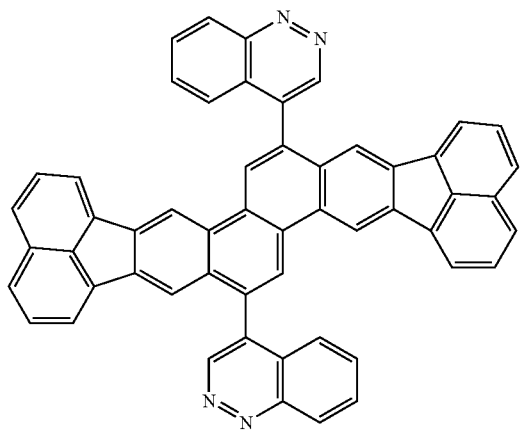
F7
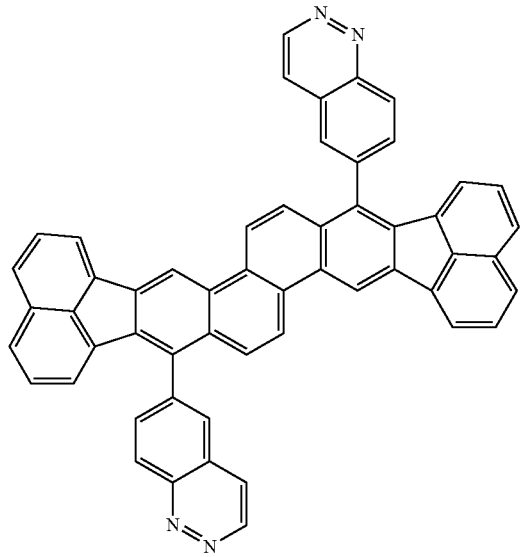
F8
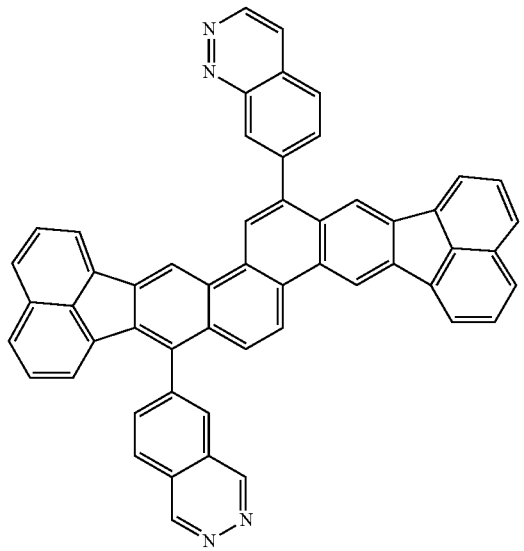
F9

-continued

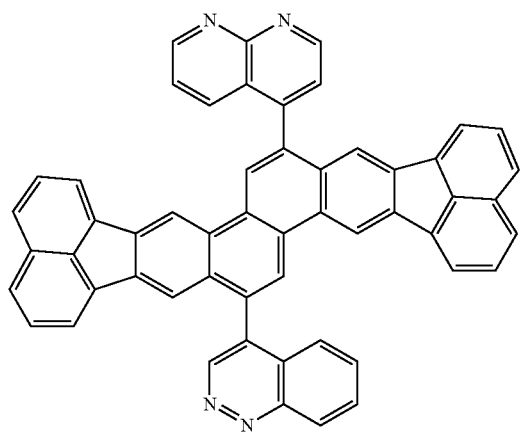

F10

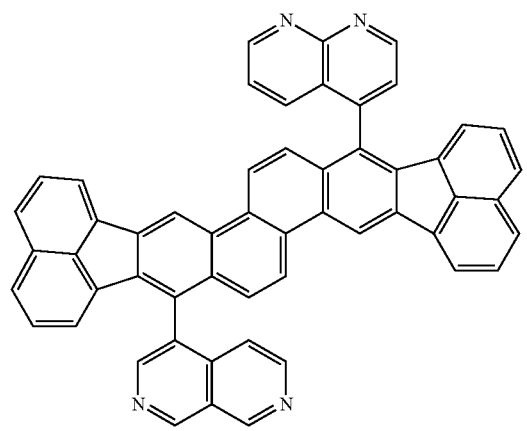

F11

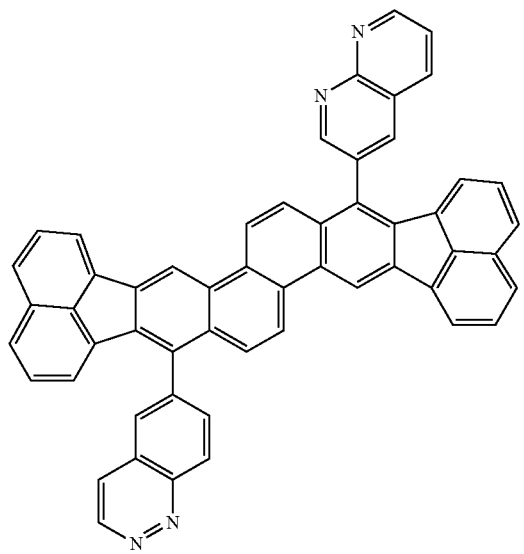

F12

Among the exemplary compounds, the compounds that belong to the A group are compounds in which a benzochalcogenophene derivative group is introduced to the basic skeleton at any one of $R_{22}$, $R_{23}$, and $R_{29}$ in the formula [1]. The compounds that belong to the A group exhibit blue light emission with a shorter wavelength and higher reduction potential than other compounds according to this embodiment. That is, the A group is a group of compounds that exhibit blue light emission with a higher color purity and higher electron acceptability. The compounds that belong to the A group can be used for light-emitting layer host materials, transport layers, and injection layers. However, if the compounds are used for light-emitting layers, the light emission efficiency decreases compared with the case where the compounds are used as a guest at low concentration.

Among the exemplary compounds, the compounds that belong to the B group are compounds in which a benzochalcogenophene derivative group is introduced to the basic skeleton at any position other than $R_{22}$, $R_{23}$, and $R_{29}$ in the formula [1]. Among the compounds according to this embodiment, the B group is a group of compounds capable of finely adjusting blue light emission and reduction potential.

Among the exemplary compounds, the compounds that belong to the C group are compounds in which three or more substituents are introduced to the basic skeleton in the formula [1] or compounds in which a substituent is further introduced to the benzochalcogenophene derivative group. By increasing the number of substituents or introducing a bulky substituent, the intermolecular interaction is suppressed. Among the compounds according to this embodiment, therefore, the C group is a group of compounds capable of further reducing concentration quenching in the form of thin film when used as a guest of the light-emitting layer.

Among the exemplary compounds, the compounds that belong to the D group are compounds in which groups represented by the formulae [105] to [109] are introduced. This can achieve high electron acceptability and blue light emission with a high color purity.

Among the exemplary compounds, the compounds that belong to the E group are compounds in which groups represented by the formulae [110] to [118] are introduced. Since the number of nitrogen atoms per introduced group is smaller than that of the D group, the electron acceptability decreases, but Tg is improved with increasing the molecular weight. This can achieve high thermal resistance and blue light emission with a high color purity.

Among the exemplary compounds, the compounds that belong to the F group are compounds in which groups represented by the formulae [119] to [124] are introduced. This can achieve high thermal resistance and high electron acceptability.

The organic compound according to this embodiment is a chemically stable compound that is suitable for blue light emission with high efficiency. Therefore, when the organic compound according to this embodiment is used as a material for organic light-emitting elements, an organic light-emitting element that has good light-emitting properties and high durability can be provided.

Organic Compound Represented by Formula [101]

First, an organic compound according to this embodiment will be described. The organic compound according to this embodiment is an organic compound represented by formula [101].

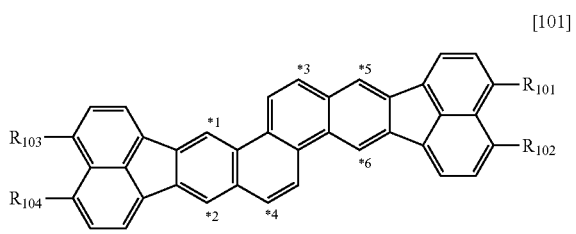

[101]

In the formula [101], a group having an azine skeleton and represented by any one of formulae [102] to [104] (hereafter may be simply referred to as a "group having an azine skeleton") is bonded to at least one of positions *1 to *6, preferably to two of positions *1 to *6. The group having an azine skeleton is bonded at a position *. When the group having an azine skeleton is bonded to a plurality of positions, the groups having an azine skeleton may be the same or different.

$R_{101}$ to $R_{104}$ represent groups each independently selected from the group consisting of a hydrogen atom, a substituted or unsubstituted aryl group, and a substituted or unsubstituted aryloxy group. $R_{101}$ to $R_{104}$ may represent a hydrogen atom. $R_{101}$ to $R_{104}$ may represent a group having no lone pair, such as an aryl group having no lone pair, to suppress intermolecular stacking.

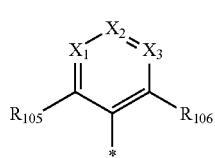

[102]

In the formula [102], $X_1$ to $X_3$ represent a carbon atom having a hydrogen atom or a substituent Y or a nitrogen atom, the carbon atom or the nitrogen atom constituting a ring. At least one of $X_1$ to $X_3$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group.

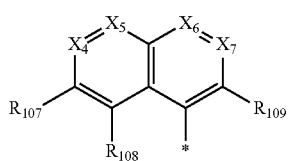

[103]

In the formula [103], $X_4$ to $X_7$ represent a carbon atom having a hydrogen atom or a substituent Y or a nitrogen atom, the carbon atom or the nitrogen atom constituting a ring. At least one of $X_4$ to $X_7$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{107}$ to $R_{109}$ represent groups each independently selected from the group consisting of a hydrogen atom, a substituted or unsubstituted alkyl group, a substituted or unsubstituted aryl group, and a substituted or unsubstituted heterocyclic group.

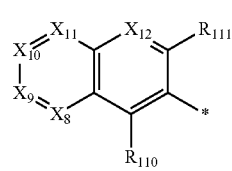

[104]

In the formula [104], $X_8$ to $X_{12}$ represent a carbon atom having a hydrogen atom or a substituent Y or a nitrogen atom, the carbon atom or the nitrogen atom constituting a ring. At least one of $X_8$ to $X_{12}$ represents a nitrogen atom.

The substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group. When a plurality of carbon atoms having the substituent Y are present, the substituents Y may be the same or different.

$R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

The group bonded to positions *1 to *6 may be a group having an azine skeleton and represented by the formula [102] or may be a group having an azine skeleton and represented by the formula [103] or [104].

Examples of the group having an azine skeleton and represented by the formula [102] include groups represented by formulae [105] to [109].

[105]
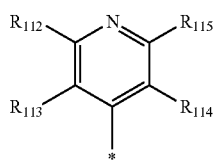

[106]
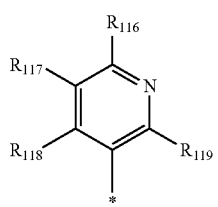

[107]
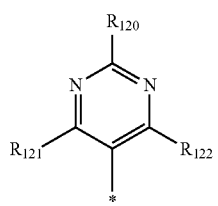

[108]
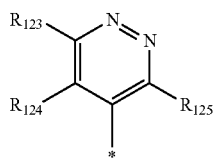

[109]
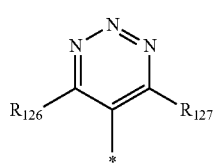

In the formulae [105] to [109], $R_{112}$ to $R_{127}$ represent groups each independently selected from the group consisting of a hydrogen atom, a substituted or unsubstituted alkyl group, a substituted or unsubstituted aryl group, and a substituted or unsubstituted heterocyclic group.

Examples of the group having an azine skeleton and represented by the formula [103] or [104] include groups represented by formulae [110] to [118].

[110]
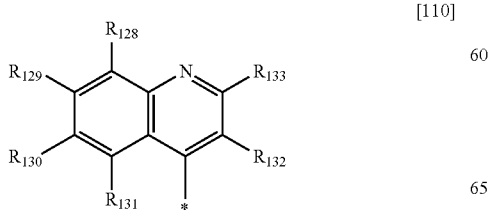

[111]
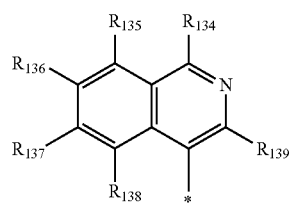

[112]
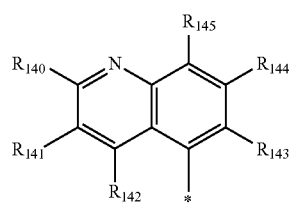

[113]
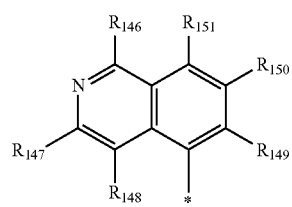

[114]
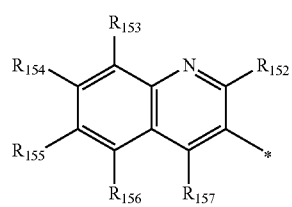

[115]
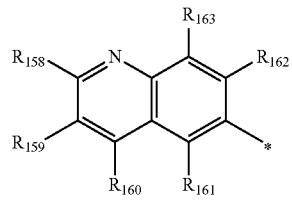

[116]
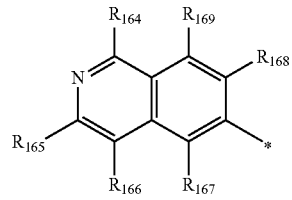

[117]
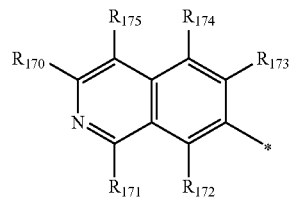

[118]

[Structure with R_176, R_177, R_178, R_179, R_180, R_181 on quinoline skeleton]

In the formulae [110] to [118], $R_{128}$ to $R_{181}$ represent groups each independently selected from the group consisting of a hydrogen atom, a substituted or unsubstituted alkyl group, a substituted or unsubstituted aryl group, and a substituted or unsubstituted heterocyclic group.

Examples of the group having an azine skeleton and represented by the formula [103] or [104] include groups represented by formulae [119] to [124].

[119]

[Structure with $R_{182}$, $R_{183}$, $R_{184}$, $R_{185}$, $R_{186}$ on naphthyridine skeleton]

[120]

[Structure with $R_{187}$, $R_{188}$, $R_{189}$, $R_{190}$, $R_{191}$]

[121]

[Structure with $R_{192}$, $R_{193}$, $R_{194}$, $R_{195}$, $R_{196}$ on cinnoline skeleton]

[122]

[Structure with $R_{196}$, $R_{197}$, $R_{199}$, $R_{200}$, $R_{201}$]

[123]

[Structure with $R_{202}$, $R_{203}$, $R_{204}$, $R_{205}$, $R_{206}$]

[124]

[Structure with $R_{207}$, $R_{208}$, $R_{209}$, $R_{210}$, $R_{211}$]

In the formulae [119] to [124], $R_{182}$ to $R_{211}$ represent groups each independently selected from the group consisting of a hydrogen atom, a substituted or unsubstituted alkyl group, a substituted or unsubstituted aryl group, and a substituted or unsubstituted heterocyclic group.

Examples of the group having an azine skeleton and represented by the formula [103] or [104] also include groups with $X_6$ and $X_7$ representing a carbon atom and groups with $X_{12}$ representing a carbon atom.

Non-limiting examples of the alkyl group represented by Y and 8105 to $R_{211}$ include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. Among them, the alkyl group may be an alkyl group having 1 to 10 carbon atoms.

Non-limiting examples of the aryl group represented by Y and $R_{110}$ to $R_{211}$ include a phenyl group, a naphthyl group, an indenyl group, a biphenyl group, a terphenyl group, a fluorenyl group, a phenanthryl group, and a triphenylenyl group. Among them, the aryl group may be an aryl group having 6 to 18 carbon atoms.

Non-limiting examples of the heterocyclic group represented by Y and 8105 to $R_{211}$ include a pyridyl group, a pyrimidyl group, a pyrazyl group, a triazyl group, an oxazolyl group, an oxadiazolyl group, a thiazolyl group, a thiadiazolyl group, a carbazolyl group, an acridinyl group, and a phenanthrolyl group. Among them, the heterocyclic group may be a heterocyclic group having 3 to 15 carbon atoms.

Non-limiting examples of the aryloxy group represented by Y and $R_{110}$ to $R_{104}$ include a phenoxy group and a thienyloxy group.

Non-limiting examples of the silyl group represented by Y include a trimethylsilyl group and a triphenylsilyl group.

Non-limiting examples of the substituent that may be further introduced to the alkyl group, the aryl group, the heterocyclic group, and the aryloxy group include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heterocyclic groups such as a pyridyl group and a pyrrolyl group; alkoxy groups such as a methoxy group, an ethoxy group, and a propoxy group; and aryloxy groups such as a phenoxy group.

Next, a method for synthesizing the organic compound according to this embodiment will be described. The organic compound according to this embodiment is synthesized through, for example, the following reaction scheme. In the following scheme, Ar' represents a group having an azine skeleton and represented by any one of the formulae [102] to [104].

Synthesis Route 1
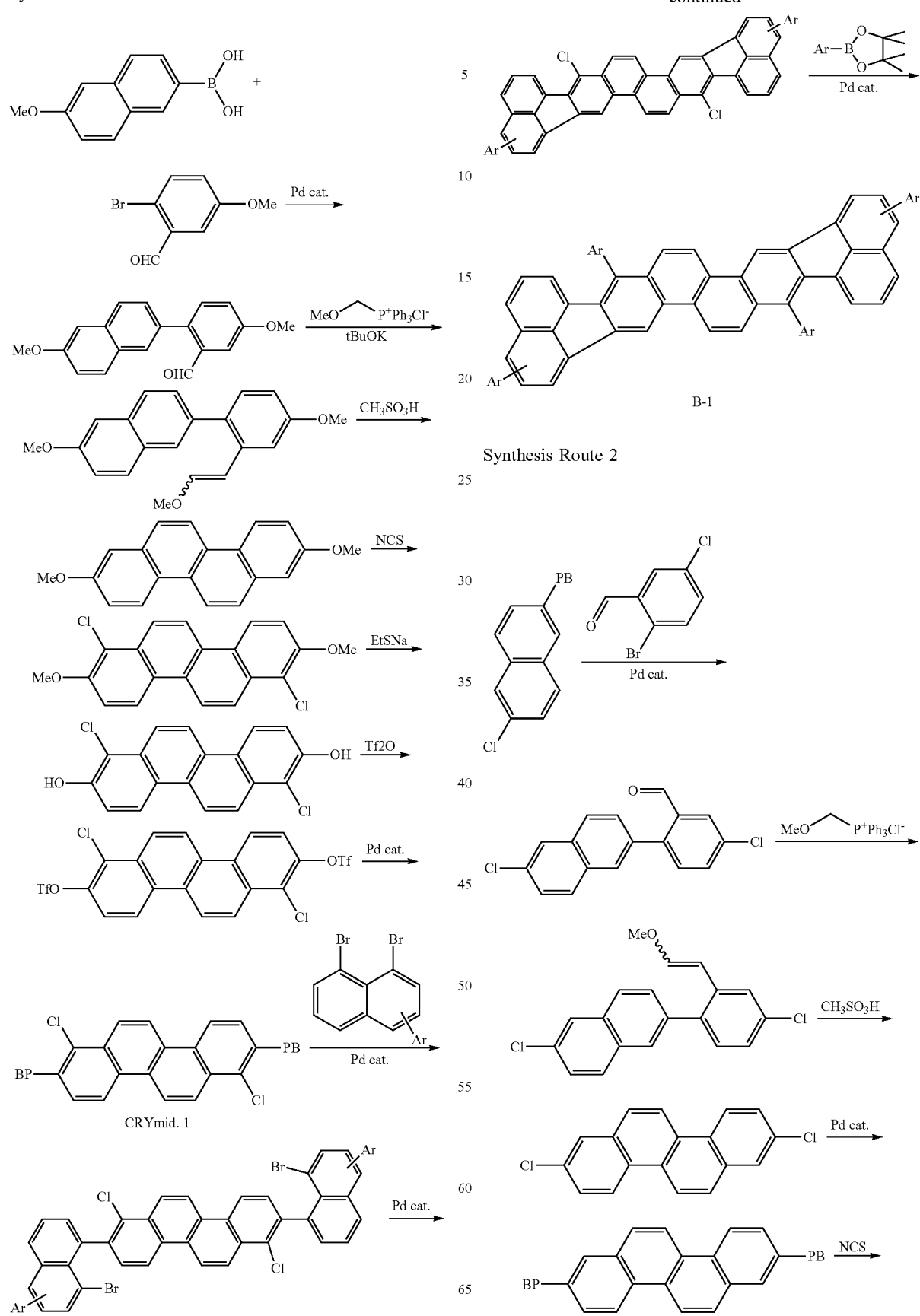

81
-continued
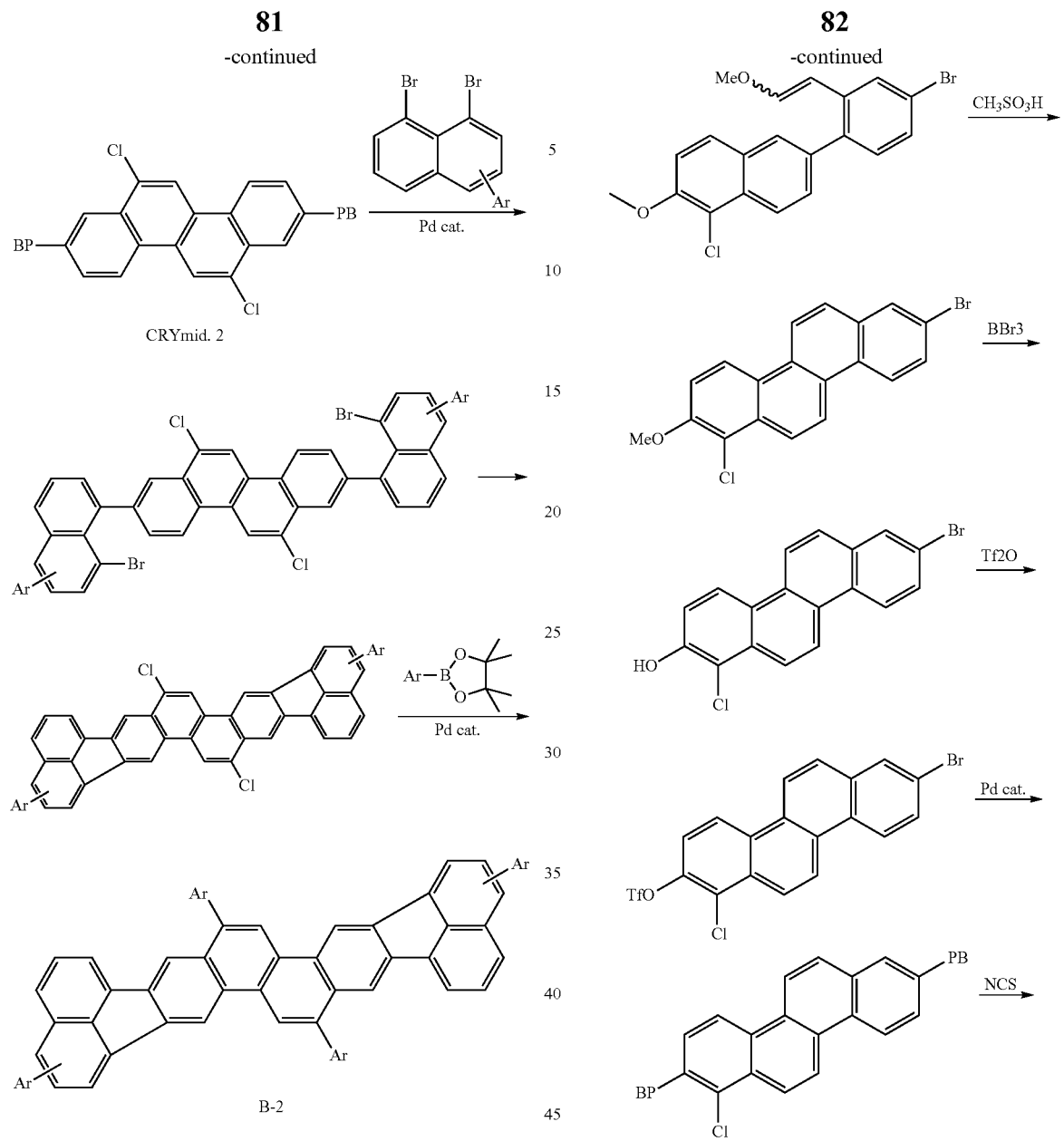
Synthesis Route 3
82
-continued
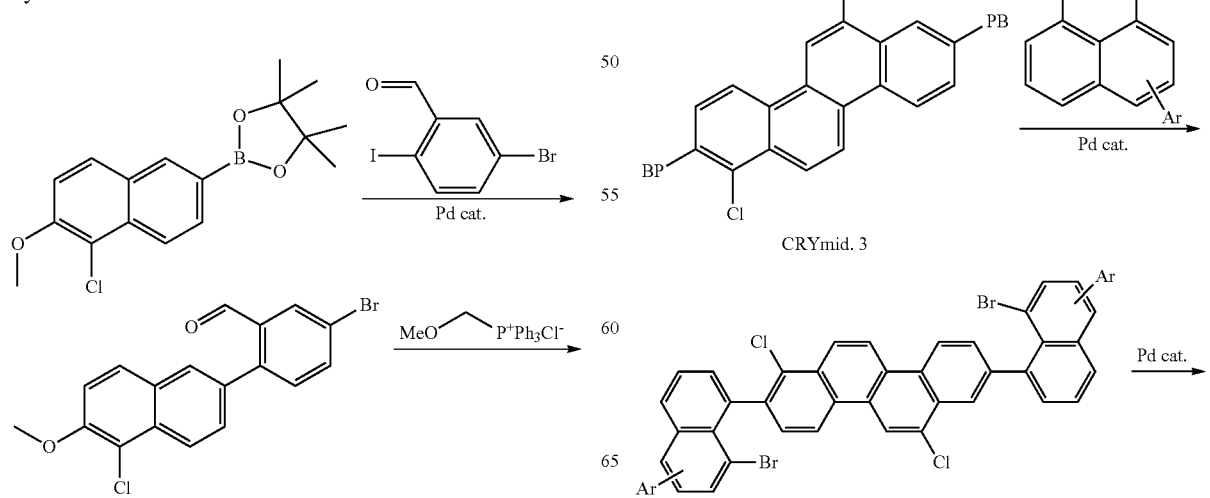

83
-continued
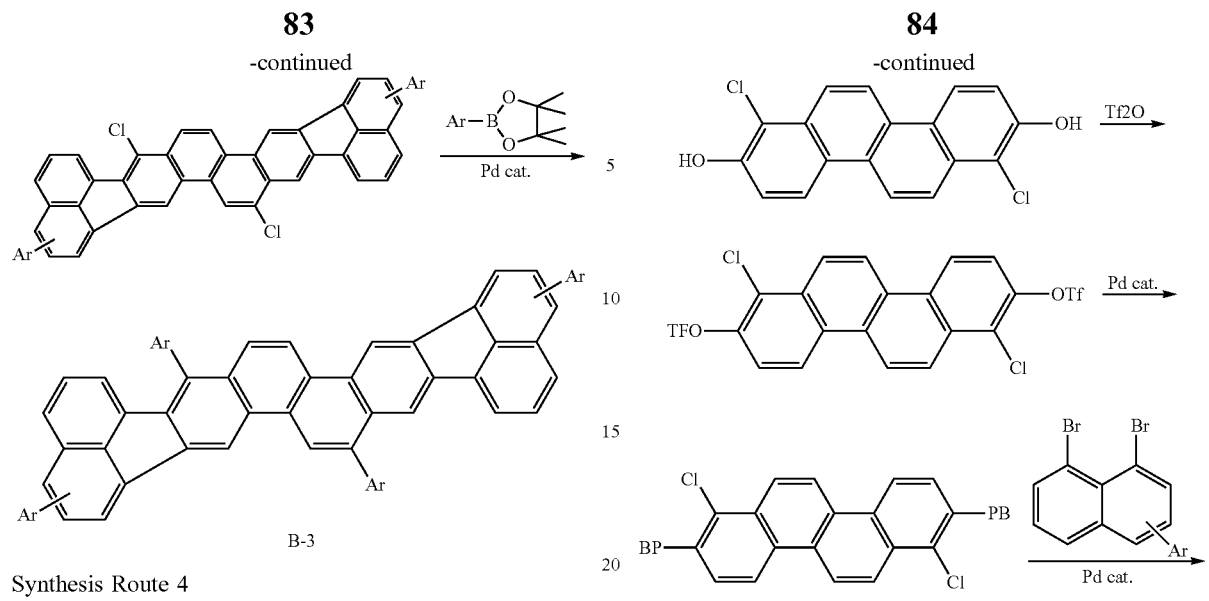
Synthesis Route 4
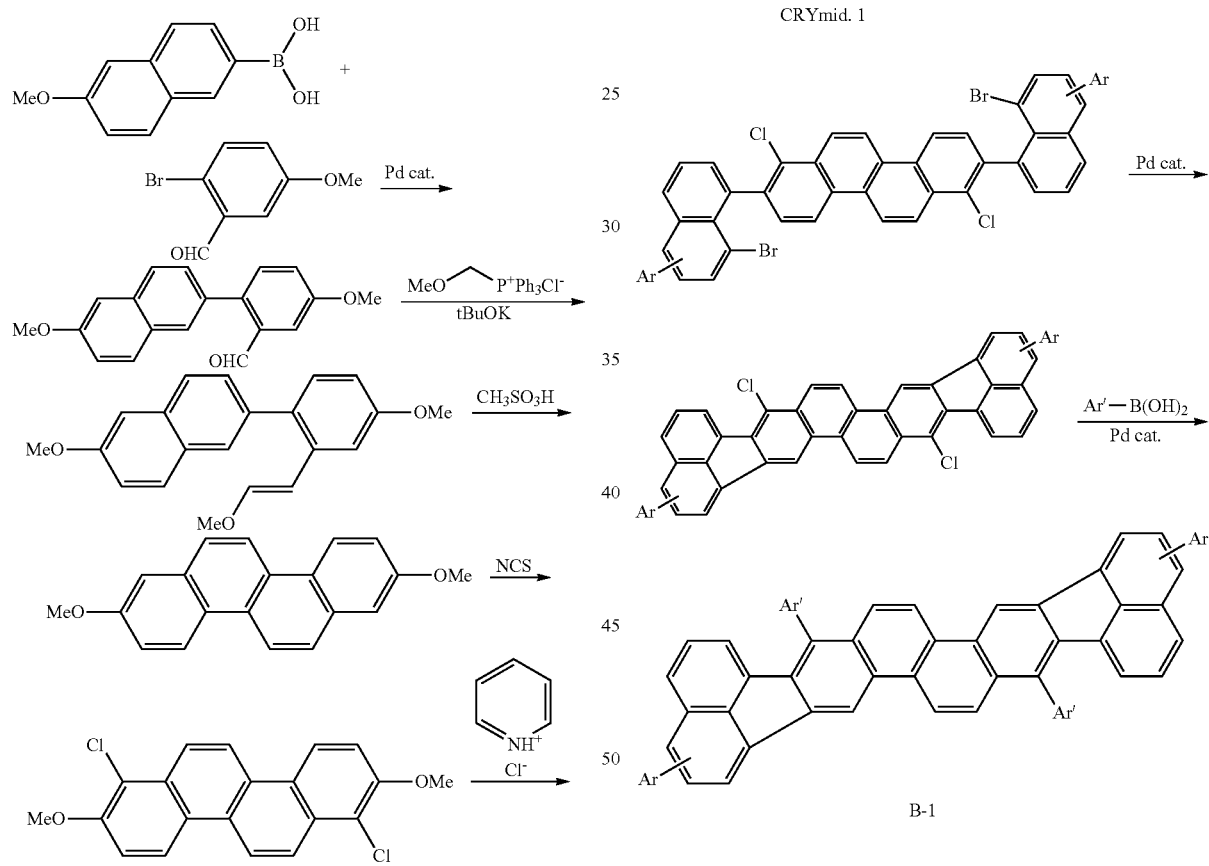
84
-continued
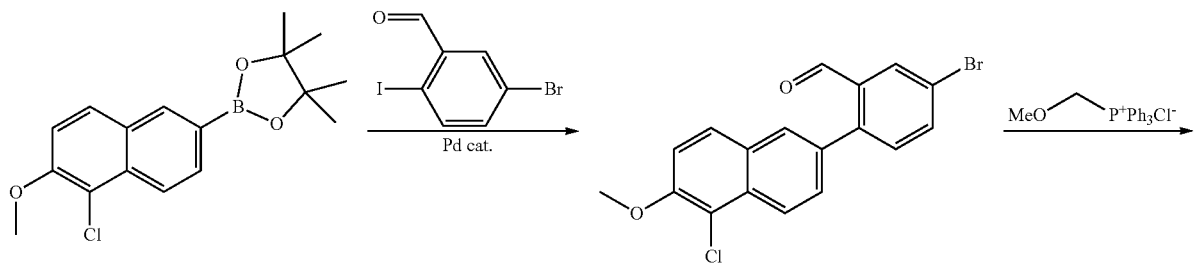
Synthesis Route 5

-continued
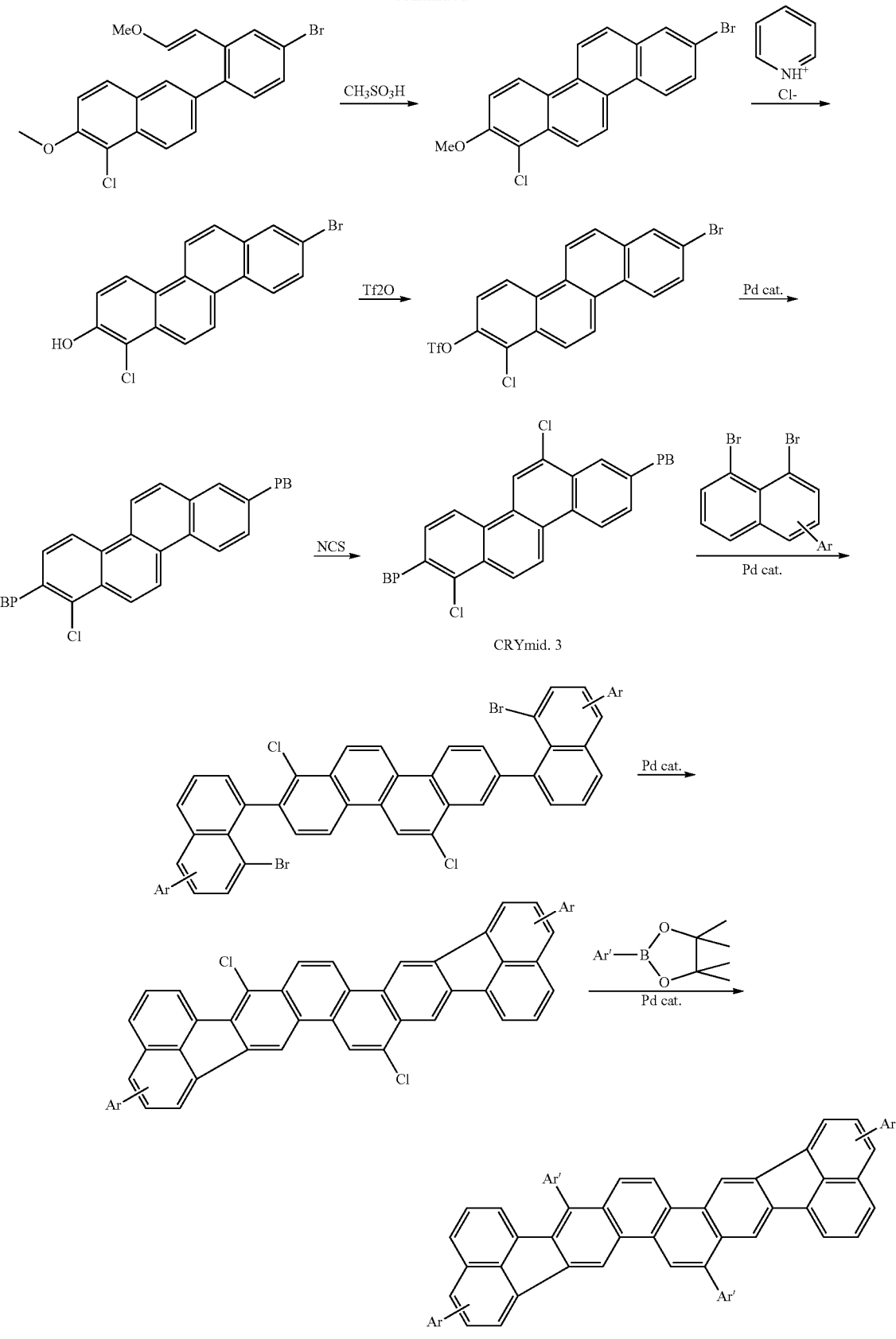
B-3

Herein, the compound represented by the formula [101] can be obtained by appropriately changing the substituents Ar and Ar'. The details of the synthesis method will be described in Examples.

Since the organic compound according to this embodiment has the following features, the organic compound is a compound that exhibits blue light emission with a high color purity and has high reduction potential and high chemical stability. Furthermore, an organic light-emitting element having a high color purity and high durability can be provided by using the organic compound.

(3) The group having an azine skeleton and serving as an electron-withdrawing substituent bonds to the basic skeleton at a position at which the electron orbital distribution of LUMO of the basic skeleton is relatively lower than that of HOMO.

(4) Nitrogen atoms in the group having an azine skeleton are arranged in a direction in which a hydrogen bond is not formed with respect to the basic skeleton.

Hereafter, these features will be described. Herein, the basic skeleton according to this embodiment refers to a skeleton in which hydrogen atoms, but not groups having an azine skeleton, are bonded to positions *1 to *6 in the formula [101] and $R_{110}$ to $R_{104}$ each represent a hydrogen atom.

(3) The group having an azine skeleton and serving as an electron-withdrawing substituent bonds to the basic skeleton at a position at which the electron orbital distribution of LUMO of the basic skeleton is relatively lower than that of HOMO.

When the organic compound represented by the formula [101] is made, the present inventors have focused on the basic skeleton itself.

To emit blue light with a high color purity, the basic skeleton itself needs to be in a blue region with a high color purity. In this embodiment, the desired emission wavelength region is a blue region with a high color purity, which is specifically a region in which the maximum emission wavelength in a dilute solution is 430 nm or more and 450 nm or less. The basic skeleton according to this embodiment is a basic skeleton suitable for desired blue light emission.

The basic skeleton according to this embodiment contributes to emitting blue light with a high color purity, but the compound has a large band gap and low electron acceptability. Organic light-emitting materials need to have high charge stability. To achieve this, high electron acceptability is required. In organic light-emitting elements, carrier recombination caused when an organic compound sandwiched between electrodes is repeatedly oxidized and reduced between its molecules allows the organic compound to have an excited state and a ground state in a repeated manner. Consequently, the organic light-emitting elements emit light. Therefore, the compound that is unstable in terms of charge transfer is chemically changed to a different compound through an oxidation-reduction process and in an excited state. This impairs the intrinsic element characteristics, which decreases the luminance of the organic light-emitting element and deteriorates the durability of the element during continuous driving. To suppress such deterioration, charge stability is required and thus high electron acceptability is required.

Accordingly, in this embodiment, the present inventors have focused on an increase in reduction potential as one of design strategies for materials having high electron acceptability, and have found the compound represented by the formula [101]. Specifically, by introducing the group having an azine skeleton as an electron-withdrawing group to the basic skeleton, the electron acceptability is improved, which can further improve the charge stability.

Although a halogen group such as a fluorine atom can be employed as an electron-withdrawing group, the fluorine atom has an oxidizing power and thus deteriorates the life of the element. A carboxy group can also be employed, but such a compound having a carboxy group is not suitable as a deposition material because the carboxy group makes it difficult to perform sublimation purification. In this embodiment, a group having an azine skeleton has been found as an electron-withdrawing substituent that has excellent deposition performance and does not deteriorate the characteristics of elements, such as durability life of elements. The group may be a group having an azine skeleton and represented by any one of the formulae [102] to [104].

Table 4 shows the exemplary compounds according to this embodiment and the comparative compounds that are compared with each other in terms of emission wavelength and reduction potential. The exemplary compounds are, for example, a compound in which an electron-withdrawing substituent having an azine skeleton is introduced to positions *3 and *4 in the formula [101], which are desired positions of the basic skeleton. The comparative compounds are compounds that do not have a group having an azine skeleton.

The emission wavelength was measured by photoluminescence measurement of a diluted toluene solution at an excitation wavelength of 350 nm at room temperature using an F-4500 manufactured by Hitachi, Ltd. The reduction potential was determined by cyclic voltammetry (CV) measurement. The CV measurement was performed using a DMF solution of 0.1 M tetrabutylammonium perchlorate (for reduction potential measurement). The reference electrode was $Ag/Ag^+$, the counter electrode was Pt, and the working electrode was glassy carbon. The scanning speed of voltage was 1.0 V/s. The measurement instrument was an electrochemical analyzer 660C manufactured by ALS.

TABLE 4

| Name of compound | Molecular structure | Maximum emission wavelength (nm) | Reduction potential (V) |
|---|---|---|---|
| Comparative compound 1-A | 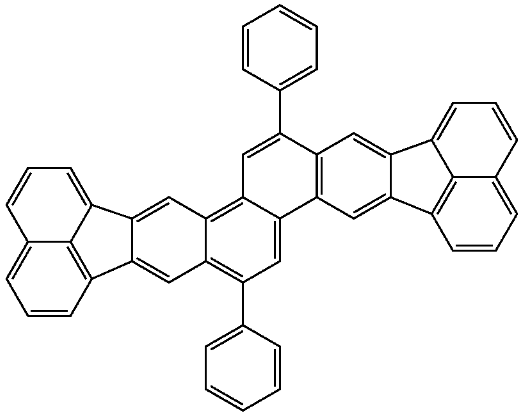 [SMILES: c1ccc(-c2cc3c4cc5c(cc4c(-c4ccccc4)cc3c3cc4c(cc23)-c2cccc3cccc-4c23)-c2cccc3cccc-5c23)cc1] | 448 | −2.08 |
| Comparative compound 1-C | 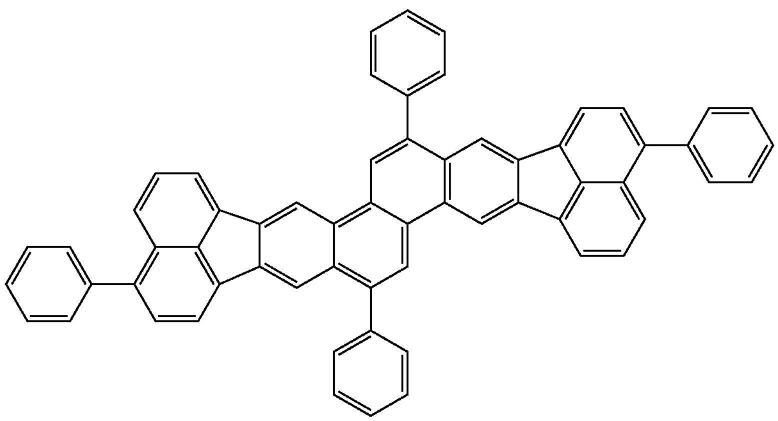 [SMILES: c1ccc(-c2ccc3c4c(cccc24)-c2cc4c(cc2-3)c(-c2ccccc2)cc2c3cc5c(cc3c(-c3ccccc3)cc42)-c2ccc(-c3ccccc3)c3cccc-5c23)cc1] | 452 | −2.01 |
| Exemplary compound D1 | 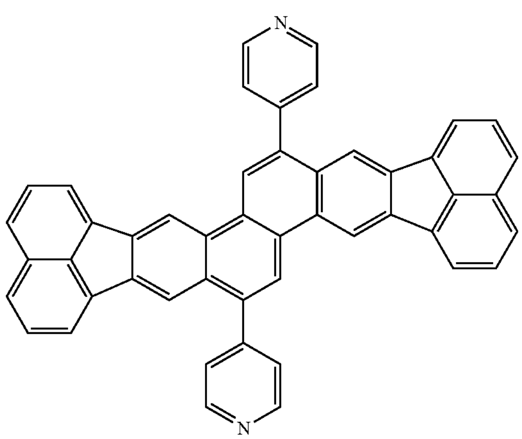 [SMILES: c1cc2c3c(cccc3c1)-c1cc3c(cc1-2)c(-c1ccncc1)cc1c2cc4c(cc2c(-c2ccncc2)cc31)-c1cccc2cccc-4c12] | 444 | −1.98 |

TABLE 4-continued

| Name of compound | Molecular structure | Maximum emission wavelength (nm) | Reduction potential (V) |
|---|---|---|---|
| Exemplary compound D11 | 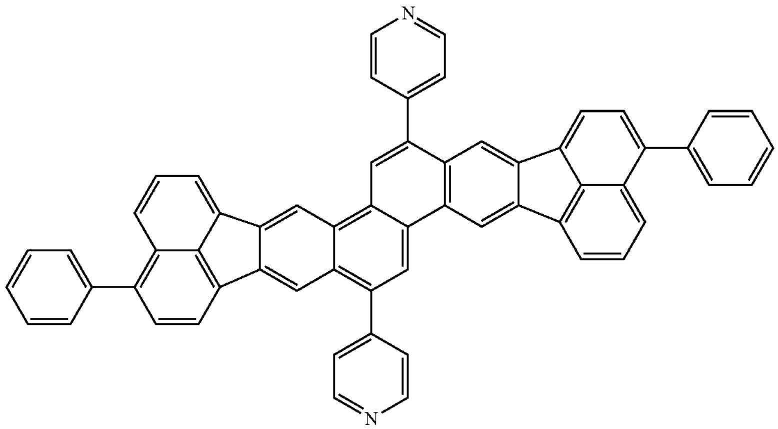 [SMILES: c1ccc(-c2ccc3c4c(cccc24)-c2cc4c(cc2-3)c(-c2ccncc2)cc2c3cc5c(cc3c(-c3ccncc3)cc42)-c2ccc(-c3ccccc3)c3cccc-5c23)cc1] | 449 | −1.87 |

Table 4 shows that the compounds according to this embodiment in which a group having an azine skeleton and serving as an electron-withdrawing substituent is introduced to desired positions have a higher reduction potential than the comparative compounds by 0.1 V or more without shifting the wavelength to longer wavelengths. That is, the compound according to this embodiment exhibits blue light emission with a high color purity and has improved electron acceptability. Hereafter, the details of the results in Table 4 and the discussion thereof will be described.

The comparative compound 1-A is a compound in which a phenyl group having no electron-withdrawing substituent is introduced to the 9 and 19 positions of a diacenaphtho[1,2-b:1',2'-k]chrysene skeleton serving as a basic skeleton. This is a compound in which the basic skeleton itself has characteristics close to those of the exemplary compound. The exemplary compound D1 has a structure in which an electron-withdrawing group having an azine skeleton is introduced to the 9 and 19 positions of the basic skeleton. The exemplary compound D1 has a higher reduction potential of −1.98 V than the comparative compound 1-A. At the same time, the exemplary compound D1 has a shorter maximum emission wavelength of 444 nm than the comparative compound 1-A. Thus, the exemplary compound D1 has a better color purity.

The comparative compound 1-C has a structure in which a phenyl group is further introduced to the 3 and 13 positions of the basic skeleton of the comparative compound 1-A. The conjugation length of the basic skeleton is increased in the longitudinal direction, which narrows the band gap. As a result, the comparative compound 1-C has a higher reduction potential than the comparative compound 1-A, but has a longer maximum emission wavelength, which deteriorates the color purity. In contrast, the exemplary compound D11 according to this embodiment has a structure in which a group having an azine skeleton is introduced to the 9 and 19 positions of the comparative compound 1-C instead of the phenyl group. The exemplary compound D11 has a higher reduction potential of −1.87 V than the comparative compound 1-C and a shorter maximum emission wavelength than the comparative compound 1-C.

This result can be considered as follows. The electron orbital distributions of HOMO and LUMO of the diacenaphtho[1,2-b:1',2'-k]chrysene skeleton serving as a basic skeleton are dependent on the positions of the basic skeleton. Therefore, the degree of effect on HOMO and LUMO is probably dependent on the positions to which an electron-withdrawing substituent is introduced. In other words, in the exemplary compounds D1 and D11, a group having an azine skeleton, which is an electron-withdrawing substituent, is introduced to the 9 and 19 positions of the basic skeleton. At these positions, the electron orbital distribution of LUMO of the basic skeleton is relatively lower than that of HOMO. Therefore, a relatively large electron withdrawing effect is exerted to HOMO and the optical band gap is widened. Consequently, the maximum emission wavelength of the exemplary compounds is shifted to shorter wavelengths than that of the comparative compounds. At the same time, the reduction potential is increased because of the electron-withdrawing effect on LUMO. Table 4 shows the results obtained when an electron-withdrawing group having an azine skeleton is introduced to the 9 and 19 positions of the basic skeleton, that is, to the positions *3 and *4 in the formula [101]. The same effect is also produced when such an electron-withdrawing group having an azine skeleton is introduced to the positions *1, *2, *5, and *6.

Figure 6A:
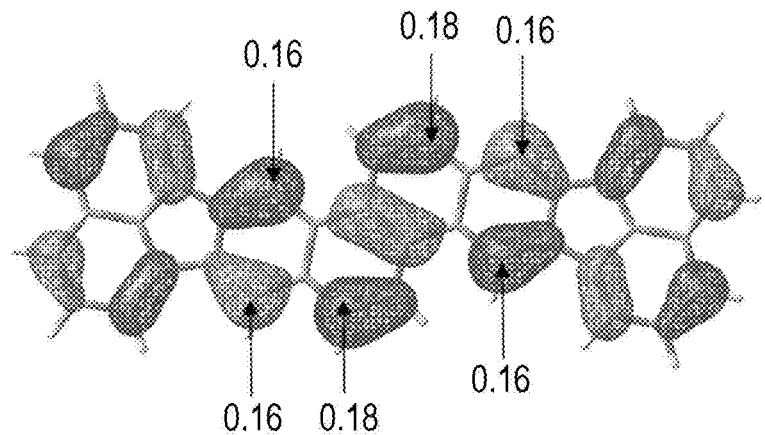
FIGS. 6A and 6B illustrate the electron orbital distributions of HOMO and LUMO of a diacenaphtho[1,2-b:1',2'-k]chrysene skeleton.
Figure 6B:
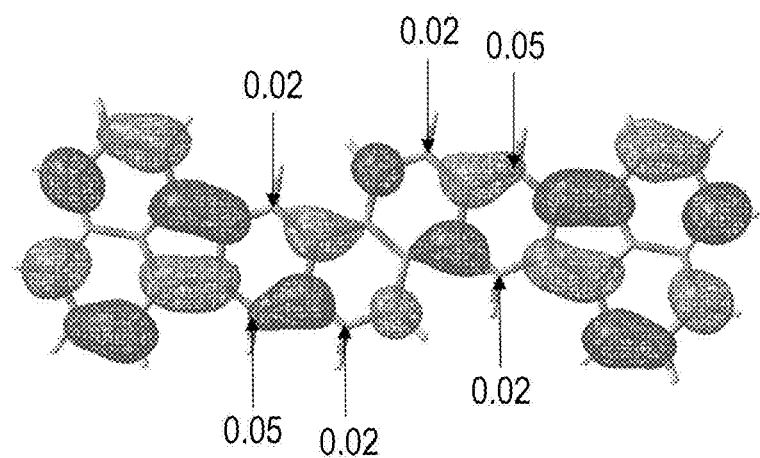

To support the above effect, the electron orbital distributions of HOMO and LUMO of the diacenaphtho[1,2-b:1',2'-k]chrysene skeleton serving as a basic skeleton were calculated and visualized using the molecular orbital calculations. FIGS. 6A and 6B illustrate the results. FIG. 6A illustrates the electron orbital distribution of HOMO, and FIG. 6B illustrates the electron orbital distribution of LUMO.

The density functional theory (DFT), which has been widely used today, was used as a calculation technique of the molecular orbital calculations. The functional was B3LYP and the basis function was 6-31G*. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A.

Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010.), which has been widely used today.

As is clear from FIGS. 6A and 6B, at the positions *1 to *6 in the formula [101] (positions indicated by arrows), the electron orbital distribution of HOMO (FIG. 6A) is relatively higher than that of LUMO (FIG. 6B). This is because the numerical values accompanied with arrows refer to orbital coefficients, and the orbital coefficients of HOMO at the positions *1 to *6 are larger than the corresponding orbital coefficients of LUMO. Therefore, when an electron-withdrawing group having an azine skeleton is introduced to the positions, the reduction potential is increased because of the electron-withdrawing effect on LUMO, but a larger electron-withdrawing effect is exerted to HOMO. As a result, the optical band gap is widened and the emission wavelength is shifted to shorter wavelengths.

(4) Nitrogen atoms in the group having an azine skeleton are arranged in a direction in which a hydrogen bond is not formed with respect to the basic skeleton.

The compound according to this embodiment has a group having an azine skeleton, which is an electron-withdrawing substituent, at the positions *1 to *6 in the formula [101], and the group having an azine skeleton is the group represented by any one of the formulae [102] to [104]. That is, nitrogen atoms in the group having an azine skeleton are arranged in a direction in which a hydrogen bond is not formed with respect to the basic skeleton. Table 5 shows the exemplary compound according to this embodiment and the comparative compounds that have nitrogen atoms at different positions, and these compounds are compared with each other in terms of emission wavelength and reduction potential.

TABLE 5

| Name of compound | Molcular structure | Maximum emission wavelength (nm) | Reduction potential (V) |
| --- | --- | --- | --- |
| Comparative compound 1-A | | 448 | −2.08 |
| Comparative compound 1-B | | 453 | −2.08 |

TABLE 5-continued

| Name of compound | Molcular structure | Maximum emission wavelength (nm) | Reduction potential (V) |
|---|---|---|---|
| Exemplary compound D13 | | 445 | −1.95 |

Table 5 shows that the exemplary compound D13 according to this embodiment has a shorter maximum emission wavelength and a higher reduction potential than the comparative compound 1-A. This effect has been described above. On the other hand, the comparative compound 1-B having a group having an azine skeleton has a longer maximum emission wavelength, but has the same reduction potential. This difference can be explained as follows.

First, since the comparative compound 1-B has a structure in which nitrogen atoms in the group having an azine skeleton are arranged closer to the basic skeleton, the lone pair on the nitrogen atoms forms a hydrogen bond at the 10 and 20 positions of the basic skeleton, which increases the planarity. This increases the degree of π conjugation on the whole molecule and narrows the band gap, which probably increases the maximum emission wavelength. In general, when the band gap is narrowed, the HOMO shifts to the high energy level and the LUMO shifts to the low energy level. In the comparative compound 1-B, however, the lone pair on the nitrogen atoms is arranged in such a direction that the lone pair forms a hydrogen bond with hydrogen atoms on the basic skeleton. This probably shifts the HOMO and LUMO to higher energy levels. The term "high HOMO/LUMO energy level" means that each orbital is closer to the vacuum level. The term "low HOMO/LUMO energy level" means that each orbital is farther from the vacuum level.

This is because the lone pair on nitrogen atoms forms a hydrogen bond with hydrogen atoms on the basic skeleton, which donates electrons from the lone pair on nitrogen atoms to the hydrogen atoms on the basic skeleton via the hydrogen bond. Therefore, electrons are donated to the basic skeleton unlike the characteristics of the electron-withdrawing group, which shifts the HOMO and LUMO to higher energy levels. That is, the tendency that the LUMO is shifted to the lower energy level as the band gap is narrowed is canceled by the electron-donating effect via the hydrogen bond. As a result, the maximum emission wavelength increases and the reduction potential does not increase. These changes are opposite to those in this embodiment.

As described above, the organic compound according to this embodiment has the above features (3) and (4). Therefore, the organic compound is a chemically stable compound that exhibits blue light emission with a high color purity and has high electron acceptability. By using this organic compound, a high-efficiency organic light-emitting element that has high durability and emits blue light with a high color purity can be provided.

The organic compound according to this embodiment will be specifically described below. However, this embodiment is not limited thereto.

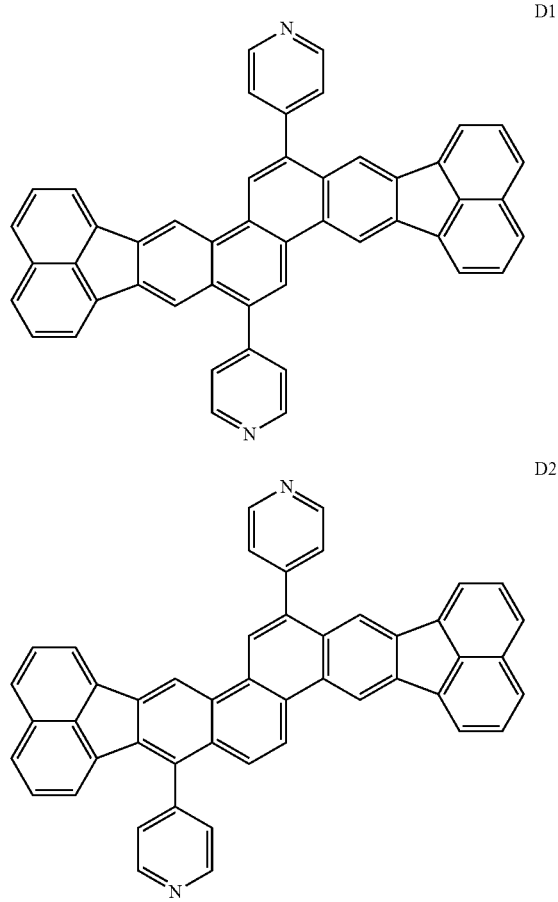

-continued
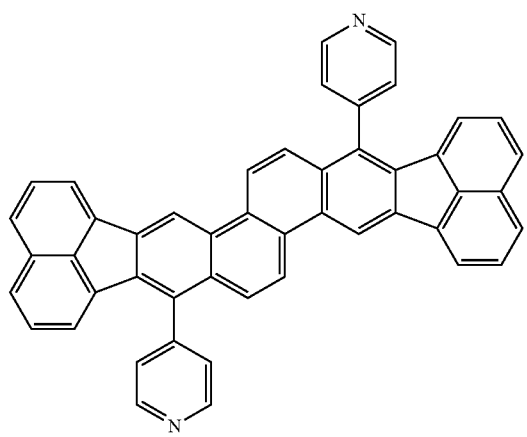
D3
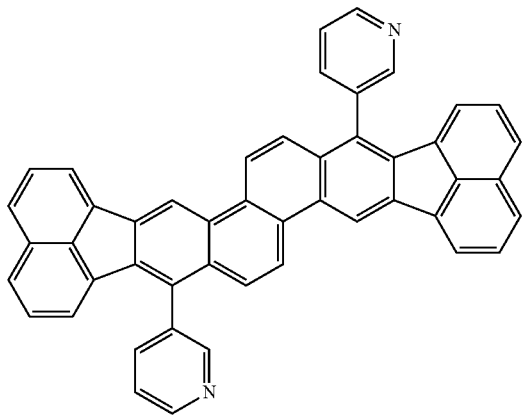
D6
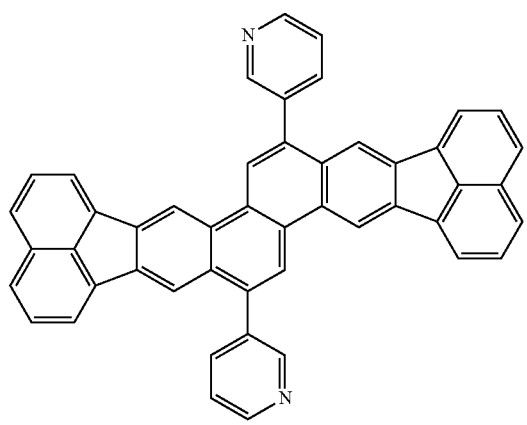
D4
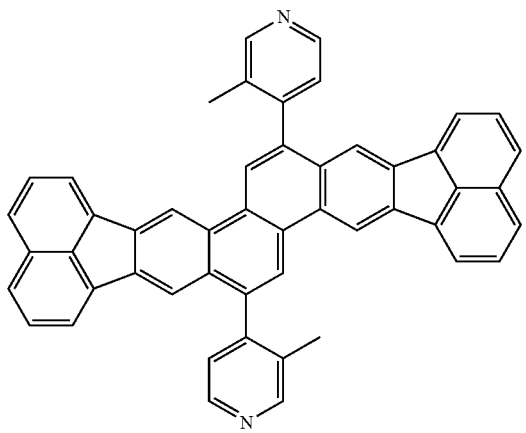
D7
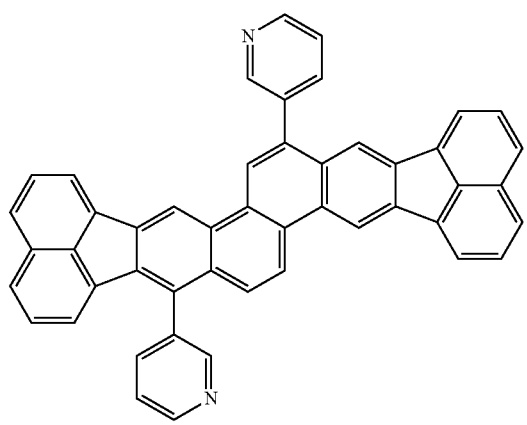
D5

D9
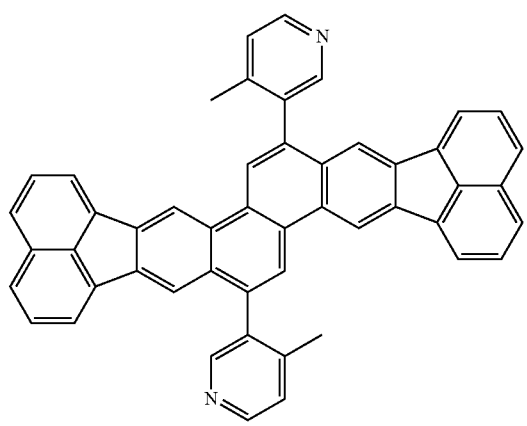
D10
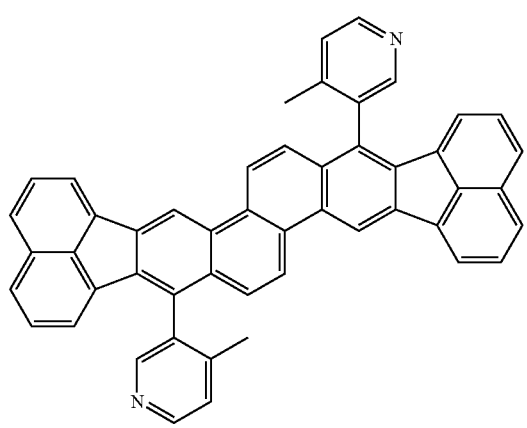
D11
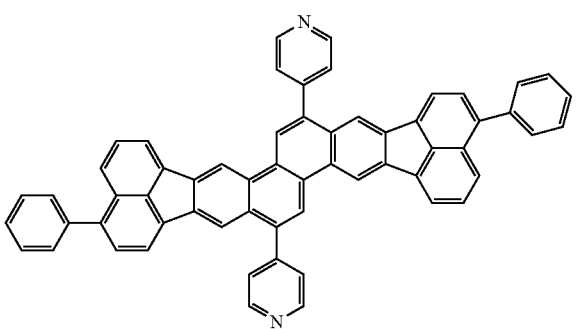
D12
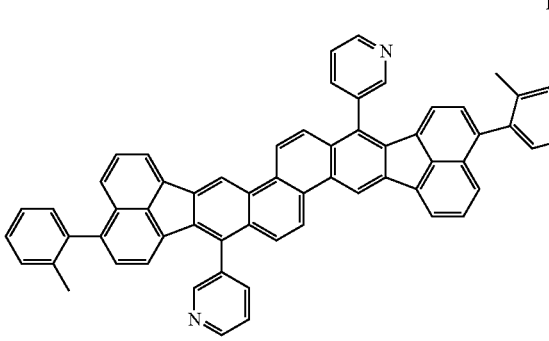
D13
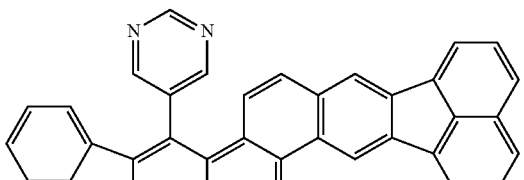
D14
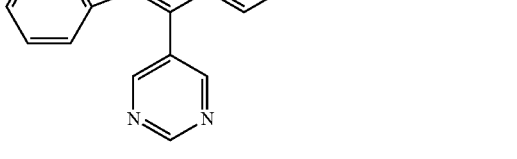
D15
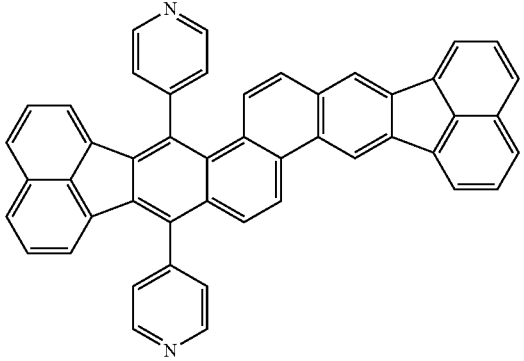
D16
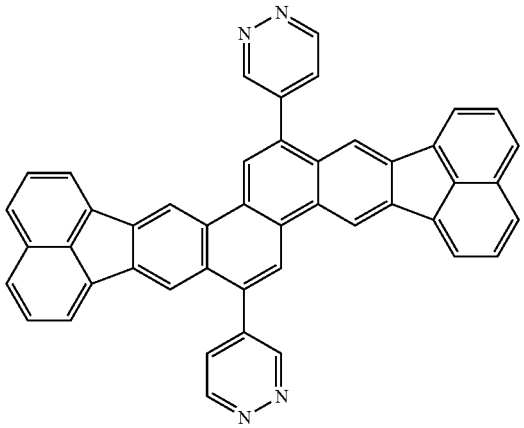

D17
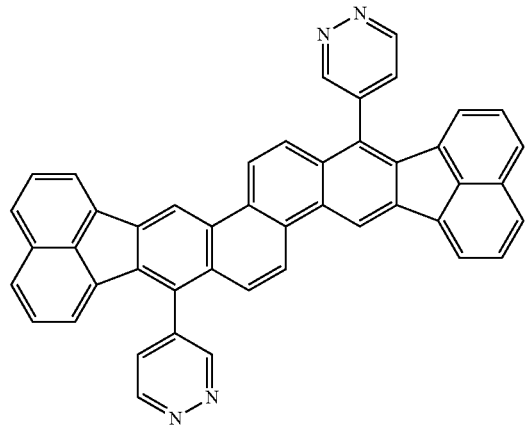
D18
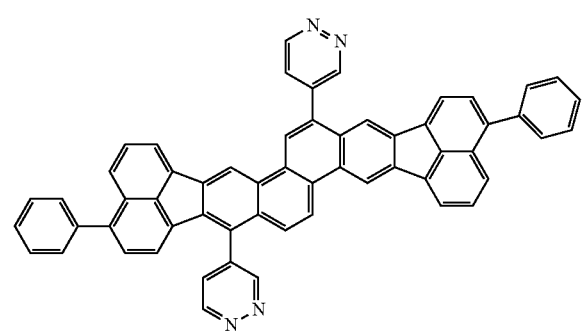
D19
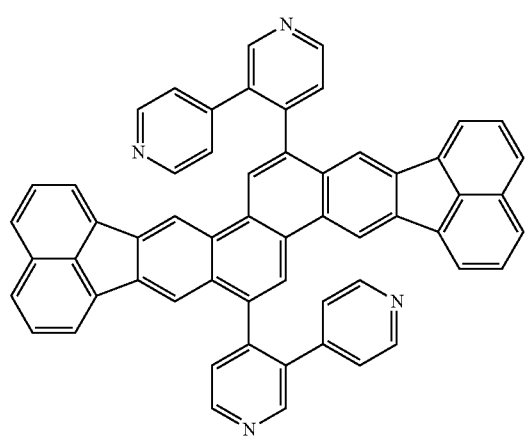
D20
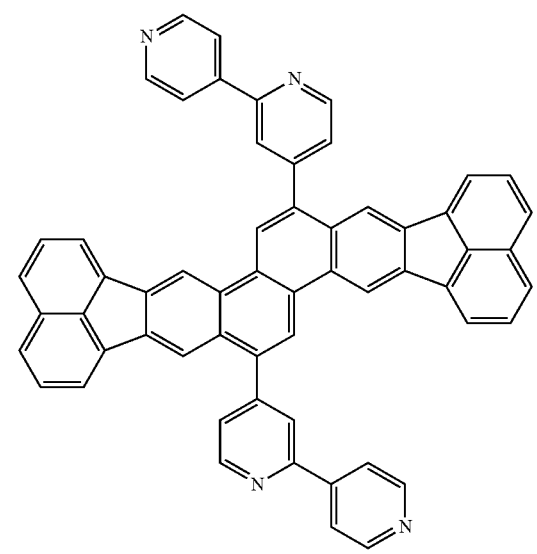
D21
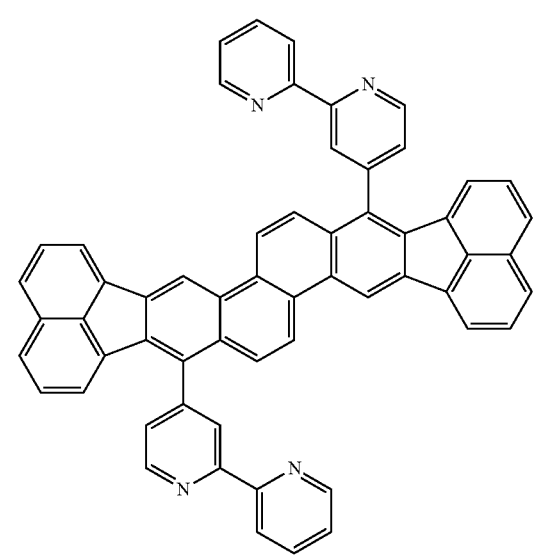
D22
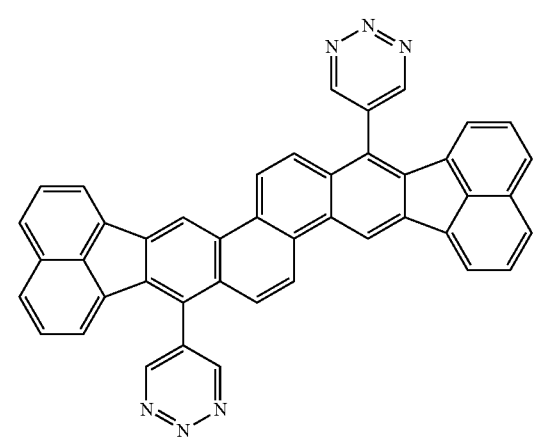

D23
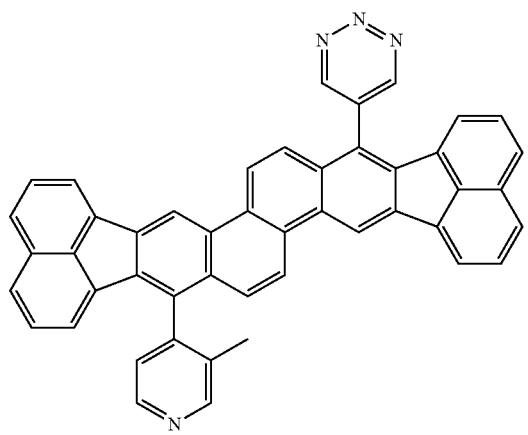
D24
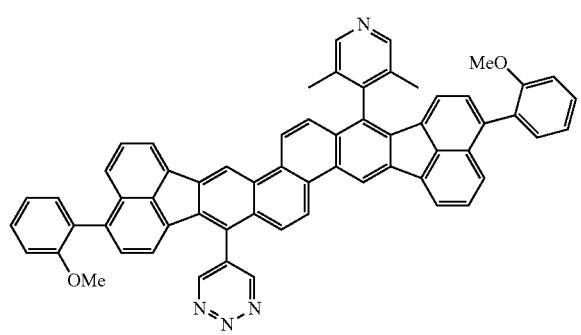
D25
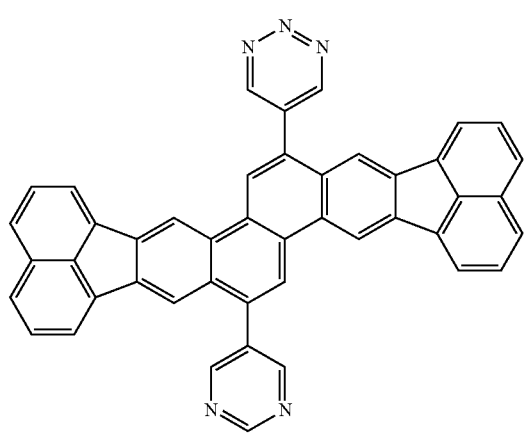
D26
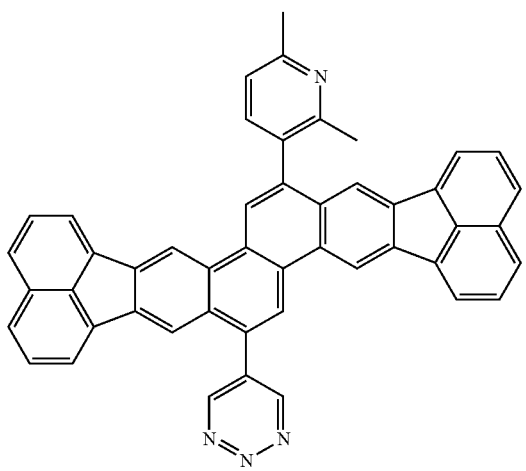
D27
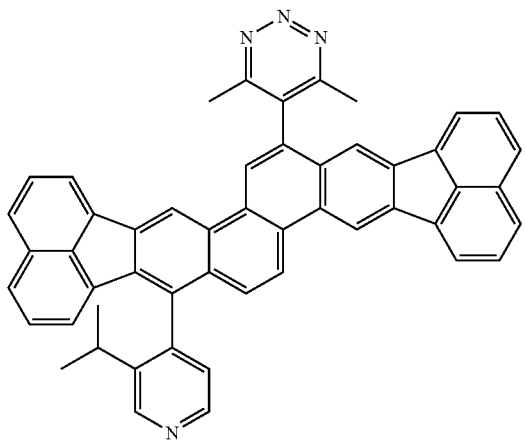
D28
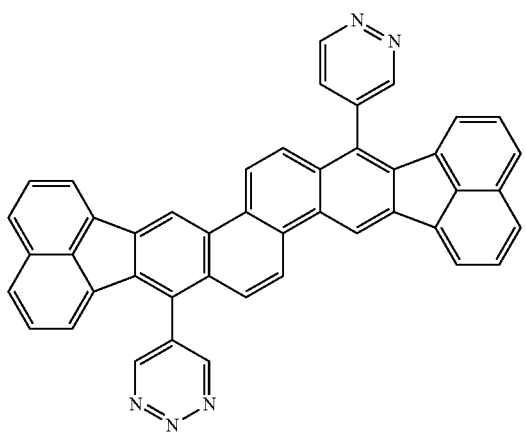

-continued
D29
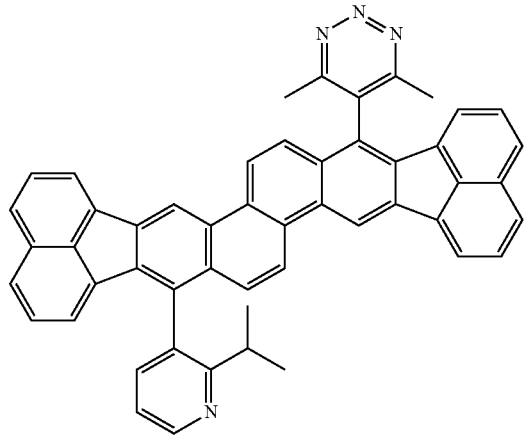
D30
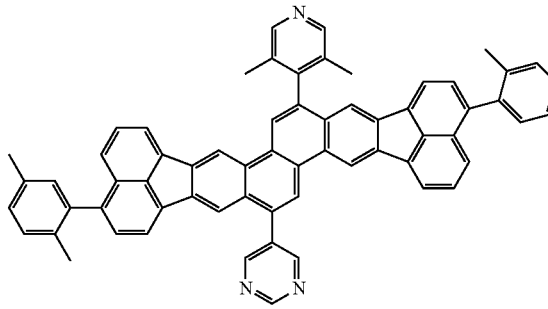
D31
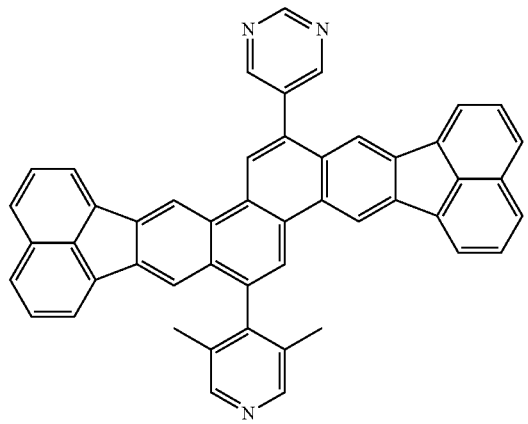
D32
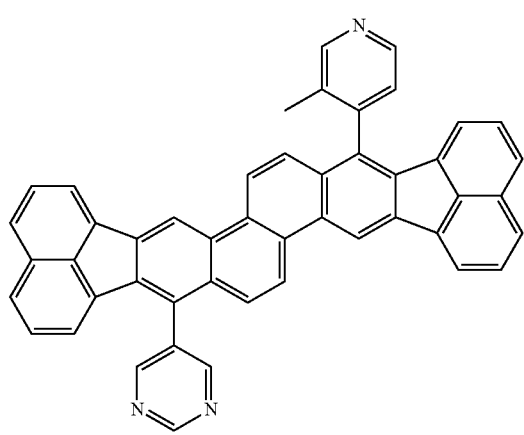
-continued
D33
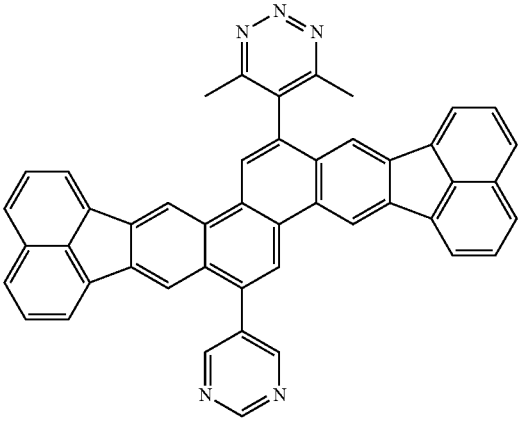
E1
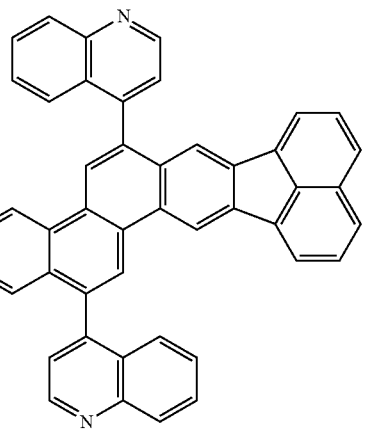
E2
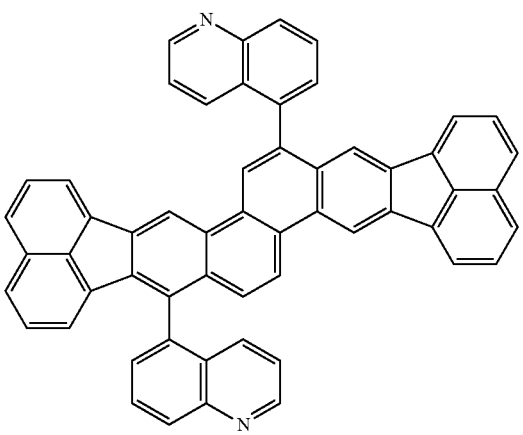

E3
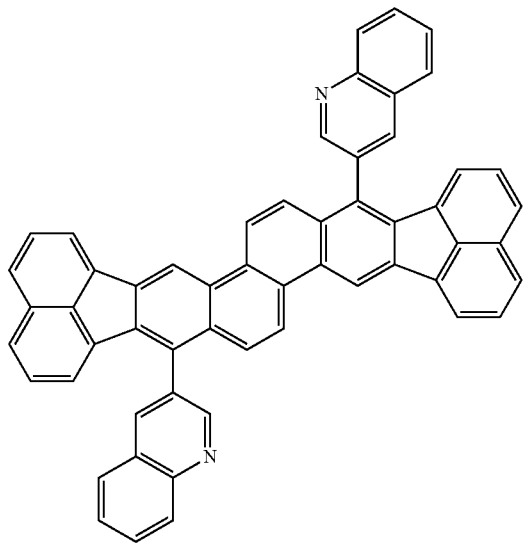
E4
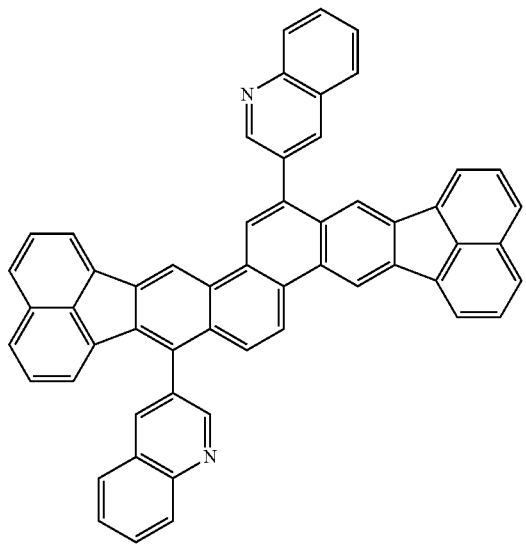
E5
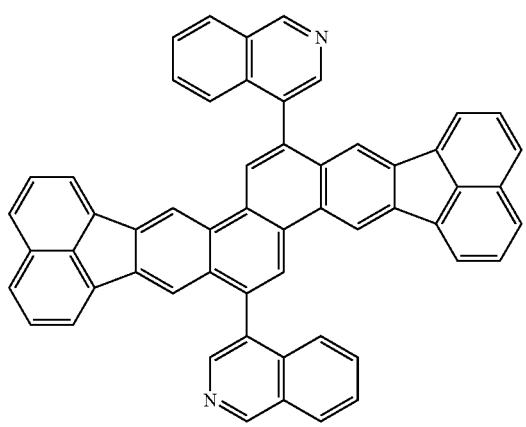
E6
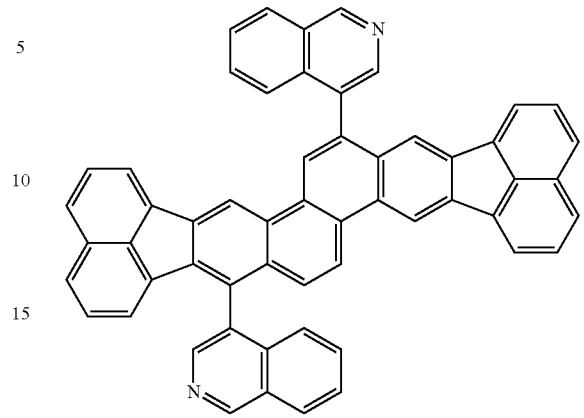
E7
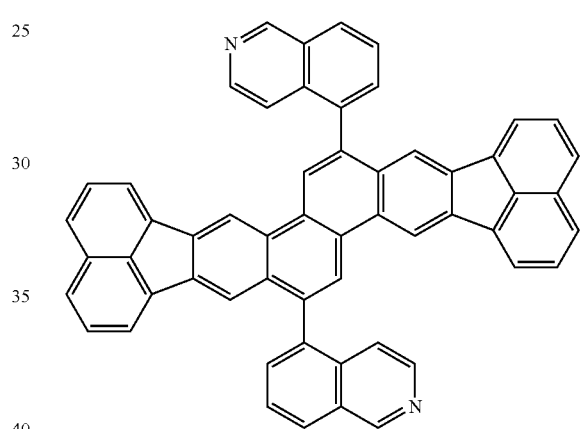
E8
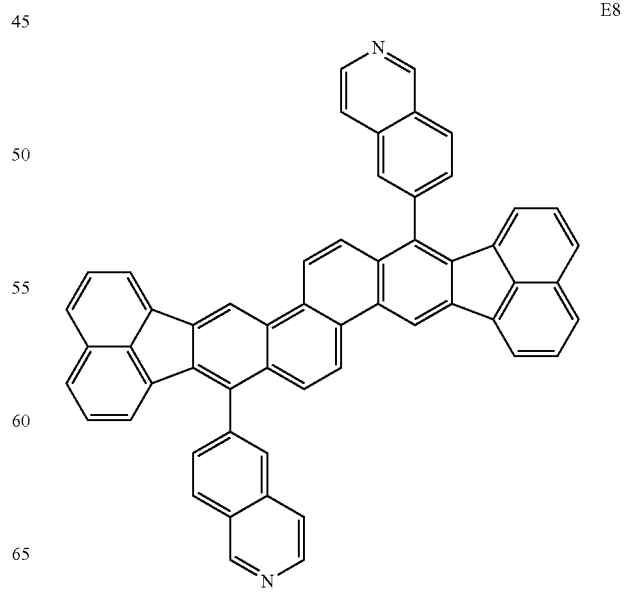

E9
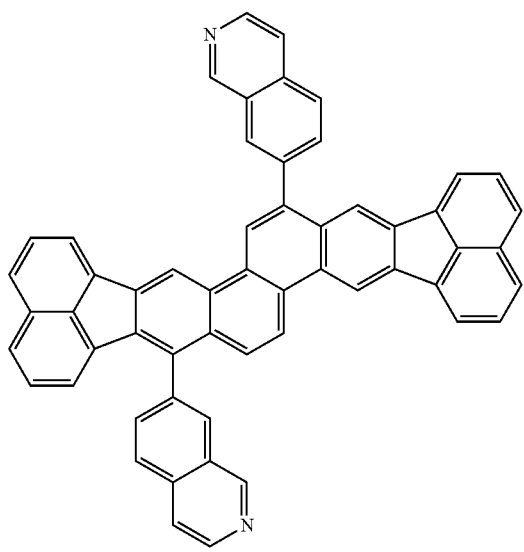
E10
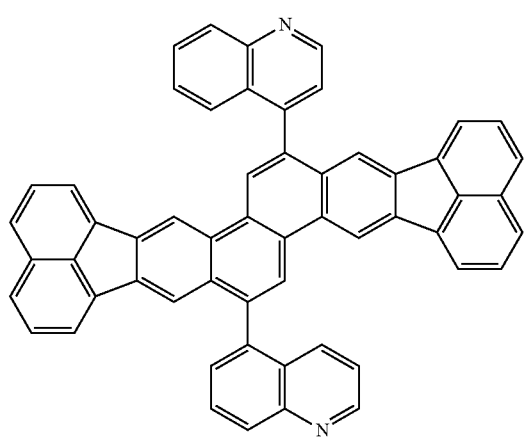
E11
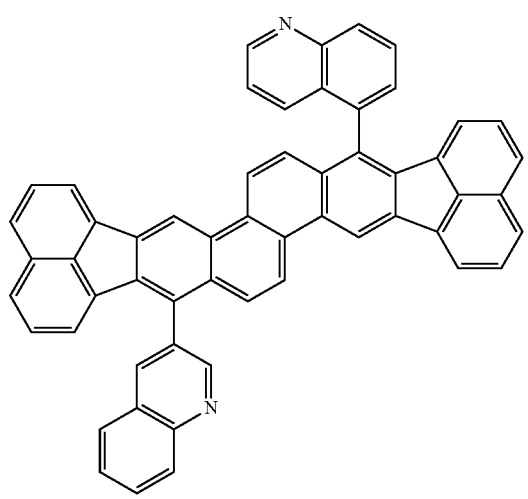
E12
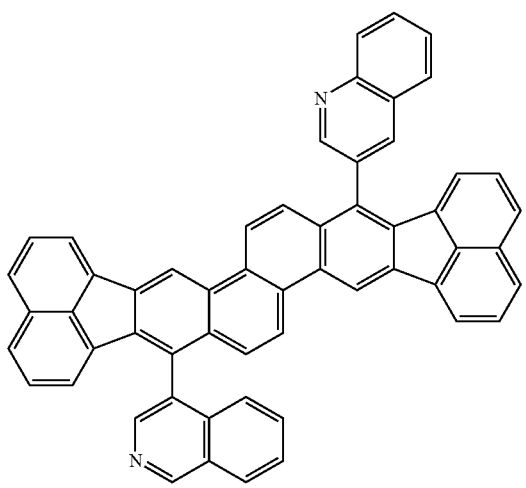
F1
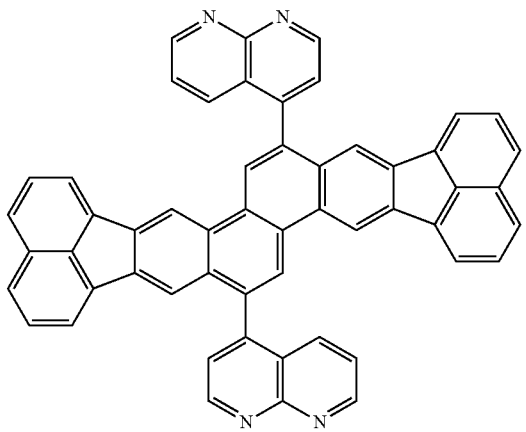
F2
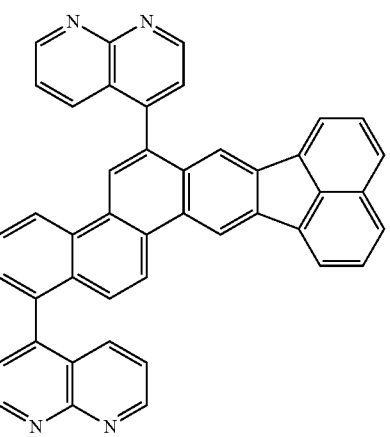

111
-continued
F3
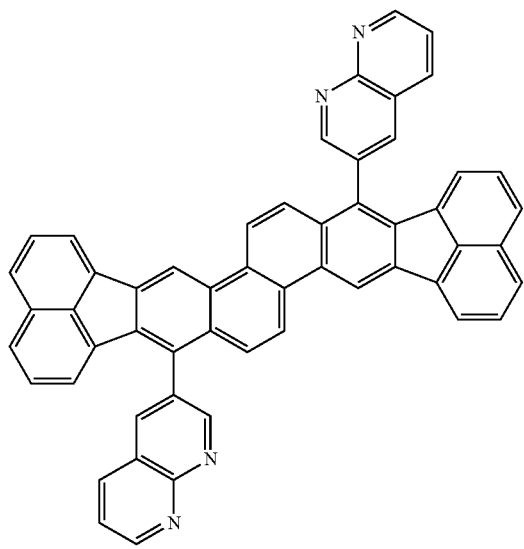
F4
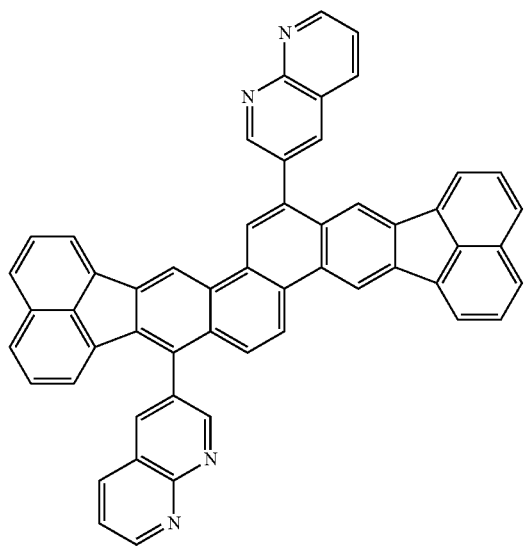
F5
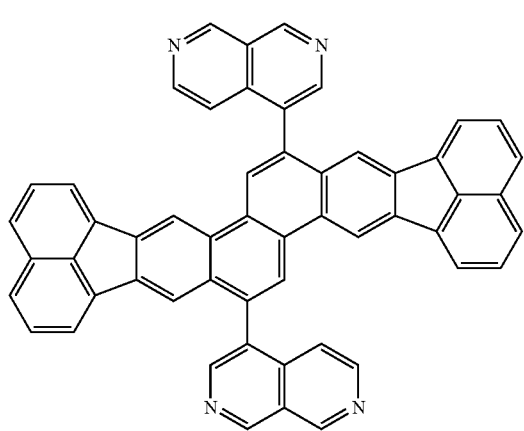
112
-continued
F6
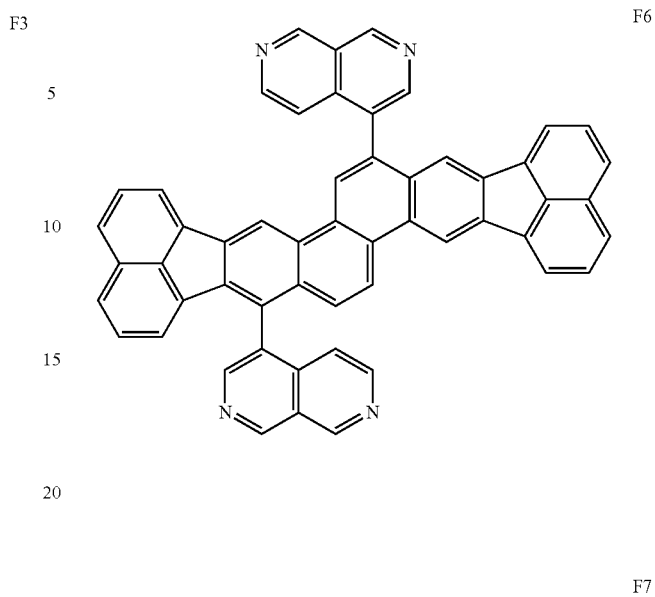
F7
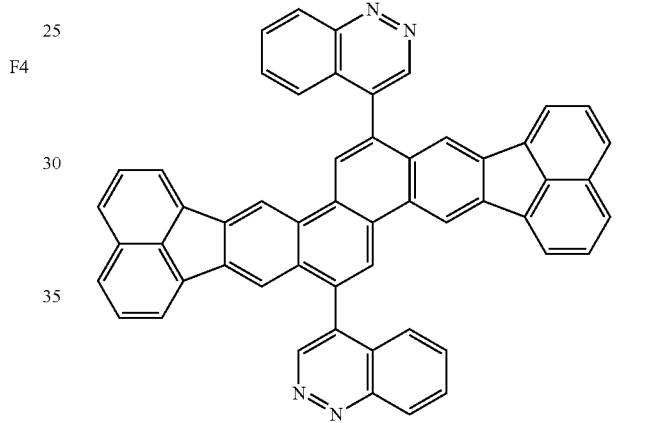
F8
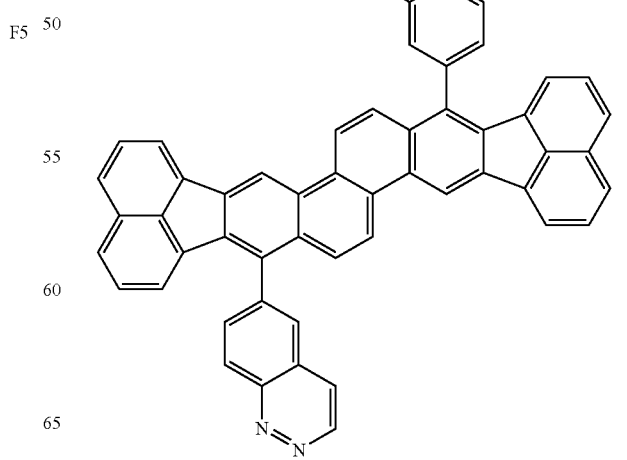

F9

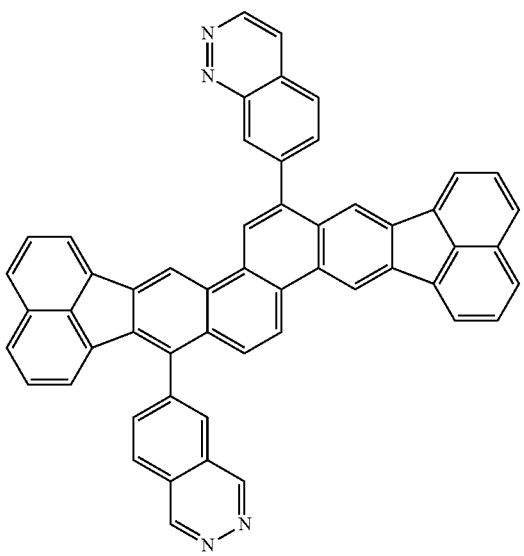

F10

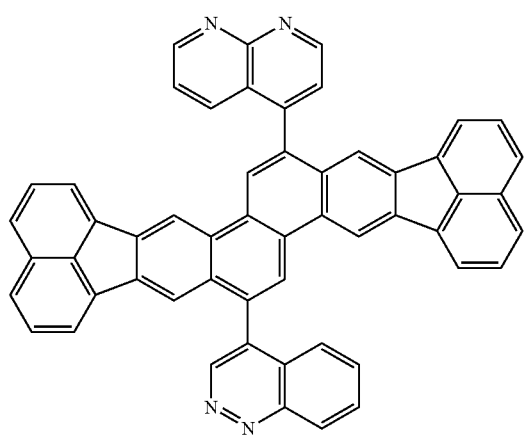

F11

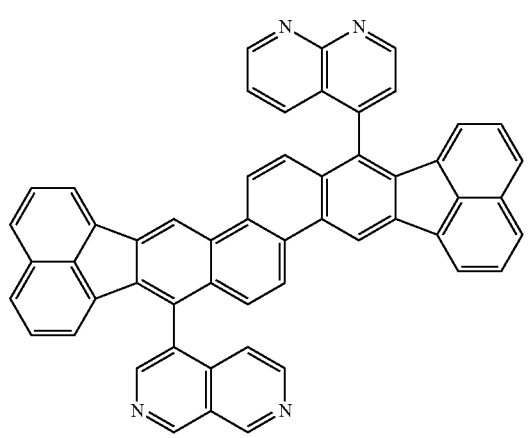

F12

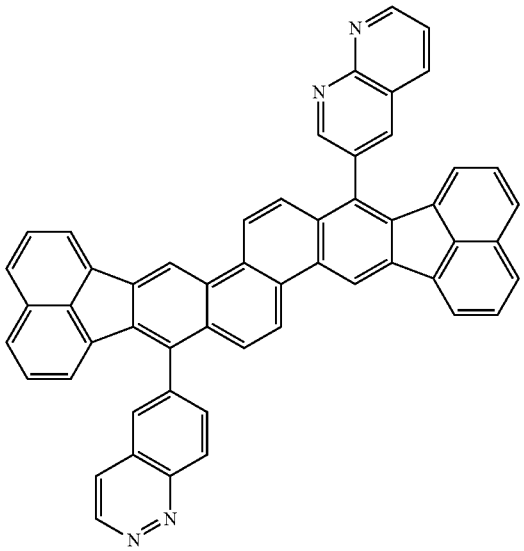

Among the exemplary compounds, the compounds that belong to the D group are compounds in which groups having an azine skeleton and represented by the formulae [105] to [109] are introduced. This can achieve high electron acceptability and blue light emission with a high color purity.

Among the exemplary compounds, the compounds that belong to the E group are compounds in which groups having an azine skeleton and represented by the formulae [110] to [118] are introduced. Since the number of nitrogen atoms per introduced group having an azine skeleton is smaller than that of the D group, the electron acceptability decreases, but Tg is improved with increasing the molecular weight. This can achieve high thermal resistance and blue light emission with a high color purity.

Among the exemplary compounds, the compounds that belong to the F group are compounds in which groups having an azine skeleton and represented by the formulae [119] to [124] are introduced. This can achieve high thermal resistance and high electron acceptability.

Organic Light-Emitting Element

Next, an organic light-emitting element according to this embodiment will be described. The organic light-emitting element according to this embodiment at least includes an anode and a cathode, which are a pair of electrodes, and an organic compound layer disposed between the electrodes. In the organic light-emitting element according to this embodiment, the organic compound layer may have a single-layer structure or a multilayer structure including a plurality of layers as long as the organic compound layer includes a light-emitting layer. When the organic compound layer has a multilayer structure including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may have a single-layer structure or a multilayer structure including a plurality of layers.

In the organic light-emitting element according to this embodiment, the organic compound according to this embodiment is contained in at least one layer of the organic compound layer. Specifically, the organic compound according to this embodiment is contained in any of the light-emitting layer, the hole injection layer, the hole transport layer, the electron blocking layer, the hole/exciton blocking layer, the electron transport layer, and the electron injection layer. The organic compound according to this embodiment may be contained in the light-emitting layer.

In the organic light-emitting element according to this embodiment, when the organic compound according to this embodiment is contained in the light-emitting layer, the light-emitting layer may be a layer formed of only the organic compound according to this embodiment or may be a layer formed of the organic compound according to this embodiment and other compounds. When the light-emitting layer is a layer formed of the organic compound according to this embodiment and other compounds, the organic compound according to this embodiment may be used as a host of the light-emitting layer or a guest of the light-emitting layer. Alternatively, the organic compound may be used as an assist material that can be contained in the light-emitting layer. Herein, the host refers to a compound having the highest mass ratio among the compounds that form the light-emitting layer. The guest refers to a compound that has a lower mass ratio than the host and that is responsible for main light emission among the compounds that form the light-emitting layer. The assist material refers to a compound that has a lower mass ratio than the host and that assists light emission of the guest among the compounds that form the light-emitting layer. The assist material is also referred to as a second host.

When the organic compound according to this embodiment is used as a guest of the light-emitting layer, the concentration of the guest is preferably 0.01 mass % or more and 20 mass % or less and more preferably 0.1 mass % or more and 5 mass % or less relative to the whole light-emitting layer.

When the organic compound according to this embodiment is used as a guest of the light-emitting layer, a material having a higher LUMO energy level than the organic compound according to this embodiment (a material having a LUMO energy level closer to the vacuum level) may be used as the host. This is because when a material having a higher LUMO energy level than the organic compound according to this embodiment is used as the host, the organic compound according to this embodiment can accept a larger amount of electrons supplied to the host of the light-emitting layer. This is particularly because when a material having a higher LUMO energy level than the organic compound represented by the formula [101] having high electron acceptability, that is, a low LUMO energy level is used as the host, the organic compound according to this embodiment can accept a larger amount of electrons supplied to the host of the light-emitting layer.

As a result of thorough studies, the present inventors have found that when the organic compound according to this embodiment is used as the host or guest of the light-emitting layer, in particular, as the guest of the light-emitting layer, an element that produces an optical output with high efficiency and high luminance and that has very high durability is provided. This light-emitting layer may have a single-layer structure or a multilayer structure, or a blue emission color that is an emission color of this embodiment can be mixed with another color by adding a light-emitting material having another emission color. The multilayer structure refers to a state in which the light-emitting layer and another light-emitting layer are stacked. In this case, the emission color of the organic light-emitting element is not limited to blue. The emission color may be specifically white or an intermediate color. In the case of white, the other light-emitting layer emits light having a color other than blue, such as red or green. The light-emitting layers are formed by a method such as vapor deposition or coating. The details of the method will be specifically described in Examples below.

The organic compound according to this embodiment can be used as a material for organic compound layers other than the light-emitting layer that constitute the organic light-emitting element according to this embodiment. Specifically, the organic compound may be used as a material for, for example, electron transport layers, electron injection layers, hole transport layers, hole injection layers, and hole blocking layers. In this case, the emission color of the organic light-emitting element is not limited to blue. The emission color may be specifically white or an intermediate color.

The organic compound according to this embodiment may be used in combination with, for example, a publicly known low-molecular-weight or high-molecular-weight compound such as a hole injection or transport compound, a compound serving as the host, a luminous compound, or an electron injection or transport compound if necessary. Examples of these compounds will be described below.

A hole injection or transport material may be a material having a high hole mobility such that injection of holes from the anode is facilitated and the injected holes can be transported to the light-emitting layer. The hole injection or transport material may also be a material having a high glass transition temperature in order to suppress the deterioration of the film quality, such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer. Non-limiting specific examples of the compound used as the hole injection or transport material are shown below.

117 118
HT1
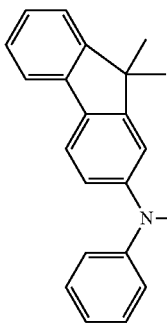
HT2
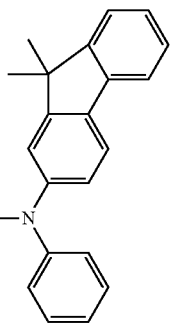
HT3
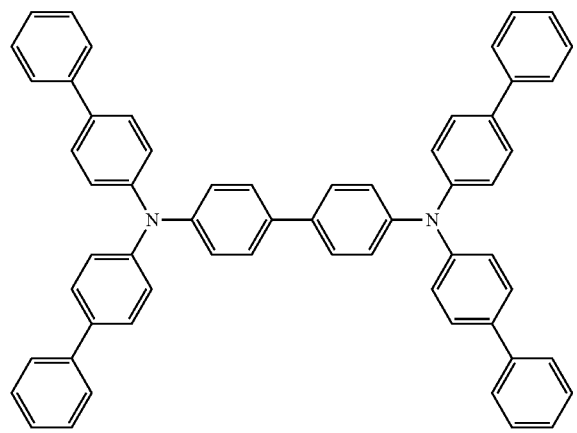
HT4
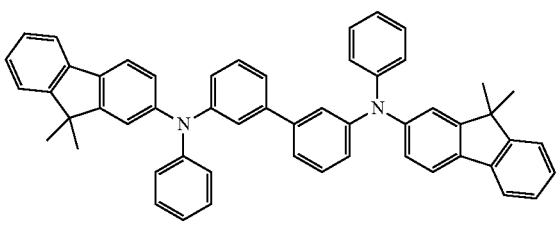
HT5
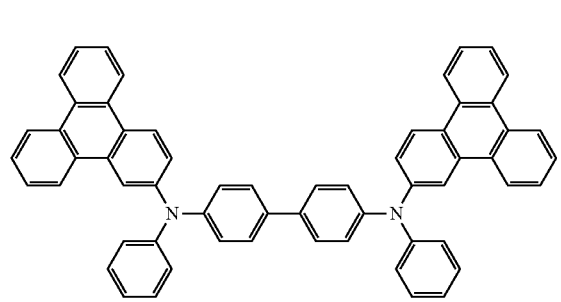
HT6
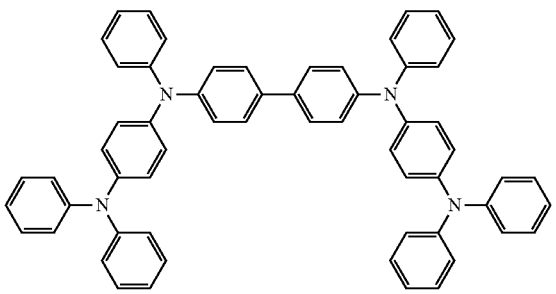
HT7
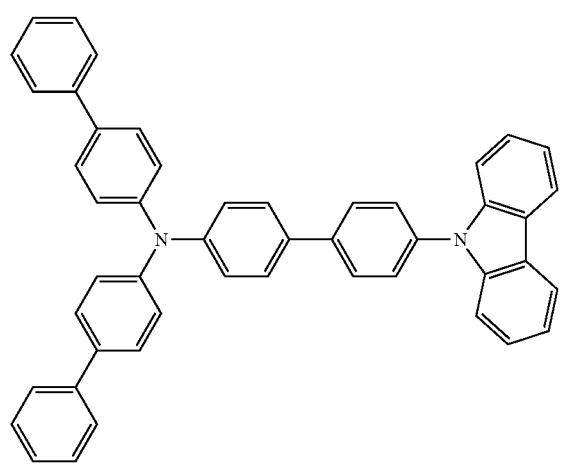
HT8
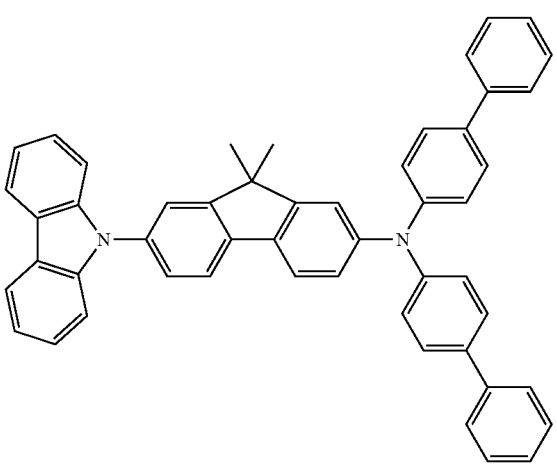

-continued
HT9
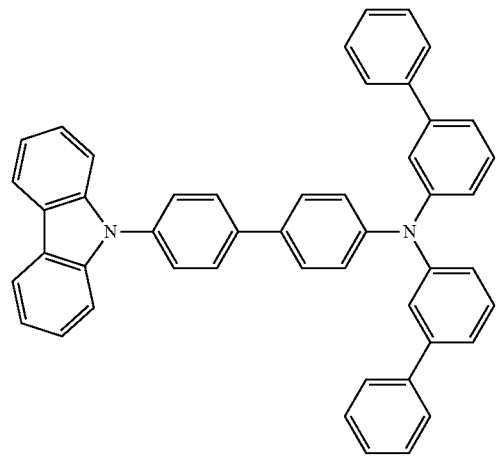
HT10
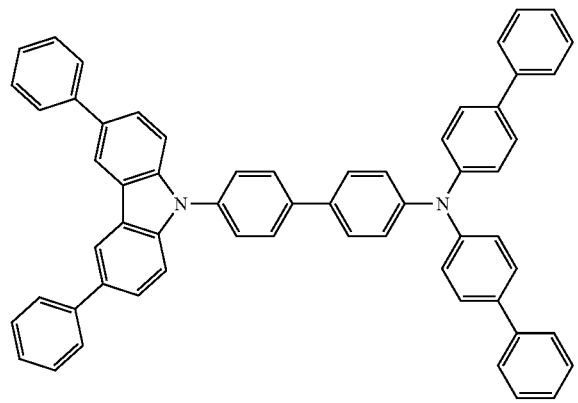
HT11
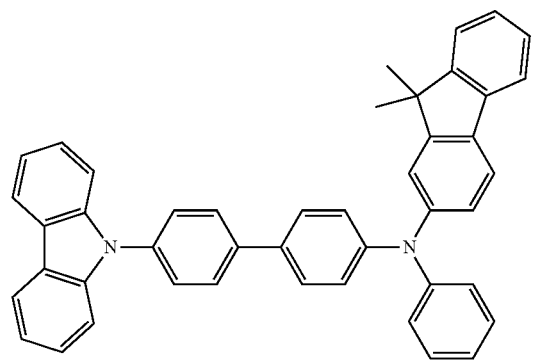
HT12
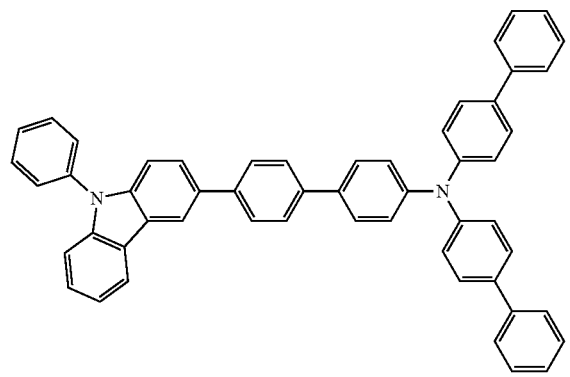
HT13
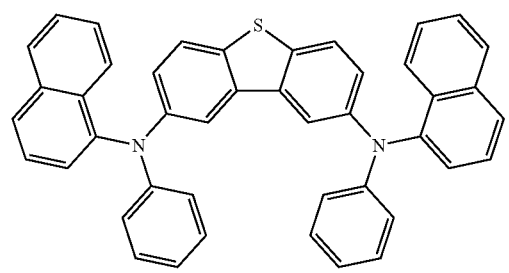
HT14
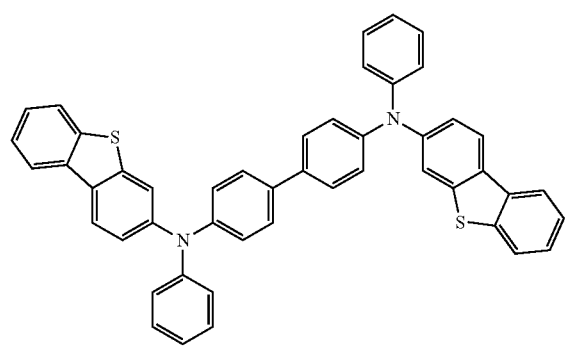
HT15
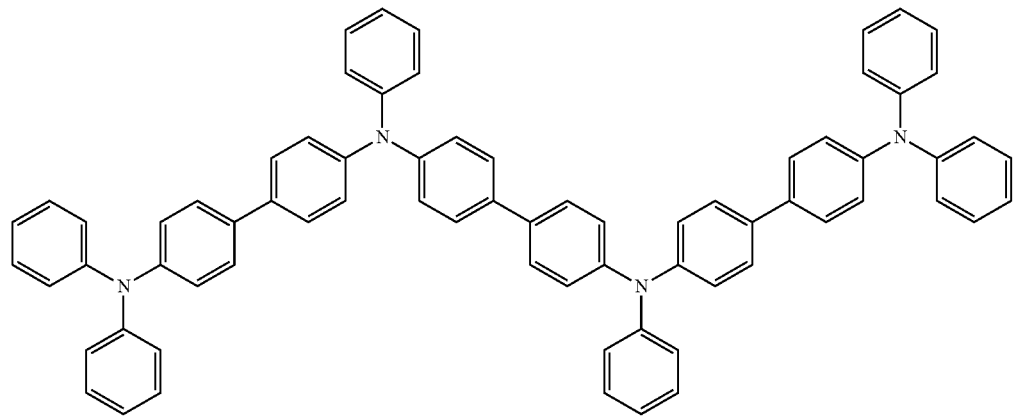

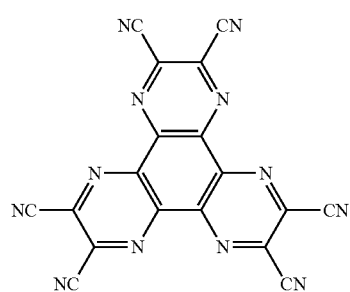
HT16

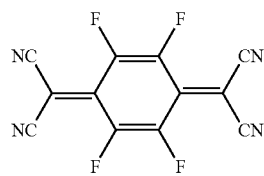
HT17

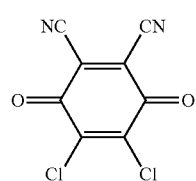
HT18

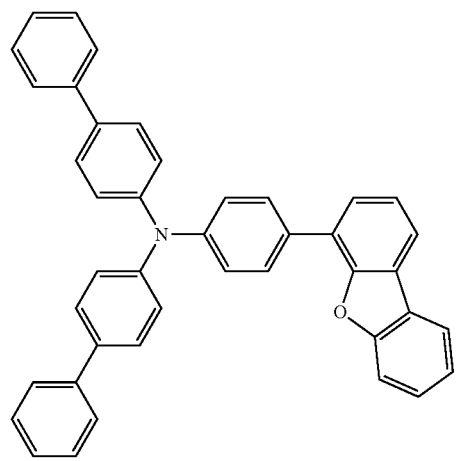
HT19

Examples of the light-emitting material mainly concerned with a light-emitting function include, in addition to the organic compound represented by the formula [1], fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives. Non-limiting specific examples of the compound used as the light-emitting material are shown below.

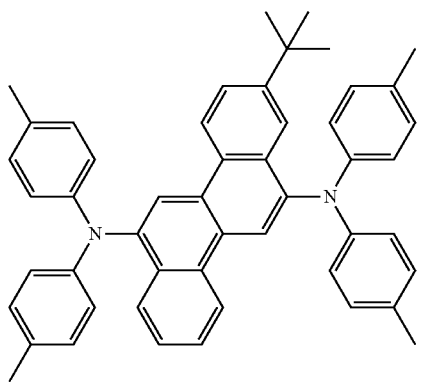
BD2

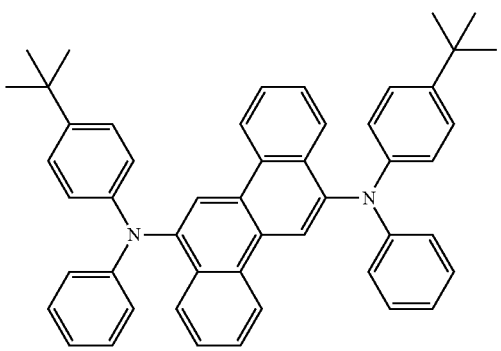
BD1

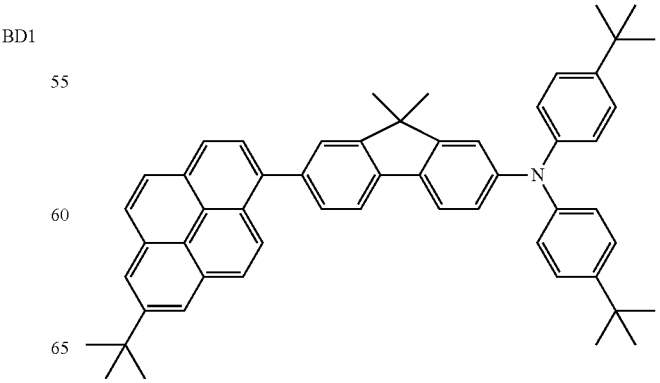
BD3

BD4
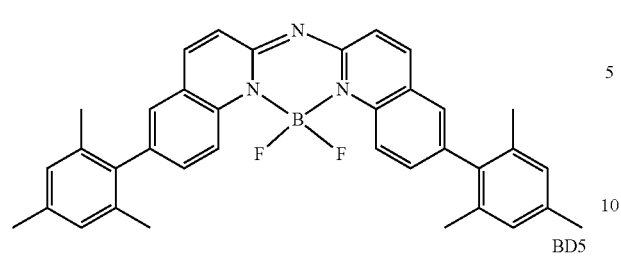
BD5
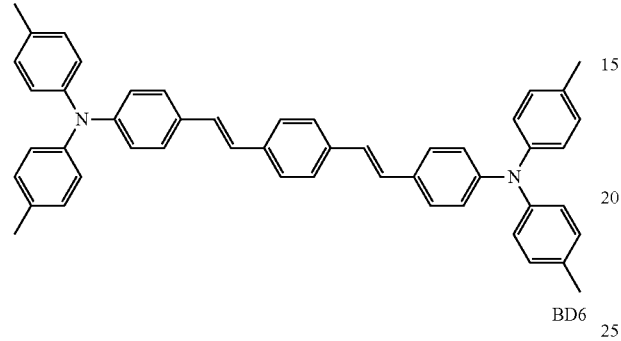
BD6
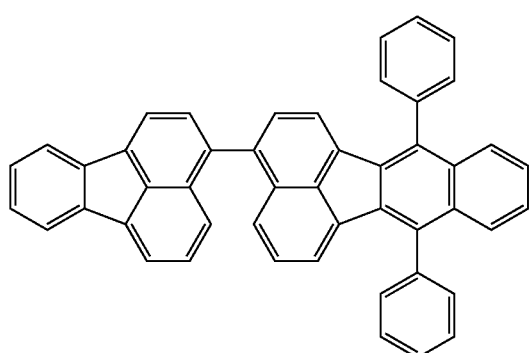
BD7
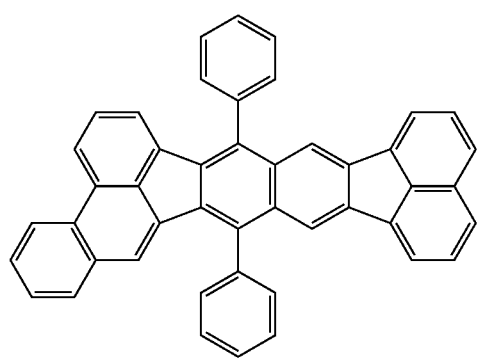
BD8
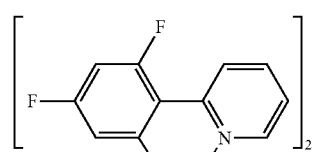
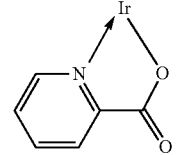
GD1
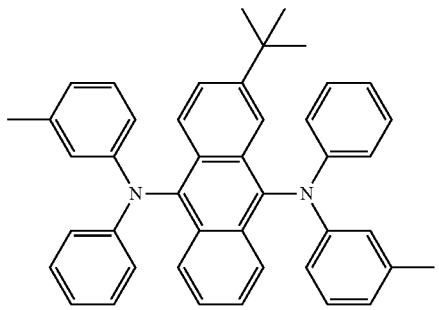
GD2
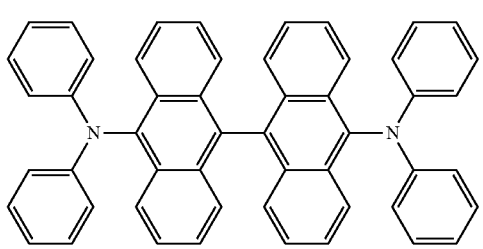
GD3
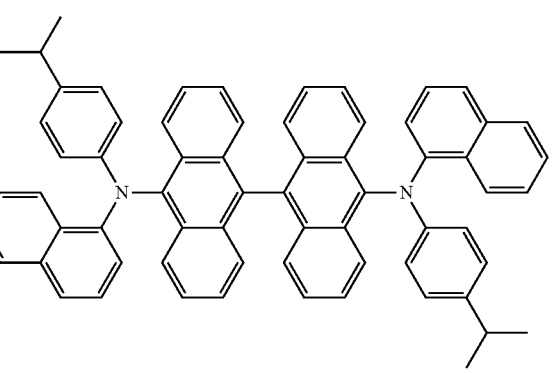
GD4
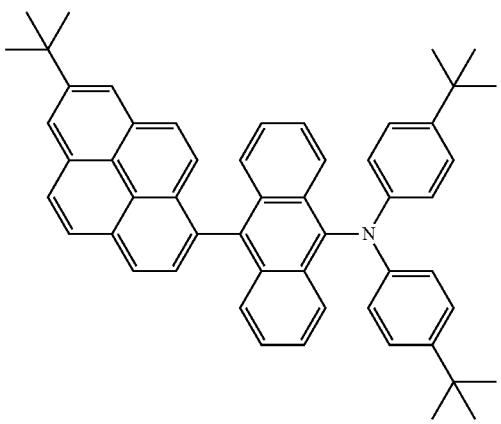

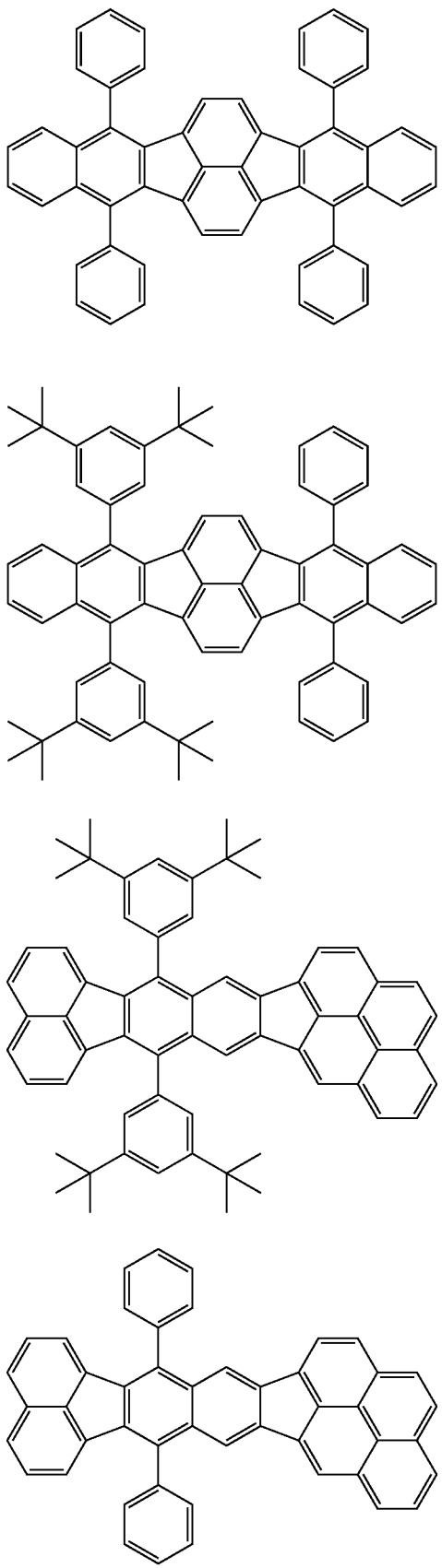
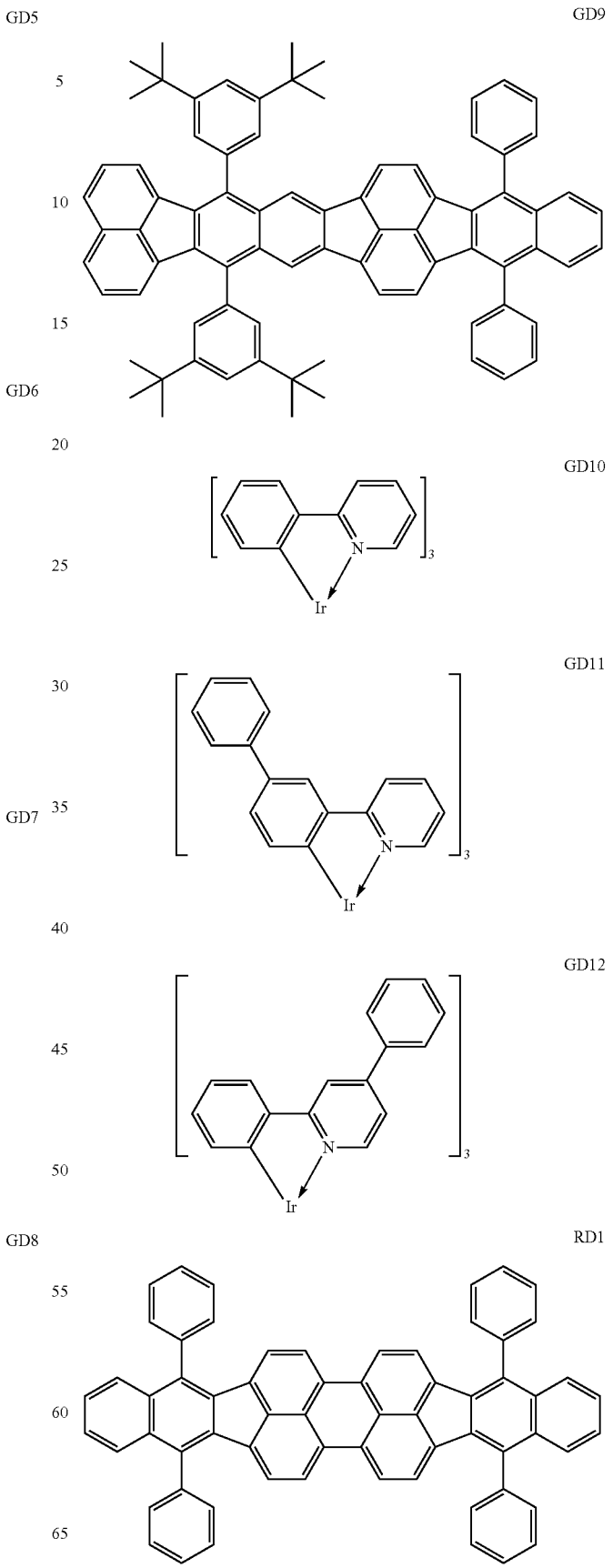

127
-continued

RD2
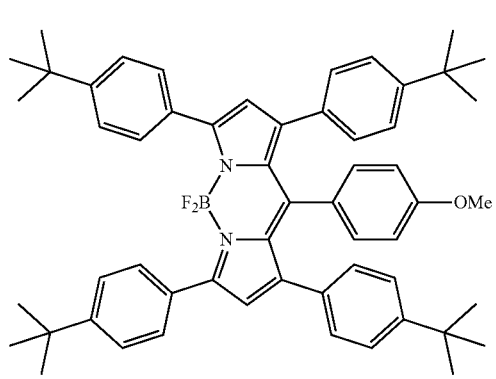

RD3
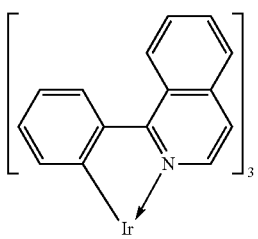

RD4
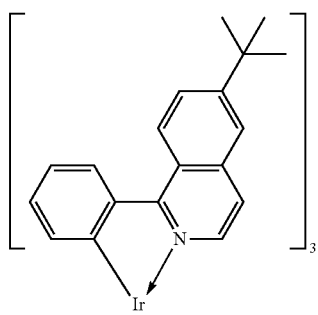

RD5
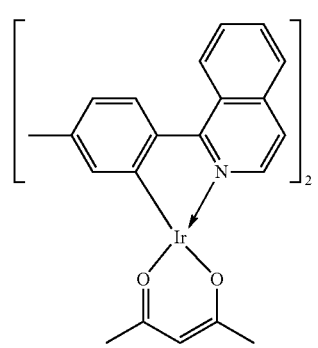

128
-continued

RD6
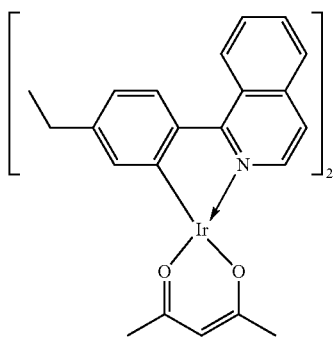

RD7
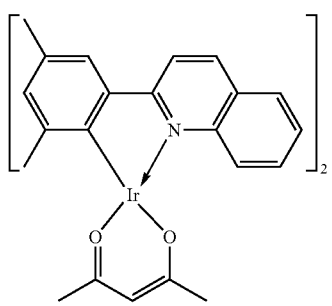

RD8
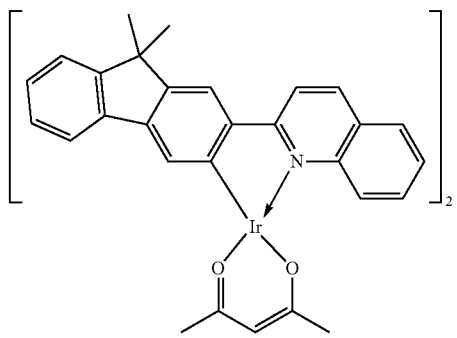

Examples of the light-emitting-layer host or light emission assist material contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes. Non-limiting specific examples of the compound used as the light-emitting-layer host or light emission assist material contained in the light-emitting layer are shown below.

EM1
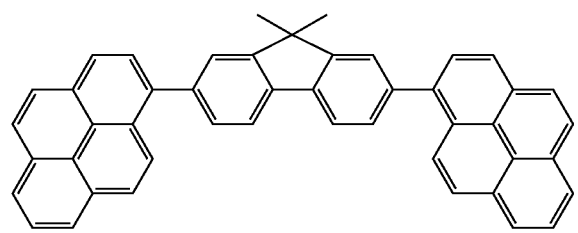
EM2
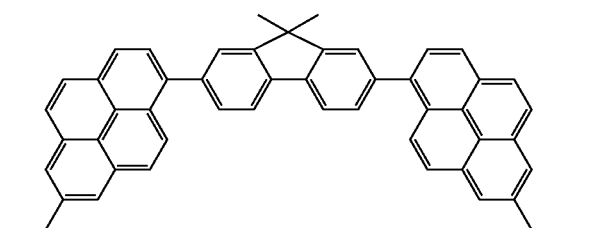
EM3
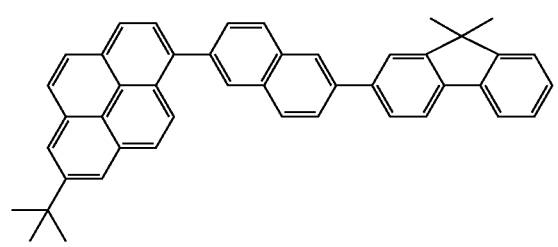
EM4
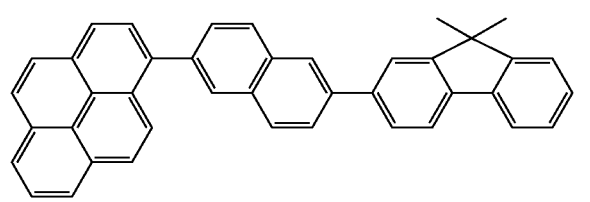
EM5
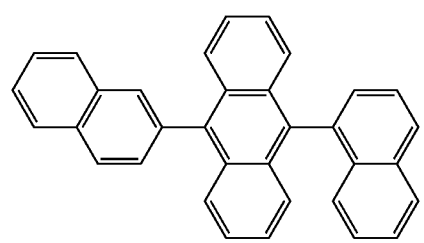
EM6
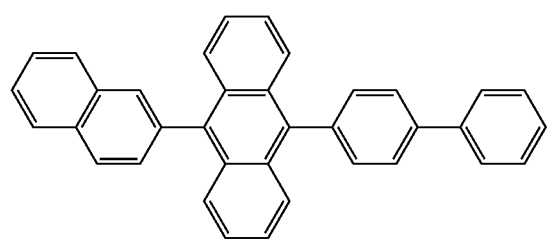
EM7
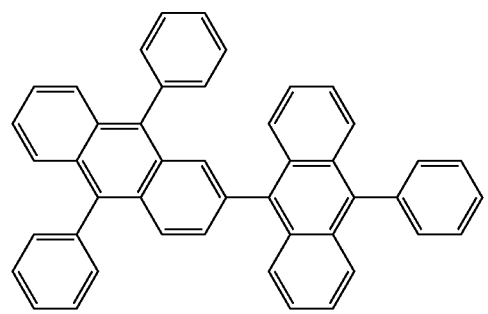
EM8
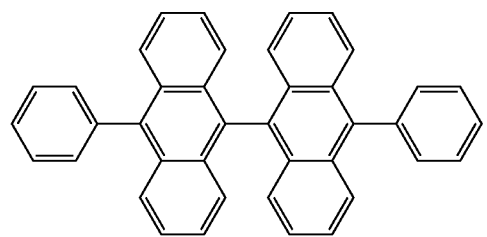
EM9
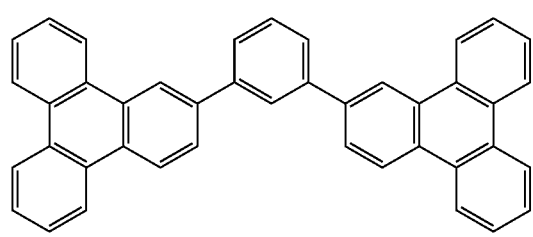
EM10
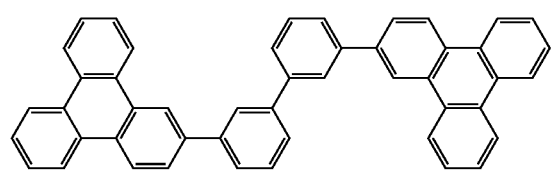
EM11
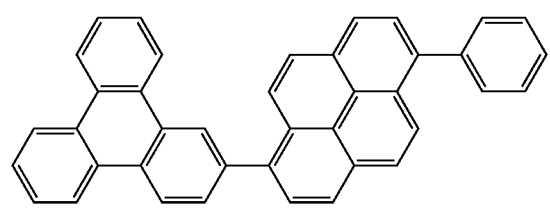
EM12
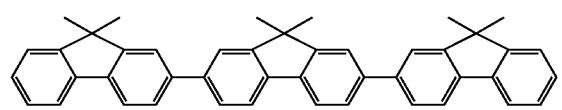

-continued
EM13
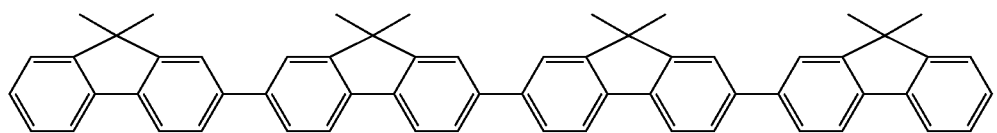
EM14
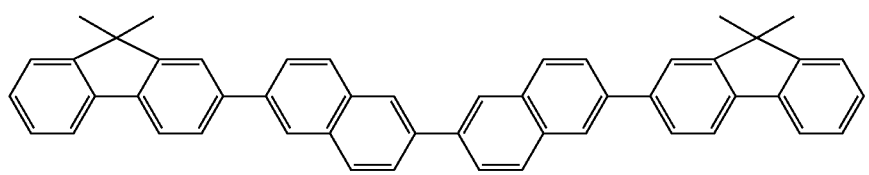
EM15
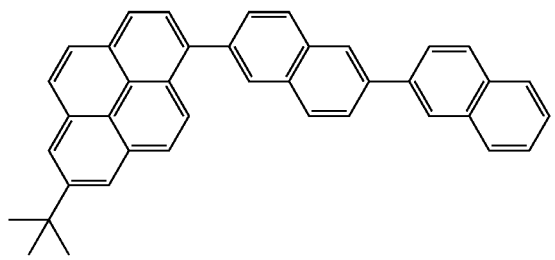
EM16
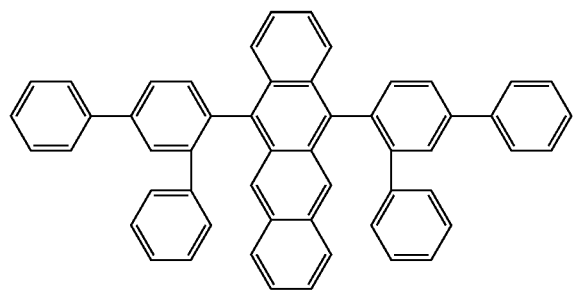
EM17
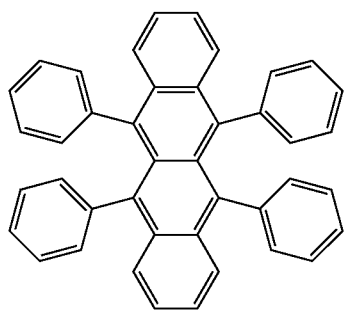
EM18
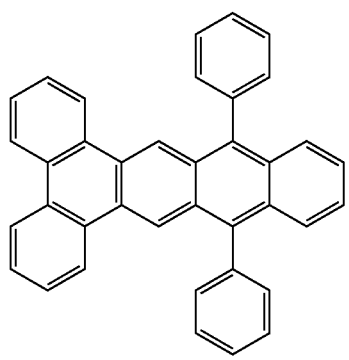
EM19
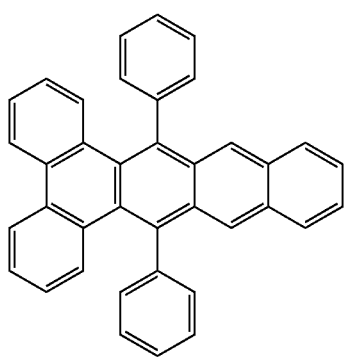
EM20
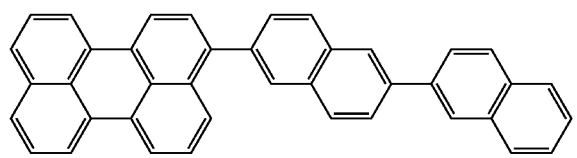

-continued
EM21
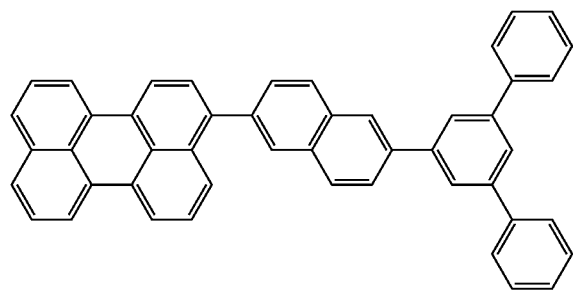
EM22
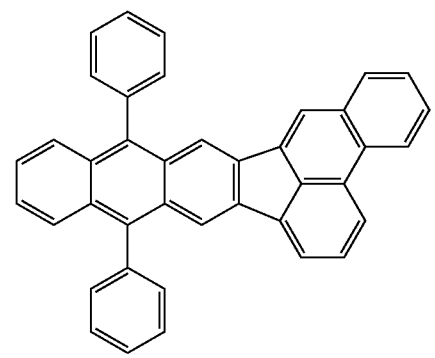
EM23
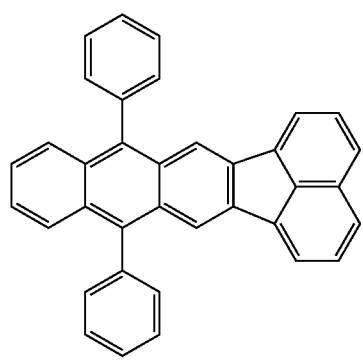
EM24
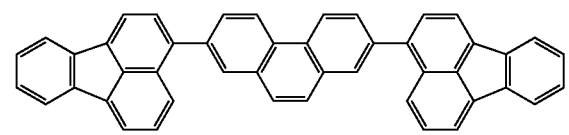
EM25
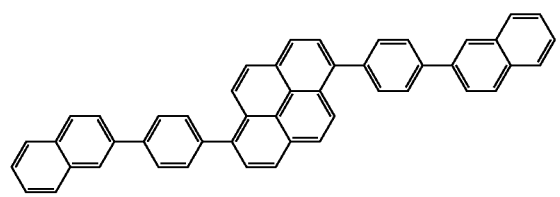
EM26
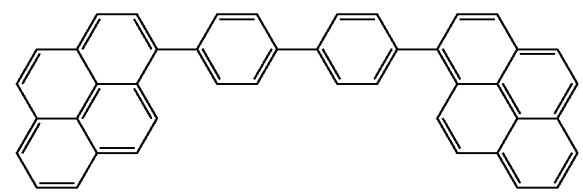
EM27
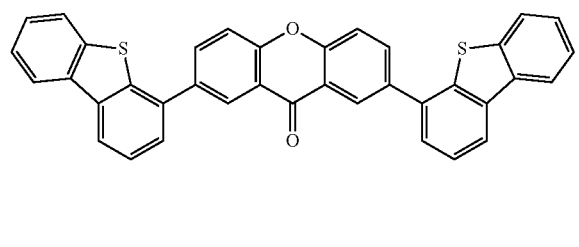
EM28
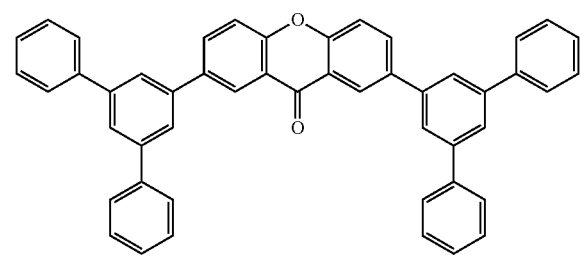
EM29
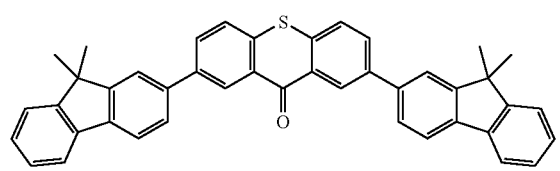
EM30
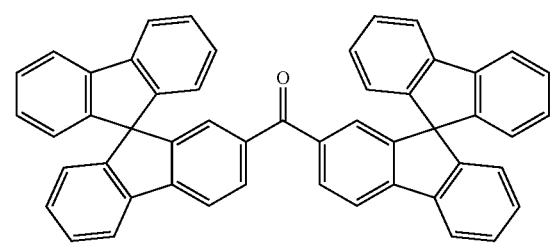

-continued
EM31
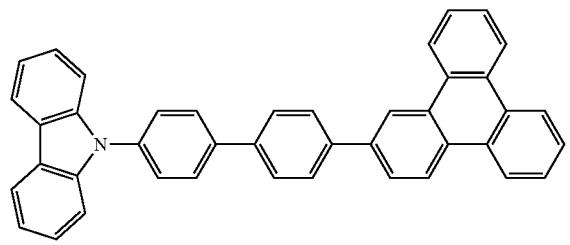
EM32
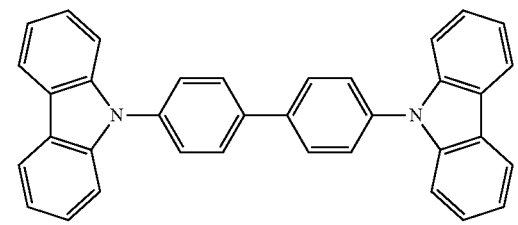
EM33
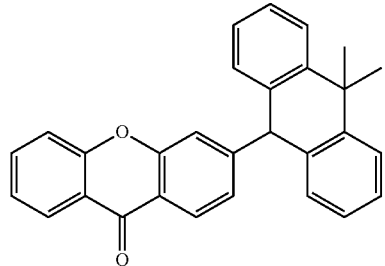
EM34
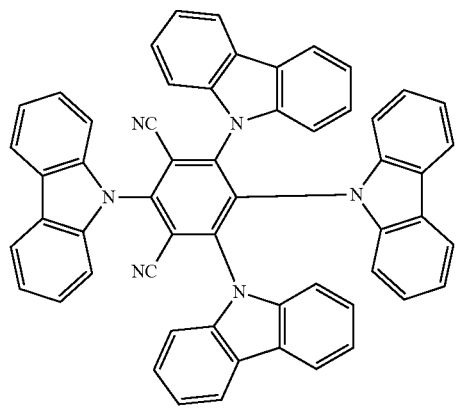
EM35
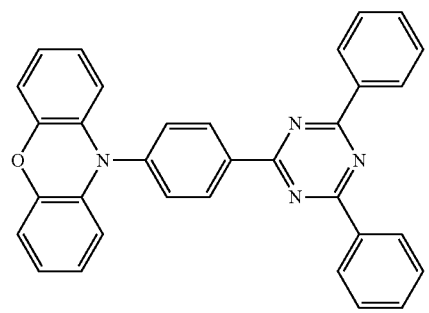
EM36
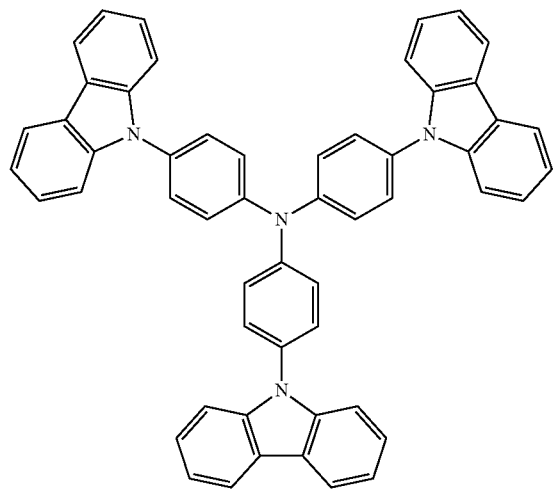
EM37
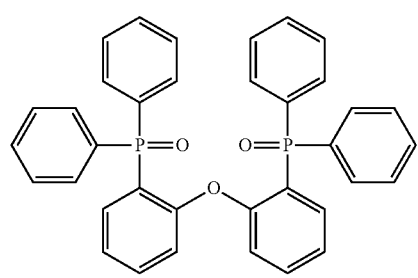
EM38
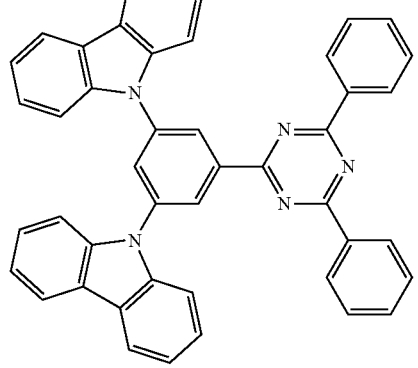

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer. Non-limiting specific examples of the compound used as the electron transport material are shown below.

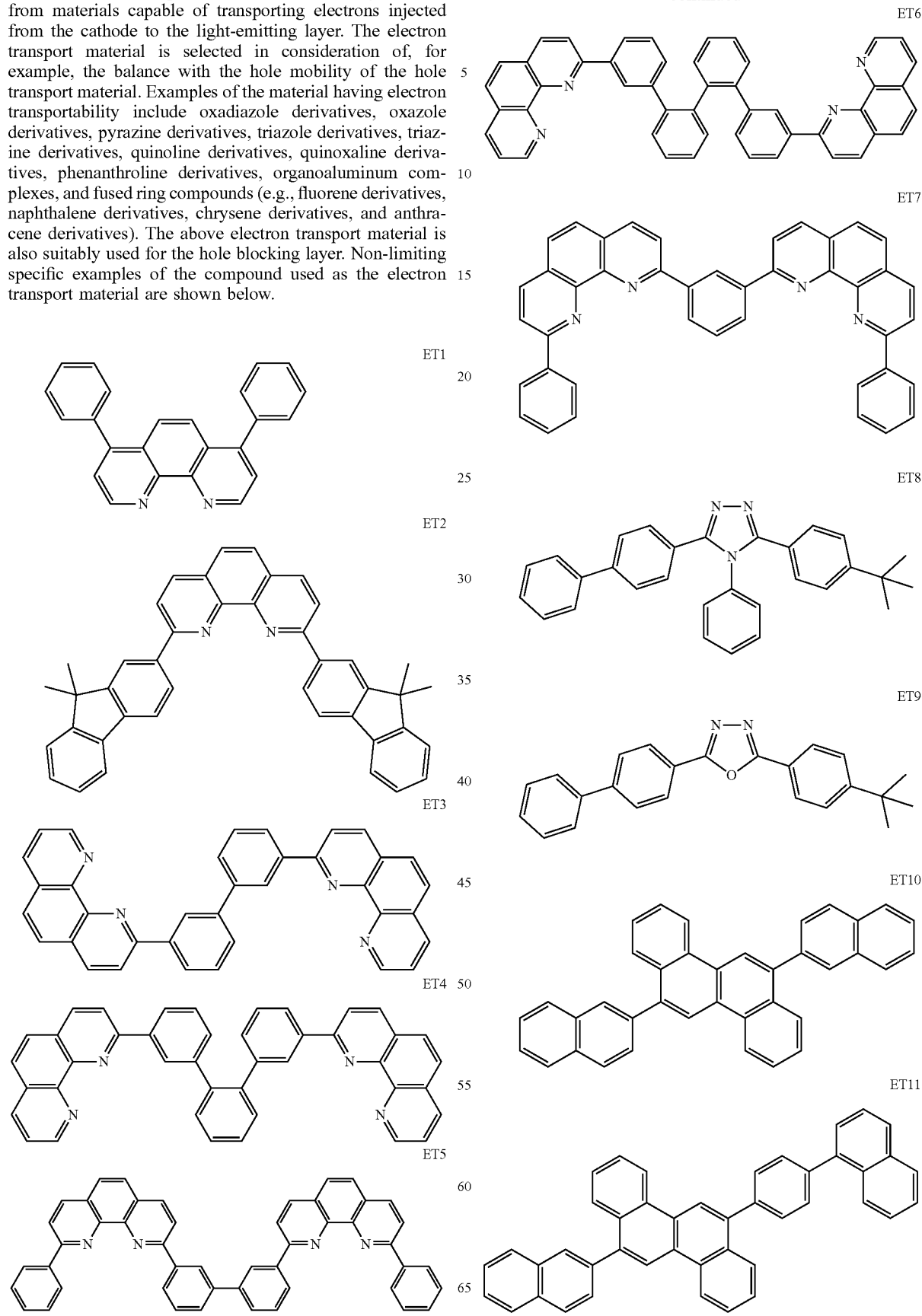

ET12
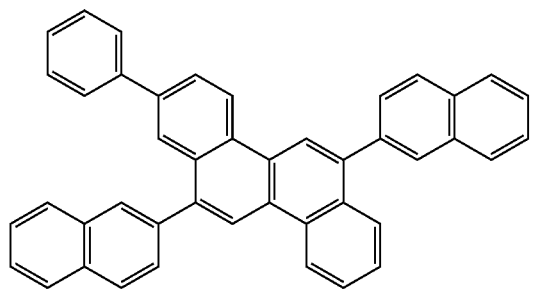
ET13
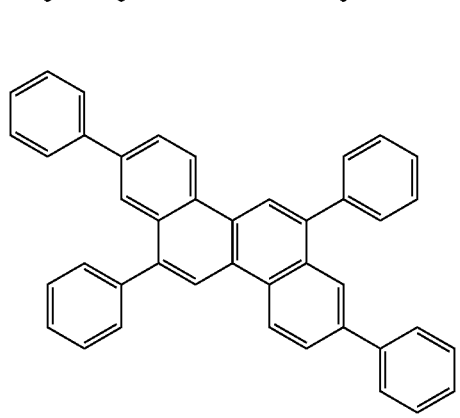
ET14
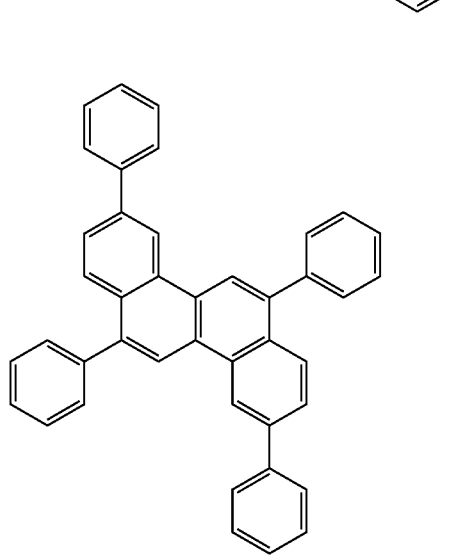
ET15
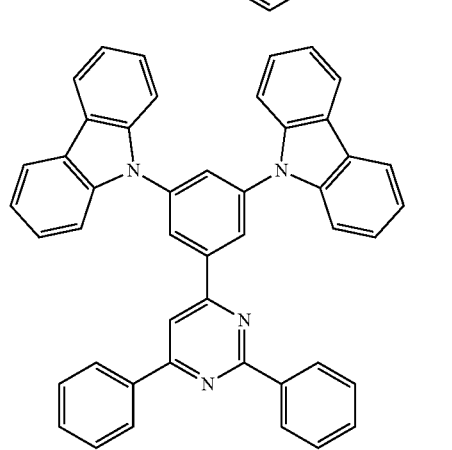
ET16
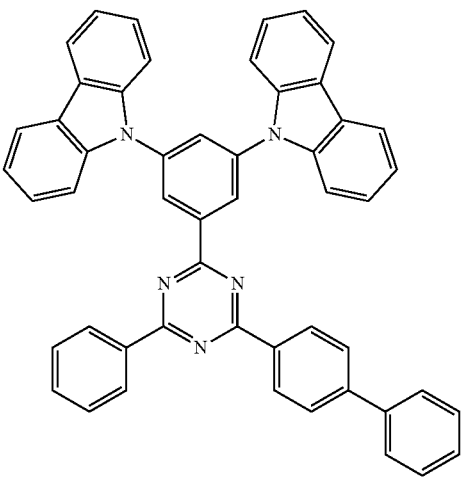
ET17
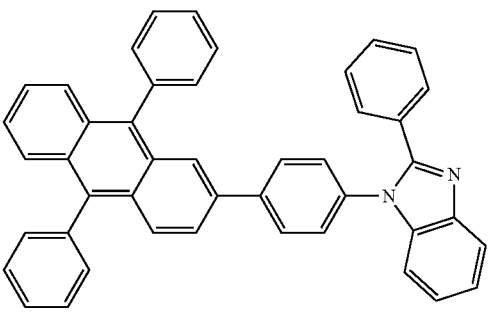
ET18
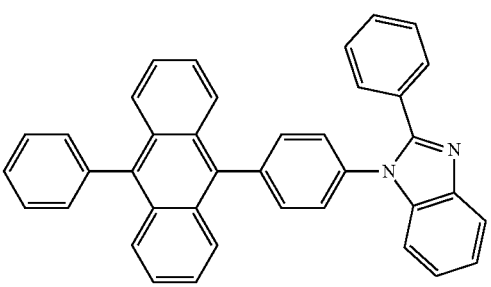
ET19

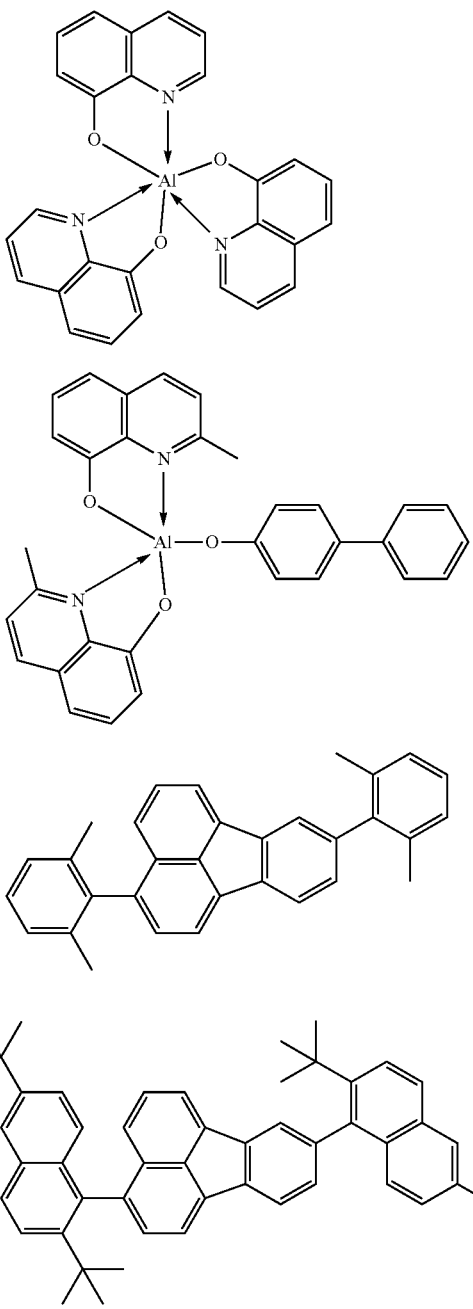

Configuration of Organic Light-Emitting Element

The organic light-emitting element is provided by forming an anode, an organic compound layer, and a cathode on a substrate. For example, a protective layer and a color filter may be disposed on the cathode. If the color filter is disposed, a planarizing layer may be disposed between the protective layer and the color filter. The planarizing layer may be formed of, for example, an acrylic resin.

Substrate

The substrate is formed of, for example, quartz, glass, silicon wafer, resin, or metal. A switching element such as a transistor and a wire may be disposed on the substrate, and an insulating layer may be disposed thereon. The insulating layer may be formed of any material as long as contact holes can be formed to establish electrical connection between the anode and the wire and the anode can be insulated from wires to which the anode is not connected. Examples of the material for the insulating layer include resins such as polyimide, silicon oxide, and silicon nitride.

Electrode

The electrode may be a pair of electrodes. The pair of electrodes may be an anode and a cathode. When an electric field is applied in a direction in which the organic light-emitting element emits light, the electrode having a high electric potential is an anode and the other electrode is a cathode. It can also be said that the electrode that supplies holes to the light-emitting layer is an anode and the electrode that supplies electrons is a cathode.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used.

These electrode materials may be used alone or in combination of two or more. The anode may have a single-layer structure or a multilayer structure.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the materials are not limited thereto. The electrode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver is preferably used and a silver alloy is more preferably used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The method for forming a cathode is not particularly limited. For example, a DC and AC sputtering method may be employed because good film coverage can be achieved to readily reduce the resistance.

Protective Layer

A protective layer may be disposed on the cathode. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into the organic compound layer. For example, after the formation of the cathode, the resulting substrate may be transferred to another chamber without breaking the vacuum, and a silicon nitride film having a thickness of 2 μm may be formed by a chemical vapor deposition (CVD) method to provide a protective layer. After the film formation by the CVD method, a protective layer may be disposed by an atomic layer deposition method (ALD method).

Color Filter

A color filter may be disposed on the protective layer. For example, a color filter provided in consideration of the size of organic light-emitting elements is disposed on another substrate, and this substrate may be bonded to the substrate on which the organic light-emitting elements have been disposed. Alternatively, a color filter may be patterned on the above-described protective layer by photolithography. The color filter may be formed of a polymer.

Planarizing Layer

A planarizing layer may be disposed between the color filter and the protective layer. The planarizing layer may be formed of an organic compound. The organic compound may be a low-molecular-weight organic compound or may be a high-molecular-weight organic compound, but is desirably a high-molecular-weight organic compound.

The planarizing layer may be disposed on and below the color filter, and both the planarizing layers may be formed of the same material or different materials. Specific examples of the material include polyvinyl carbazole resin, polycarbonate resin, polyester resin, ABS resin, acrylic resin, polyimide resin, phenolic resin, epoxy resin, silicone resin, and urea resin.

Counter Substrate

A counter substrate may be disposed on the planarizing layer. The name of the counter substrate is derived from the fact that the counter substrate is disposed at a position corresponding to that of the above-described substrate. The counter substrate may be formed of the same material as the above-described substrate.

Organic Compound Layer

The organic compound layers (e.g., a hole injection layer, a hole transport layer, an electron blocking layer, a light-emitting layer, a hole blocking layer, an electron transport layer, and an electron injection layer) that constitute the organic light-emitting element according to an embodiment of the present disclosure are formed by the following method.

The organic compound layers that constitute the organic light-emitting element according to an embodiment of the present disclosure can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed.

When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination.

Non-limiting examples of the binder resin include polyvinyl carbazole resin, polycarbonate resin, polyester resin, ABS resin, acrylic resin, polyimide resin, phenolic resin, epoxy resin, silicone resin, and urea resin.

These binder resins may be used alone as a homopolymer or in combination as a mixture of two or more as a copolymer. Furthermore, publicly known additives such as a plasticizer, an antioxidant, and an ultraviolet absorber may be optionally used in combination.

Application of Organic Light-Emitting Element According to Embodiment of the Present Disclosure The organic light-emitting element according to an embodiment of the present disclosure can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit. The display apparatus includes a plurality of pixels, and at least one of the plurality of pixels may include the organic light-emitting element according to this embodiment and a transistor connected to the organic light-emitting element.

The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

Next, a display apparatus according to this embodiment will be described with reference to the attached drawings. FIG. 1 is a schematic sectional view illustrating an example of a display apparatus including organic light-emitting elements and TFT elements connected to the organic light-emitting elements. The TFT element is an example of active elements.

The display apparatus 10 in FIG. 1 includes a substrate 11 made of glass or the like and a moisture proof film 12 that is disposed on the substrate 11 and protects TFT elements or organic compound layers. The display apparatus 10 also includes metal gate electrodes 13, gate insulating films 14, and semiconductor layers 15.

Each of the TFT elements 18 includes a semiconductor layer 15, a drain electrode 16, and a source electrode 17. An insulating film 19 is disposed on the TFT element 18. An anode 21 that constitutes an organic light-emitting element 26 and the source electrode 17 are connected to each other through a contact hole 20.

The form of electrical connection between electrodes (anode 21 and cathode 23) included in the organic light-emitting element 26 and electrodes (source electrode 17 and drain electrode 16) included in the TFT element 18 is not limited to the form illustrated in FIG. 1. That is, it suffices that one of the anode 21 and the cathode 23 is electrically connected to one of the source electrode 17 and the drain electrode 16 of the TFT element 18.

In the display apparatus 10 in FIG. 1, an organic compound layer 22 is illustrated as if having a single-layer structure, but may have a multilayer structure. A first protective layer 24 and a second protective layer 25 for suppressing the deterioration of the organic light-emitting element 26 are disposed on the cathode 23.

In the display apparatus 10 in FIG. 1, a transistor is used as a switching element. Instead, an MIM element may be used as a switching element.

The transistor used in the display apparatus 10 in FIG. 1 is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements.

The transistor included in the display apparatus 10 in FIG. 1 may be formed in a substrate such as a Si substrate. Herein, the phrase "formed in a substrate" means that a transistor is produced by processing the substrate itself, such as a Si substrate. That is, a transistor formed in a substrate can be regarded as a transistor integrally formed with a substrate.

In the organic light-emitting element according to this embodiment, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "in a substrate". The size of a display unit determines whether a transistor is disposed in a substrate or a TFT is used. For example, in the case of a size of about 0.5 inches, the organic light-emitting element may be disposed on a Si substrate.

Figure 2:
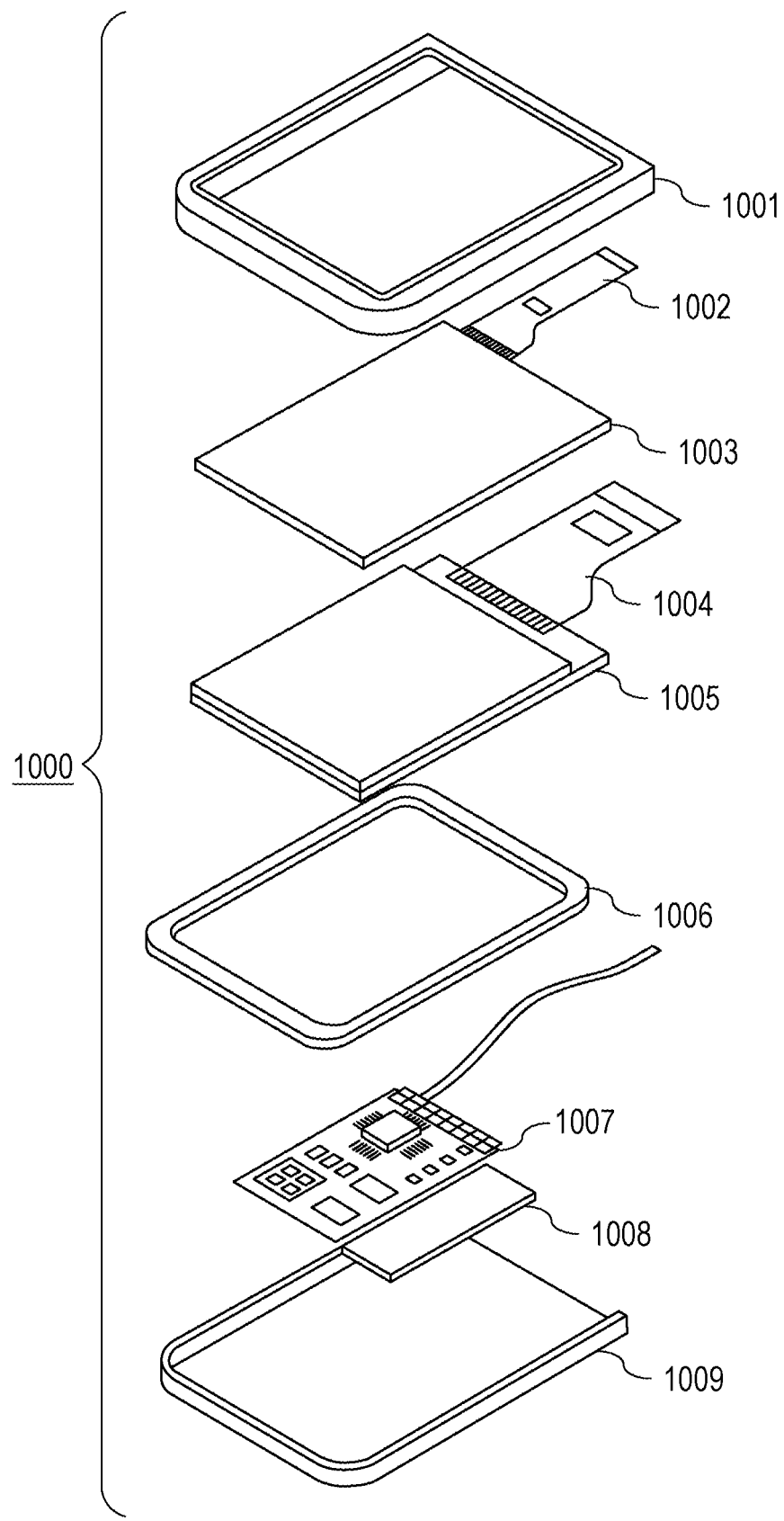
FIG. 2 schematically illustrates an example of a display apparatus according to an embodiment of the present disclosure.

FIG. 2 schematically illustrates an example of a display apparatus according to this embodiment. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. A transistor is printed on the circuit board 1007. The battery 1008 is not necessarily disposed if the display apparatus is not a mobile apparatus. Even if the display apparatus is a mobile apparatus, the battery 1008 may be disposed at a different position.

The display apparatus according to this embodiment may be used in a display unit of a photoelectric conversion apparatus such as an image pickup apparatus that includes an optical unit including a plurality of lenses and an image pickup element configured to receive light that has passed through the optical unit. The image pickup apparatus may include a display unit configured to display information obtained by the image pickup element. The display unit may be a display unit exposed to the outside of the image pickup apparatus or a display unit disposed in a viewfinder. The image pickup apparatus may be a digital camera or a digital camcorder.

Figure 3A:
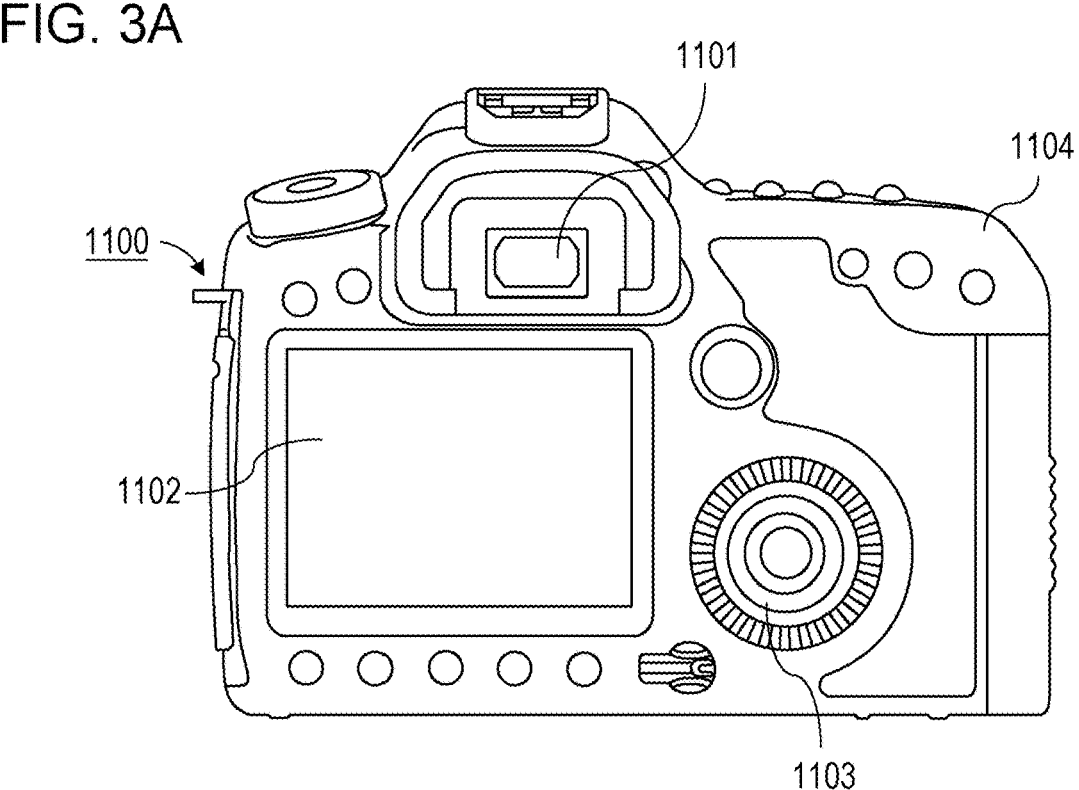
FIG. 3A schematically illustrates an example of an image pickup apparatus according to an embodiment of the present disclosure.

FIG. 3A schematically illustrates an example of an image pickup apparatus according to this embodiment. An image pickup apparatus 1100 may include a viewfinder 1101, a rear display 1102, an operating unit 1103, and a housing 1104. The viewfinder 1101 may include the display apparatus according to this embodiment. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Therefore, the display apparatus including the organic light-emitting element according to this embodiment may be used. This is because the organic light-emitting element has a high response speed. The display apparatus including the organic light-emitting element can be more suitably used than these apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

The display apparatus according to this embodiment may include red, green, and blue color filters. The red, green, and blue color filters may be disposed in a delta arrangement.

The display apparatus according to this embodiment may be used in a display unit of an electronic apparatus such as a mobile terminal. The display unit may have both a display function and an operational function. Examples of the mobile terminal include cellular phones such as smartphones, tablet computers, and head-mounted displays.

Figure 3B:
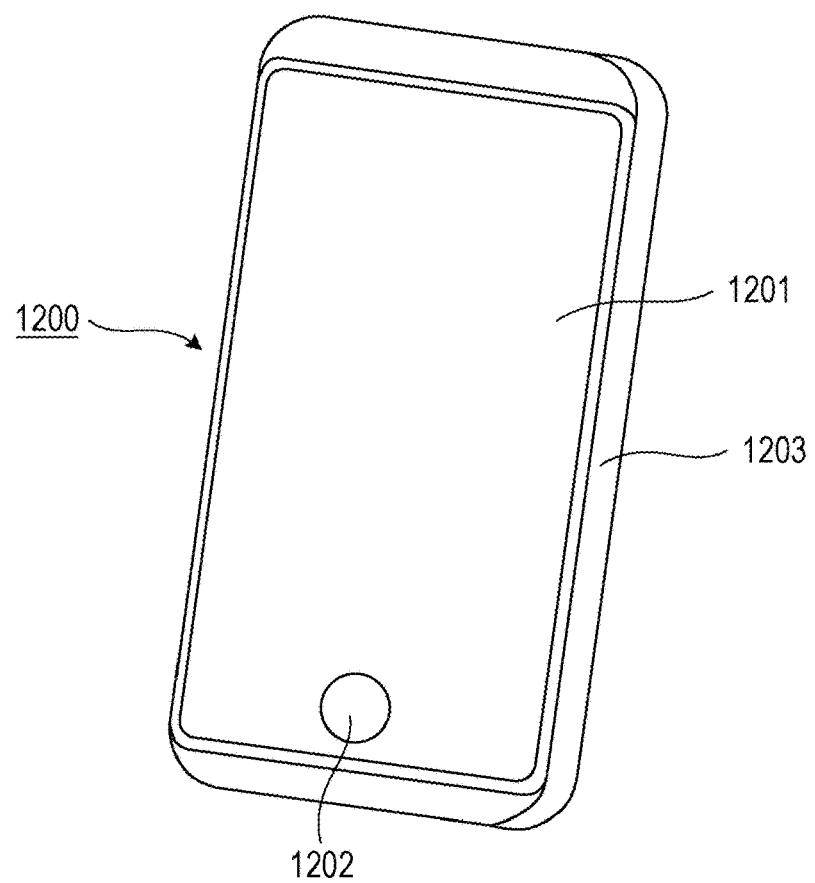
FIG. 3B schematically illustrates an example of an electronic apparatus according to an embodiment of the present disclosure.

FIG. 3B schematically illustrates an example of an electronic apparatus according to this embodiment. An electronic apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. An electronic apparatus including a communication unit may be referred to as a communication apparatus.

Figure 4A:
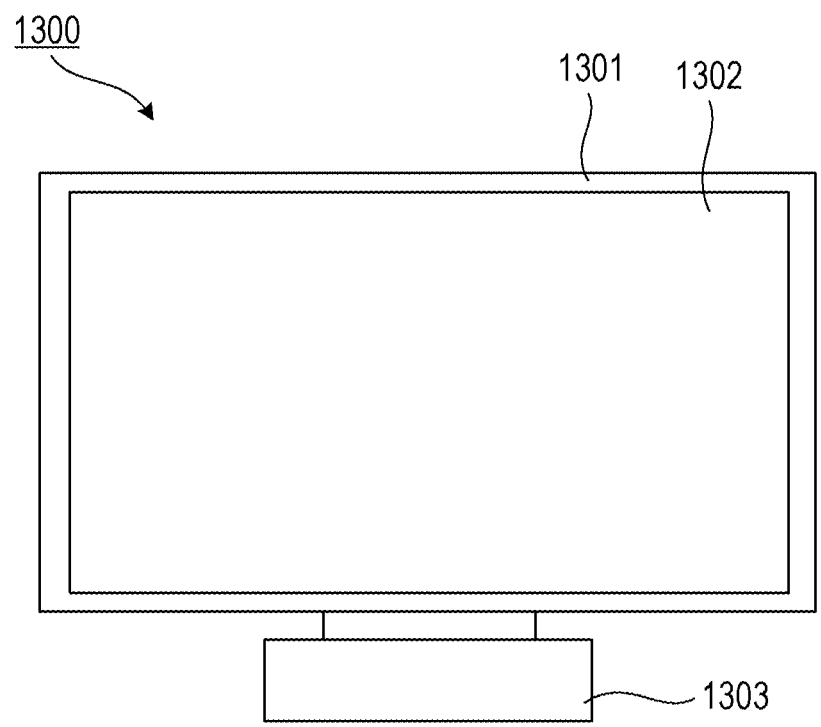
FIG. 4A schematically illustrates an example of a display apparatus according to an embodiment of the present disclosure.
Figure 4B:
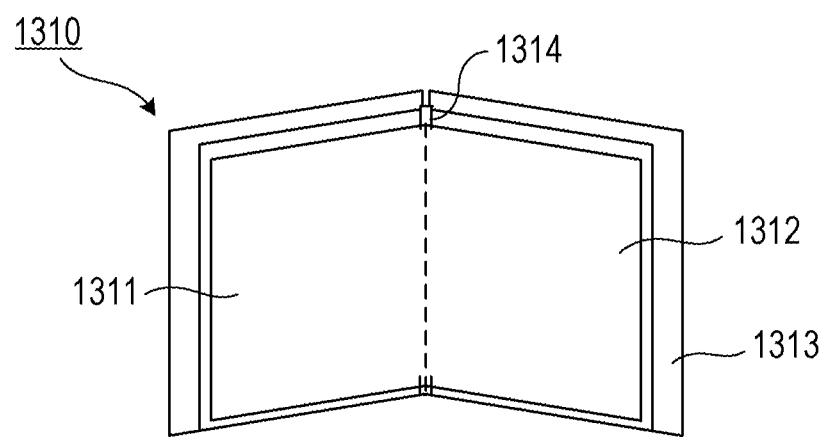
FIG. 4B schematically illustrates an example of a foldable display apparatus.

FIGS. 4A and 4B schematically illustrate examples of display apparatuses according to this embodiment. FIG. 4A illustrates a display apparatus such as a television monitor or a PC monitor. A display apparatus 1300 includes a frame 1301 and a display unit 1302. A light-emitting device according to this embodiment may be used for the display unit 1302. The display apparatus 1300 includes the frame 1301 and a base 1303 that supports the display unit 1302. The form of the base 1303 is not limited to that in FIG. 4A. The lower side of the frame 1301 may also serve as a base. The frame 1301 and the display unit 1302 may be curved. The radius of curvature may be 5000 mm or more and 6000 mm or less.

FIG. 4B schematically illustrates another example of the display apparatus according to this embodiment. A display apparatus 1310 in FIG. 4B is a so-called foldable display apparatus. The display apparatus 1310 includes a first display unit 1311, a second display unit 1312, a housing 1313, and a bending point 1314. The first display unit 1311 and the second display unit 1312 may include the light-emitting device according to this embodiment. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Figure 5A:
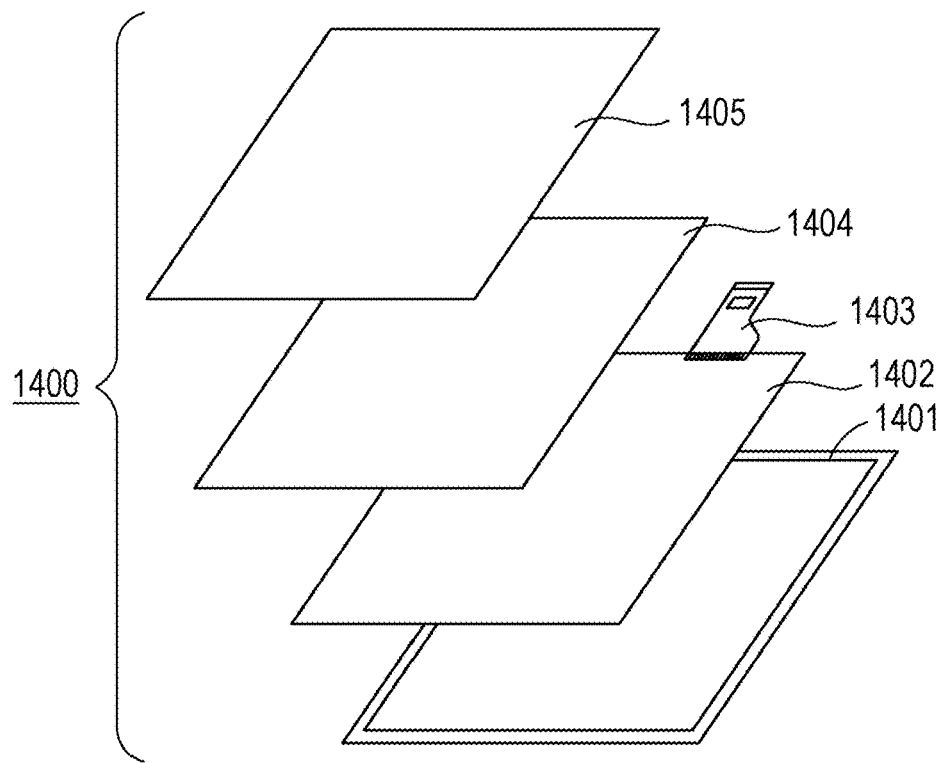
FIG. 5A schematically illustrates an example of a lighting apparatus according to an embodiment of the present disclosure.

FIG. 5A schematically illustrates an example of a lighting apparatus according to this embodiment. A lighting apparatus 1400 may include a housing 1401, a light source 1402, a circuit board 1403, and an optical filter 1404 and a light diffusion unit 1405 that transmit light emitted from the light source 1402. The light source 1402 may include the organic light-emitting element according to this embodiment. The optical filter 1404 may be a filter for improving the color rendering of the light source. The light diffusion unit 1405 used for lighting up or the like effectively diffuses light from the light source and allows the light to reach a wide area. The optical filter 1404 and the light diffusion unit 1405 may be disposed on the light-emitting side of the lighting apparatus. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to this embodiment and a power supply circuit connected to the organic light-emitting element. The power supply circuit is a circuit that converts an alternating voltage to a direct voltage. The color "white" has a color temperature of 4200 K and the color "natural white" has a color temperature of 5000 K. The lighting apparatus may include a color filter.

The lighting apparatus according to this embodiment may include a heat dissipation unit. The heat dissipation unit dissipates heat in the apparatus to the outside and is formed of, for example, a metal having a high specific heat or a liquid silicon.

Figure 5B:
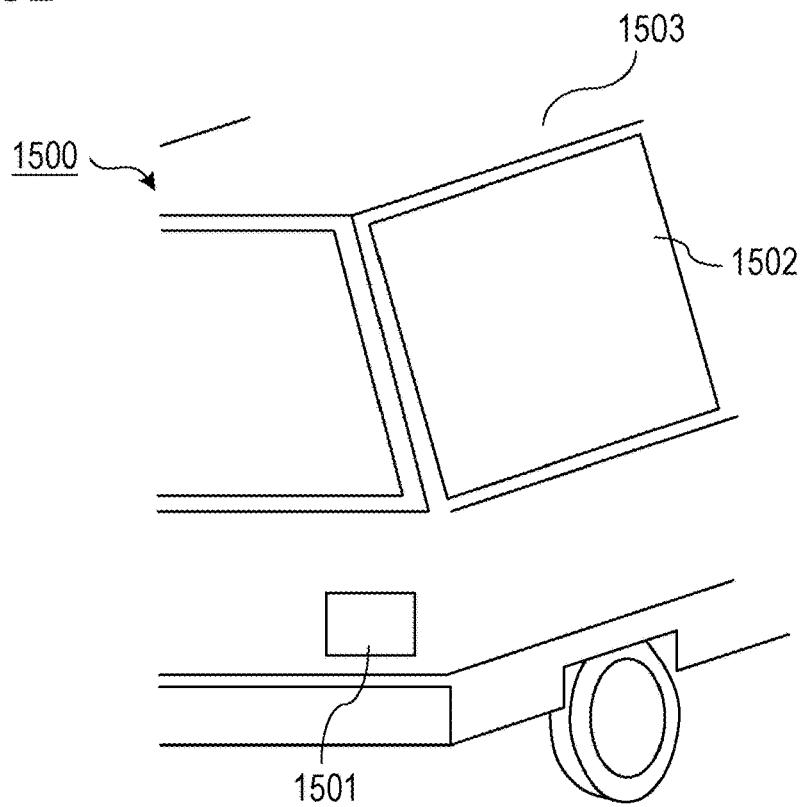
FIG. 5B schematically illustrates an example of an automobile including a lighting fixture for vehicles according to an embodiment of the present disclosure.

FIG. 5B schematically illustrates an automobile that is an example of a moving object according to this embodiment. The automobile includes a tail lamp that is an example of a lighting fixture. An automobile 1500 includes a tail lamp 1501, and the tail lamp may be lit through, for example, application of the brake.

The tail lamp 1501 may include the organic light-emitting element according to this embodiment. The tail lamp 1501 may include a protective member that protects the organic light-emitting element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative.

The automobile 1500 may include a car body 1503 and windows 1502 attached to the car body 1503. The windows 1502 may be transparent displays as long as the windows 1502 are not a front or rear window of the automobile. The transparent display may include the organic light-emitting element according to this embodiment. In this case, members, such as an electrode, included in the organic light-emitting element are formed of a transparent material.

The moving object according to this embodiment may be, for example, a ship, an aircraft, or a drone. The moving object may include a body and a lighting fixture disposed on the body. The lighting fixture may emit light for allowing the position of the body to be recognized. The lighting fixture may include the organic light-emitting element according to this embodiment.

As described above, use of an apparatus including the organic light-emitting element according to this embodiment allows stable display with a good image quality for a long time.

EXAMPLES

Hereafter, the present disclosure will be described based on Examples. However, the present disclosure is not limited thereto.

Example 1 (Synthesis of Exemplary Compound A1)

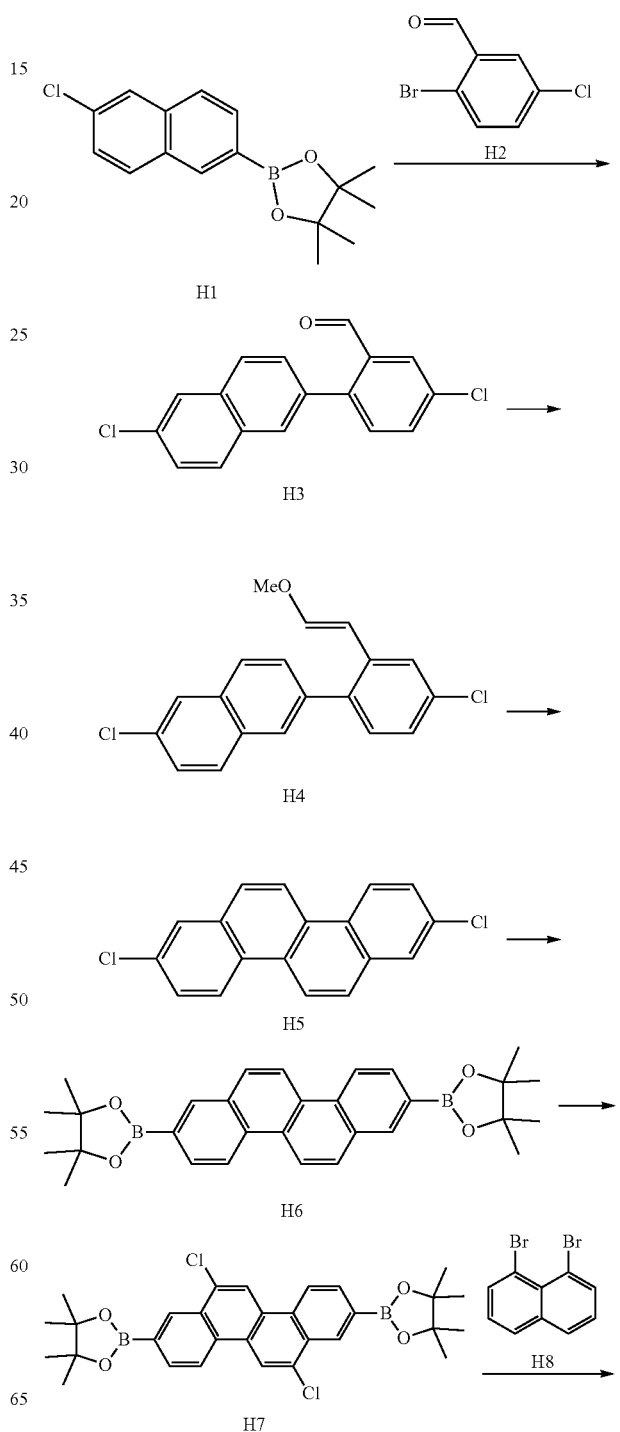

-continued

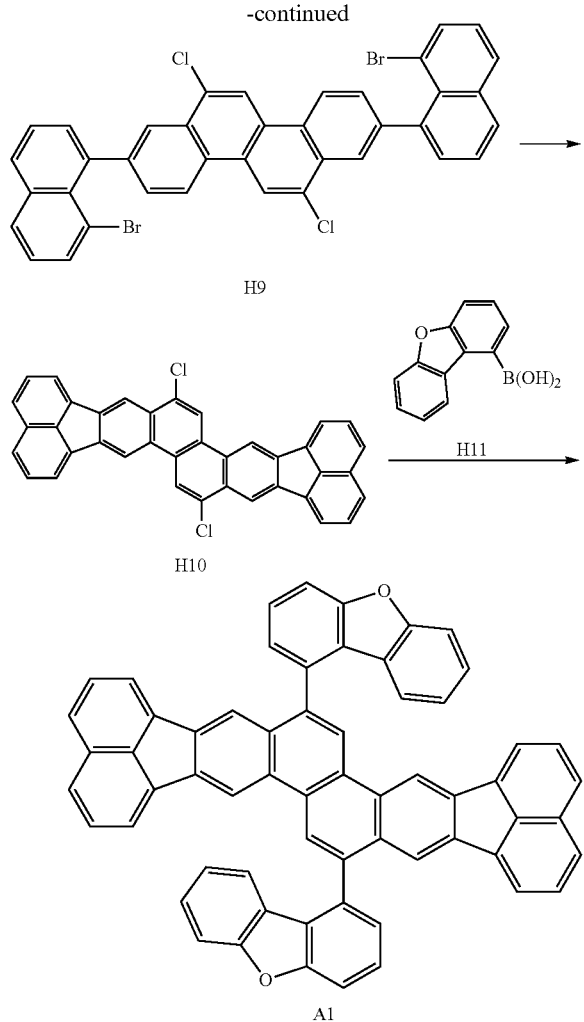

(1) Synthesis of Compound H3

The following reagents and solvents were charged into a 500 ml recovery flask.
Compound H1: 7.23 g (25.1 mmol)
Compound H2: 5.00 g (22.8 mmol)
Pd(PPh$_3$)$_4$: 790 mg (1.14 mmol)
Sodium carbonate: 9.66 g (91.2 mmol)
Toluene: 200 ml
Ethanol: 100 ml
Water: 100 ml Subsequently, the reaction solution was heated to 90° C. in a nitrogen stream, and stirring was performed at this temperature (90° C.) for 5 hours. After the completion of the reaction, extraction was performed using toluene and water. The resulting product was concentrated, purified by silica gel column chromatography (heptane:toluene=1:1), and then washed by dispersion with methanol to obtain 5.5 g of a white compound H3 (yield: 80%).

(2) Synthesis of Compound H4

The following reagent and solvent were charged into a 200 ml recovery flask.
(Methoxymethyl)triphenylphosphonium chloride: 12.8 g (41.5 mmol)
Tetrahydrofuran: 50 ml Subsequently, the following reagent was gradually added dropwise to the reaction solution in a nitrogen stream at room temperature.
Potassium t-butoxide [1.0 M tetrahydrofuran solution]

Subsequently, the reaction solution was stirred at this temperature (room temperature) for 1 hour, and then the following mixed solution was gradually added dropwise thereto at room temperature.
Compound H3: 5.0 g (16.6 mmol)
Tetrahydrofuran: 50 ml After the completion of the reaction, extraction was performed using toluene and water. The resulting product was concentrated, purified by silica gel column chromatography (heptane:toluene=1:1), and then washed by dispersion with methanol to obtain 4.48 g of a white compound H4 (yield: 82%).

(3) Synthesis of Compound H5

The following reagent and solvent were charged into a 200 ml recovery flask.
Compound H4: 4.00 g (12.1 mmol)
Dichloromethane: 100 ml Subsequently, the reaction solution was cooled to 0° C. in a nitrogen stream, and the following reagent was added dropwise to the reaction solution.
Methanesulfonic acid: 1.75 g (18.2 mmol)

Subsequently, the reaction solution was stirred at room temperature for 3 hours. After the completion of the reaction, 50 ml of methanol was added thereto and stirring was performed at 0° C. for 30 minutes. The resulting product was then separated and washed with water and methanol to obtain 3.09 g of a white compound H5 (yield: 86%).

(4) Synthesis of Compound H6

The following reagents and solvent were charged into a 500 ml recovery flask.
Compound H5: 3.00 g (10.1 mmol)
bis(pinacolborane): 10.3 g (40.4 mmol)
Pd(dba)$_2$: 580 mg (1.01 mmol)
P(Cy)$_3$: 850 mg (3.03 mmol)
Potassium acetate: 3.96 mg (40.4 mmol)
o-Xylene: 300 ml Subsequently, the reaction solution was heated to 150° C. in a nitrogen stream, and stirring was performed at this temperature (150° C.) for 7 hours. After the completion of the reaction, celite filtration was performed. The resulting product was concentrated and washed by dispersion with heptane to obtain 3.93 g of a white compound H6 (yield: 81%).

(5) Synthesis of Compound H7

The following reagents and solvent were charged into a 500 ml recovery flask.
Compound H6: 3.8 g (7.91 mmol)
NCS: 5.28 g (39.6 mmol)
Methanesulfonic acid: 227 mg (2.37 mmol)
DMF: 380 ml Subsequently, the reaction solution was heated to 65° C. in a nitrogen stream, and stirring was performed at this temperature (65° C.) for 7 hours. After the completion of the reaction, filtration was performed. The resulting product was purified by silica gel column chromatography (toluene) and then washed by dispersion with heptane to obtain 2.17 g of a white compound H7 (yield: 50%).

(6) Synthesis of Compound H9

The following reagents and solvent were charged into a 200 ml recovery flask.
Compound H7: 2.00 g (3.64 mmol)
Compound H8: 4.17 g (14.6 mmol)
PdCl$_2$(PPh$_3$)$_2$: 128 mg (0.18 mmol)
Sodium carbonate: 1.54 g (14.6 mmol)
DMSO: 100 ml Subsequently, the reaction solution was heated to 90° C. in a nitrogen stream, and stirring was performed at this temperature (90° C.) for 5 hours. After the completion of the reaction, 100 ml of methanol was added thereto and stirring was performed at room temperature for 30 minutes. After that, filtration was performed. The resulting product was purified by silica gel column chromatography (heptane:chlorobenzene=3:1) and then washed by dispersion with methanol to obtain 1.24 g of a white compound H9 (yield: 48%).

(7) Synthesis of Compound H10

The following reagents and solvent were charged into a 100 ml recovery flask.

Compound H9: 1.00 g (1.41 mmol)
Pd(dba)$_2$: 81 mg (0.14 mmol)
P(Cy)$_3$: 119 mg (0.42 mmol)
Potassium acetate: 415 mg (4.23 mmol)
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 523 mg of a dark green compound H10 (yield: 68%).

(8) Synthesis of Exemplary Compound A1

The following reagents and solvent were charged into a 200 ml recovery flask.

Compound H10: 100 mg (0.18 mmol)
Compound H11: 229 mg (1.08 mmol)
Pd(OAc)$_2$: 4 mg (0.02 mmol)
s-phos: 18 mg (0.05 mmol)
Potassium carbonate: 149 g (1.08 mmol)
DMSO: 10 ml Subsequently, the reaction solution was heated to 100° C. in a nitrogen stream, and stirring was performed at this temperature (100° C.) for 6 hours. After the completion of the reaction, 100 ml of methanol was added thereto and stirring was performed at room temperature for 30 minutes. After that, filtration was performed. The resulting product was purified by silica gel column chromatography (chlorobenzene) and then washed by dispersion with heptane/toluene to obtain 76 mg of a yellow exemplary compound A1 (yield: 52%).

The emission spectrum of a toluene solution of the exemplary compound A1 at 1×10$^{-5}$ mol/L was determined by photoluminescence measurement at an excitation wavelength of 350 nm using an F-4500 manufactured by Hitachi, Ltd. As a result, a spectrum having the maximum intensity at 444 nm was obtained.

The exemplary compound A1 was subjected to mass spectrometry using MALDI-TOF-MS (Autoflex LRF manufactured by Bruker).

MALDI-TOF-MS

Measured value: m/z=809, Calculated value: $C_{62}H_{32}O_2$=809

Example 2 (Synthesis of Exemplary Compound A2)

An exemplary compound A2 was synthesized with reference to Example 1, except that the raw material H1 was changed to the raw material H12 in the above scheme and the raw material H2 was changed to a raw material H13 in the following scheme. The measured value of mass spectrometry performed in the same manner as in Example 1 was m/z=809.

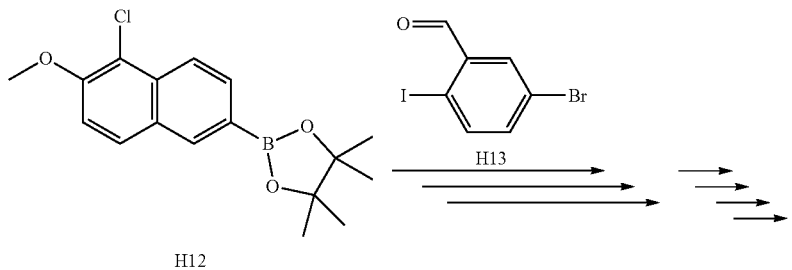

H12

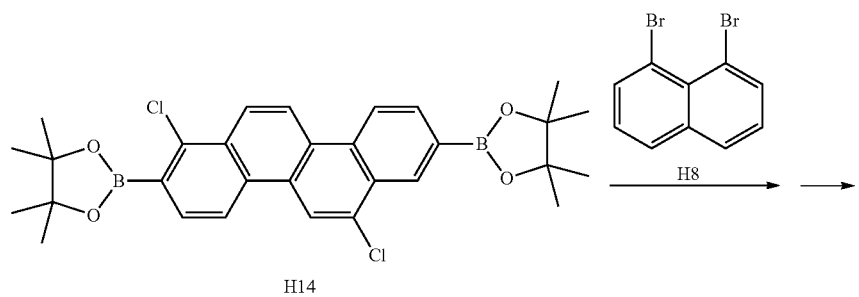

H14

153 154
-continued
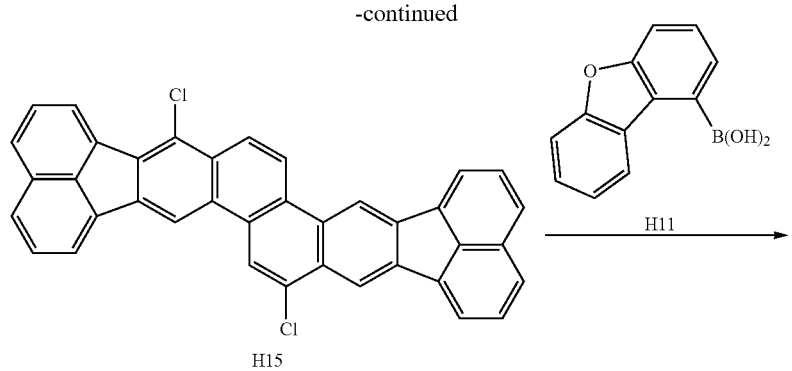
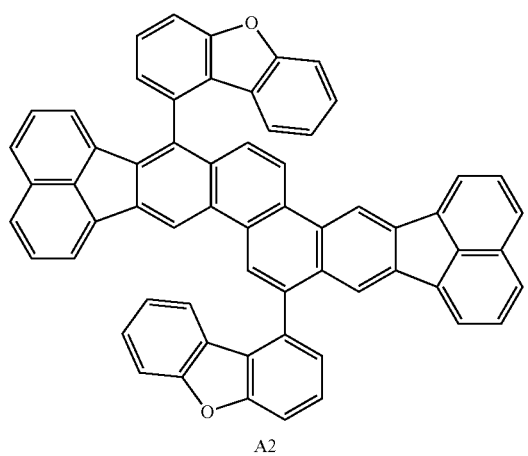
A2
Example 3 (Synthesis of Exemplary Compound A3)
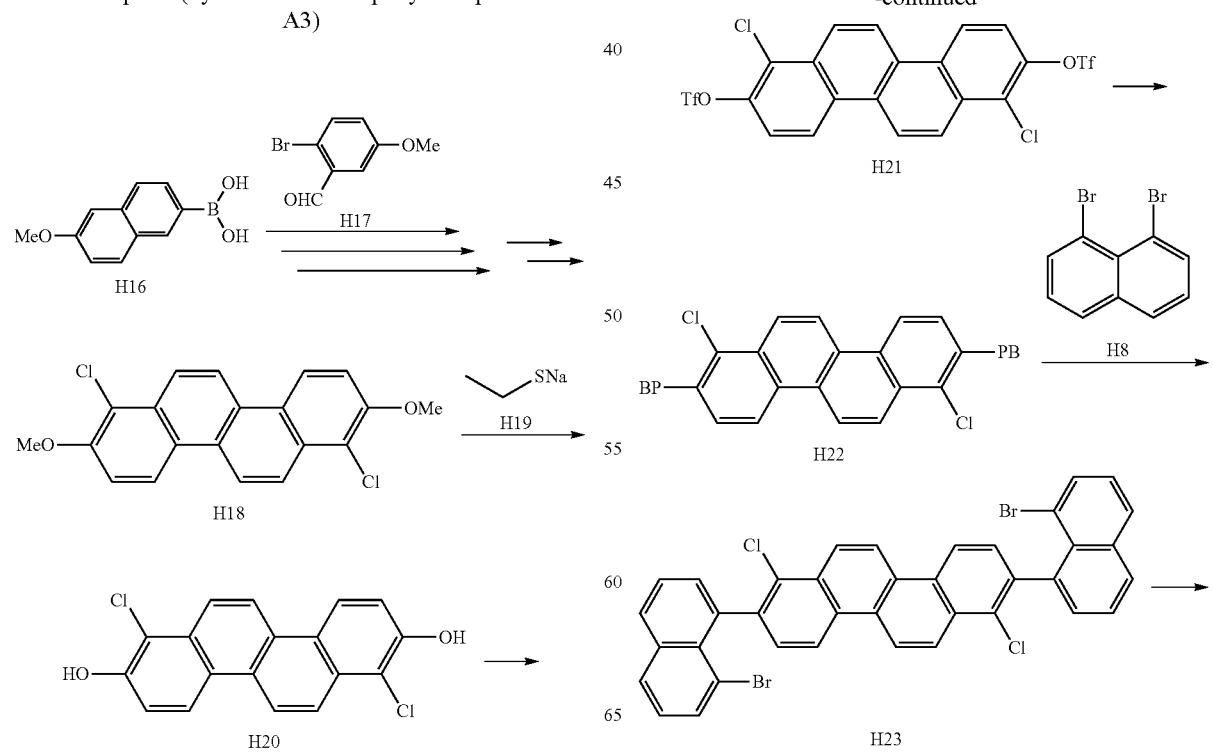

-continued

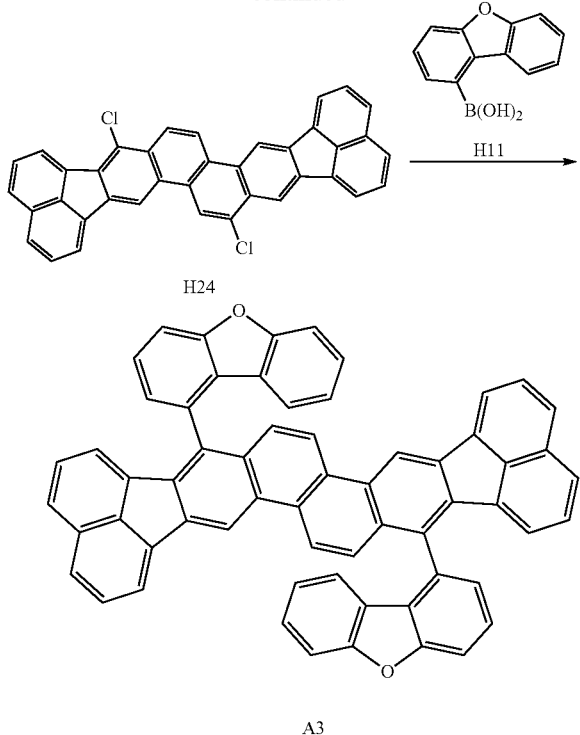

(1) Synthesis of Compound H18
An intermediate H18 was synthesized in the same manner as in Example 1, except that the raw materials H1 and H2 were changed to the above raw materials H16 and H17, respectively.

(2) Synthesis of Compound H20
The following reagents and solvent were charged into a 500 ml recovery flask.
Compound H18: 3.6 g (10.0 mmol)
Sodium ethanethiolate H19: 3.36 g (40.0 mmol)
DMF: 280 ml Subsequently, the reaction solution was heated to 60° C. in a nitrogen stream, and stirring was performed at this temperature for 7 hours. After the completion of the reaction, an aqueous ammonium chloride solution was added thereto, and filtration was performed. The resulting product was washed by dispersion with 100 ml of water to obtain 2.46 g of a white compound $H_2O$ (yield: 75%).

(3) Synthesis of Compound H21
The following reagents and solvent were charged into a 500 ml recovery flask.
Compound H20: 2.4 g (7.29 mmol)
Pyridine: 3.5 ml
Methylene chloride: 240 ml Subsequently, 4.78 ml (29.1 mmol) of trifluoromethanesulfonic anhydride was added dropwise to the reaction solution under ice-cold conditions, and stirring was performed at room temperature for 2 hours. After the completion of the reaction, 200 ml of ice water was added thereto and the organic layer was extracted. The organic layer was concentrated and purified by silica gel column chromatography (mixture of toluene and heptane) to obtain 3.54 g of a white compound H21 (yield: 82%).

(4) Synthesis of Compound H22
The following reagents and solvent were charged into a 500 ml recovery flask.
Compound H21: 3.5 g (6.37 mmol)
bis(pinacolborane): 9.71 g (38.2 mmol)
Pd(dppf)$_2$Cl$_2$: 453 mg (0.637 mmol)
Potassium acetate: 2.50 g (25.5 mmol)
Dioxane: 200 ml Subsequently, the reaction solution was heated to 100° C. in a nitrogen stream, and stirring was performed at this temperature for 7 hours. After the completion of the reaction, celite filtration was performed. The resulting product was concentrated and washed by dispersion with heptane to obtain 3.18 g of a gray compound H22 (yield: 91%).

(5) Synthesis of Compound H23
The following reagents and solvent were charged into a 200 ml recovery flask.
Compound H22: 2.00 g (2.83 mmol)
Compound H8: 2.43 g (8.48 mmol)
Pd(PPh$_3$)$_2$Cl$_2$: 199 mg (0.28 mmol)
Sodium carbonate: 1.80 g (17.0 mmol)
DMSO: 100 ml Subsequently, the reaction solution was heated to 90° C. in a nitrogen stream, and stirring was performed at this temperature for 5 hours. After the completion of the reaction, 100 ml of water was added thereto and stirring was performed at room temperature for 30 minutes. After that, filtration was performed. The resulting product was purified by silica gel column chromatography (mixture of heptane and chlorobenzene) and then washed by dispersion with methanol to obtain 0.76 g of a yellow compound H23 (yield: 38%).

(6) Synthesis of Compound H24
The following reagents and solvent were charged into a 100 ml recovery flask.
Compound H23: 0.75 g (1.06 mmol)
Pd(PPh$_3$)$_2$Cl$_2$: 77 mg (0.11 mmol)
DBU: 5.0 ml
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 417 mg of a dark green compound H24 (yield: 72%).

(7) Synthesis of Exemplary Compound A3
The following reagents and solvents were charged into a 300 ml recovery flask.
Compound H24: 300 mg (0.55 mmol)
Compound H11: 466 mg (2.20 mmol)
Pd(OAc)$_2$: 4 mg (0.02 mmol)
s-phos: 18 mg (0.05 mmol)
Potassium phosphate: 0.458 g (2.16 mmol)
Xylene: 150 ml
Water: 15 ml Subsequently, the reaction solution was heated to 120° C. in a nitrogen stream, and stirring was performed at this temperature for 7 hours. After the completion of the reaction, filtration was performed. The resulting product was purified by silica gel column chromatography (toluene) and then washed by dispersion with heptane to obtain 227 mg of a yellow exemplary compound A3 (yield: 51%).

The emission spectrum of a toluene solution of the exemplary compound A3 at $1 \times 10^{-5}$ mol/L was determined by photoluminescence measurement at an excitation wavelength of 350 nm using an F-4500 manufactured by Hitachi, Ltd. As a result, a spectrum having the maximum intensity at 445 nm was obtained.

Furthermore, the exemplary compound was subjected to mass spectrometry using MALDI-TOF-MS (Autoflex LRF manufactured by Bruker).
MALDI-TOF-MS
Measured value: m/z=809, Calculated value: $C_{62}H_{32}O_2$=809

Examples 4 to 21 (Synthesis of Exemplary Compounds)

As shown in Tables 6 to 8, exemplary compounds in Examples 4 to 21 were synthesized in the same manner as in Examples 1 to 3, except that the raw materials H1, H12, and H16 in Examples 1 to 3 were changed to a raw material 1, the raw materials H2, H13, and H17 were changed to a raw material 2, the raw material H8 was changed to a raw material 3, and the raw material H11 was changed to a raw material 4. The measured value m/z of mass spectrometry performed in the same manner as in Examples 1 to 3 is also shown.

TABLE 6

| Example | Exemplary compound | Raw material 1 | Raw material 2 |
|---|---|---|---|
| 4 | A7 | | |
| 5 | A8 | | |
| 6 | A9 | | |

TABLE 6-continued
7 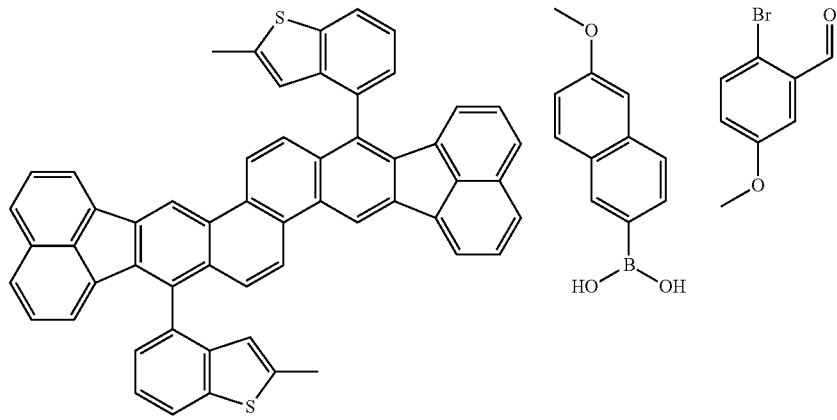
A12
8 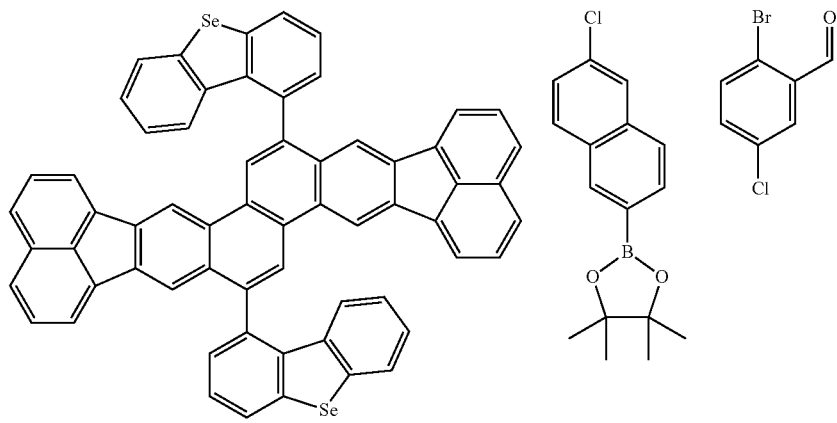
A21
9 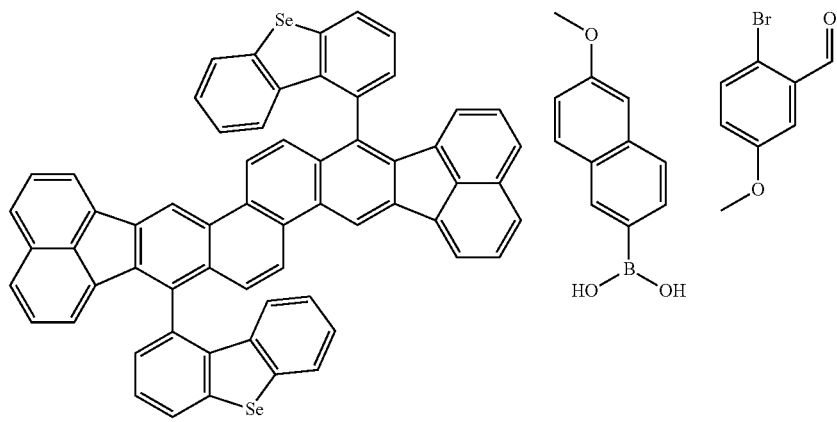
A23

TABLE 6-continued
| | | Raw material 3 | Raw material 4 | m/z |
|---|---|---|---|---|
| 10 | 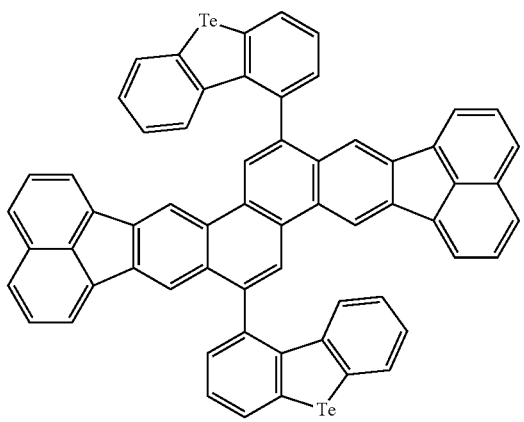 A24 | | 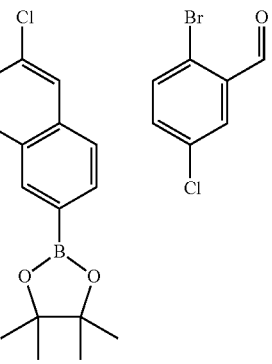 | |
| 4 | | Br Br (naphthalene) | dibenzothiophene-B(OH)₂ | 841 |
| 5 | | Br Br (naphthalene) | dibenzothiophene-B(OH)₂ | 841 |
| 6 | | Br Br (naphthalene) | dibenzothiophene-B(OH)₂ | 841 |
| 7 | | Br Br (naphthalene) | methylbenzothiophene-Bpin | 769 |
| 8 | | Br Br (naphthalene) | dibenzoselenophene-Bpin | 935 |

TABLE 6-continued
| | | | |
|---|---|---|---|
| 9 | 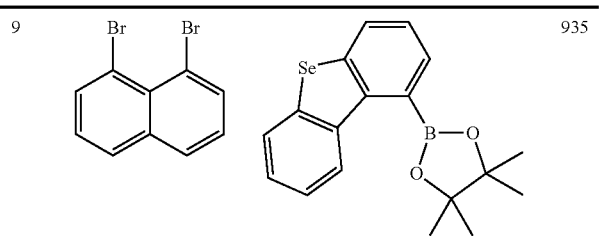 | | 935 |
| 10 | 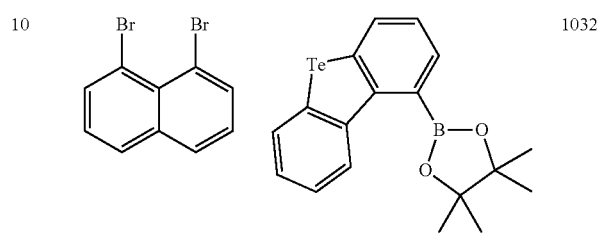 | | 1032 |
TABLE 7
| Example | Exemplary compound | Raw material 1 | Raw material 2 |
|---|---|---|---|
| 11 | 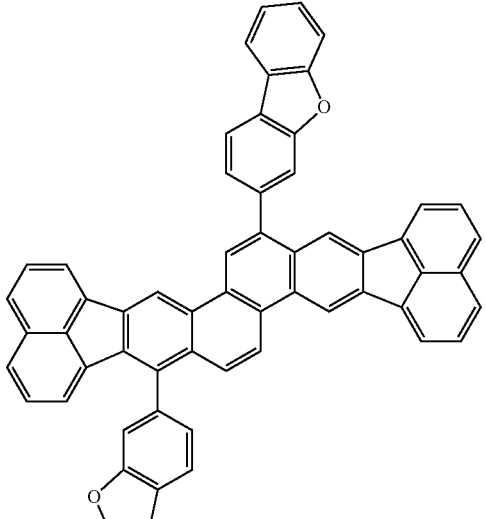\
B2 | 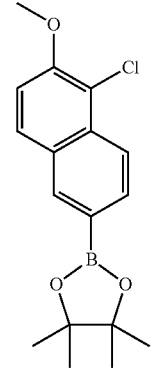 [SMILES: COc1ccc2cc(B3OC(C)(C)C(C)(C)O3)ccc2c1Cl] | 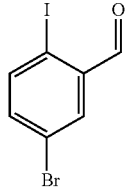 |

TABLE 7-continued
| 12 | 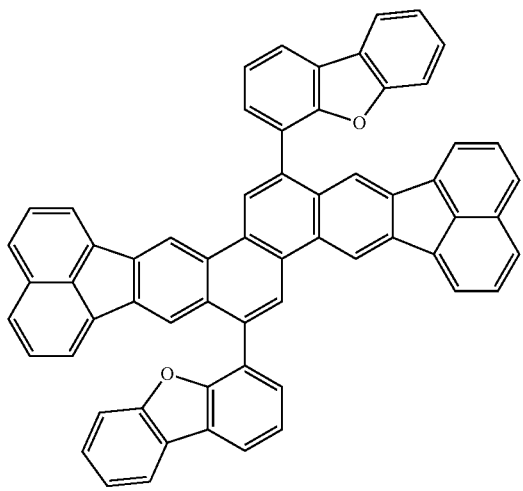 B9 | 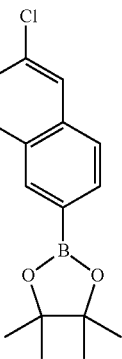 | 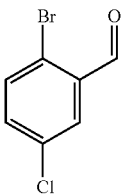 |
| --- | --- | --- | --- |
| 13 | 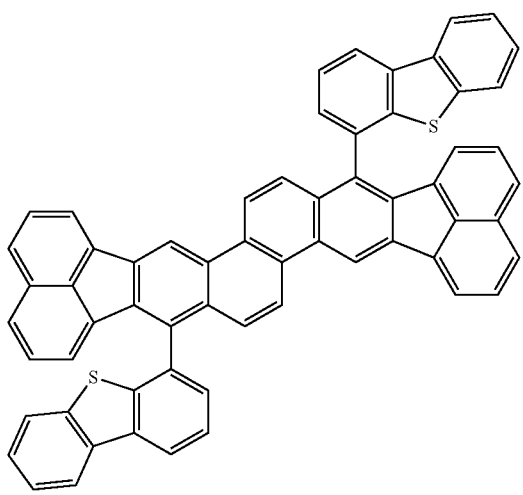 B14 | 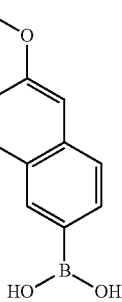 | 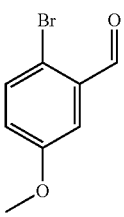 |
| 14 | 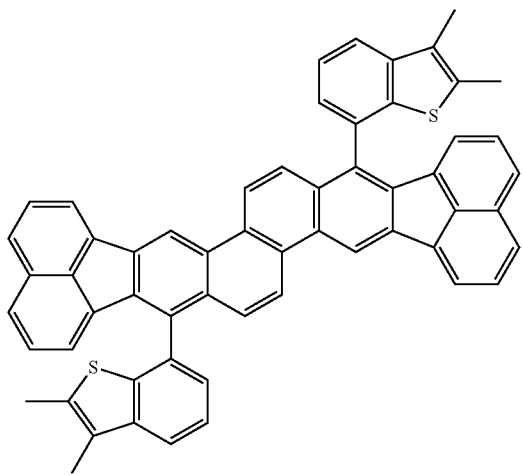 B16 | 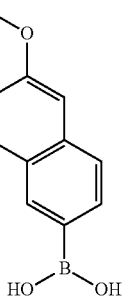 | 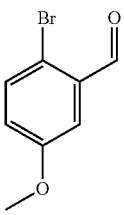 |

TABLE 7-continued
| | | Raw material 3 | Raw material 4 | |
|---|---|---|---|---|
| 15 | 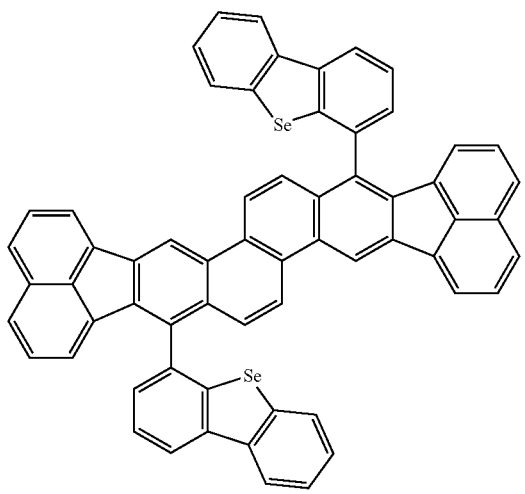
B25 | 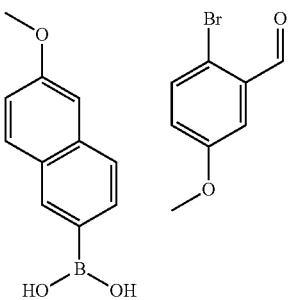 | | |
| 16 | 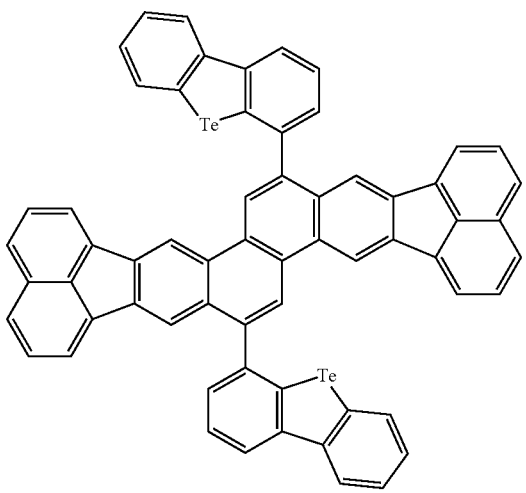
B28 | 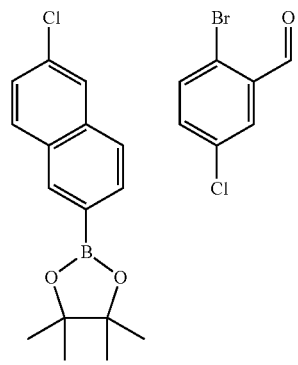 | | |
| Example | Raw material 3 | Raw material 4 | m/z |
|---|---|---|---|
| 11 | | | 809 |

TABLE 7-continued
| | | | |
|---|---|---|---|
| 12 | 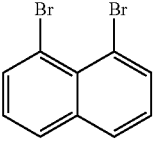 [SMILES: Brc1cccc2cccc(Br)c12] | 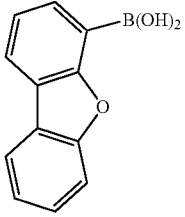 [SMILES: OB(O)c1cccc2c1oc1ccccc12] | 809 |
| 13 | 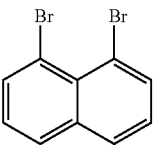 [SMILES: Brc1cccc2cccc(Br)c12] | 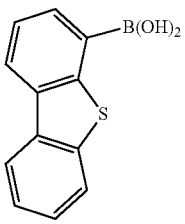 [SMILES: OB(O)c1cccc2c1sc1ccccc12] | 841 |
| 14 | 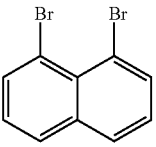 [SMILES: Brc1cccc2cccc(Br)c12] | 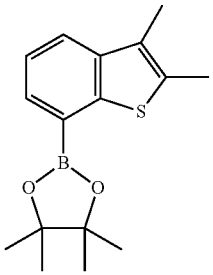 | 797 |
| 15 | 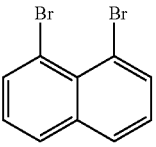 | 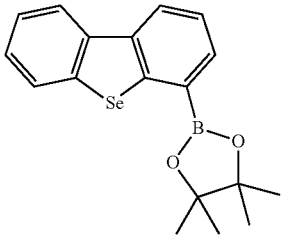 [SMILES: CC1(C)OB(c2cccc3c2[se]c2ccccc23)OC1(C)C] | 935 |
| 16 | 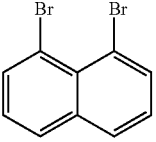 [SMILES: Brc1cccc2cccc(Br)c12] | 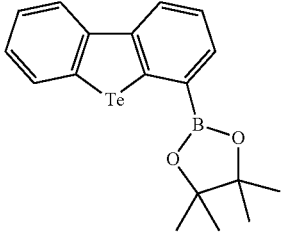 | 1032 |

TABLE 8
| Example | Exemplary compound | Raw material 1 | Raw material 2 |
|---|---|---|---|
| 17 | 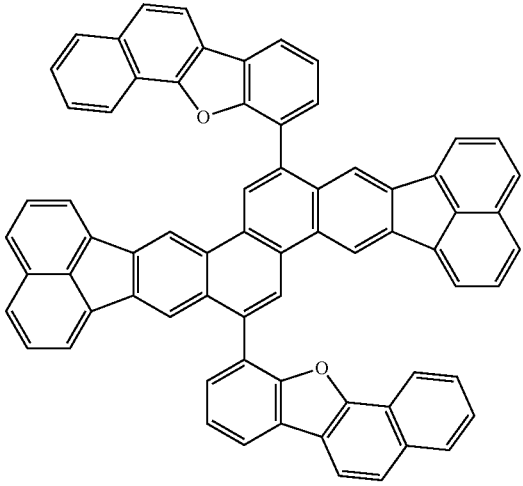<br>C1 | 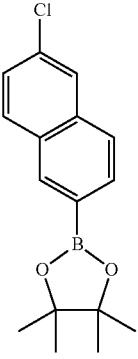 [SMILES: CC1(C)OB(c2ccc3cc(Cl)ccc3c2)OC1(C)C] | 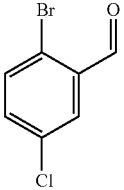 |
| 18 | 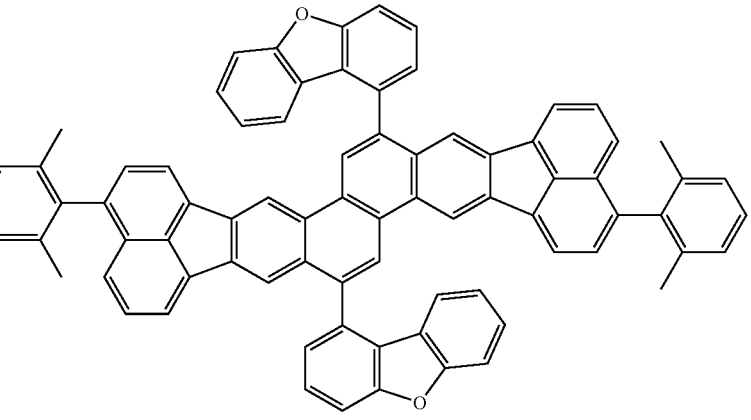<br>C3 | 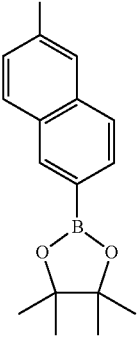 | 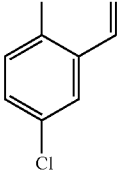 |
| 19 | 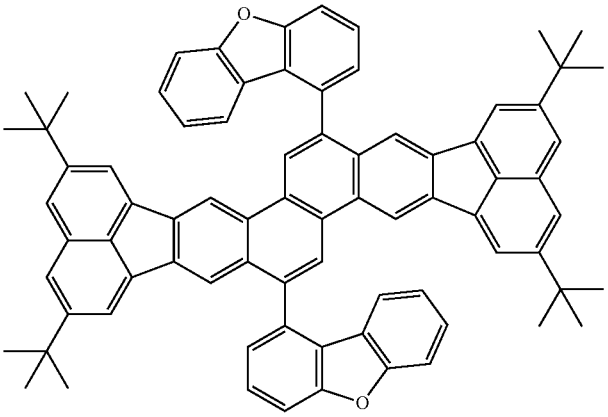<br>C8 | 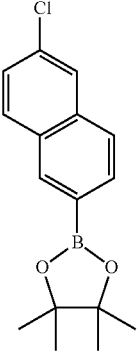 [SMILES: CC1(C)OB(c2ccc3cc(Cl)ccc3c2)OC1(C)C] | 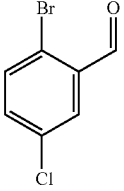 |

TABLE 8-continued
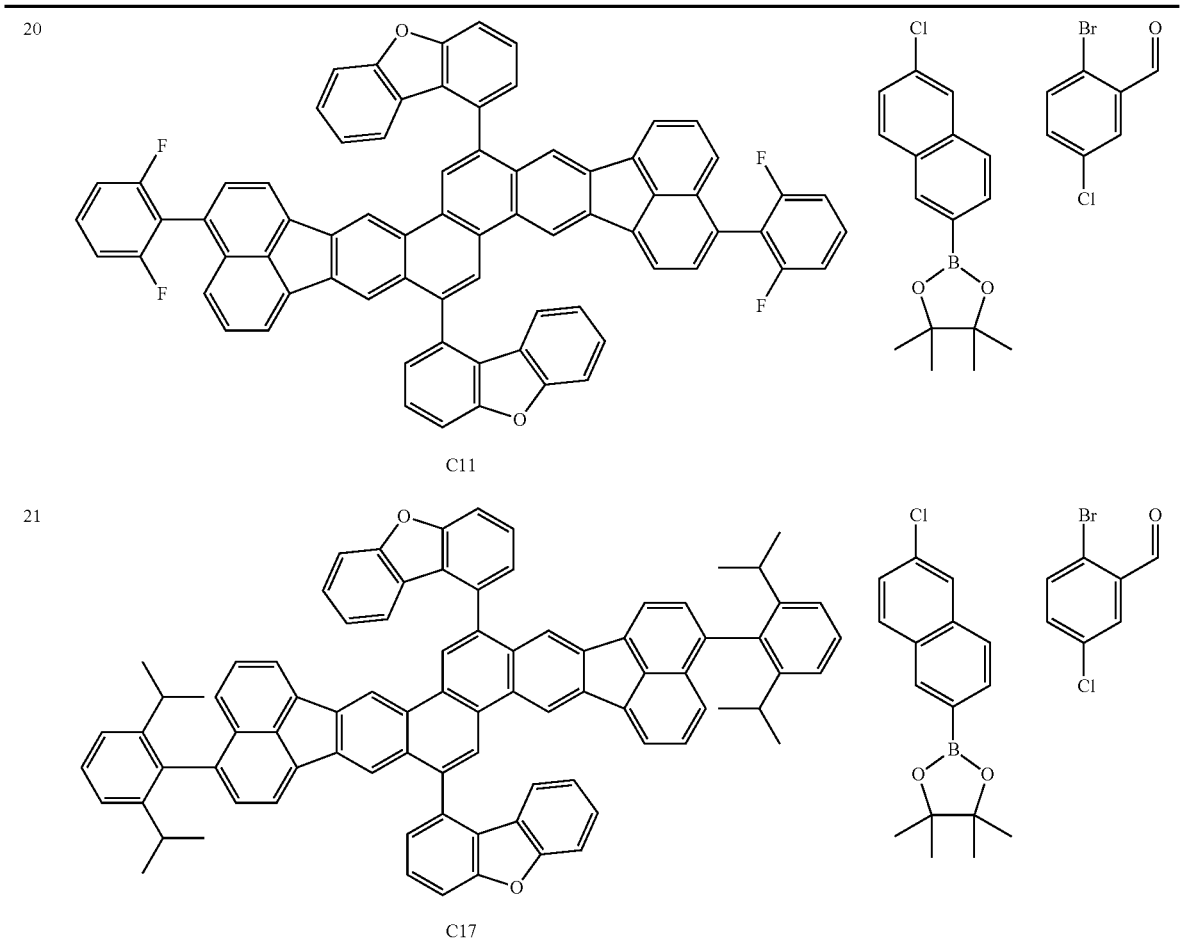

TABLE 8-continued
| | | | |
|---|---|---|---|
| 19 | | 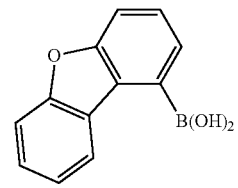 | 1033 |
| 20 | 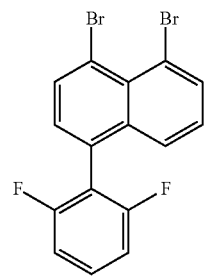 | 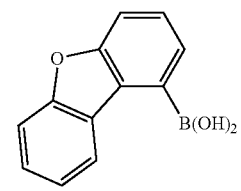 | 1033 |
| 21 | 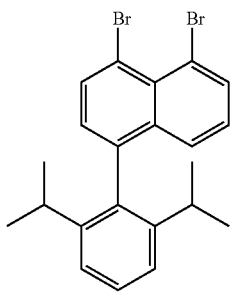 [SMILES: CC(C)c1cccc(C(C)C)c1-c1ccc(Br)c2c(Br)cccc12] | 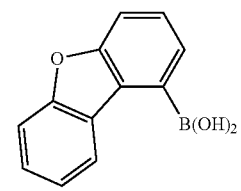 | 1129 |
Example 22 (Synthesis of Exemplary Compound C14)
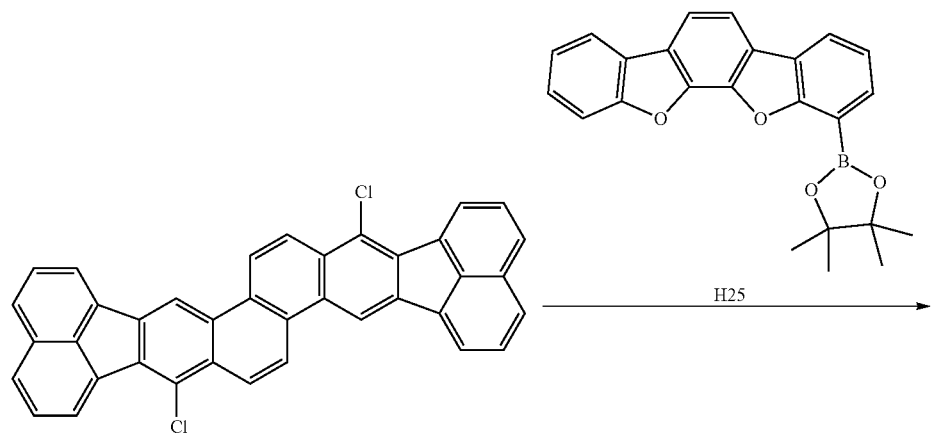

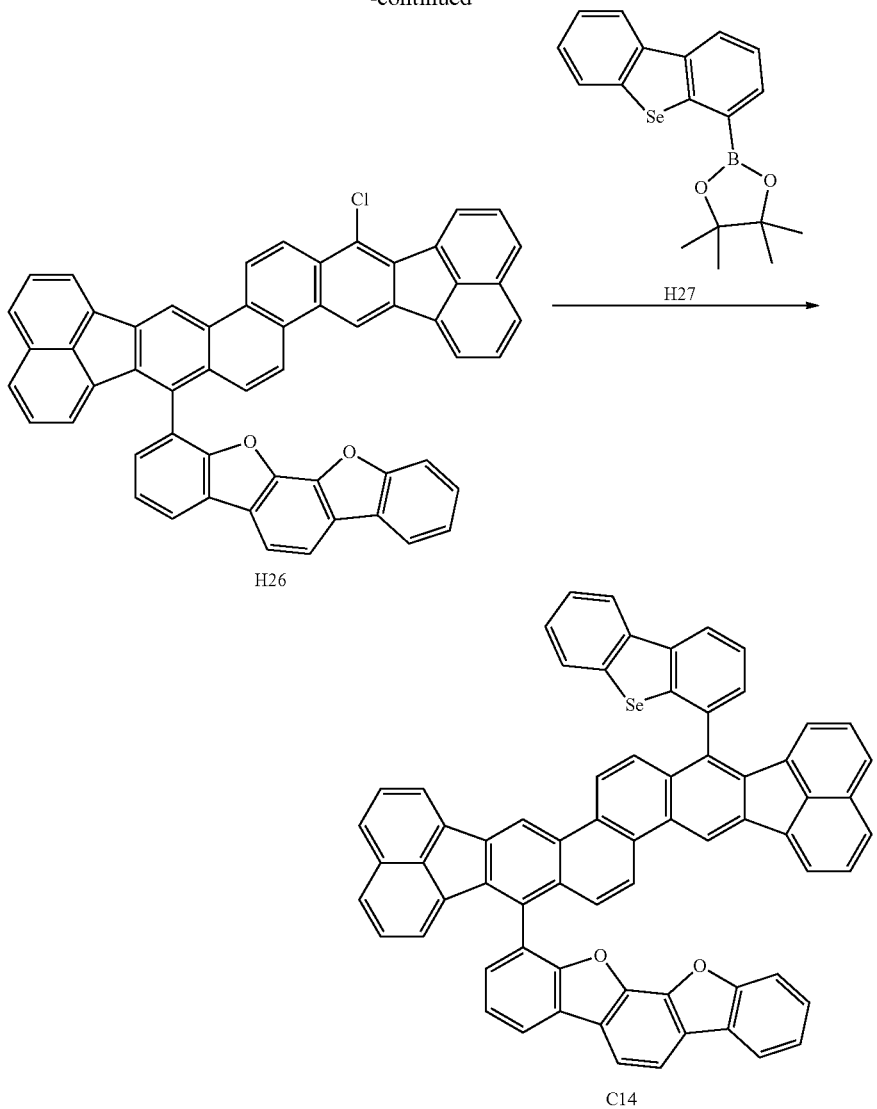

(1) Synthesis of Compound H26

The following reagents and solvents were charged into a 300 ml recovery flask.

Compound H24: 300 mg (0.55 mmol)
Compound H25: 211 mg (0.55 mmol)
Pd(OAc)$_2$: 4 mg (0.02 mmol)
s-phos: 18 mg (0.05 mmol)
Potassium phosphate: 0.229 g (1.08 mmol)
Xylene: 150 ml
Water: 15 ml Subsequently, the reaction solution was heated to 120° C. in a nitrogen stream, and stirring was performed at this temperature for 3 hours. After the completion of the reaction, filtration was performed. The resulting product was purified by silica gel column chromatography (toluene) and then washed by dispersion with heptane to obtain 148 mg of a compound H26 (yield: 35%).

(2) Synthesis of Exemplary Compound C14

The following reagents and solvents were charged into a 100 ml recovery flask.

Compound H26: 140 mg (0.18 mmol)
Compound H27: 129 mg (0.36 mmol)
Pd(OAc)$_2$: 2 mg (0.01 mmol)
s-phos: 9 mg (0.25 mmol)
Potassium phosphate: 0.114 g (0.54 mmol)
Xylene: 70 ml
Water: 7 ml Subsequently, the reaction solution was heated to 120° C. in a nitrogen stream, and stirring was performed at this temperature for 5 hours. After the completion of the reaction, filtration was performed. The resulting product was purified by silica gel column chromatography (toluene) and then washed by dispersion with heptane to obtain 74 mg of a yellow exemplary compound C14 (yield: 43%).

The exemplary compound C14 was subjected to mass spectrometry using MALDI-TOF-MS (Autoflex LRF manufactured by Bruker).

MALDI-TOF-MS

Measured value: m/z=962, Calculated value: $C_{54}H_{34}O_2Se$=962

Example 23 (Synthesis of Exemplary Compound D1)

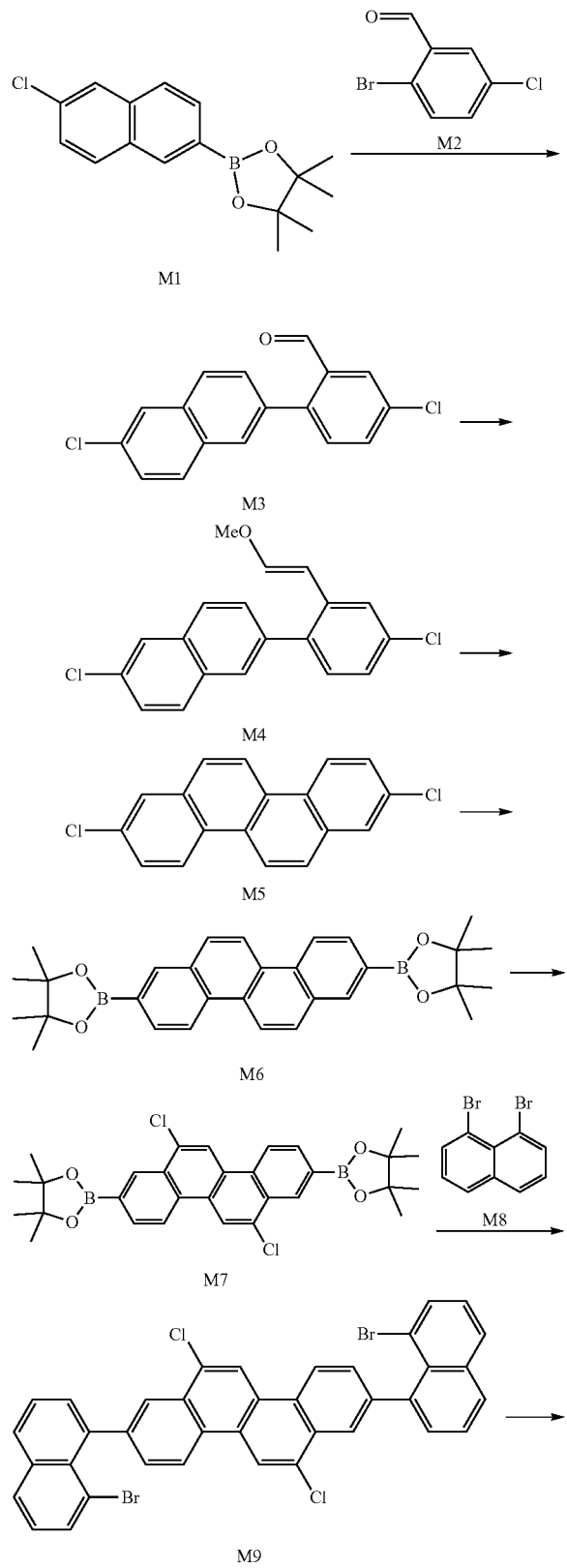

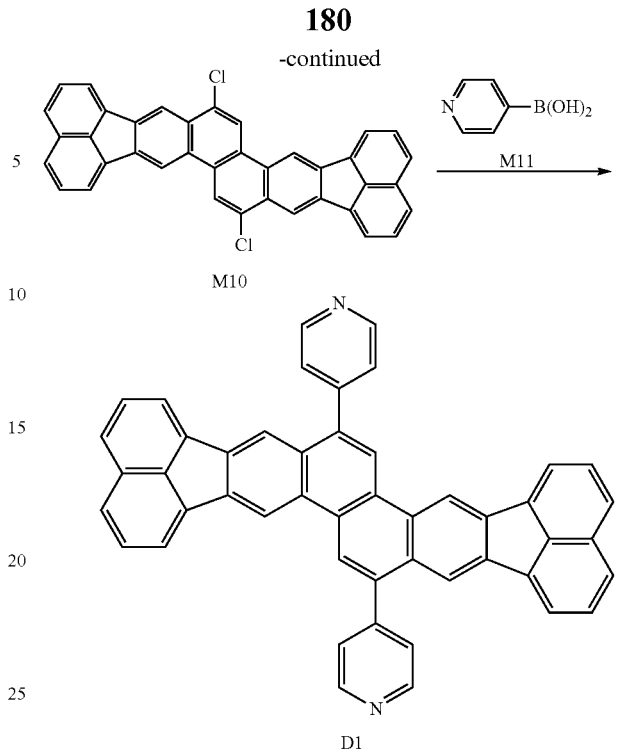

(1) Synthesis of Compound M3

The following reagents and solvent were charged into a 500 ml recovery flask.

Compound M1: 7.23 g (25.1 mmol)
Compound M2: 5.00 g (22.8 mmol)
Pd(PPh$_3$)$_4$: 790 mg (1.14 mmol)
Sodium carbonate: 9.66 g (91.2 mmol)
Toluene: 200 ml
Ethanol: 100 ml
Water: 100 ml Subsequently, the reaction solution was heated to 90° C. in a nitrogen stream, and stirring was performed at this temperature (90° C.) for 5 hours. After the completion of the reaction, extraction was performed using toluene and water. The resulting product was concentrated, purified by silica gel column chromatography (heptane:toluene=1:1), and then washed by dispersion with methanol to obtain 5.5 g of a white compound M3 (yield: 80%).

(2) Synthesis of Compound M4

The following reagents and solvent were charged into a 200 ml recovery flask.

(Methoxymethyl)triphenylphosphonium chloride: 12.8 g (41.5 mmol)
Tetrahydrofuran: 50 ml Subsequently, the following reagent was gradually added dropwise to the reaction solution in a nitrogen stream at room temperature.

Potassium t-butoxide [1.0 M tetrahydrofuran solution]

Subsequently, the reaction solution was stirred at this temperature (room temperature) for 1 hour, and then the following mixed solution was gradually added dropwise thereto at room temperature.

Compound M3: 5.0 g (16.6 mmol)
Tetrahydrofuran: 50 ml

After the completion of the reaction, extraction was performed using toluene and water. The resulting product was concentrated, purified by silica gel column chromatography (heptane:toluene=1:1), and then washed by dispersion with methanol to obtain 4.48 g of a white compound M4 (yield: 82%).

(3) Synthesis of Compound M5

The following reagent and solvent were charged into a 200 ml recovery flask.

Compound M4: 4.00 g (12.1 mmol)
Dichloromethane: 100 ml

Subsequently, the reaction solution was cooled to 0° C. in a nitrogen stream, and the following reagent was added dropwise to the reaction solution.

Methanesulfonic acid: 1.75 g (18.2 mmol)

Subsequently, the reaction solution was stirred at room temperature for 3 hours. After the completion of the reaction, 50 ml of methanol was added thereto and stirring was performed at 0° C. for 30 minutes. The resulting product was then separated and washed with water and methanol to obtain 3.09 g of a white compound M5 (yield: 86%).

(4) Synthesis of Compound M6

The following reagents and solvent were charged into a 500 ml recovery flask.

Compound M5: 3.00 g (10.1 mmol)
bis(pinacolborane): 10.3 g (40.4 mmol)
Pd(dba)$_2$: 580 mg (1.01 mmol)
P(Cy)$_3$: 850 mg (3.03 mmol)
Potassium acetate: 3.96 mg (40.4 mmol)
o-Xylene: 300 ml Subsequently, the reaction solution was heated to 150° C. in a nitrogen stream, and stirring was performed at this temperature (150° C.) for 7 hours. After the completion of the reaction, celite filtration was performed. The resulting product was concentrated and washed by dispersion with heptane to obtain 3.93 g of a white compound M6 (yield: 81%).

(5) Synthesis of Compound M7

The following reagent and solvent were charged into a 500 ml recovery flask.

Compound M6: 3.8 g (7.91 mmol)
NCS: 5.28 g (39.6 mmol)
Methanesulfonic acid: 227 mg (2.37 mmol)
DMF: 380 ml Subsequently, the reaction solution was heated to 65° C. in a nitrogen stream, and stirring was performed at this temperature (65° C.) for 7 hours. After the completion of the reaction, filtration was performed. The resulting product was purified by silica gel column chromatography (toluene) and then washed by dispersion with heptane to obtain 2.17 g of a white compound M7 (yield: 50%).

(6) Synthesis of Compound M9

The following reagents and solvent were charged into a 200 ml recovery flask.

Compound M7: 2.00 g (3.64 mmol)
Compound M8: 4.17 g (14.6 mmol)
PdCl$_2$(PPh$_3$)$_2$: 128 mg (0.18 mmol)
Sodium carbonate: 1.54 g (14.6 mmol)
DMSO: 100 ml Subsequently, the reaction solution was heated to 90° C. in a nitrogen stream, and stirring was performed at this temperature (90° C.) for 5 hours. After the completion of the reaction, 100 ml of methanol was added thereto and stirring was performed at room temperature for 30 minutes. After that, filtration was performed. The resulting product was purified by silica gel column chromatography (heptane: chlorobenzene=3:1) and then washed by dispersion with methanol to obtain 1.24 g of a white compound M9 (yield: 48%).

(7) Synthesis of Compound M10

The following reagents and solvent were charged into a 100 ml recovery flask.

Compound M9: 1.00 g (1.41 mmol)
Pd(dba)$_2$: 81 mg (0.14 mmol)
P(Cy)$_3$: 119 mg (0.42 mmol)
Potassium acetate: 415 mg (4.23 mmol)
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 523 mg of a dark green compound M11 (yield: 68%).

(8) Synthesis of Exemplary Compound D1

The following reagents and solvent were charged into a 200 ml recovery flask.

Compound M10: 200 mg (0.36 mmol)
Compound M11: 221 mg (1.80 mmol)
Pd(OAc)$_2$: 8 mg (0.04 mmol)
s-phos: 36 mg (0.10 mmol)
Potassium carbonate: 298 g (2.16 mmol)
DMSO: 20 ml Subsequently, the reaction solution was heated to 100° C. in a nitrogen stream, and stirring was performed at this temperature (100° C.) for 6 hours. After the completion of the reaction, 100 ml of methanol was added thereto and stirring was performed at room temperature for 30 minutes. After that, filtration was performed. The resulting product was purified by silica gel column chromatography (chlorobenzene) and then washed by dispersion with heptane/toluene to obtain 146 mg of a yellow exemplary compound D1 (yield: 65%).

The emission spectrum of a toluene solution of the exemplary compound D1 at 1×10$^{-5}$ mol/L was determined by photoluminescence measurement at an excitation wavelength of 350 nm using an F-4500 manufactured by Hitachi, Ltd. As a result, a spectrum having the maximum intensity at 444 nm was obtained.

The exemplary compound D1 was subjected to mass spectrometry using MALDI-TOF-MS (Autoflex LRF manufactured by Bruker).

MALDI-TOF-MS

Measured value: m/z=630, Calculated value: $C_{48}H_{26}N_2$=630

Example 24 (Synthesis of Exemplary Compound D2)

An exemplary compound D2 was synthesized in the same manner as in Example 23, except that the raw material M1 was changed to the raw material M12 in the above scheme and the raw material M2 was changed to a raw material M13 in the following scheme. The measured value of mass spectrometry performed in the same manner as in Example 23 was m/z=630.

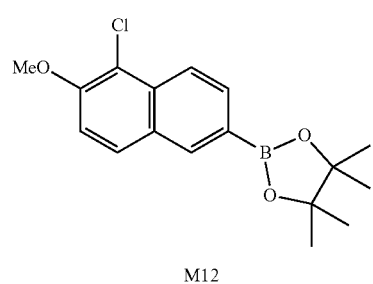
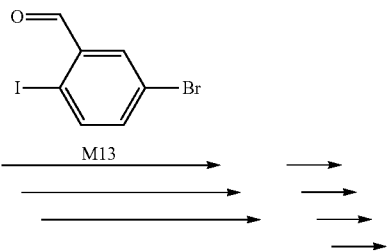
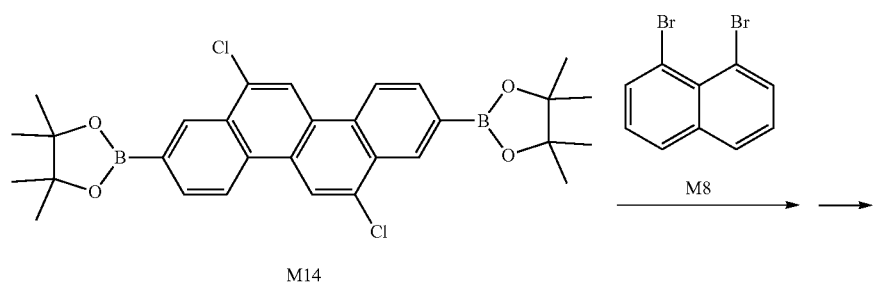
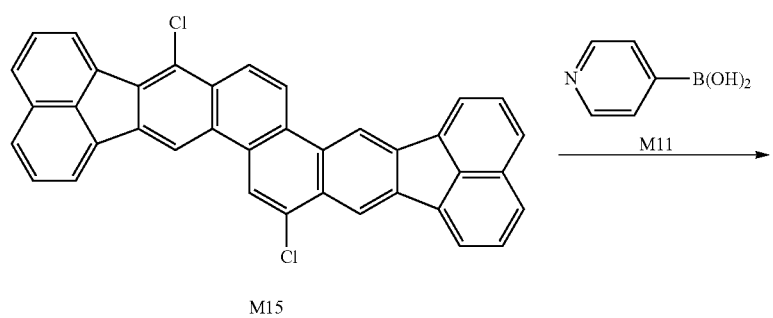
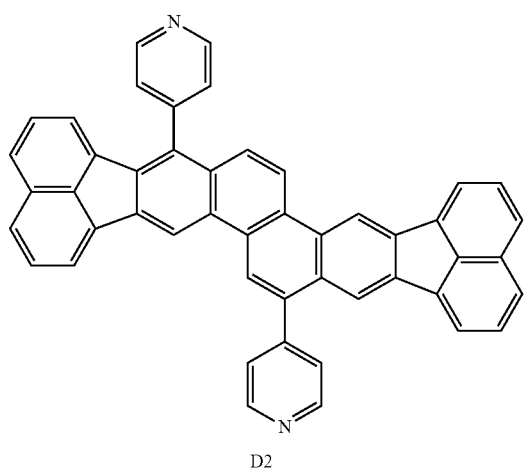

Example 25 (Synthesis of Exemplary Compound D3)

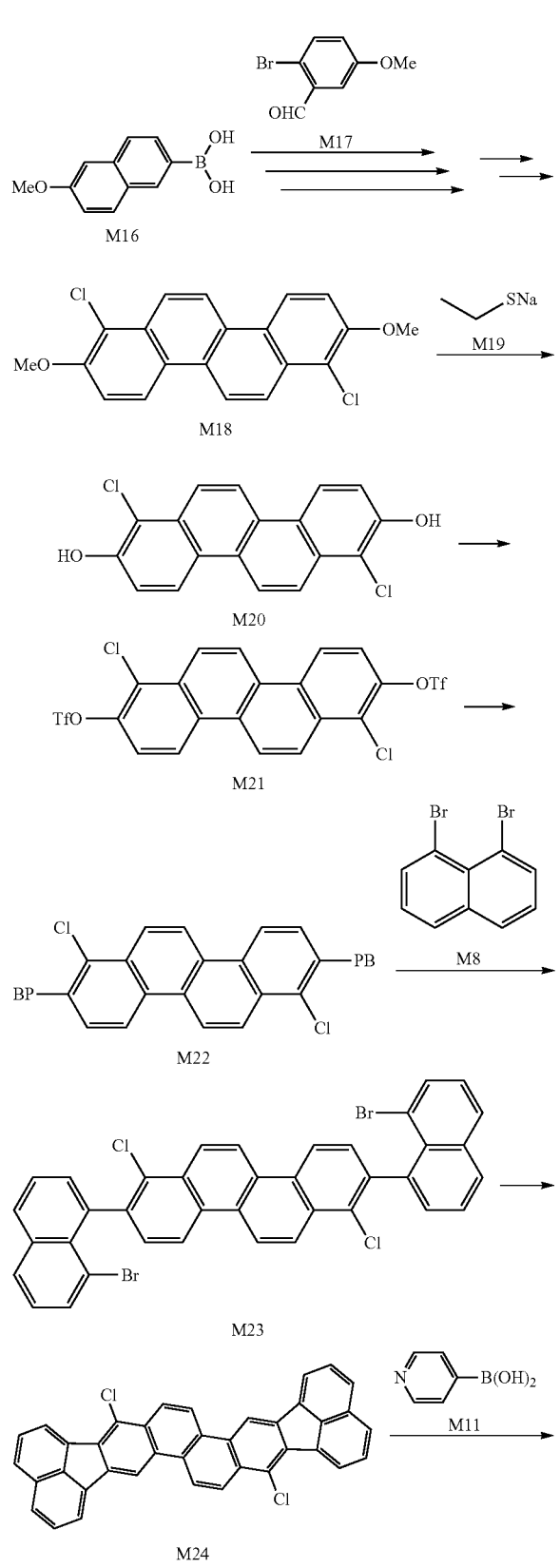

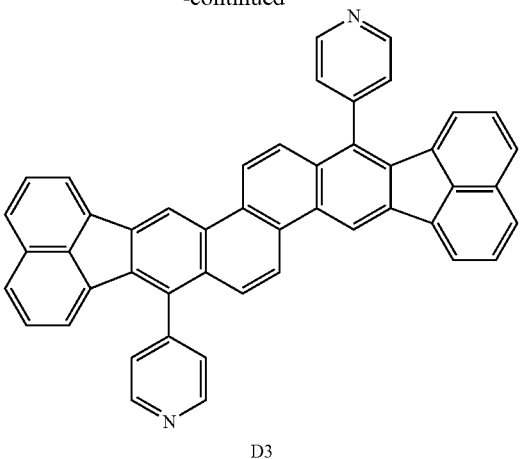

D3

(1) Synthesis of Compound M18

An intermediate M18 was synthesized in the same manner as in Example 23, except that M1 was changed to M16 and M2 was changed to M17.

(2) Synthesis of Compound M20

The following reagent and solvent were charged into a 500 ml recovery flask.
  Compound M18: 3.6 g (10.0 mmol)
  Sodium ethanethiolate M19: 3.36 g (40.0 mmol)
  DMF: 280 ml Subsequently, the reaction solution was heated to 60° C. in a nitrogen stream, and stirring was performed at this temperature for 7 hours. After the completion of the reaction, an aqueous ammonium chloride solution was added thereto, and filtration was performed. The resulting product was washed by dispersion with 100 ml of water to obtain 2.46 g of a white compound M20 (yield: 75%).

(3) Synthesis of Compound M21

The following reagents and solvent were charged into a 500 ml recovery flask.
  Compound M20: 2.4 g (7.29 mmol)
  Pyridine: 3.5 ml
  Methylene chloride: 240 ml Subsequently, 4.78 ml (29.1 mmol) of trifluoromethanesulfonic anhydride was added dropwise to the reaction solution under ice-cold conditions, and stirring was performed at room temperature for 2 hours. After the completion of the reaction, 200 ml of ice water was added thereto and the organic layer was extracted. The organic layer was concentrated and purified by silica gel column chromatography (mixture of toluene and heptane) to obtain 3.54 g of a white compound M21 (yield: 82%).

(4) Synthesis of Compound M22

The following reagents and solvent were charged into a 500 ml recovery flask.
  Compound M21: 3.5 g (6.37 mmol)
  bis(pinacolborane): 9.71 g (38.2 mmol)
  $Pd(dppf)_2Cl_2$: 453 mg (0.637 mmol)
  Potassium acetate: 2.50 g (25.5 mmol)
  Dioxane: 200 ml Subsequently, the reaction solution was heated to 100° C. in a nitrogen stream, and stirring was performed at this temperature for 7 hours. After the completion of the reaction, celite filtration was performed. The resulting product was concentrated and washed by dispersion with heptane to obtain 3.18 g of a gray compound M22 (yield: 91%).

(5) Synthesis of Compound M23

The following reagents and solvent were charged into a 200 ml recovery flask.

Compound M22: 2.00 g (2.83 mmol)
Compound M8: 2.43 g (8.48 mmol)
$Pd(PPh_3)_2Cl_2$: 199 mg (0.28 mmol)
Sodium carbonate: 1.80 g (17.0 mmol)
DMSO: 100 ml Subsequently, the reaction solution was heated to 90° C. in a nitrogen stream, and stirring was performed at this temperature for 5 hours. After the completion of the reaction, 100 ml of water was added thereto and stirring was performed at room temperature for 30 minutes. After that, filtration was performed. The resulting product was purified by silica gel column chromatography (mixture of heptane and chlorobenzene) and then washed by dispersion with methanol to obtain 0.76 g of a yellow compound M23 (yield: 38%).

(6) Synthesis of Compound M24

The following reagents and solvent were charged into a 100 ml recovery flask.

Compound M23: 0.75 g (1.06 mmol)
$Pd(PPh_3)_2Cl_2$: 77 mg (0.11 mmol)
DBU: 5.0 ml
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 417 mg of a dark green compound M24 (yield: 72%).

(7) Synthesis of Exemplary Compound D3

The following reagents and solvents were charged into a 300 ml recovery flask.

Compound M24: 300 mg (0.55 mmol)
Compound M11: 271 mg (2.20 mmol)
$Pd(OAc)_2$: 4 mg (0.02 mmol)
s-phos: 18 mg (0.05 mmol)
Potassium phosphate: 0.458 g (2.16 mmol)
Xylene: 150 ml
Water: 15 ml Subsequently, the reaction solution was heated to 120° C. in a nitrogen stream, and stirring was performed at this temperature for 7 hours. After the completion of the reaction, filtration was performed. The resulting product was purified by silica gel column chromatography (toluene) and then washed by dispersion with heptane to obtain 211 mg of a yellow exemplary compound D3 (yield: 61%).

The emission spectrum of a toluene solution of the exemplary compound D3 at $1\times10^{-5}$ mol/L was determined by photoluminescence measurement at an excitation wavelength of 350 nm using an F-4500 manufactured by Hitachi, Ltd. As a result, a spectrum having the maximum intensity at 444 nm was obtained.

Furthermore, the exemplary compound was subjected to mass spectrometry using MALDI-TOF-MS (Autoflex LRF manufactured by Bruker).

MALDI-TOF-MS

Measured value: m/z=630, Calculated value: $C_{48}H_{26}N_2=630$

Examples 26 to 36 (Synthesis of Exemplary Compounds)

As shown in Tables 9 and 10, exemplary compounds in Examples 26 to 36 were synthesized in the same manner as in Examples 23 to 25, except that the raw materials M1, M12, and M16 in Examples 23 to 25 were changed to a raw material 1, the raw materials M2, M13, and M17 were changed to a raw material 2, the raw material M8 was changed to a raw material 3, and the raw material M11 was changed to a raw material 4. The measured value m/z of mass spectrometry performed in the same manner as in Examples 23 to 25 is also shown.

TABLE 9

| Example | Exemplary compound | Raw material 1 | Raw material 2 |
|---|---|---|---|
| 26 | 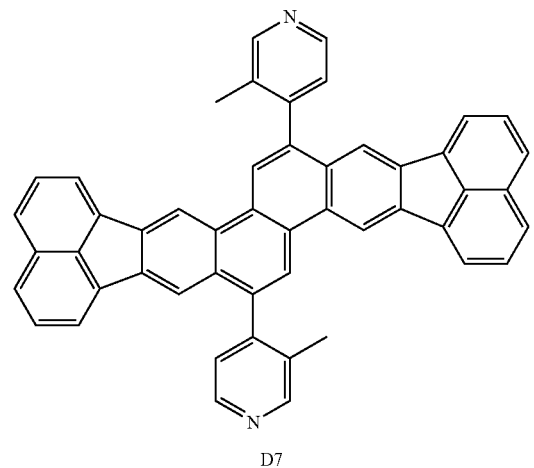<br>D7 | M1 | M2 |

TABLE 9-continued
| 27 | 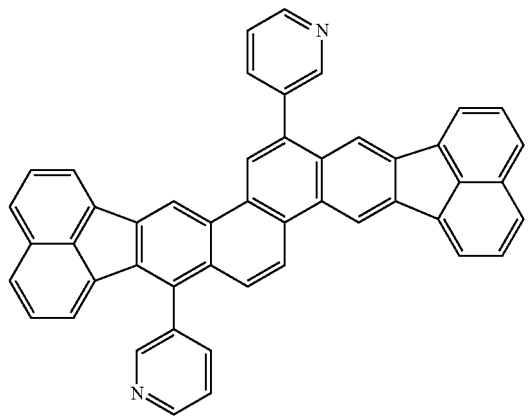<br>D5 | M12 | M13 |
| --- | --- | --- | --- |
| 28 | 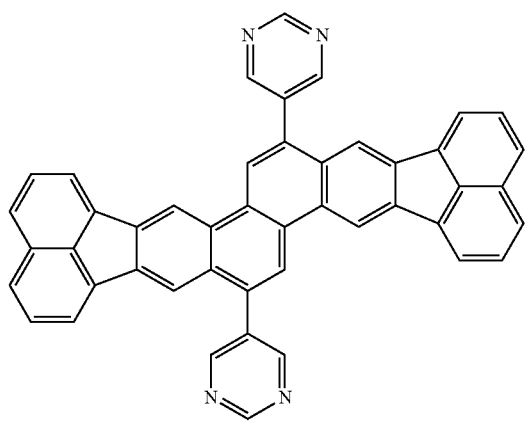<br>D13 | M1 | M2 |
| 29 | 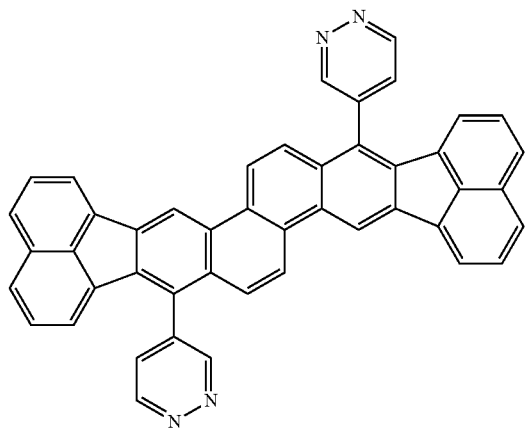<br>D17 | M16 | M17 |

TABLE 9-continued
30 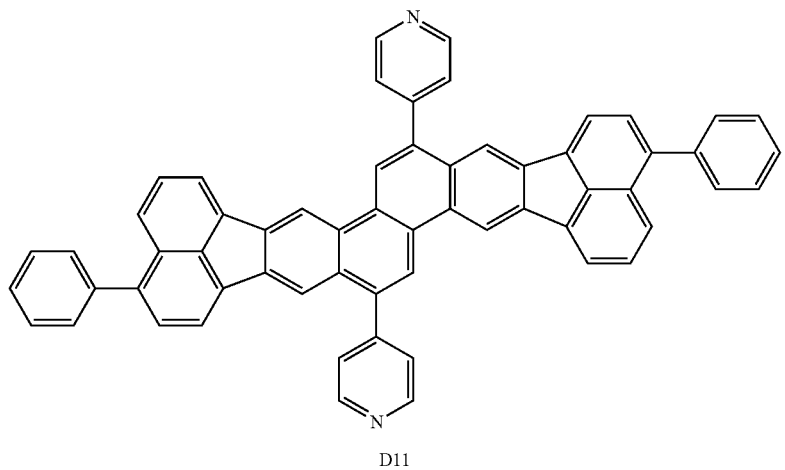
D11
M1　M2
31 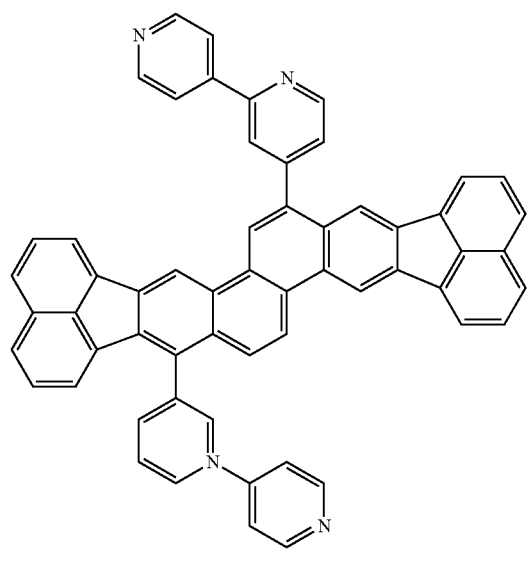
D20
M12　M13
| Example | Raw material 3 | Raw material 4 | m/z |
|---|---|---|---|
| 26 | M8 | ![pyridine with methyl and B(OH)2] | 658 |
| 27 | M8 | ![pyridine-B(OH)2] | 630 |
| 28 | M8 | ![pyrimidine-B(OH)2] | 632 |
| 29 | M8 | ![pyridazine-B(OH)2] | 632 |

TABLE 9-continued
| | | | | |
|---|---|---|---|---|
| 30 | 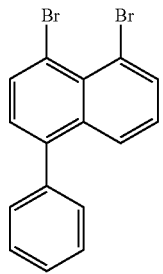 [SMILES: Brc1cccc2c(-c3ccccc3)ccc(Br)c12] | | M11 | 782 |
| 31 | | 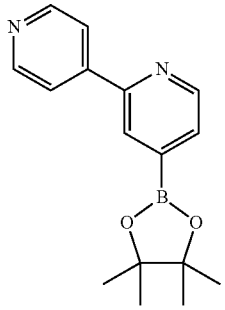 [SMILES: CC1(C)OB(c2ccnc(-c3ccncc3)c2)OC1(C)C] | M8 | 784 |
TABLE 10
| Example | Exemplary compound | Raw material 1 | Raw material 2 | Raw material 3 | Raw material 4 | m/z |
|---|---|---|---|---|---|---|
| 32 | 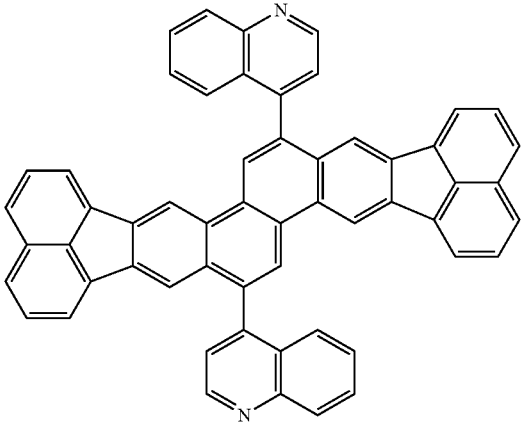<br>E1 | M1 | M2 | M8 | 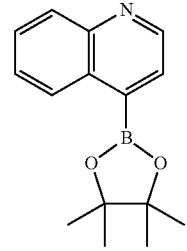 [SMILES: CC1(C)OB(c2ccnc3ccccc23)OC1(C)C] | 730 |

TABLE 10-continued
| Example | Exemplary compound | Raw material 1 | Raw material 2 | Raw material 3 | Raw material 4 | m/z |
|---|---|---|---|---|---|---|
| 33 | 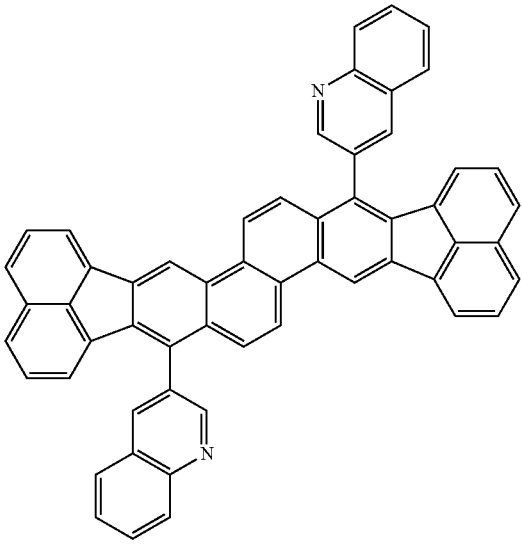<br>E3 | M16 | M17 | M8 | 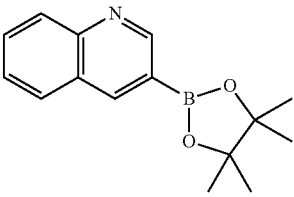 [SMILES: CC1(C)OB(c2cnc3ccccc3c2)OC1(C)C] | 730 |
| 34 | 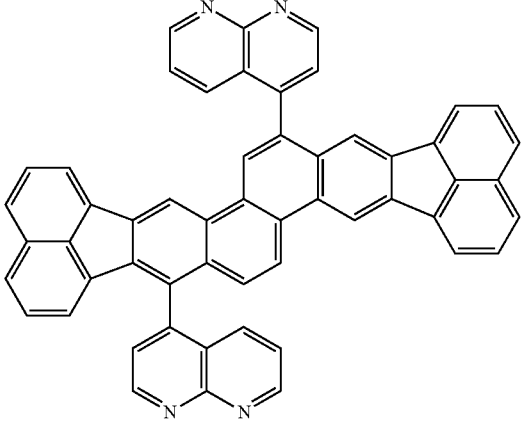<br>F2 | M12 | M13 | M8 | 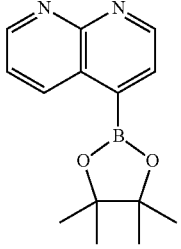 [SMILES: CC1(C)OB(c2ccnc3ncccc23)OC1(C)C] | 732 |
| 35 | 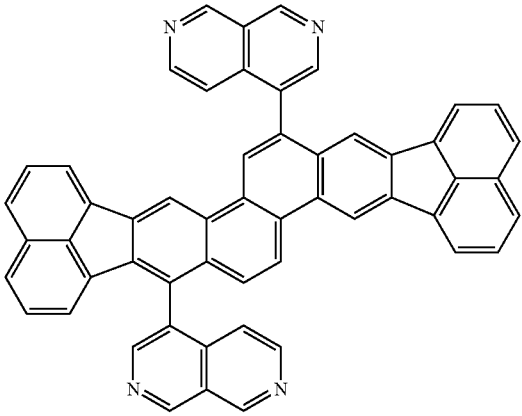<br>F6 | M12 | M13 | M8 | 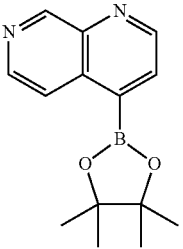 [SMILES: CC1(C)OB(c2ccnc3cnccc23)OC1(C)C] | 732 |

TABLE 10-continued

| Example | Exemplary compound | Raw material 1 | Raw material 2 | Raw material 3 | Raw material 4 | m/z |
|---|---|---|---|---|---|---|
| 36 | 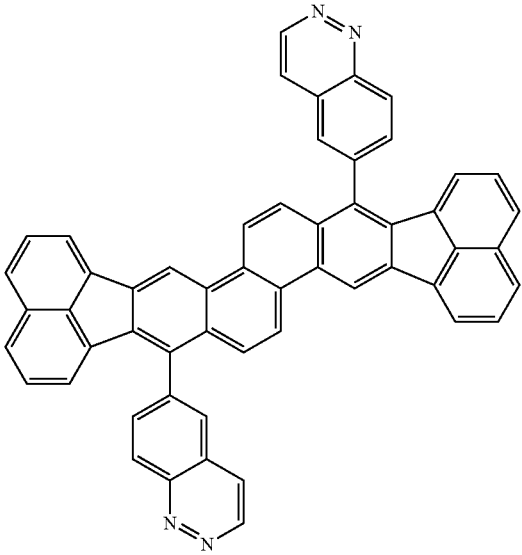<br>F8 | M16 | M17 | M8 | 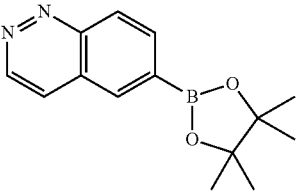 [SMILES: CC1(C)OB(c2ccc3nnccc3c2)OC1(C)C] | 732 |

Example 37 (Synthesis of Exemplary Compound D22)

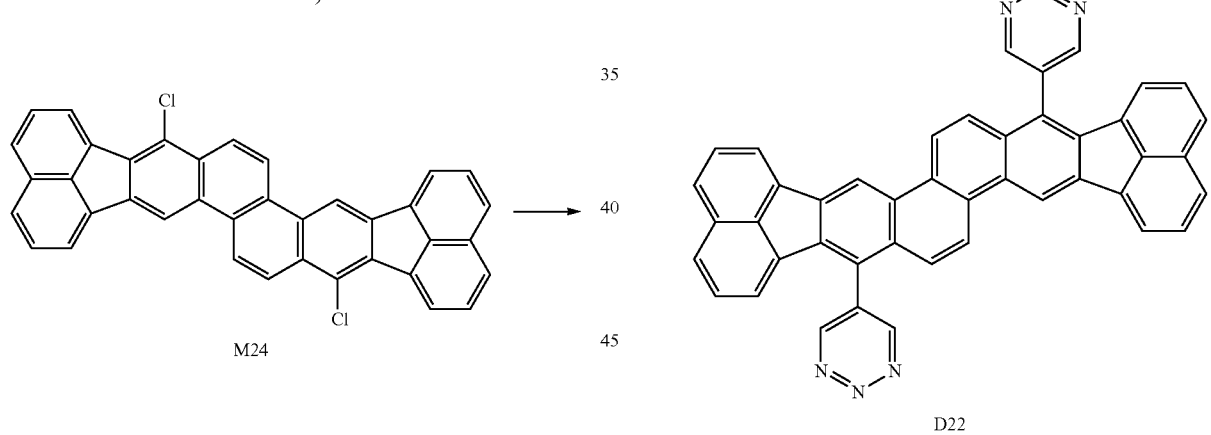

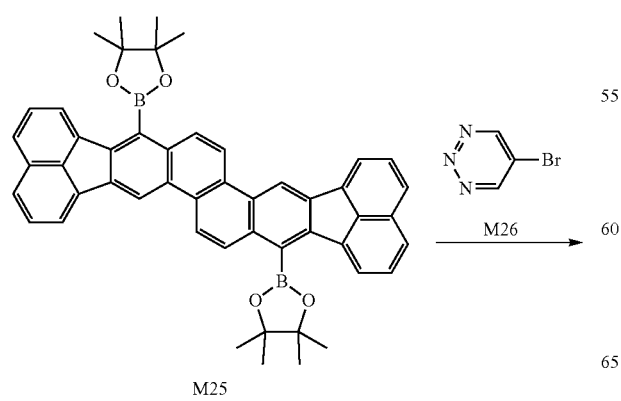

(1) Synthesis of Compound M25

The following reagents and solvent were charged into a 500 ml recovery flask.

Compound M24: 556 mg (1.01 mmol)
bis(pinacolborane): 1.03 g (4.04 mmol)
Pd(dba)$_2$: 58 mg (0.10 mmol)
P(Cy)$_3$: 85 mg (0.30 mmol)
Potassium acetate: 392 mg (4.04 mmol)
o-Xylene: 300 ml Subsequently, the reaction solution was heated to 150° C. in a nitrogen stream, and stirring was performed at this temperature (150° C.) for 7 hours. After the completion of the reaction, celite filtration was performed. The resulting product was concentrated and washed by dispersion with heptane to obtain 404 mg of a gray compound M25 (yield: 55%).

(2) Synthesis of Exemplary Compound D22

The following reagents and solvent were charged into a 200 ml recovery flask.
Compound M25: 200 mg (0.27 mmol)
Compound M26: 87 mg (1.80 mmol)
Pd(OAc)$_2$: 8 mg (0.04 mmol)
s-phos: 36 mg (0.10 mmol)
Potassium carbonate: 298 g (2.16 mmol)
DMSO: 50 ml Subsequently, the reaction solution was heated to 100° C. in a nitrogen stream, and stirring was performed at this temperature (100° C.) for 6 hours. After the completion of the reaction, 100 ml of methanol was added thereto and stirring was performed at room temperature for 30 minutes. After that, filtration was performed. The resulting product was purified by silica gel column chromatography (chlorobenzene) and then washed by dispersion with heptane/toluene to obtain 103 mg of a yellow exemplary compound D22 (yield: 60%).

The emission spectrum of a toluene solution of the exemplary compound D22 at 1×10$^{-5}$ mol/L was determined by photoluminescence measurement at an excitation wavelength of 350 nm using an F-4500 manufactured by Hitachi, Ltd. As a result, a spectrum having the maximum intensity at 442 nm was obtained.

Example 38 (Synthesis of Exemplary Compound D23)

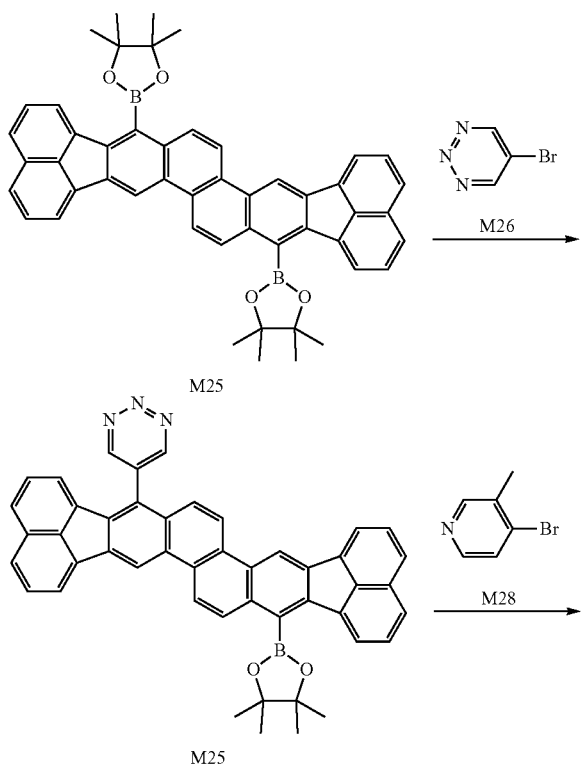

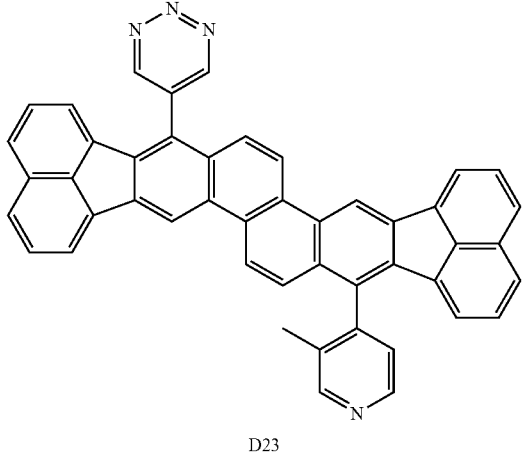

D23

The following reagents and solvent were charged into a 200 ml recovery flask.
Compound M25: 200 mg (0.27 mmol)
Compound M26: 43 mg (0.27 mmol)
Pd(OAc)$_2$: 8 mg (0.04 mmol)
s-phos: 36 mg (0.10 mmol)
Potassium carbonate: 298 g (2.16 mmol)
DMSO: 50 ml Subsequently, the reaction solution was heated to 100° C. in a nitrogen stream, and stirring was performed at this temperature (100° C.) for 3 hours. After the reaction solution was cooled to room temperature, the following reagents were added thereto.
Compound M28: 93 mg (0.54 mmol)
Pd(OAc)$_2$: 8 mg (0.04 mmol)
s-phos: 36 mg (0.10 mmol)
Potassium carbonate: 298 g (2.16 mmol)

Subsequently, the reaction solution was heated to 100° C. in a nitrogen stream, and stirring was performed at this temperature (100° C.) for 6 hours. After the completion of the reaction, 100 ml of methanol was added thereto and stirring was performed at room temperature for 30 minutes. After that, filtration was performed. The resulting product was purified by silica gel column chromatography (chlorobenzene) and then washed by dispersion with heptane/toluene to obtain 17 mg of a yellow exemplary compound D23 (yield: 10%).

Furthermore, the exemplary compound was subjected to mass spectrometry using MALDI-TOF-MS (Autoflex LRF manufactured by Bruker).
MALDI-TOF-MS
Measured value: m/z=647, Calculated value: $C_{47}H_{26}N_4$=647

Examples 39 to 48 (Synthesis of Exemplary Compounds)

As shown in Tables 11 and 12, exemplary compounds in Examples 39 to 48 were synthesized in the same manner as in Examples 37 and 38, except that the raw material M25 in Example 37 was changed to a raw material 5, the raw material M26 in Examples 37 and 38 was changed to a raw material 6, and the raw material M28 in Example 38 was changed to a raw material 7. The measured value m/z of mass spectrometry performed in the same manner as in Examples 23 to 25 is also shown.

TABLE 11
| Example | Exemplary compound | Raw material 5 | Raw material 6 | Raw material 7 | m/z |
|---|---|---|---|---|---|
| 39 | 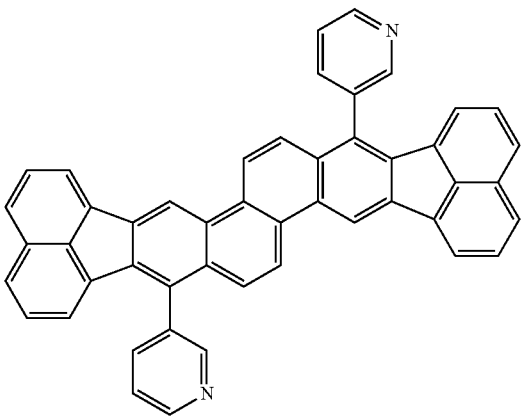<br>D6 | M15 | 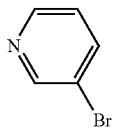 | — | 630 |
| 40 | 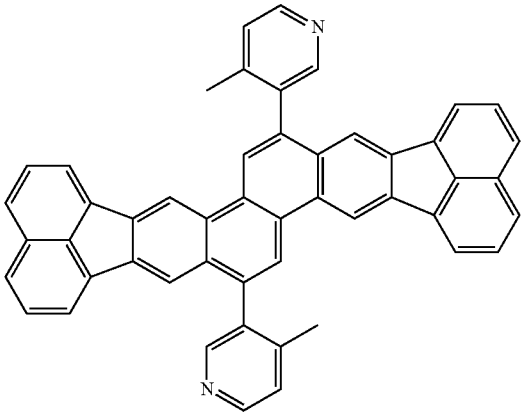<br>D9 | M10 | 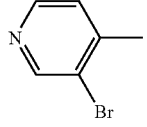 | — | 658 |
| 41 | 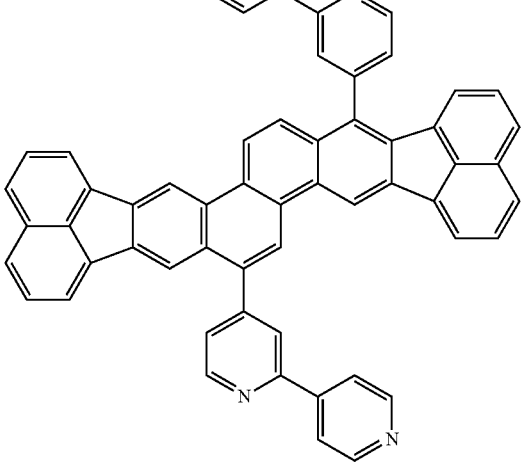<br>D20 | M15 | 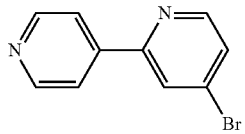 [SMILES: Brc1ccnc(-c2ccncc2)c1] | — | 784 |

TABLE 11-continued
| Example | Exemplary compound | Raw material 5 | Raw material 6 | Raw material 7 | m/z |
|---|---|---|---|---|---|
| 42 | 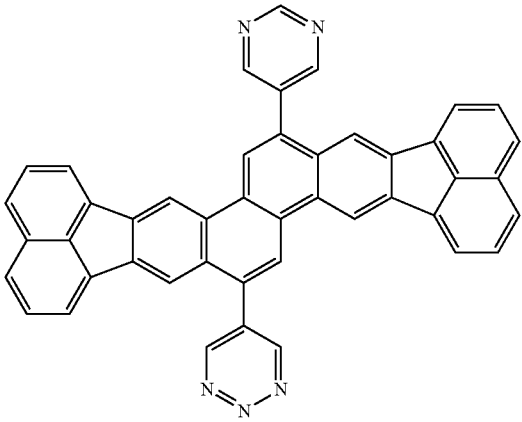<br>D25 | M12 | M26 | 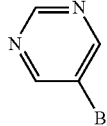 | 633 |
| 43 | 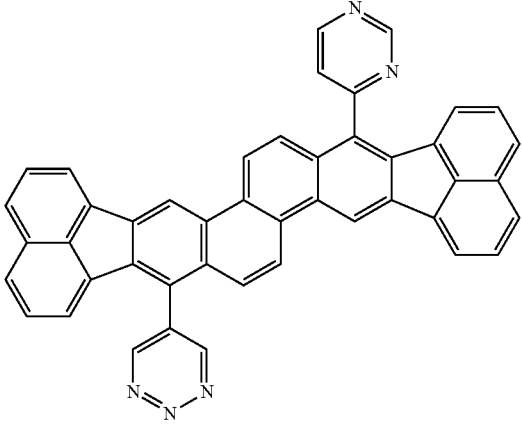<br>D28 | M16 | M26 | 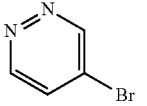 | 633 |
| 44 | 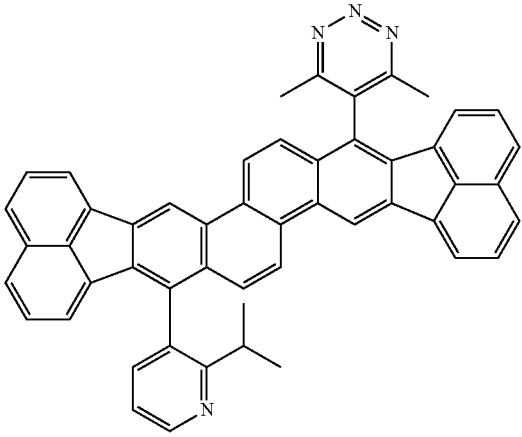 [SMILES: Cc1nnnc(C)c1-c1c2c(cc3c1ccc1c4cc5c(c(-c6cccnc6C(C)C)c4ccc31)-c1cccc3cccc-5c13)-c1cccc3cccc-2c13] | M16 | 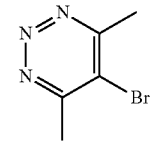 |  | 702 |

TABLE 12
| Example | Exemplary compound | Raw material 5 | Raw material 6 | Raw material 7 | m/z |
|---|---|---|---|---|---|
| 45 | 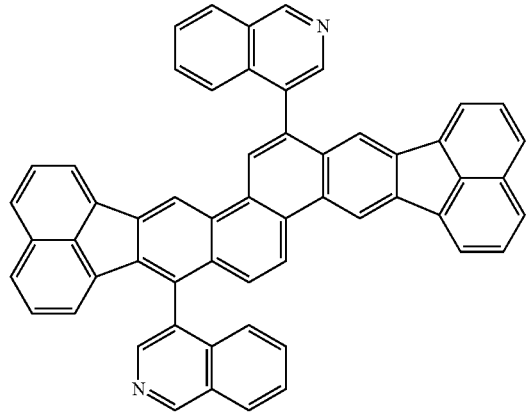<br>E5 | M15 | 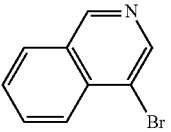 [SMILES: Brc1cncc2ccccc12] | — | 730 |
| 46 | 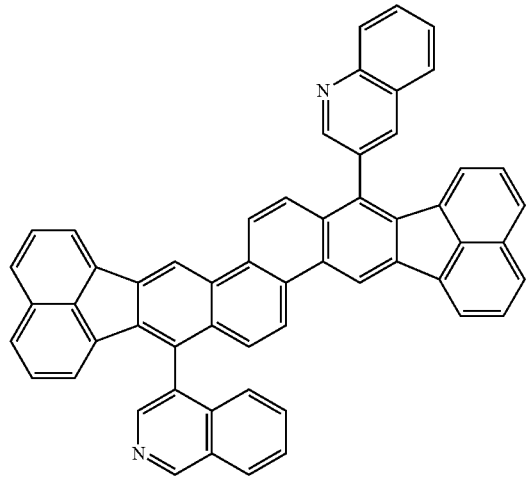<br>E12 | M16 | 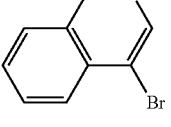 | 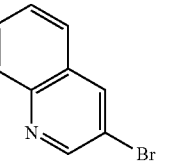 | 730 |
| 47 | 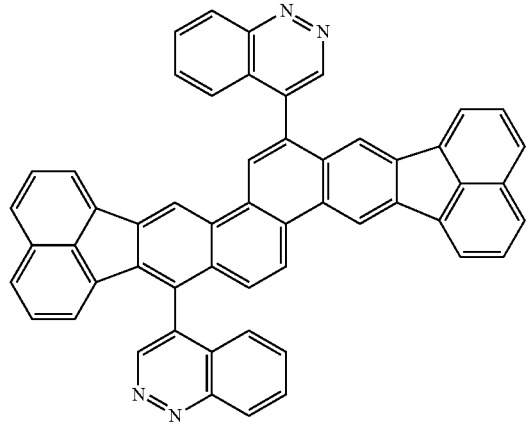<br>F7 | M12 | 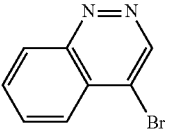 [SMILES: Brc1cnnc2ccccc12] | — | 732 |

TABLE 12-continued

| Example | Exemplary compound | Raw material 5 | Raw material 6 | Raw material 7 | m/z |
|---|---|---|---|---|---|
| 48 | 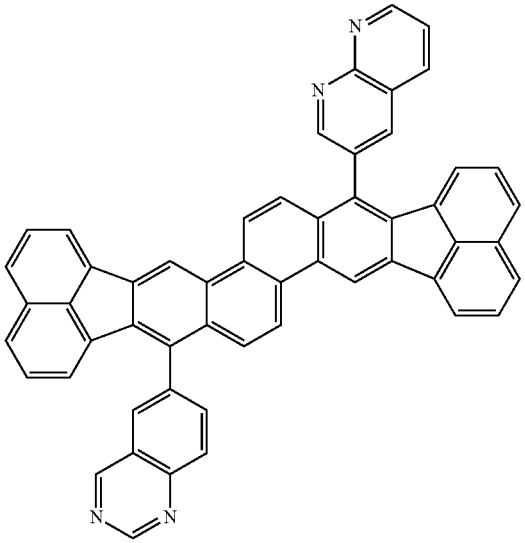<br>F12 | M16 | 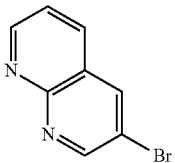 [SMILES: Brc1cnc2ncccc2c1] | 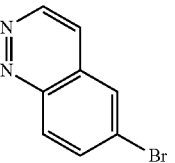 [SMILES: Brc1ccc2nnccc2c1] | 732 |

Example 49

In this Example, a bottom-emission organic EL element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process. Subsequently, the organic EL layers and the electrode layer shown in Table 13 were successively formed on the ITO substrate by performing vacuum vapor deposition through resistance heating in a vacuum chamber. At this time, the electrode area of a counter electrode (metal electrode layer, cathode) was set to 3 mm$^2$.

TABLE 13

| | Material | | Thickness (nm) |
|---|---|---|---|
| Cathode | Al | | 100 |
| Electron injection layer (EIL) | LiF | | 1 |
| Electron transport layer (ETL) | ET2 | | 15 |
| Hole blocking layer (HBL) | ET12 | | 15 |
| Light-emitting layer (EML) | Host EM4<br>Guest A1 | Mass ratio<br>EM4:A1 = 99:1 | 20 |
| Electron blocking layer (EBL) | HT12 | | 15 |
| Hole transport layer (HTL) | HT3 | | 30 |
| Hole injection layer (HIL) | HT16 | | 5 |

The characteristics of the obtained element were measured and evaluated. The light-emitting element had a maximum emission wavelength of 445 nm and a maximum external quantum efficiency (E.Q.E) of 5.9%, and emitted blue light with a chromaticity of (X, Y)=(0.15, 0.06). For the measurement instrument, specifically, the current-voltage characteristics were measured with a microammeter 4140B manufactured by Hewlett-Packard Company, and the emission luminance was measured with a BM7 manufactured by TOPCON Corporation. Furthermore, a continuous driving test at a current density of 80 mA/cm$^2$ was performed to measure a time (LT95) taken when the luminance decrease reached 5%. The time was 100 hours. Table 14 shows the measurement results.

Examples 50 to 62 and Comparative Examples 1 and 2

Organic light-emitting elements were produced by the same method as in Example 49, except that the compounds were appropriately changed to those listed in Table 14. The characteristics of the obtained elements were measured and evaluated in the same manner as in Example 49. Table 14 shows the measurement results.

TABLE 14

| | HIL | HTL | EBL | EML Host | EML Guest | HBL | ETL | E.Q.E [%] | LT95 [h] | Blue chromaticity coordinates (x, y) |
|---|---|---|---|---|---|---|---|---|---|---|
| Example 49 | HT16 | HT3 | HT12 | EM4 | A1 | ET12 | ET2 | 5.9 | 100 | (0.15, 0.06) |
| Example 50 | HT16 | HT3 | HT12 | EM4 | A2 | ET12 | ET2 | 6.0 | 105 | (0.15, 0.06) |
| Example 51 | HT16 | HT3 | HT11 | EM1 | A3 | ET12 | ET2 | 6.0 | 110 | (0.15, 0.06) |
| Example 52 | HT16 | HT2 | HT12 | EM4 | A7 | ET12 | ET2 | 5.9 | 105 | (0.14, 0.07) |
| Example 53 | HT16 | HT3 | HT11 | EM3 | A8 | ET10 | ET2 | 6.0 | 110 | (0.14, 0.07) |
| Example 54 | HT16 | HT2 | HT8 | EM3 | A12 | ET12 | ET3 | 5.8 | 95 | (0.14, 0.08) |
| Example 55 | HT16 | HT3 | HT11 | EM3 | A21 | ET12 | ET2 | 5.9 | 100 | (0.15, 0.06) |
| Example 56 | HT16 | HT2 | HT12 | EM4 | A23 | ET12 | ET2 | 6.0 | 105 | (0.15, 0.06) |
| Example 57 | HT16 | HT3 | HT11 | EM3 | A24 | ET12 | ET2 | 5.9 | 95 | (0.15, 0.06) |
| Example 58 | HT16 | HT2 | HT8 | EM6 | B2 | ET12 | ET3 | 5.9 | 100 | (0.14, 0.11) |
| Example 59 | HT16 | HT2 | HT12 | EM8 | B14 | ET10 | ET2 | 6.0 | 105 | (0.14, 0.10) |
| Example 60 | HT16 | HT2 | HT12 | EM3 | B25 | ET10 | ET2 | 6.0 | 100 | (0.14, 0.10) |
| Example 61 | HT16 | HT2 | HT12 | EM4 | C11 | ET12 | ET2 | 6.2 | 95 | (0.14, 0.10) |
| Example 62 | HT16 | HT2 | HT11 | EM4 | C17 | ET12 | ET3 | 6.0 | 95 | (0.15, 0.09) |
| Comparative Example 1 | HT16 | HT3 | HT12 | EM1 | Comparative compound 1-a | ET12 | ET2 | 4.7 | 75 | (0.14, 0.13) |
| Comparative Example 2 | HT16 | HT3 | HT12 | EM4 | Comparative compound 1-b | ET10 | ET2 | 5.5 | 75 | (0.14, 0.11) |

Table 14 shows that the 5% degradation lifetime (LT95) in Comparative Example 1 in which the comparative compound 1-a described in PTL 1 was used and in Comparative Example 2 in which the comparative compound 1-b was used was 80 hours or shorter, which was worse than the light-durability characteristics of the blue light-emitting elements in Examples. In contrast, the elements including the organic compound according to this embodiment had high durability. This is because the compound according to this embodiment has a benzochalcogenophene derivative group and thus has high electron acceptability and high charge stability.

The external quantum efficiency in Comparative Example 1 was 5% or less, which was lower than that of the blue light-emitting elements in Examples. In contrast, the elements including the organic compound according to this embodiment had high-efficient blue light emission characteristics. This is because the compound according to this embodiment has a benzochalcogenophene derivative group and thus the concentration quenching in the form of thin film can be reduced.

Example 63

In this Example, a top-emission organic EL element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A multilayer film of Al and Ti having a thickness of 40 nm was formed on a glass substrate by a sputtering method and patterned by photolithography to form an anode. At this time, the electrode area of a counter electrode (metal electrode layer, cathode) was set to 3 mm$^2$. Subsequently, the cleaned substrate on which the electrode had been formed and materials were placed in a vacuum evaporation system (manufactured by ULVAC, Inc.), and the system was evacuated to a pressure of $1.3 \times 10^{-4}$ Pa ($1 \times 10^{-6}$ Torr) and then UV/ozone cleaning was performed. Subsequently, layers shown in Table 15 were formed. Lastly, sealing was performed in a nitrogen atmosphere.

TABLE 15

| | Material | | | Thickness (nm) |
|---|---|---|---|---|
| Cathode | Mg Ag | | Mass ratio Mg:Ag = 50:50 | 10 |
| Electron injection layer (EIL) | | LiF | | 1 |
| Electron transport layer (ETL) | | ET2 | | 25 |
| Hole blocking layer (HBL) | | ET12 | | 80 |
| Second light-emitting layer (2nd EML) | Second host Second guest (blue dopant) | EM1 A1 | Mass ratio EM1:A1 = 99:1 | 15 |
| First light-emitting layer (1st EML) | First host First guest (red dopant) Third guest (green dopant) | EM1 RD1 GD7 | Mass ratio EM1:RD1:GD7 = 96.7:0.3:3.0 | 10 |
| Electron blocking layer (EBL) | | HT7 | | 10 |
| Hole transport layer (HTL) | | HT2 | | 20 |

TABLE 15-continued

| | Material | Thickness (nm) |
|---|---|---|
| Hole injection layer (HIL) | HT16 | 5 |

The characteristics of the obtained element were measured and evaluated. The obtained element exhibited good white light emission. Furthermore, a continuous driving test at an initial luminance of 1000 cd/m² was performed to measure a luminance decrease after 100 hours. Table 16 shows the results.

Examples 64 to 68 and Comparative Example 3

Organic light-emitting elements were produced by the same method as in Example 63, except that the compounds were appropriately changed to those listed in Table 16. The characteristics of the obtained elements were measured and evaluated in the same manner as in Example 63. Table 16 shows the measurement results.

TABLE 16

| | 1st EML | | | 2nd EML | | Luminance decrease [%] |
|---|---|---|---|---|---|---|
| | First host | First guest | Third guest | Second host | Second guest | |
| Example 63 | EM1 | RD1 | GD7 | EM1 | A1 | 15 |
| Example 64 | EM1 | RD1 | GD7 | EM3 | A3 | 13 |
| Example 65 | EM1 | RD1 | GD6 | EM1 | A7 | 13 |
| Example 66 | EM4 | RD1 | GD6 | EM4 | A9 | 14 |
| Example 67 | EM1 | RD1 | GD7 | EM1 | A21 | 15 |
| Example 68 | EM2 | RD1 | GD6 | EM2 | C11 | 18 |
| Comparative Example 3 | EM4 | RD1 | GD6 | EM4 | Comparative compound 1-a | 23 |

Table 16 shows that the organic light-emitting element including the comparative compound 1-a had a luminance decrease of 23%. This is because when the comparative compound is used as a guest, the reduction potential is low and the electron acceptability is not sufficient and therefore the organic light-emitting elements have poor chemical stability. In contrast, the elements including the organic compound according to this embodiment had high durability. This is because the compound according to this embodiment has a benzochalcogenophene derivative group and thus has high electron acceptability and high charge stability.

Thus, the organic compound according to this embodiment has high electron acceptability due to its high reduction potential, contributes to high light emission efficiency due to reduced concentration quenching, and exhibits blue light emission with a high color purity. Accordingly, when the organic compound according to this embodiment is used for organic light-emitting elements, the organic light-emitting elements have high light emission efficiency and high driving durability.

Example 69

In this Example, a bottom-emission organic EL element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process. Subsequently, the organic EL layers and the electrode layer shown in Table 17 were successively formed on the ITO substrate by performing vacuum vapor deposition through resistance heating in a vacuum chamber. At this time, the electrode area of a counter electrode (metal electrode layer, cathode) was set to 3 mm².

TABLE 17

| | Material | | | Thickness (nm) |
|---|---|---|---|---|
| Cathode | Al | | | 100 |
| Electron injection layer (EIL) | LiF | | | 1 |
| Electron transport layer (ETL) | ET2 | | | 10 |
| Hole blocking layer (HBL) | ET12 | | | 20 |
| Light-emitting layer (EML) | Host EM3 Guest D1 | Mass ratio EM3:D1 = 99.3:0.7 | | 30 |
| Electron blocking layer (EBL) | HT12 | | | 15 |
| Hole transport layer (HTL) | HT3 | | | 30 |
| Hole injection layer (HIL) | HT16 | | | 5 |

The characteristics of the obtained element were measured and evaluated. The light-emitting element had a maximum emission wavelength of 447 nm and a maximum external quantum efficiency (E.Q.E) of 5.9%, and emitted blue light with a chromaticity of (X, Y)=(0.15, 0.08). For the measurement instrument, specifically, the current-voltage characteristics were measured with a microammeter 4140B manufactured by Hewlett-Packard Company, and the emission luminance was measured with a BM7 manufactured by TOPCON Corporation. Furthermore, a continuous driving test at a current density of 100 mA/cm² was performed to measure a time (LT95) taken when the luminance decrease reached 5%. The time was more than 100 hours.

Examples 70 to 81 and Comparative Examples 4 and 5

Organic light-emitting elements were produced by the same method as in Example 69, except that the compounds were appropriately changed to those listed in Table 18. The characteristics of the obtained elements were measured and evaluated in the same manner as in Example 69. Table 18 shows the measurement results.

TABLE 18

| | HIL | HTL | EBL | EML Host | EML Guest | HBL | ETL | E.Q.E [%] | LT95 [h] | Blue chromaticity coordinates (x, y) |
|---|---|---|---|---|---|---|---|---|---|---|
| Example 70 | HT16 | HT3 | HT12 | EM4 | D1 | ET12 | ET2 | 5.9 | 120 | (0.15, 0.08) |
| Example 71 | HT16 | HT2 | HT10 | EM3 | D2 | ET12 | ET2 | 5.8 | 125 | (0.15, 0.08) |
| Example 72 | HT16 | HT1 | HT11 | EM4 | D11 | ET12 | ET2 | 6.1 | 130 | (0.15, 0.09) |
| Example 73 | HT16 | HT2 | HT10 | EM3 | D13 | ET10 | ET2 | 5.7 | 120 | (0.14, 0.08) |
| Example 74 | HT16 | HT3 | HT8 | EM3 | D20 | ET12 | ET3 | 5.6 | 110 | (0.14, 0.09) |
| Example 75 | HT16 | HT2 | HT8 | EM6 | E2 | ET12 | ET3 | 5.8 | 100 | (0.14, 0.07) |
| Example 76 | HT16 | HT2 | HT10 | EM8 | E3 | ET10 | ET2 | 5.8 | 105 | (0.14, 0.10) |
| Example 77 | HT16 | HT2 | HT12 | EM4 | F2 | ET12 | ET2 | 5.7 | 110 | (0.14, 0.10) |
| Example 78 | HT16 | HT3 | HT10 | EM4 | D22 | ET16 | ET2 | 5.7 | 130 | (0.14, 0.08) |
| Example 79 | HT16 | HT2 | HT12 | EM1 | D29 | ET12 | ET3 | 5.9 | 125 | (0.14, 0.09) |
| Example 80 | HT16 | HT2 | HT11 | EM2 | E12 | ET10 | ET3 | 5.9 | 130 | (0.15, 0.09) |
| Example 81 | HT16 | HT3 | HT12 | EM2 | F12 | ET12 | ET2 | 5.8 | 120 | (0.15, 0.10) |
| Comparative Example 4 | HT16 | HT3 | HT10 | EM2 | Comparative compound 1-A | ET12 | ET2 | 5.2 | 70 | (0.14, 0.13) |
| Comparative Example 5 | HT16 | HT3 | HT12 | EM3 | Comparative compound 1-B | ET10 | ET2 | 5.1 | 75 | (0.14, 0.15) |

Table 18 shows that the elements in Comparative Examples 4 and 5 had a 5% degradation lifetime of 100 hours or shorter, which was poor durability, whereas the elements including the organic compound according to this embodiment had a 5% degradation lifetime of longer than 100 hours. In Comparative Examples 4 and 5, the chromaticity coordinates were (0.14, 0.13) and (0.14, 0.15), respectively. The color reproduction range of sRGB is more widened in Examples than in Comparative Examples. This is because the compound according to an embodiment of the present disclosure contributes to emitting blue light with a shorter wavelength. The element including the organic compound according to an embodiment of the present disclosure has good blue light-emitting properties and high durability.

Example 82

In this Example, a top-emission organic EL element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film having a thickness of 40 nm was formed on a glass substrate by a sputtering method and patterned by photolithography to form an anode. At this time, the electrode area of a counter electrode (metal electrode layer, cathode) was set to 3 mm$^2$. Subsequently, the cleaned substrate on which the electrode had been formed and materials were placed in a vacuum evaporation system (manufactured by ULVAC, Inc.), and the system was evacuated to a pressure of $1.3 \times 10^{-4}$ Pa ($1 \times 10^{-6}$ Torr) and then UV/ozone cleaning was performed. Subsequently, layers shown in Table 19 were formed. Lastly, sealing was performed in a nitrogen atmosphere.

TABLE 19

| | Material | | | Thickness (nm) |
|---|---|---|---|---|
| Cathode | Mg | | Mass ratio | 10 |
| | Ag | | Mg:Ag = 50:50 | |
| Electron injection layer (EIL) | LiF | | | 1 |
| Electron transport layer (ETL) | ET2 | | | 30 |
| Hole blocking layer (HBL) | ET12 | | | 75 |
| Second light-emitting layer (2nd EML) | Second host | EM1 | Mass ratio | 10 |
| | Second guest (blue dopant) | D1 | EM1:D1 = 99.4:0.6 | |
| First light-emitting layer (1st EML) | First host | EM1 | Mass ratio | 10 |
| | First guest (red dopant) | RD1 | EM1:RD1:GD6 = 97.2:0.3:2.5 | |
| | Third guest (green dopant) | GD6 | | |
| Electron blocking layer (EBL) | HT8 | | | 10 |
| Hole transport layer (HTL) | HT2 | | | 20 |
| Hole injection layer (HIL) | HT16 | | | 5 |

The characteristics of the obtained element were measured and evaluated. The obtained element exhibited good white light emission. Furthermore, a continuous driving test at an initial luminance of 1000 cd/m$^2$ was performed to measure a luminance decrease after 100 hours. The luminance decrease was 14%.

Examples 83 to 89 and Comparative Example 6

Organic light-emitting elements were produced by the same method as in Example 82, except that the compounds were appropriately changed to those listed in Table 20. The characteristics of the obtained elements were measured and evaluated in the same manner as in Example 82. Table 20 shows the measurement results.

TABLE 20

| | 1st EML | | | 2nd EML | | Luminance decrease [%] |
|---|---|---|---|---|---|---|
| | First host | First guest | Third guest | Second host | Second guest | |
| Example 83 | EM1 | RD1 | GD6 | EM1 | D2 | 13 |
| Example 84 | EM1 | RD1 | GD7 | EM2 | D6 | 15 |
| Example 85 | EM1 | RD1 | GD6 | EM1 | D12 | 12 |
| Example 86 | EM4 | RD1 | GD6 | EM4 | E2 | 18 |
| Example 87 | EM4 | RD1 | GD7 | EM3 | F2 | 16 |
| Example 88 | EM2 | RD1 | GD6 | EM2 | D23 | 14 |
| Example 89 | EM1 | RD1 | GD7 | EM1 | E11 | 16 |
| Comparative Example 6 | EM4 | RD1 | GD7 | EM3 | Comparative compound 1-A | 25 |

Table 20 shows that the luminance decrease was 25% in Comparative Example 6 in which the comparative compound 1-A was used. This is because when the comparative compound is used as a guest, the reduction potential is low and the electron acceptability is not sufficient and therefore the organic light-emitting elements have poor chemical stability.

The organic compound according to an embodiment of the present disclosure is a compound that is suitable for blue light emission and has high chemical stability. Therefore, when the organic compound according to an embodiment of the present disclosure is used as a material for organic light-emitting elements, an organic light-emitting element that has good light-emitting properties and high durability can be provided.

The organic compound represented by the formula [1] according to an embodiment of the present disclosure contributes to high light emission efficiency due to reduced concentration quenching, has high electron acceptability due to its high reduction potential, and exhibits blue light emission with a high color purity.

The organic compound represented by the formula [101] according to an embodiment of the present disclosure is a blue light-emitting material having a high reduction potential, high electron acceptability, and a high color purity.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Applications No. 2019-204601, filed Nov. 12, 2019, No. 2019-211187, filed Nov. 22, 2019, and No. 2020-120637, filed Jul. 14, 2020, which are hereby incorporated by reference herein in their entirety.

What is claimed is:

1. An organic compound represented by formula [1],

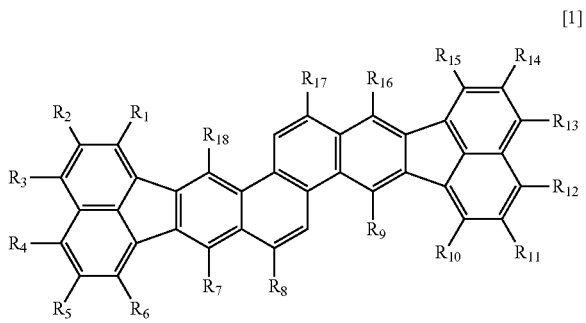

[1]

wherein in the formula [1], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, a silyl group, and a group represented by any one of formulae [2], [3], and [102] to [104], at least one of $R_1$ to $R_{18}$ represents a group represented by any one of the formulae [2], [3], and [102] to [104], the group represented by any one of the formulae [2] and [3] is a group bonded at any one of $R_{19}$ to $R_{32}$,

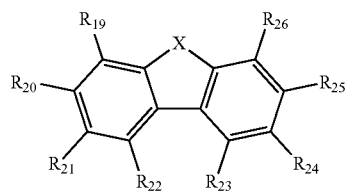

[2]

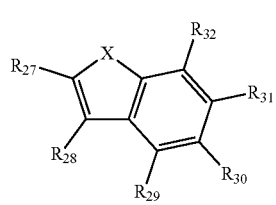

[3]

in the formulae [2] and [3], $R_{19}$ to $R_{32}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted aryloxy group, and a silyl group, $R_{19}$ to $R_{32}$ may form a ring with a group adjacent thereto, each X is independently selected from the group consisting of an oxygen atom, a sulfur atom, a selenium atom, and a tellurium atom,

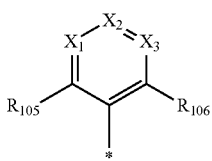

[102]

in the formula [102], $X_1$ to $X_3$ represent a carbon atom having a hydrogen atom or a substituent Y or a nitrogen atom, the carbon atom or the nitrogen atom constituting a ring, at least one of $X_1$ to $X_3$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, $R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group,

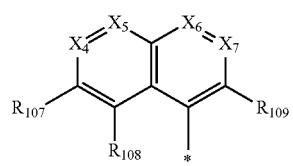

[103]

in the formula [103], $X_4$ to $X_7$ represent a carbon atom having a hydrogen atom or a substituent Y or a nitrogen atom, the carbon atom or the nitrogen atom constituting a ring, at least one of $X_4$ to $X_7$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, $R_{107}$ to $R_{109}$ represent groups each independently selected from the group consisting of a hydrogen atom, a substituted or unsubstituted alkyl group, a substituted or unsubstituted aryl group, and a substituted or unsubstituted heterocyclic group,

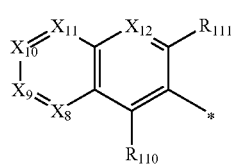

[104]

in the formula [104], $X_8$ to $X_{12}$ represent a carbon atom having a hydrogen atom or a substituent Y or a nitrogen atom, the carbon atom or the nitrogen atom constituting a ring, at least one of $X_8$ to $X_{12}$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, and $R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

2. The organic compound according to claim 1, wherein at least one of $R_1$ to $R_{18}$ represents a group represented by any one of the formulae [2] and [3].

3. The organic compound according to claim 1, wherein a number of the group represented by any one of the formulae [2], [3], and [102] to [104] is 1 or more and 4 or less.

4. The organic compound according to claim 1, wherein a number of the group represented by any one of the formulae [2], [3], and [102] to [104] is 1 or more and 2 or less.

5. The organic compound according to claim 1, wherein at least one of $R_3$, $R_4$, $R_7$, $R_8$, $R_9$, $R_{12}$, $R_{13}$, $R_{16}$, $R_{17}$, and $R_{18}$ represents a group represented by any one of the formulae [2], [3], and [102] to [104].

6. The organic compound according to claim 1, wherein at least one of $R_7$, $R_8$, $R_9$, $R_{16}$, $R_{17}$, and $R_{18}$ represents a group represented by any one of the formulae [2], [3], and [102] to [104].

7. The organic compound according to claim 1, wherein the group represented by any one of the formulae [2] and [3] is a group bonded at any one of $R_{22}$, $R_{23}$, and $R_{29}$.

8. The organic compound according to claim 1, wherein at least one of $R_1$ to $R_{18}$ represents a group represented by a dibenzofuranyl group or a dibenzothiophenyl group.

9. The organic compound according to claim 1, wherein $R_1$ to $R_{18}$ are each independently selected from the group consisting of a hydrogen atom and a group represented by any one of the formulae [2], [3], and [102] to [104].

10. The organic compound according to claim 1, wherein $R_1$, $R_6$, $R_{10}$, and $R_{15}$ represent a hydrogen atom.

11. The organic compound according to claim 1, wherein $R_3$, $R_4$, $R_{12}$, and $R_{13}$ represent a hydrogen atom.

12. The organic compound according to claim 1, wherein $R_7$, $R_9$, $R_{16}$, and $R_{18}$ represent a hydrogen atom.

13. An organic compound represented by formula [101],

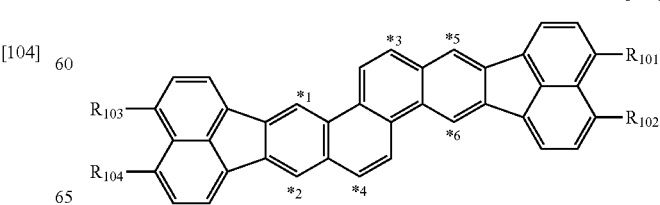

[101]

wherein in the formula [101], a group having an azine skeleton and represented by any one of formulae [102] to [104] is bonded at a position * to at least one of positions *1 to *6, when the group having an azine skeleton and represented by any one of the formulae [102] to [104] is bonded to a plurality of the positions *1 to *6, the groups having an azine skeleton and represented by any one of the formulae [102] to [104] may be the same or different, $R_{101}$ to $R_{104}$ represent groups each independently selected from the group consisting of a hydrogen atom, a substituted or unsubstituted aryl group, and a substituted or unsubstituted aryloxy group,

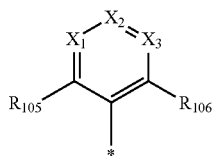

[102]

in the formula [102], $X_1$ to $X_3$ represent a carbon atom having a hydrogen atom or a substituent Y or a nitrogen atom, the carbon atom or the nitrogen atom constituting a ring, at least one of $X_1$ to $X_3$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, $R_{105}$ and $R_{106}$ represent groups each independently selected from the group consisting of a hydrogen atom, a substituted or unsubstituted alkyl group, a substituted or unsubstituted aryl group, and a substituted or unsubstituted heterocyclic group,

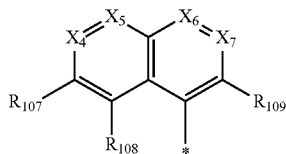

[103]

in the formula [103], $X_4$ to $X_7$ represent a carbon atom having a hydrogen atom or a substituent Y or a nitrogen atom, the carbon atom or the nitrogen atom constituting a ring, at least one of $X_4$ to $X_7$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, $R_{107}$ to $R_{109}$ represent groups each independently selected from the group consisting of a hydrogen atom, a substituted or unsubstituted alkyl group, a substituted or unsubstituted aryl group, and a substituted or unsubstituted heterocyclic group,

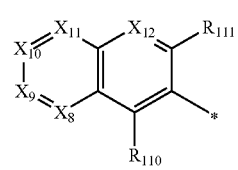

[104]

in the formula [104], $X_8$ to $X_{12}$ represent a carbon atom having a hydrogen atom or a substituent Y or a nitrogen atom, the carbon atom or the nitrogen atom constituting a ring, at least one of $X_8$ to $X_{12}$ represents a nitrogen atom, the substituent Y is a group selected from the group consisting of a substituted or unsubstituted alkyl group, a substituted or unsubstituted aryl group, a substituted or unsubstituted heterocyclic group, a substituted or unsubstituted aryloxy group, and a silyl group, when a plurality of carbon atoms having the substituent Y are present, the substituents Y may be the same or different, and $R_{110}$ and $R_{111}$ represent groups each independently selected from the group consisting of a hydrogen atom, a substituted or unsubstituted alkyl group, a substituted or unsubstituted aryl group, and a substituted or unsubstituted heterocyclic group.

14. The organic compound according to claim 13, wherein the group having an azine skeleton and represented by any one of the formulae [102] to [104] is bonded to two of the positions *1 to *6.

15. The organic compound according to claim 13, wherein the group bonded to the at least one of positions *1 to *6 is a group having an azine skeleton and represented by the formula [102].

16. The organic compound according to claim 15,
wherein the group having an azine skeleton and represented by the formula [102] is selected from groups represented by formulae [105] to [109], and

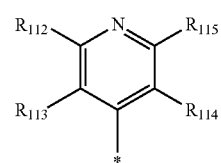

[105]

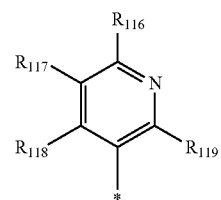

[106]

[107]
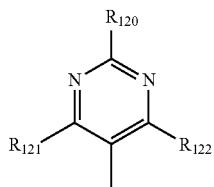

[108]
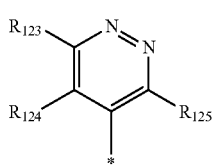

[109]
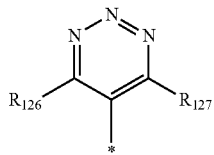

in the formulae [105] to [109], $R_{112}$ to $R_{127}$ represent groups each independently selected from the group consisting of a hydrogen atom, a substituted or unsubstituted alkyl group, a substituted or unsubstituted aryl group, and a substituted or unsubstituted heterocyclic group.

17. The organic compound according to claim 13, wherein the group bonded to the at least one of positions *1 to *6 is a group having an azine skeleton and represented by the formula [103] or [104].

18. The organic compound according to claim 17,
wherein the group having an azine skeleton and represented by the formula [103] or [104] is selected from groups represented by formulae [110] to [118], and

[110]
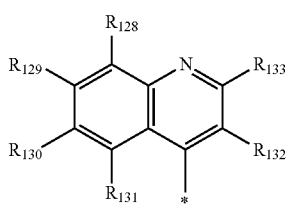

[111]
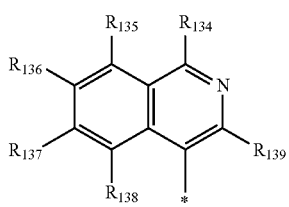

[112]
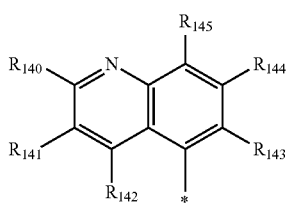

[113]
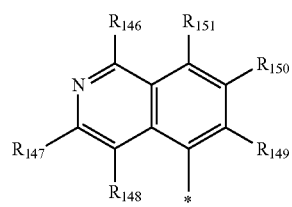

[114]
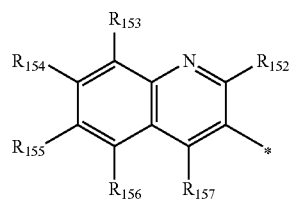

[115]
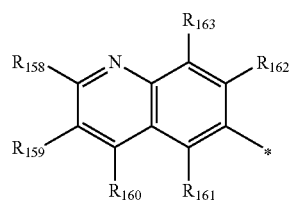

[116]
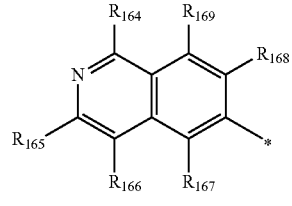

[117]
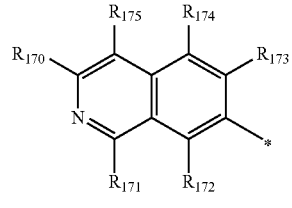

[118]
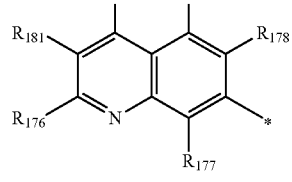

in the formulae [110] to [118], $R_{128}$ to $R_{181}$ represent groups each independently selected from the group consisting of a hydrogen atom, a substituted or unsubstituted alkyl group, a substituted or unsubstituted aryl group, and a substituted or unsubstituted heterocyclic group.

19. The organic compound according to claim 17,
wherein the group having an azine skeleton and represented by the formula [103] or [104] is selected from groups represented by formulae [119] to [124], and

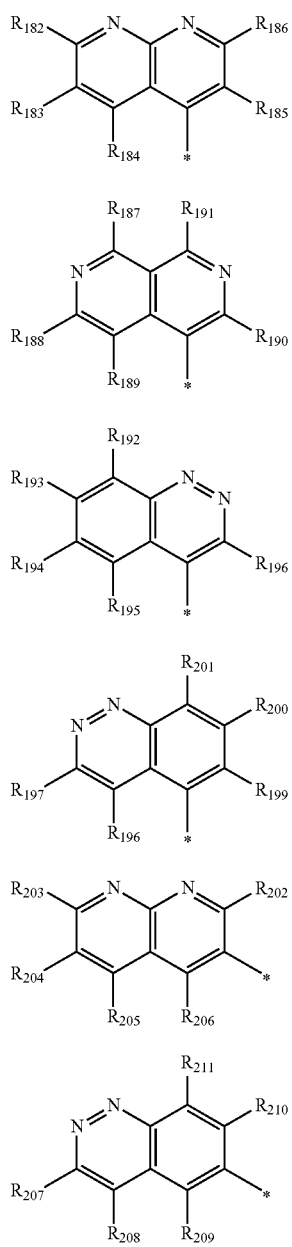

in the formulae [119] to [124], $R_{182}$ to $R_{211}$ represent groups each independently selected from the group consisting of a hydrogen atom, a substituted or unsubstituted alkyl group, a substituted or unsubstituted aryl group, and a substituted or unsubstituted heterocyclic group.

20. The organic compound according to claim 17, wherein the group having an azine skeleton and represented by the formula [103] or [104] is a group with $X_6$ and $X_7$ representing the carbon atom or a group with $X_{12}$ representing the carbon atom.

21. The organic compound according to claim 13, wherein $R_{101}$ to $R_{104}$ represent a hydrogen atom.

22. The organic compound according to claim 13, wherein $R_{101}$ to $R_{104}$ represent a group having no lone pair.

23. An organic light-emitting element comprising:
an anode;
a cathode; and
an organic compound layer disposed between the anode and the cathode,
wherein at least one layer in the organic compound layer includes the organic compound according to claim 1.

24. The organic light-emitting element according to claim 23, wherein the layer including the organic compound is a light-emitting layer.

25. The organic light-emitting element according to claim 23, wherein the organic light-emitting element emits blue light.

26. The organic light-emitting element according to claim 24,
wherein the organic compound layer further includes another light-emitting layer disposed together with the light-emitting layer so as to form a multilayer structure, and
the other light-emitting layer emits light having a color different from a color of light emitted from the light-emitting layer.

27. The organic light-emitting element according to claim 26, wherein the organic light-emitting element emits white light.

28. A display apparatus comprising a plurality of pixels,
wherein at least one of the plurality of pixels includes the organic light-emitting element according to claim 23 and a transistor connected to the organic light-emitting element.

29. A photoelectric conversion apparatus comprising:
an optical unit including a plurality of lenses;
an image pickup element that receives light which has passed through the optical unit; and
a display unit that displays an image captured by the image pickup element,
wherein the display unit includes the organic light-emitting element according to claim 23.

30. An electronic apparatus comprising:
a display unit including the organic light-emitting element according to claim 23;
a housing in which the display unit is disposed; and
a communication unit that is disposed in the housing and communicates with an external unit.

31. A lighting apparatus comprising:
a light source including the organic light-emitting element according to claim 23; and
a light diffusion unit or an optical filter that transmits light emitted from the light source.

32. A moving object comprising:
a lighting fixture including the organic light-emitting element according to claim 23; and
a body on which the lighting fixture is disposed.

33. An image forming apparatus comprising:
a photosensitive member;
an exposure light source configured to exposure the photosensitive member,
wherein the exposure light source includes the organic light-emitting element according to claim 23.

* * * * *